United States Patent [19]
Paoletti

[11] Patent Number: 5,482,713
[45] Date of Patent: Jan. 9, 1996

[54] EQUINE HERPESVIRUS RECOMBINANT POXVIRUS VACCINE

[75] Inventor: Enzo Paoletti, Albany, N.Y.

[73] Assignee: Health Research Incorporated, Albany, N.Y.

[21] Appl. No.: 124,668

[22] Filed: Sep. 21, 1993

Related U.S. Application Data

[60] Division of Ser. No. 502,834, Apr. 4, 1990, Pat. No. 5,338, 683, which is a continuation-in-part of Ser. No. 394,488, Aug. 16, 1989, abandoned, which is a continuation-in-part of Ser. No. 339,004, Apr. 17, 1989, abandoned, said Ser. No. 502,834is a continuation-in-part of Ser. No. 90,209, Aug. 27, 1987, abandoned, which is a division of Ser. No. 622,135, Jun. 19, 1984, Pat. No. 4,722,848, which is a continuation-in-part of Ser. No. 446,824, Dec. 8, 1982, Pat. No. 4,603, 112, which is a continuation-in-part of Ser. No. 334,456, Dec. 24, 1981, Pat. No. 4,769,330.

[51] Int. Cl.⁶ ............... A61K 39/285; A61K 39/275; A61K 39/245; A61K 39/27
[52] U.S. Cl. ................... 424/199.1; 424/186.1; 424/229.1; 935/65; 435/235.1
[58] Field of Search ................ 435/235.1, 69.1, 435/172.3, 235.1; 424/89, 186.1, 199.1, 229.1; 935/65

[56] References Cited

U.S. PATENT DOCUMENTS 5,242,829  9/1993  Panicali et al. ............. 424/199.1

FOREIGN PATENT DOCUMENTS 8903429  4/1989  WIPO ............. C12N 15/00
9001546  2/1990  WIPO ............. C12N 15/00

OTHER PUBLICATIONS

Stokes, A. et al. 1989, *J. Gen. Virol.* vol. 70 pp. 1173–1183.
Van Drunen–Littel–van den Hurk et al., 1989, *J. Virol.* vol. 63, pp. 2159–2168.
Whalley, J. M. et al. 1989, *J. Gen. Virol.* vol. 70 pp. 383–394.
Riggio, M. P. et al. 1989, *J. Virol.* vol. 63 pp. 1123–1133.
Taylor, J. et al. 1988, *Vaccine* vol. 6 pp. 497–503.
Allen, G. P. et al., 1987, J. Virol. vol. 61 pp. 2454–2461.
Allen, G. P. et al. 1988, J. Virol. vol. 62 pp. 2850–2858.
Cremer, K. J. et al. 1985, Science vol. 228 pp. 737–740.
Piccini, A. et al. 1987, Meth. Enzymol. vol. 153 pp. 545–563.

*Primary Examiner*—Mary E. Mosher
*Attorney, Agent, or Firm*—Curtis, Morris & Safford

[57] ABSTRACT

What is described is a recombinant poxvirus, such as vaccinia virus, fowlpox virus and canarypox virus, containing foreign DNA from herpesvirus. In one embodiment, the foreign DNA is expressed in a host by the production of a herpesvirus glycoprotein. In another embodiment, the foreign DNA is expressed in a host by the production of at least two, particularly two or three, herpesvirus glycoproteins. What is also described is a vaccine containing the recombinant poxvirus for inducing an immunological response in a host animal inoculated with the vaccine. By the present invention, the barrier of maternal immunity in a newborn offspring can be overcome or avoided.

11 Claims, 83 Drawing Sheets

```
290  ACACCCTCTGTGTTGTTGCCCAACCGTGTCCGTTCCGTTTCGGTAGAAGACGGAGACGCCCGTCTCTACGGCTAAATGCGTACCGAGCACCCGGG  1190
       T   P   S   V   F   V   A   P   T   V   S   V   S   V   E   D   G   D   A   V   C   T   A   K   C   V   P   S   T   G
320  GTGTTCGTATCGTGGTCAGTGAACGACCACCAGGGGTTCCGTCCAAGACATGACAACGGAGTCTGCCCTAGCCACTCGGGATTG           1280
       V   F   V   S   W   S   V   N   D   H   L   P   G   V   P   S   Q   D   M   T   T   G   V   C   P   S   H   S   G   L
350  GTTAACATGCAAAGCCGCCGCCCTCTCAGAAGAGAATGGGGAGGGAGTATAGCTGCATAATAGAGGGGTACCCCGACGGCCTGCCT           1370
       V   N   M   Q   S   R   R   P   L   S   E   E   N   G   E   R   E   Y   S   C   I   I   E   G   Y   P   D   G   L   P
380  ATGTTTCGGACACAGTGGTATATGACGGCCTCCCCGATTGTTGAGGACAGGCCGGTTTTGACGAGCATCATCGCAGTTACTTGCGGGGCC       1460
       M   F   S   D   T   V   V   Y   D   A   S   P   I   V   E   D   R   P   V   L   T   S   I   I   A   V   T   C   G   A
410  GCGGCACTGGGCGCTGGTCGTCTCTCATCACAGCCCGTCTCTGTTTTTACTGCTCCAAGCCCTCACAGGCCGTACAAGAAGTCTGACTTTTAG    1550
       A   L   A   L   V   V   L   I   T   A   V   C   F   Y   C   S   K   P   S   Q   A   P   Y   K   K   S   D   I   -
440  GCTGGACCGCTCTCCCCAACAACCTATTGTCAAACTCACTCTCGAGAATATGGCACTAAAATATGCGTTATACGCTAGGTGGGCTCCCCACAAGTCGTCC  1640
470  GCATAGGCCAACCGTACGACCCGGTGATATTTATAAAGCCATTATACTCTGCGGTATACGCTGATCTCTATGCGGCCCTAACGTCTAAGTAAAA  1730
     GTGTTACAATCGCGACCCGGTCGAAGATTGAAGATGAAGATTATAAATTACTACAGCTGGAAACCGTTGGGTTT                        1820
     CAACATGGCAGGAGACCCAACAGCTGCGATGCAGAGACCCAACAGCTGAAACCGCC                                          1884
```

| FIG.6A |
|--------|
| FIG.6B |
| FIG.6C |

```
AACGTTGGGTTGTTACCGCATCTCAAGGAGGAACTAGCTCGGTTTATGATTACTGCG
                                                        114
GCTAAAGGTAATTGGTCAATTAGCGAGTTTCAAAGGTTTTATTGCTTTGAGGGAGTG

ACAGGTGTGACGGCCACGCAGCGGCTGGCGTGGAAATATATCGGGGAGCTCATCCTA
                                                        228
GCCGCCGCAGTATTCTCCTCGGTTTTCCACTGTGGAGAGGTGCGCCTCCTGCGCGCA

GATCGTACCTACCCGGACTCCAGCGGCGCACAGCGCTGCGTGAGCGGCATTTACATA
                                                        342
ACCTACGAGGCGTCATGTCCTCTGGTTGCCGTTCTGTCGGCGGCTCCACATGGGGCA
              M  S  S  G  C  R  S  V  G  G  S  T  W  G

ATTGGCGCGGAGACGGTGGTGATTTACGACAGCGACGTGTTCTCTCTCCTGTATGCA
 N  W  R  G  D  G  G  D  L  R  Q  R  R  V  L  S  P  V  C
                                                        456
GTGCTCCAGCAGCTGGCTCCTGGATCGGGAGCCAACTAGGCAATGTTGGAAACTTAC
 S  A  P  A  A  G  S  W  I  G  S  Q  L  G  N  V  G  N  L
15
TCGCCACCCCCCACCCGCTGGGAAAGCCGGCATCATCGAGGGTGGGCACAATAGTTC
 L  A  T  P  H  P  L  G  K  P  A  S  S  R  V  G  T  I  V
                                                        570
TAGCCTGTTTGTTGCTTTTTGGAAGCTGTGTTGTTAGAGCCGTACCCACCACGCCAA
 L  A  C  L  L  L  F  G  S  C  V  V  R  A  V  P  T  T  P
53
GCCCCCCAACTAGTACTCCCACTTCCATGTCAACGCACTCCCATGGGACAGTAGACC
 S  P  P  T  S  T  P  T  S  M  S  T  H  S  H  G  T  V  D
                                                        684
CTACGCTGCTCCCCACAGAAACGCCCGACCCACTCAGACTGGCTGTGCGCGAGTCCG
 P  T  L  L  P  T  E  T  P  D  P  L  R  L  A  V  R  E  S
91
GTATACTCGCTGAGGATGGAGACTTTTACACCTGCCCACCGCCTACCGGATCCACCG
 G  I  L  A  E  D  G  D  F  Y  T  C  P  P  P  T  G  S  T
                                                        798
TCGTACGCATCGAACCACCTAGAACTTGCCCCAAGTTTGACCTTGGGAGAAACTTCA
 V  V  R  I  E  P  P  R  T  C  P  K  F  D  L  G  R  N  F
129                                                     *
CGGAGGGGATTGCTGTTATTTTTAAGGAAAACATCGCTCCCTACAAATTCAGGGCAA
 T  E  G  I  A  V  I  F  K  E  N  I  A  P  Y  K  F  R  A
                                                        912
ACGTATACTACAAGGACATCGTTGTAACACGTGTGTGGAAAGGATACAGCCATACGT
 N  V  Y  Y  K  D  I  V  V  T  R  V  W  K  G  Y  S  H  T
167
CCCTGTCCGACAGATACAATGACAGGGTTCCGGTTTCGGTGGAGGAGATCTTCGGTC
 S  L  S  D  R  Y  N  D  R  V  P  V  S  V  E  E  I  F  G
                                                        1026
TCATCGACAGTAAGGGAAAATGTTCGTCAAAGGCCGAGTACCTCAGAGATAACATCA
 L  I  D  S  K  G  K  C  S  S  K  A  E  Y  L  R  D  N  I
205
TGCACCACGCGTACCACGACGACGAGGACGAGGTGGAGCTTGATTTGGTGCCGTCCA
 M  H  H  A  Y  H  D  D  E  D  E  V  E  L  D  L  V  P  S
                                                        1140
AGTTTGCAACTCCGGGGGCCAGAGCCTGGCAGACCACCAACGATACTACGTCTTACG
 K  F  A  T  P  G  A  R  A  W  Q  T  T  N  D  T  T  S  Y
```

FIG. 6A

```
243
TGGGTGGATGCCATGGAGGCACTACACGTCAACGTCTGTCAACTGCATCGTCGAGG
 V  G  W  M  P  W  R  H  Y  T  S  T  S  V  N  C  I  V  E
                                                        1254
AGGTGGAGGCGCGGTCCGTCTACCCCTACGACTCCTTCGCCCTGTCCACCGGTGATA
 E  V  E  A  R  S  V  Y  P  Y  D  S  F  A  L  S  T  G  D
281
TTGTGTACGCGTCTCCGTTTTACGGCCTGAGGGCTGCCGCTCGCATAGAGCACAATA
 I  V  Y  A  S  P  F  Y  G  L  R  A  A  A  R  I  E  H  N
                                                        1368
GCTACGCGCAGGAGCGTTTCAGGCAAGTTGAAGGGTACAGGCCCCGCGACTTAGACA
 S  Y  A  Q  E  R  F  R  Q  V  E  G  Y  R  P  R  D  L  D
319
GTAAACTACAAGCCGAAGAGCCGGTTACCAAAAATTTTATCACTACCCCGCATGTCA
 S  K  L  Q  A  E  E  P  V  T  K  N  F  I  T  T  P  H  V
                                                        1482
CCGTCAGCTGGAACTGGACCGAGAAGAAAGTCGAGGCGTGTACGCTGACCAAATGGA
 T  V  S  W  N  W  T  E  K  K  V  E  A  C  T  L  T  K  W
357                *
AAGAGGTCGACGAACTCGTCAGGGACGAGTTCCGCGGGTCCTACAGATTTACTATTC
 K  E  V  D  E  L  V  R  D  E  F  R  G  S  Y  R  F  T  I
                                                        1596
GATCCATCTCGTCTACGTTTATCAGTAACACTACTCAATTTAAGTTGGAAAGTGCCC
 R  S  I  S  S  T  F  I  S  N  T  T  Q  F  K  L  E  S  A
395                            *
CCCTTACTGAATGTGTATCCAAAGAAGCAAAGGAAGCCATAGACTCGATATACAAAA
 P  L  T  E  C  V  S  K  E  A  K  E  A  I  D  S  I  Y  K
                                                        1710
AGCAGTACGAGTCTACGCACGTCTTTAGCGGTGATGTGGAATATTACCTGGCACGCG
 K  Q  Y  E  S  T  H  V  F  S  G  D  V  E  Y  Y  L  A  R
433
GGGGGTTCTTAATTGCATTCAGACCTATGCTCTCCAACGAACTCGCCAGGCTGTACC
 G  G  F  L  I  A  F  R  P  M  L  S  N  E  L  A  R  L  Y
                                                        1824
TGAACGAGCTTGTGAGATCTAACCGCACCTACGACCTAAAAAATCTATTGAACCCCA
 L  N  E  L  V  R  S  N  R  T  Y  D  L  K  N  L  L  N  P
471                   *
ATGCAAACAATAACAATAACACCACGCGAAGACGCAGGTCTCTCCTGTCAGTACCAG
 N  A  N  N  N  N  T  T  R  R  R  R  S  L  L  S  V  P
       *  *                                             1938
AACCTCAGCCAACCCAAGATGGTGTGCATAGAGAACAAATTCTACATCGCTTGCACA
 E  P  Q  P  T  Q  D  G  V  H  R  E  Q  I  L  H  R  L  H
509
AACGAGCAGTGGAGGCAACGGCAGGTACCGATTCTTCCAACGTCACCGCCAAACAGC
 K  R  A  V  E  A  T  A  G  T  D  S  S  N  V  T  A  K  Q
                                              *         2052
TGGAGCTCATCAAAACCACGTCGTCTATCGAGTTTGCCATGCTACAGTTTGCATACG
 L  E  L  I  K  T  T  S  S  I  E  F  A  M  L  Q  F  A  Y
547
ATCACATCCAATCCCACGTCAATGAAATGCTAAGTAGAATAGCAACTGCGTGGTGTA
 D  H  I  Q  S  H  V  N  E  M  L  S  R  I  A  T  A  W  C
                                                        2166
CCCTCCAAAACAAAGAGCGGACCCTATGGAACGAAATGGTGAAGATTAACCCGAGCG
 T  L  Q  N  K  E  R  T  L  W  N  E  M  V  K  I  N  P  S
                                                    *
```

FIG. 6B

```
585
CCATAGTCTCCGCAACCCTTGACGAGCGAGTTGCAGCGAGGGTCCTGGGGGACGTGA
 A  I  V  S  A  T  L  D  E  R  V  A  A  R  V  L  G  D  V
                                                      2280
TAGCTATAACGCACTGCGCCAAAATAGAGGGCAACGTGTACTTGCAAAACTCCATGC
 I  A  I  T  H  C  A  K  I  E  G  N  V  Y  L  Q  N  S  M
623
GCTCGATGGACAGTAACACGTGCTACTCCCGCCCCCCGTAACATTTACAATTACTA
 R  S  M  D  S  N  T  C  Y  S  R  P  P  V  T  F  T  I  T
                                                      2394
AGAATGCAAACAACAGAGGGTCGATAGAAGGCCAGCTGGGAGAGGAGAACGAGATTT
 K  N  A  N  N  R  G  S  I  E  G  Q  L  G  E  E  N  E  I
661
TCACGGAGCGCAAGCTGATCGAGCCGTGCGCCCTCAATCAGAAGCGCTACTTTAAGT
 F  T  E  R  K  L  I  E  P  C  A  L  N  Q  K  R  Y  F  K
                                                      2508
TTGGCAAAGAGTACGTTTACTACGAGAACTACACGTTCGTCCGCAAAGTGCCCCCCA
 F  G  K  E  Y  V  Y  Y  E  N  Y  T  F  V  R  K  V  P  P
699                              *
CGGAAATCGAGGTTATCAGCACGTACGTTGAACTAAACTTGACCCTTTTGGAAGACC
 T  E  I  E  V  I  S  T  Y  V  E  L  N  L  T  L  L  E  D
                                       *              2622
GCGAGTTTCTGCCCCTGGAGGTGTACACGCGGGCTGAGCTGGAGGACACCGGCCTGC
 R  E  F  L  P  L  E  V  Y  T  R  A  E  L  E  D  T  G  L
737
TAGACTACAGCGAAATACAGCGCCGCAACCAGCTCCACGCTCTCAGGTTTTACGACA
 L  D  Y  S  E  I  Q  R  R  N  Q  L  H  A  L  R  F  Y  D
                                                      2736
TCGACAGCGTGGTCAACGTGGACAATACCGCAGTGATTATGCAGGGGATCGCCAGCT
 I  D  S  V  V  N  V  D  N  T  A  V  I  M  Q  G  I  A  S
775
TTTTCAAGGGCCTGGGTAAAGTGGGGGAGGCCGTGGGAACGCTCGTTCTCGGCGCCG
 F  F  K  G  L  G  K  V  G  E  A  V  G  T̲ ̲L̲ ̲V̲ ̲L̲ ̲G̲ ̲A̲
                                                      2850
CCGGCGCTGTTGTTTCAACCGTATCTGGAATAGCTTCGTTTTTAAACAACCCATTTG
 ̲A̲ ̲G̲ ̲A̲ ̲V̲ ̲V̲ ̲S̲ ̲T̲ ̲V̲ ̲S̲ ̲G̲ ̲I̲ ̲A̲ ̲S̲ ̲F̲ ̲L̲ ̲N̲ ̲N̲ ̲P̲ ̲F̲
813
GGGGGCTAGCCATCGGCCTGCTGGTAATCGCCGGCCTGGTAGCTGCGTTTTTTGCTT
 ̲G̲ ̲G̲ ̲L̲ ̲A̲ ̲I̲ ̲G̲ ̲L̲ ̲L̲ ̲V̲ ̲I̲ ̲A̲ ̲G̲ ̲L̲ ̲V̲ ̲A̲ ̲A̲ ̲F̲ ̲F̲ ̲A̲
                                                      2964
ACAGATATGTAATGCAGATCCGCAGTAACCCCATGAAAGCTCTATACCCCATAACAA
 Y  R  Y  V  M  Q  I  R  S  N  P  M  K  A  L  Y  P  I  T
851
CAAAGGCCTTGAAAAACAAAGCCAAAACTTCCTACGGCCAGAACGAGGAGGACGATG
 T  K  A  L  K  N  K  A  K  T  S  Y  G  Q  N  E  E  D  D
                                                      3078
GGAGCGACTTTGATGAGGCCAAGCTTGAAGAGGCTCGCGAAATGATCAAATACATGT
 G  S  D  F  D  E  A  K  L  E  E  A  R  E  M  I  K  Y  M
889
CTATGGTTTCGGCCCTGGAAAAGCAGGAAAAGAAAGCTATAAAGAAAAACAGTGGGG
 S  M  V  S  A  L  E  K  Q  E  K  K  A  I  K  K  N  S  G
                                                      3192
TTGGCCTGATCGCCAGTAACGTCTCAAAGCTGGCCCTGCGAAGGCGCGGTCCCAAAT
 V  G  L  I  A  S  N  V  S  K  L  A  L  R  R  R  G  P  K
927             *
ATACCCGACTCCAACAGAACGATACCATGGAAAATGAAAAAATGGTTTAAACATGTT
 Y  T  R  L  Q  Q  N  D  T  M  E  N  E  K  M  V  -
                        *                             3306
T̲A̲A̲T̲A̲A̲A̲TATTATGACACGTACTCAAAGTGTGACCTCATATTTGCATAACCACTTTC
965                                                   3351
TAGTTCCGGCCCCAAGGATATTTAAGCCTAGTATCTCCGCCGAGG
```

FIG. 6C

Construction of plasmids containing EHV-1 gp14

Modification of the 5' end of EHV-1 gp14

Removal of extraneous EHV-1 DNA

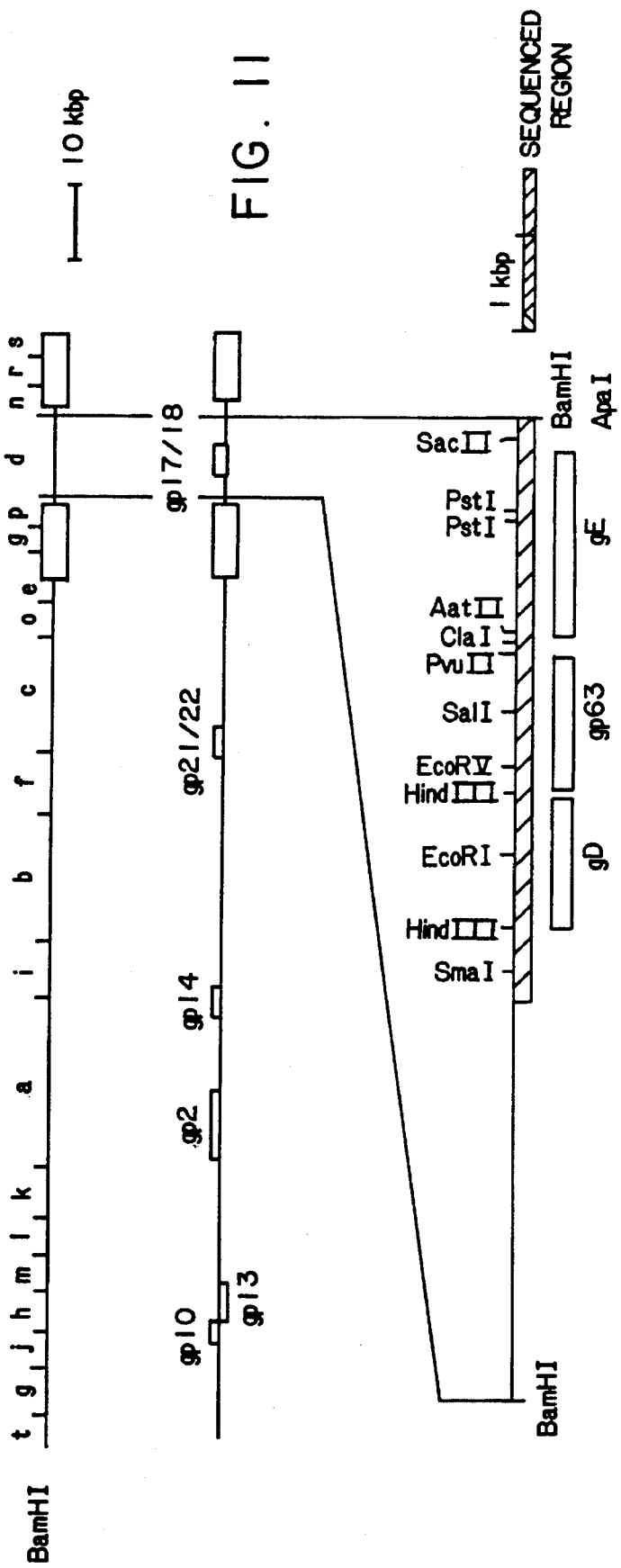

| FIG.12 |
|---|
| FIG.12A |
| FIG.12B |
| FIG.12C |
| FIG.12D |
| FIG.12E |
| FIG.12F |
| FIG.12G |
| FIG.12H |
| FIG.12I |
| FIG.12J |
| FIG.12K |
| FIG.12L |

1 CAGGGGTCGTCGGGTAGCCTCAGGGGTCACACACAACACCAGACCGTTGACTCCTTCTC

69 CAGACGACACCTATGACGATACAAATCACCTAACGGTAGGAACAATTCAATAGAGATCGTGCCTCAGC

137 TCCCGCCAGACCGACCCATCATAGAGCTGGGGGAGGCGACTCTCAGAAAAACTTTATGGAGGCGTCC

205 TGTACTGTGGAGACTAACTCAGGCTTGGCGATTTTTTGAAAATCGGCAAGCGTAGACGCGTT

273 TAATCGGGAACTACTCATACTCGGCTGATGCGCAATGGGTACCGTTTACGCCCTCGTATCTACGC

341 TTAGAGTTCCGTGGTTAAATGTTATTCCACTAACAAAAATTACTTGCGCTTGCCCCACGAATCTA

409 GTCGCCGGCGATGGGGAGGACCTCAACTCATGTACCACCAAATCAACCACCAATACGTGTCCGGGCCA

FIG.12A

```
477  ACAGGCGCACCCATATTTTTTCTCTGCGAAAGGGCACAGGGCTGTGTGTATCACATCAGAACTGGTGT

545  CCCAGCCCACAATAACTTGGTCAGTTGGATCAGATAGGTTGCGTAACGATGGATTTTCTCAGACGTGG
                                   Sma I
613  TATGGAATACAGCCCCGGGGGTGTGTGGTATACTGCGCAGCAGGTTCGCATTCACCGCCACCACCTGGCGC

681  TTTGGATCAACATCAAAGGACTATCTCTGTGAGGTCAGCGCATCGGACTCAAAGACGAGCGATTACAA

749  AGTGCTACCCAACGCCCCACTCAACTTCGCTTTAGTGGCTGCGACCAGCTAACAGTGACAA

817  TTTTATGCCTGCTGCTGTGCTTGTACTGTATGTTAACCCGCCCCCGAGCGTCTGTATATTAACTCAAA

885  AATTATCCCTTCGCCTTTACAACCAGTGGTGGCGTGTATGCAGAAGCGTGCCACCGCCCCTGGTACGTG
```

FIG. 12B

```
                                              HindIII
 953 TTTTTCAATAAACGAAGCATGTCTACCTTCAAGCTTATGATGGATGGACGTTTGGTTTTTGCCATGGC
                     M  S  T  F  K  L  M  M  D  G  R  L  V  F  A  M  A    17

1021 AATCGCGATCTTGAGCGTTGTGCTCTCTTGTGGAACATGCGAGAAAGCCAAGCGTGCCGGTTCGAGGAC
      I  A  I  L  S  V  V  L  S  C  G  T  C  E  K  A  K  R  A  V  R  G    59
                     _____↑

1089 GCCAGGATAGGCCAAAGGAGTTCCACCACCCGTTATTAACGACCAAGTAAAAAATGTTGACTTGCTAC
      R  Q  D  R  P  K  E  F  P  P  P  R  Y  N  Y  T  I  L  T  R  Y  N  A    82
                                       *******          *****

1157 ACTGCGCTAGCATCACCGTTTATTAACGACCAAGTAAAAAATGTTGACTTGCGGATTGTTACTGCTAC
      T  A  L  A  S  P  F  F  I  N  D  Q  V  K  N  V  D  L  R  I  V  T  A  T   105
      **

1225 GCGCCCATGTGAAATGATAGCGCTAAGACAAACATAGACTCAATCCTGAAGGAGCTGGCCG
      R  P  C  E  M  I  A  L  I  A  K  T  N  I  D  S  I  L  K  E  L  A   127

1293 CTGCCCAAAAAACTTATTCCGCCAGACTCACCTGGTTTAAAATTATGCCAACGTGTGCAACGCCTATA
      A  A  Q  K  T  Y  S  A  R  L  T  W  F  K  I  M  P  T  C  A  T  P  I   150

1361 CACGATGTTAGTTATATGAAATGCAACCCGAAGCTATCATTGCAATGTGTGATGAGAGATCAGACAT
      H  D  V  S  Y  M  K  C  N  P  K  L  S  F  A  M  C  D  E  R  S  D  I   173
```

FIG. 12C

```
1429 ACTATGGCAAGCTAGTTTAATTACTATGGCTGCTGAAACTGACGATGAACTTGGACTTGTACTGGCAG
      L  W  Q  A  S  L  I  T  M  A  A  E  T  D  D  E  L  G  L  V  L  A   195

1497 CCCCTGCACATTCTGCCTCGGGACTGTATCGCCGTGTTATAGAAATCGACGGAAGGCGAATTACACG
      A  P  A  H  S  A  S  G  L  Y  R  R  V  I  E  I  D  G  R  R  I  Y  T  218
                                                        EcoRI

1565 GACTTTTCTGTAACTATTCCCAGTGAACGGTGTCCGATTGCCTTTGAGCAAAACTTTGGCAATCCGA
      D  F  S  V  T  I  P  S  E  R  C  P  I  A  F  E  Q  N  F  G  N  P  D  241

1633 TCGGTGTAAAACTCCAGAGCAGTACTCGCGGGGAGAAGTTTTACACGTCGGTTTCTTGGTGAATTCA
      R  C  K  T  P  E  Q  Y  S  R  G  E  V  F  T  R  R  F  L  G  E  F   263

1701 ACTTCCCACAAGGAGAGCATATGACATGGTTGAAGTTCTGTTCGTCTACGATGGTGGAAACCTACCA
      N  F  P  Q  G  E  H  M  T  W  L  K  F  W  F  V  Y  D  G  G  N  L  P  286

1769 GTGCAGTTTATGAAGCCCAGCATTCGCCAAGACCCGTGCCTCCGGATAACCACCCTGGATTGATTC
      V  Q  F  Y  E  A  Q  A  F  A  R  P  V  P  P  D  N  H  P  G  F  D  S  309

1837 TGTTGAGTCGGAGATTACACAAATAAAACAGACCCGAAACCAGGCCAGGCGGACCCCAAACCCAATC
      V  E  S  E  I  T  Q  N  K  T  D  P  K  P  G  Q  A  D  P  K  P  N   331
                                 *******

1905 AGCCTTTTAAGTGGCCCAGCATCAAACACTTGCCCCAAGACTCGATGAGGTGGATGAGGTCATAGAG
      Q  P  F  K  W  P  S  I  K  H  L  A  P  R  L  D  E  V  D  E  V  I  E  354
```

FIG. 12D

```
1973 CCCGTAACAAAGCCCCCAAAAACGTCTAAGAGCAACTCTACGTTTGTGGGCATCAGGCGTCGGTTTGGG
     P  V  T  K  P  P  K  T  S  K  S  N  S  T  F  V  G  I  S  V  G  L  G    377
                                 * * * * * * *

2041 TATCGCCGGCCTAGTATTGGTGGGGCGTCATTCTATACGTCTGCTTGCGTCGGAAGAAGAACTGAAAA
     I  A  G  L  V  L  V  G  V  I  L  Y  V  C  L  R  R  K  K  E  L  K       379

2109 AGTCTGCACAGAACGGCTTGACTCGCCTACGCTCGACCTTTAAGGATGTTAAATATACCCAGCTTCCG
     K  S  A  Q  N  G  L  T  R  L  R  S  T  F  K  D  V  K  Y  T  Q  L  P    402
                                                HindIII 2177 TAAACAGTGTTGCCGTAACCTGCTGGGAGGTGTCCAACGGCCTTAAAGCTTCGCGGTTTGGAGATATAAC
     ---

2245 GCACAACCTACAACAAACGCGACACAGCAAGTAGTAGTCGCTATGCCAAACTCACTGGGATGTTCAG
                                                M  A  K  L  T  G  M  F  S    9

2313 CGCTGCGATATTACTGTCTATGGCTATATGCTCAACCGCAATCATATATCGCGGAGAACATATGAGCA
     A  A  I  L  L  S  M  A  I  C  S  T  A  I  I  Y  R  G  E  H  M  S       31

2381 TGTACCTAAACGCCAGTCTCGAGTTGCCGTGTACCCACTGATCAGTCCCTGTTTTGGTTGGCCAC
     M  Y  L  N  A  S  E  F  A  V  Y  P  T  D  Q  S  L  V  L  V  G  H       54
                  * * * * * *

2449 TTGCTCTTTCTCGACGGACAACGCTTACCCACCAACTATAGTGGGCTGATCGAATTGATTCATTA
     L  L  F  L  D  G  Q  R  L  P  T  T  N  Y  S  G  L  I  E  L  I  H  Y    77
```

FIG.12E

2517 CAACTACTCCAGCGTTTGCTACACTGTTATCCAAACGATATCGTATGAATCATGCCCGTGTAGCCA
     N Y S S V C Y T V I Q T I S Y E S C P R V A   99
     *****                                 ***

2585 ACAATGCTTTCAGATCGTGCCTCCACAAACTTCTAAGCACTACCACGACTATTCCGAGTCAATGCC
     N N A F R S C L H K T S K H Y H D Y F R V N A   122
                                              *****

2653 TCTGTTGAAACCAACGTTCTCTTAAACATCACAAAGCCTCACAGATTCCGGGGTATATCCT
     S V E T N V L L N I T K P Q P T D S G A Y I L   145
                            *****

2721 TCGCGTAAAACTTGACCACGCGCCAACCGCAGATGTTTTTGGAGTTTCCGCCTTTGTTTACGATCTAA
     R V K L D H A P T A D V F G V S A F V Y D L   167

2789 AATCTAAAACGGTCCCCGATCCAATGCCCACACAAACGGTAGAACCTACAACGAGCTATGTGTCG
     K S K T V P D P M P T T Q T V E P T T S Y V S   190

2857 ACTCCCACATACGACTATACCGATGACGTAACCACCGAAACTGAATCCACATCTACCCAACA
     T P T Y D Y T D D V T T E T E S T S T Q Q   213

2925 GGGCGATGACCTCCACTCAAACCCCTAGCGCTACAATGGGAACCCAGCTAACCACAGAGCTGCCGACAA
     A M T S T Q T P S A T W G T Q L T T E L P T   235

FIG. 12F

```
2993 ACGAAACTGTGGTTATTGGTCAGGAGGCCCTGTTATGCCATTGGTTCCAGCCATCGACACAAGGGTGCCG
      N  E  T  V  V  I  G  Q  E  A  L  L  C  H  W  F  Q  P  S  T  R  V  P    258
      *******

3061 ACCCTGTATCTGCATCTGTTGGGACGCACTGGCAATCTCCCGGAAGATGTTCTACTGGTCGAAGACTC
      T  L  Y  L  H  L  L  G  R  T  G  N  L  P  E  D  V  L  L  V  E  D  S    281

3129 TGAGTTTCTTCGTACCACATCGCCTGCACATAGGCCTTCTGCATCACCCGCTGACGGTGATGATTTTA
      E  F  L  R  T  T  S  P  A  H  R  P  S  A  S  P  A  D  G  D  D  F       303

3197 AACAGACAAACTCAACTTCCCTTAAGGCCGCAACAAGATCGTCGCAATGGTGGTTATCCCGACCGCG
      K  Q  T  N  S  L  K  A  R  N  K  I  V  A  M  V  V  I  P  T  A          326
      *******

3265 TGTGTACTAATGCTCCTCGTTGGTGGTTGTCGGTGCCGTGCCAAACATTATT
      C  V  L  M  L  L  L  V  V  G  A  I  N  G  A  V  R  K  H  L  L          349

3333 GAGTTGCGCAAGCCGCAGGATCTACCGCTCCGGACAGGGGGCGGGGGASAAERRR
      S  C  A  S  R  R  I  Y  R  S  G  Q  G  G  G  A  S  A  A  E  R  R  R    371

3401 TGACTTGCGGTCCTACTTTAGCCGGTCATCGGAGTCGCTGGCCGACGATACAACCGTCATCTACCTC
      L  T  C  G  P  T  L  A  A  S  S  E  S  L  A  D  D  T  T  V  I  Y  L    394
                                                                    PvuII

3469 CAACCCCCAAACCTTCGAAGAAACCAAGTTGGAGACCGATCCGCTTATGGAACAGCTGAACCGGAAA
      Q  P  P  N  L  R  R  K  P  S  W  R  P  I  R  L  W  N  S  ---          413
```

FIG. 12G

```
3537 CTGGAGGCCATCAAAGAAGAATCATAGTTGTGTGGGGTAGATGGGGTTGGTATTAAAGTTTGTGTATTA
     ClaI
3605 TCGATTTTATATTTATTAAAATTTGTGAAACATAAACATCTTGTGCAATGTTTACATTATTGTGATT

3673 GGGACGGTCCACTGGGAGTGGTACAACTCGGGTTTAAAGCTCTGGATGTTTGGTAGGAAACTCACAG
                       AatII
3741 TTCTCCACTTGGCGTCAAAGCAATCAGAGCGTCTAATTCGAAGTAGAAGCTCACAATGGAGCTGTTGG
                                                           M  E  L  L
                                                                        4
3809 CCGCAAGTCGCGGCTTGTATATTTTTGGCTAGTAACAGTACTCGATGCGTGGGAGTCCAACAAGTT
      A  A  S  R  A  C  I  F  F  G  L  V  T  V  L  D  A  W  G  V  Q  Q  V
                                                                        27
3877 GAACTTTCCGAGGGGGCTTGGGCTATGATCGACGGAAGGGACGTTTTAACCCCTACTAACACAACTAC
      E  L  S  E  G  A  W  A  M  I  D  G  R  D  V  L  T  P  T  N  T  T  T
                                                             * * * * * * *
                                                                       50
3945 TCGGGTCACAAAGGCCTGACGTTTTGAACCCTCCCGGTTGCGCTGGCGACATATCAGTTAAGA
      R  V  T  K  A  W  T  F  L  E  T  P  P  G  C  A  G  D  I  S  V  K
                                                                       72
4013 AGGTGTGCGTGAGCCATAGTCTGTGCGAAGATAACATTATAATAGGAAAGCACTGTAACCTCTTAACT
      K  V  C  V  S  H  S  L  C  E  D  N  I  I  I  G  K  H  C  N  L  L  T
                                                                       95
```

FIG.12H

```
4081 GGGGAACATGGCATTGCCGTTGGCCGAGTTTAACGTAGTAAACGGATCGCTGCGCAGAACAGACGATGT
        G  E  H  G  I  A  L  A  E  F  N  V  V  N  G  S  L  R  R  T  D  D  V   118
                                            * * * * * * *

4149 GTACTTTGTGAATGGTACAGTCTTTCCAATCCTTGCCGAAACCCGCAGCGTCCTACAAATCCATAGGG
        Y  F  V  N  G  T  V  F  P  I  L  A  E  T  R  S  V  L  Q  I  H  R     140
                 * * * * * * *

4217 CAACCCCCTCTATCGCCAGGGGTTACACCCTCCACGTTTCCATCGACGGAATGATGAAACACTCCGTC
        A  T  P  S  I  A  G  V  Y  T  L  H  V  S  I  D  G  M  M  K  H  S  V  163

4285 GTGCTGCTCACCGTCAAGAAGCCGCCCAAACCGCAACCACGCTTGCGCGTTAAGACCCC
        V  L  L  T  V  K  K  P  P  K  Q  P  Q  P  Q  P  R  L  R  V  K  T  P   186

4353 GCCACCCGTAACCGTTCCTCAGGTTCCCGTAAAGACCCACGGATTTGTGTGCACGGATACCACT
        P  P  V  T  V  P  Q  V  P  V  K  T  H  T  D  F  V  V  H  G  Y  H     208

4421 CGGCGGTGTACCGTGATGGCCGTGAATCTTTCGAGCTGTCGGTGAACCTGAGTCACATATCGTAGAGCCC
        S  R  V  Y  R  D  G  E  S  F  E  L  S  V  N  L  E  S  H  I  V  E  P  231

4489 AGCTTCAGCGCCGAGATTCAGTGGTACTATATGAATACATCATCGTCATCATGCGATCTATTTCGAGT
        S  F  S  A  E  I  Q  W  Y  Y  M  N  T  S  S  S  C  D  L  F  R  V     254
                                   * * * * * * *
```

FIG.12I

```
                                         Pst I
4625 TCACATCCCCCATCAGAGCGACCAAGATCCTACACCGGGTGTATGGAAACTGCAGCGATCATGAAAT
      F  T  S  P  I  R  A  T  K  I  L  H  R  V  Y  G  N  C  S  D  H  G  N   299
                                                       * * * * * * *

4693 TCGTGGCCTTCTAGGTGCCATAGCACTCTGCTGGGCAATCGTCTATACTTTATTCAACCAGCACAGAA
      S  W  P  S  R  C  H  S  T  L  L  G  N  R  L  Y  F  I  Q  P  A  Q  N   322

4761 CAGAGTGGACCTGTTGTTCAAAGACACTCCCGCGTCGGCTACCGGGCTGTATGTGTTTGTATTATTGT
      R  V  D  L  L  F  K  D  T  P  A  S  A  T  G  L  Y  V  F  V  L  L      344

4829 ACAACGGACATCCGGAGGCGTGGACGTATACGCTGCTGTCAACCGCAAATCACTTTATGAATGTGCTT
      Y  N  G  H  P  E  A  W  T  Y  T  L  L  S  T  A  N  H  F  M  N  V  L   367

4897 ACTGACGTGACCCGCCCCAGGCTAGGAGAGCACTTTTATACGGACCTCGGGCACAAATCATCACTCC
      T  D  V  T  R  P  R  L  G  E  H  F  Y  T  D  L  G  H  K  I  I  T  P   390

4965 TCATCCATCTGTAGCTACCACTGAAGAGTTGGGAGCTTGGACTCGACACTACCCTGCCTTTTTGCTGG
      H  P  S  V  A  T  T  E  E  L  G  A  W  T  R  H  Y  L  A  F  L  L      412

5033 TTATTATCTGCACGTGCCGCTAGTTGCATTGGTGGTGTGGGGCTGTATTCTCTACATCCGA
      V  I  I  C  T  C  A  A  L  L  V  A  L  V  V  W  G  C  I  L  Y  I  R   435

FIG. 12J
```

```
5101 AGCAACCGTAAGCCGTATGAAGTGCTGAACCCCTTTGAAAACGGTTTACAGAGGCGTTCCAAGCAACGA
      S  N  R  K  P  Y  E  V  L  N  P  F  F  E  T  V  Y  T  S  V  P  S  N  D
                                                                         458

5169 CCCCTCGGACGAGAGTCTTGGTGTGTTTGAGCGCCTAGCTTCGGACTCCTTCGACTCTGATT
      P  S  D  E  V  L  V  F  E  R  L  A  S  D  S  D  D  S  F  D  S  D
                                                                     480

5237 CAGACGAAGAGAGTTGGAATACCCACCACTCCCAAACCAGCTCCCACAGTCCCACCATACCAGTTGTA
      S  D  E  E  L  E  Y  P  P  P  P  P  K  P  A  P  Q  L  P  P  Y  Q  F  V
                                                                         503

5305 GACGGGGGAGACGCCCCTAGCGGCAGGTCCGGATTCAAGGTTTGGTTCCGCGATACACCCGAGCGTC
      D  G  G  D  A  P  S  G  R  S  G  F  K  V  W  F  R  D  T  P  E  A  S
                                                                     526

5373 CCCGGTTCCTCTTCATAAACCAACGCTACAGGGTCCAGACCGGGTAGCCGGGTAGCCGTCGAAGCTAAAGT
      P  V  P  L  H  K  P  T  L  Q  G  P  D  Y  S  R  V  A  S  K  L  K
                                                                   548

5441 CGATACTAAAAATGAGCAGCAACAGCGATAACACAGAGTGCTTCCGGGAGTCAACTATGCCGAGGAA
      S  I  L  K  ---
                552

5509 TGCGCAAGCTAAACGCTAAACGCAACCCTGTCAGAAACAGCACCTTTCAAGAGTATCTCGCCGTAACGCGGTTA

5577 TCCCAGATCCGGCTCAACCTCCGATTCCGACGAGACTACACAACCAGATCAAAGTACGAGTCAGATG

5645 TCAGCGAGTTTAAAAAAATGATCTGGAAACTCTACCTCCCCAAAGGCTGAGCCGCAAGCTCAG
```

FIG. 12K

```
5713  AAGGCCGAGCCTGATGCTGCTGGAAGTAGGAGCCAGTCAGCACCACTAGCTACATCTTAAACGAATGGGT
5781  GGCTCCTATGATTGGGCATTTCTGGCAATGTGTATGAGTTGTGCTTTTCAAATAAAACAAACAT
5849  TAACCCCTGTAAACATCCGTTTGTCTACTGTGTATGATAGAGTTAAACCCAACCCTAGAGAGTTATGT
                                                    Sac II
5917  ATTTAATCCCCTGGGACCCCGCGGAAGTCATATATCCCTCGGCCCCCTCATTTGGGCGCACATTGCCT
5985  GCCCGGCGGCAGTCTTACTCCCTTAGCTCGCCCTCTTGCATAAGATAAACTATTCCCCTCCCAGCTAG
6053  TTTCACCCACCAGATTAAGCGGAGGTTTTCCCTCTCAGCCGATCACTTTTCACCACCGAAGAACAGGCCC
6121  TCATCGGTTTCCCTCCGTGTTTTCCCATCCATCTATCCAACCACTACATTTCATGGAGAAGGCGGAG
6189  GCTGCCCGCAGTGTTATACCCCGTCAGTTTCCAACCCCCAGCTACCGTGAAGCGGTATGTCCGACCA
                                            Pst I
6257  AGAAGTAAGCGAAGAACAATCTGCTGGAGATGCCTGGGTGTCTGCAGCAATGCCAGCGCAGAGGCGGT
6325  GGCTCGTGCCGCTACCTCCACCGGAATTGATAACACTAACGACTACACGTACACCGCTGCTTCTGAGA
       BamHI
6393  ATGGGGATCC
```

FIG. 12L

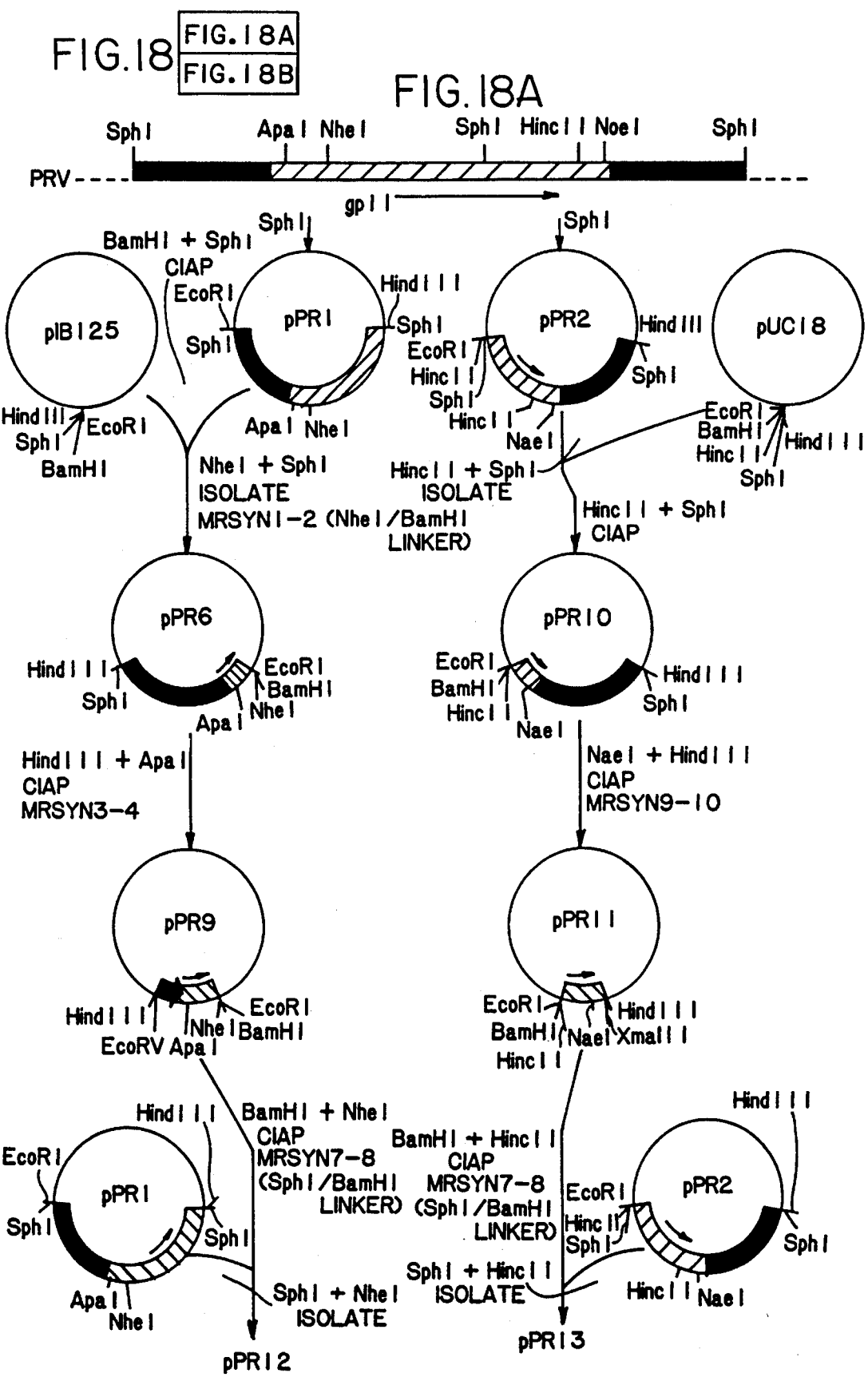

FIG. 19A

| FIG. 19A | FIG. 19B |
|---|---|
| FIG. 19C | FIG. 19D |

FIG. 19

```
AACGTGGCCTCCTGCCGCACCTGAAGGAGGCTGGCGCGCTTCATGTGGCCCGGCGATTGGTGCTCAGCGAGGTCCGCGCTTCTACCG          90

CTTCCAGACGGCCGGCGTAACGCGGCCACCCAGGCCTCGGCGATATATCCGCGGCTGGTGCTGAGCTGGCGGTTGCAGTCTTCAGTCCGT        180

CTTCCACTGCGGGGACGTCGAGGTCCTCCGCGGATCGCTTCGCGGACGCGCTTCGACCTGTACCTGACCTACGAGGCGTCATGCCCGCT        270
                                                                               M  P  A

GGTGGCGGTCTTTGGCGGGCGCATCGGCGCCCGGGCCACCACGGCGCCCTGCTCGACGTCTTTGCCTCGACTGCTCCACACCAC           360
 G  G  G  L  W  R  G  P  R  G  H  H  R  P  G  H  H  G  G  A  G  L  G  R  L  W  P  A  P  H  H
 4

GCTGCAGCTGCGGCGGGCCGCGCCTAGCCGCGGCTAGCGCCCCGCGCTCCGCGCCCCGCCGCGCTGCGCCGTGCGCCGTGACGCGG           450
 A  A  A  R  G  A  V  A  L  A  L  L  L  A  L  A  A  A  P  P  C  G  A  A  A  V  T  R
 34

GCCACCTCGGCCTGCCGCCGACGCCCCCGACGGCGAGTACGGCGAGTACGGCGACCTGGACGCCCGTGCCGCCGAGCGGCACCGCTTC         540
 A  T  S  A  S  P  T  P  G  T  G  A  T  P  N  D  V  S  A  E  A  S  L  G  E  I  E  A  F  S
 64

CCCGGCCCCTCGGAGGCCCCGGACGGCGAGTACGGCGACCTGGACGCCCGGACCGCCGTGCGCGCCGCCGCCACCGAGCGGCACCGCTTC      630
 P  G  P  S  E  A  P  D  G  E  Y  G  D  L  D  A  R  T  A  V  R  A  A  A  T  E  R  H  R  F
 94

TACGTCTGCCCGCCGCCGTCCGGCTCCACGGTGGTGCGGCTGGAGCCCGAGCAGGCCTGCCCGAGTACTGCCAGGGGCGCAACTTCACG        720
 Y  V  C  P  P  P  S  G  S  T  V  V  R  L  E  P  E  Q  A  C  P  E  Y  S  Q  G  R  N  F  T
 124

GAGGGGATCGCCGTGCTCTTCAAGGAGAACATCGCCCCGCACAAGTTCAAGGCCAAGCACATCTACTACAAGAACGTCATCGTCACGACCGTG    810
 E  G  I  A  V  L  F  K  E  N  I  A  P  H  K  F  K  A  H  I  Y  Y  K  N  V  I  V  T  T  V
```

FIG. 19B

```
154  TGGTCCGGGAGCACGTACGGCCATCACGAACCGCTTCACAGACCGCTGCCCGTGCAGGACATCACGGACGTGATCGACCGC   900
      W  S  G  S  T  Y  A  A  I  T  N  R  F  T  D  R  V  P  V  P  V  Q  D  I  T  D  V  I  D  R
184  CGCGGCAAGTGCGTCTCCAAGGCCGAGTACGTGCGCAACAACCACAAGGTGACCGCCTTCGACCGGGACGAGAACCCCGTCGAGGTGGAC   990
      R  G  K  C  V  S  K  A  E  Y  V  R  N  N  H  K  V  T  A  F  D  R  D  E  N  P  V  E  V  D
214  CTGCGCCCCTCGCGCCTGAACGCCCTGGCACACCAAGACACTACACCAAGATCGGCGCCGCCGGGCTTCTAC  1080
      L  R  P  S  R  L  N  A  L  G  T  R  G  W  H  T  T  N  D  T  Y  T  K  I  G  A  A  G  F  Y
244  CACACGGGCACCTCCGTCAACTGCATCGTCGAGGAGGTGGAGGCGCGCTCGGTGTACCCCTACGACTCCTTCGCCCTGTCCACGGGGAC   1170
      H  T  G  T  S  V  N  C  I  V  E  E  V  E  A  R  S  V  Y  P  Y  D  S  F  A  L  S  T  G  D
274  ATTGTGTACATGTCCCCCTTCTACGGCCTGCGCGAGGGGGCCCACGGGGAGCACATCGGCTACGCGCCCGGCTTCCAGCAGGTGGAG   1260
      I  V  Y  M  S  P  F  Y  G  L  R  E  G  A  H  G  E  H  I  G  Y  A  P  G  R  F  Q  Q  V  E
304  CACTACTACCCCATGGACTGGACCTGGCCTCCGGCGACTGGAACTTCTACGCACGGCCACTTCACGGTGGCC   1350
      H  Y  Y  P  M  D  W  T  W  P  P  G  D  W  N  F  Y  A  R  P  L  T  V  A
304  CACTACTACCCCATCGACCTGGACTCGCGGCTGCGCGCCTCCGAGAGCGTGACGCGCAACTTCCTACGCACCCCACTTCACGGTGGCC   1350
      H  Y  Y  P  I  D  L  D  S  R  L  R  A  S  E  S  V  T  R  N  F  L  R  T  P  H  F  T  V  A
334  TGGGACTGGGCCCCCAAGACGCGGCGGGTGTGCAGCCTGGCCAAGTGGCGCGAGGCCGAGGAGATGACCCGAGACGAGCGGACGGC   1440
      W  D  W  A  P  K  T  R  R  V  C  S  L  A  K  W  R  E  A  E  E  M  T  R  D  E  T  R  D  G
364  TCCTTCCGCTTCACGTCGCGTGCCCTGGGGGCCTCCTTCGTCAGCGACGTCACGCAGCTGGACCTGCAGCGCGTGCACCTGGGCGACTGC   1530
      S  F  R  F  T  S  R  A  L  G  A  S  F  V  S  D  V  T  Q  L  D  L  Q  R  V  H  L  G  D  C
394
```

FIG. 19C

```
      GTCCTCCGGAGGCCTCGGAGGCCATCGACGCCTACAACAGCACGCACGTGCTGGCCGGCGACAGGCCCGAGGTG   1620
      V  L  R  E  A  S  E  A  I  D  A  I  Y  R  R  Y  N  S  T  H  V  L  A  G  D  R  P  E  V
424
      TACCTCGCCCGCGGGGGCTTCGTGGTGGCCTTCCGCCCGCTGATCTCGAACGAGCTGGCGCAGCTGTACGCGCGAGCTCGAGCGCCTC   1710
      Y  L  A  R  G  G  F  V  V  A  F  R  P  L  I  S  N  E  L  A  Q  L  Y  A  R  E  L  E  R  L
454
      GGCCTCGCCGGCGTCGTGGGCCCCGCCGCCCCGGCCGCCCGCGCCCGGCGCTCCCCCGGGCCCGGCCGCGGGCACCCCGGAGCCGCCG   1800
      G  L  A  G  V  V  G  P  A  A  P  A  A  A  R  R  R  S  P  G  P  A  G  T  P  E  P  P
484
      GCCGTCAACGGCACCGGGCACCTGCGCATCACCACGGGCTCGGCGGAGTTTGCGCGCCTGCAGTTCACCTACGACCATATCCAGGCCAC   1890
      A  V  N  G  T  G  H  L  R  I  T  T  G  S  A  E  F  A  R  L  Q  F  T  Y  D  H  I  Q  A  H
514
      GTGAACGACATGCTGGGCCGCATCGCCGCCGCCTGGTGCGAGCTGCAGAACAAGGACCGCACCCTGTGGAGCGAGATGTCGCGCCTGAAC   1980
      V  N  D  M  L  G  R  I  A  A  A  W  C  E  L  Q  N  K  D  R  T  L  W  S  E  M  S  R  L  N
544
      CCCAGCGCCGTGGCCACGGCCGCGCTCGGCCAGCGCGTCTCGGCACGTATGCTCGGCGACGTGATGGCCATCTCGCGCTGTGTCGAGGTG   2070
      P  S  A  V  A  T  A  A  L  G  Q  R  V  S  A  R  M  L  G  D  V  M  A  I  S  R  C  V  E  V
574
      CGCGGCGGCGTGTACGTGCAGAACTCCATGCGCGTGCCGGGCGAGCGCGGCACGTGCTACAGCCGGCCGCTGGTCACCTTCGAGCACAAC   2160
      R  G  G  V  Y  V  Q  N  S  M  R  V  P  G  E  R  G  T  C  Y  S  R  P  L  V  T  F  E  H  N
604
      GGCACGGGCGTGATCGAGGGCCAGCTCGGCGACGACAACGAGCTCCTCATCTCGCGCGACCTGATCGAGCCCTGCACCGGCAACCACCGG   2250
      G  T  G  V  I  E  G  Q  L  G  D  D  N  E  L  L  I  S  R  D  L  I  E  P  C  T  G  N  H  R
634
      CGCTACTTTAAGCTGGGGAGCGGGTACTGTGTACTACGAGGACTACAACTACGTGCGCATGGTTGAGGTGCCGGAGACGATCAGCACGCGG   2340
      R  Y  F  K  L  G  S  G  Y  Y  V  Y  Y  E  D  Y  N  Y  V  R  M  V  E  V  P  E  T  I  S  T  R
```

FIG. 19D

```
664  GTGACCCTGAACCTGACGCTGCTGGAGGACCGCGAGTTCCTGCCCCTCGAGGTGTACACGCGCGAGGAGCTCGCCGACACGGGCCTCCTG      2430
      V  T  L  N  L  T  L  L  E  D  R  E  F  L  P  L  E  V  Y  T  R  E  E  L  A  D  T  G  L  L
694  GACTACAGCGAGATCCAGCGCCGCAACCAGCTGCATGCCCTGAAGTTCTACGACATCGACCGCGTGGTCAAGGTGGACCACAACGTGGTG      2520
      D  Y  S  E  I  Q  R  R  N  Q  L  H  A  L  K  F  Y  D  I  D  R  V  V  K  V  D  H  N  V  V
724  CTGCTGCGCGGGCATCGCCAACTTCTTCCAGGGCCTCGGCGACGTGGGCGCAGCTGTCGGCAAGGTGGTCCTGGGTGCCACGGGCGCCGTG      2610
      L  L  R  G  I  A  N  F  F  Q  G  L  G  D  V  G  A  A  V  G  K  V  V  L  G  A  T  G  A  V
754  ATCTCGGCCGTCGGCGGCATGGTGTCCTTCCTGTCCAACCCCTTCGGGGCCAACCCCCGCCAACCCCGTCTACCCCGTCTACCCCGTCTGGTCGCG    2700
      I  S  A  V  G  G  M  V  S  F  L  S  N  P  F  G  A  L  A  I  G  L  L  V  L  A  G  L  V  A
784  GCCTTCCTGGCCTACCGGCACATCTCGCGCCTGCGCCGCAACCCCATGAAGGCCCTGTACCCCGTCACGACGAAGACGCTCAAGGAGGAC      2790
      A  F  L  A  Y  R  H  I  S  R  L  R  R  N  P  M  K  A  L  Y  P  V  T  T  K  T  L  K  E  D
814  GGCGTCGACGAGGGCGACGTGGACGAGGGCGACGTGGACGAGGCCAAGCTGGACCAGGCCCGGGACATGATCCGTTACATGTCGATCGTGTCGGCCCTCGAGCAG  2880
      G  V  D  E  G  D  V  D  E  A  K  L  D  Q  A  R  D  M  I  R  Y  M  S  I  V  S  A  L  E  Q
844  CAGGAGCACAAGGCGCGCAAGAAGAACAGCGGGCCCGCTGCTGGCCAGCCGCGTCGGGGCGATGGCCACGCGGCGGCGGCACTACCAG      2970
      Q  E  H  K  A  R  K  K  N  S  G  P  A  L  L  A  S  R  V  G  A  M  A  T  R  R  R  H  Y  Q
874  CGCCTCGAGAGCGAGGACCCCGACGCCCTGTAGTCCCCGCGGGAAACAATAAAGATGCCTTGTTTGGCAACACGTCTCGGCGTCCG      3060
      R  L  E  S  E  D  P  D  A  L
904  TCT
```

FIG. 21

| FIG.2IA |
|---------|
| FIG.2IB |

FIG.2IA

```
                                                                                    90
AGGGGGACCACGTCCGCTGCGCCTGCGCCGGCGTACCGGGCTCGCCGGGCGTGAGCGGGGCCCTGCTGGTGCAGGCGTACGTGAC
                                                                                    180
CGTCGCCATGTGCGCCACTAGCATTAAATCCGTTTCCTGATTCACGCCCACGCTCGTTTTAAAACCGATGGGGACGGGGG
                                                                                    270
CCATTCGCACGGCCATGGCCTCGCTGGCGTGCGATGCTCGCTGGCGCTCTACGGGGCATCGCCGGCGCCGTCGACC
          M  A  S  L  A  R  A  M  L  A  L  L  A  L  Y  A  A  A  I  A  A  P  S  T
                                                                                    360
ACGACGGGCTCGACACGACGCCCAACGGGGGGGGGCAACAGCAGGAGGAGAACTCTCCCCTCTCCCCGAGCCCCCGCCG
  T  A  L  D  T  T  P  N  G  G  G  G  G  N  S  S  E  G  E  L  S  P  S  P  P  P  T  P  A
26                                                                                  450
CCCGCCCTCGCCCGGAGGGCGGTCTCGACGCCCCCGGTTCCGCGCAGGAAGCCCCGCGGAACAACAACCGG
  P  A  S  P  E  A  G  A  V  S  T  P  P  V  P  P  P  S  V  S  R  R  K  P  P  R  N  N  R
56                                                                                  540
ACGCGGGTCCACGGCGACAAGGCCACCGCCCACGGCCGGGAGGCGTTCTCGGCGCGTTGTCTCGGGGGTGGGGGACGCG
  T  R  V  H  G  D  K  A  T  A  H  G  R  K  R  K  I  V  C  R  E  R  L  F  S  A  R  Y  G  D  A
86                                                                                  630
GTCAGCTTCGGGTGCGCCGTCTTCCCGCGCCGGGAGACCTTCGAGGTCCGCTTCTACCGGCGCCGGCGCTTCCGCTCCCCGACGCC
  V  S  F  G  C  A  V  F  P  R  A  G  E  T  F  E  V  R  F  Y  R  R  R  G  R  F  R  S  P  D  A
116                                                                                 720
GACCCCGAGTACTTTGACGAGCCCCCGCGAGCTCCCGGCCTCTTCAGCTCGGCCAACGCCTCCGCCCACGCG
  D  P  E  Y  F  D  E  P  P  R  P  E  L  P  R  E  R  L  L  F  S  S  A  N  A  S  L  A  H  A
146                                                                                 810
GACGGCGCTCGCCCGTCGTCGTCGAGGGCGAGCGCGCCACGGTCGCCAACGTCAGCGGCGAGGTGTCCGTGCGGGTGGCCGCGGAC
  D  A  L  A  P  V  V  V  E  G  E  R  A  T  V  A  N  V  S  G  E  V  S  V  R  V  A  A  D
```

```
176                                                                                    900
    GCCGAGACCGAGGGCGTCTACACGTGGCGCGTGTCCGCCAACGGCACCGAGGTCCGGAGCGCCAACGTCTCGCTCCTGTACAGC
     A  E  T  E  G  V  Y  T  W  R  V  L  S  A  N  G  T  E  V  R  S  A  N  V  S  L  L  L  Y  S
206                                                                                    990
    CAGCCCGAGTTCGGCCTGAGCGCCCCGGTCCTCTTCGGTGAGCCCTTCCGGGCCGTGTGCGTCGACAGCACTACCCGCGGGCGC
     Q  P  E  F  G  L  S  A  P  P  V  L  F  G  E  P  F  R  A  V  C  V  V  R  D  Y  Y  P  R  R
236                                                                                    1080
    AGCGTGCGCCTGCGCTGGTTCGCGGACGAGCACCCGGTTGACAACAGCACCGTGGCCGACGAGCTGGGGCGCCGC
     S  V  R  L  R  W  F  A  D  E  H  P  V  D  A  A  F  V  T  N  S  T  V  A  D  E  L  G  R  R
266                                                                                    1170
    ACGGCGGTCTCCGTGGTGAACGTGACGCGCGCCGACGTCCCGGGACGCCGGCGGCGTCTCGCCAGCCTGCGC
     T  R  V  S  V  N  V  T  R  A  D  V  P  G  L  A  A  A  D  A  A  D  A  L  A  P  S  L  R
296                                                                                    1260
    TGCGAGGCCGTGTGGTACCGCGACAGCGTGGCCTCGCAGCGCTTCTCGGAGGCCCTGCGCCCCCACGTCTACCACCCGGGGTCTCG
     C  E  A  V  W  Y  R  D  S  V  A  S  Q  R  F  S  E  A  L  R  P  H  V  Y  H  P  A  A  V  S
326                                                                                    1350
    GTGGCGCTTCGTCGAGGGCTTCGCCGTCTGCGACGGCCTCTGCGTGCCCGAGGCCGAGGCCCGGCTGGCCTGGTCCGACCACGCCGACACC
     V  R  F  V  E  G  F  A  V  C  D  G  L  C  V  P  P  E  A  R  L  A  W  S  D  H  A  A  D  T
356                                                                                    1440
    GTCTACCACCTGGGCGCCTGCGAGCACCCGGGCCTGCTCAACGTGCGGAGCGCCCGTCCGTCGACCTCGACGGGCCCGTCGAC
     V  Y  H  L  G  A  C  A  E  H  P  G  L  L  N  V  R  S  A  R  P  L  S  D  L  D  G  P  V  D
385                                                                                    1530
    TACACCTGCCGCCTCGAGGGCCTGCCCTCGCAGCTGCCCGTCTTCGAGGACACGCAGCGCTACGACGCCTCCGCCTCGGTGAGCTGG
     Y  T  C  R  L  E  G  L  P  S  Q  L  P  V  F  E  D  T  Q  R  Y  D  A  S  P  A  S  V  S  W
416                                                                                    1620
    CCCGTCGTGAGCAGCATGATCGTCGTCATCGCGGGCATCGGGATCCTGGCTGGTCATCATGGCGACGTGCGTCTACTACCGC
     P  V  V  S  S  M  I  V  V  I  A  G  I  G  I  L  A  J  V  L  V  I  M  A  T  C  V  Y  Y  R
446                                                                                    1710
    CAGGCGGGGCCCGTGACGTCCCCGCCCCCCACGTCGAATCAATAAACGACAGCGAGTCCGGCCCTCGGCCTTGTGTG
     Q  A  G  P
476  1724
    TGTCGGCGGCCC
```

| FIG. 23A |
|----------|
| FIG. 23B |

FIG. 23A

```
                                                                          90
TGACCCGGCCCCGACTCCCCGGATTCCCCCTCTCTCACGGGTGTCCATCTTCAATAAAGTATGTCTCAAACACCTAATTTG
                                                                         180
CGTACGGGCCTTGCTCTTACGGGGGGTGCGATCCAGGCCCCAGGTCCATAAAATTGGGTTGGGCGCCCAGGTTCCCATACACTCACCTG
                                                                         270
CCAGCGGCCATGCTGTCTCGCAGGCTGCTATTGGCGGGCGACGCTCGCCCGGACGCTGGTCGCCCGGCGCGACCGTGCCGCCGACCT
    M  L  L  A  A  L  L  A  A  L  V  A  R  T  T  L  G  A  D  V  D  A  V  P  A  P  T
                                                                         360
TCCCCCGCCCCGGTACCCGAGTCGTGGCAGTGCTGACGCTGCCCCTTCGCCCTCGTCGCCCGGACGTCTACC
 F  P  P  A  Y  P  Y  T  E  S  W  Q  L  T  L  T  T  V  P  S  P  F  V  G  P  A  D  V
 28                                                                      450
ACACGGGCCCCTGGAGGACCCGTGTGGCCAGGTGGTGGACCGGCTGCTGAACGAGGCGGTGGCCCACC
  H  T  R  P  L  E  D  P  C  G  V  V  A  L  I  S  D  P  Q  V  D  R  L  L  N  E  A  V  A  H
 58                                                                      540
GGCGGCCCACGTACCGGCATCGGGAACGGGTGCGCGCACCTGCTGTACTTTATCGAGTACGCCGACTGCG
  R  P  T  Y  R  A  H  V  A  N  Y  R  I  A  D  G  C  A  H  L  L  Y  F  I  E  Y  A  D  C
 88                                                                      630
ACCCCAGGCAGATCTTTGGGCGCTGCCGCCGCCGCCGCACCACGCCGATGTGGTGGACCCCGTCGCGGACTACATGTTCCCACGGAGGACG
  D  P  R  Q  I  F  G  R  C  R  R  R  T  T  P  M  W  T  P  S  A  D  Y  M  F  P  T  E  D
```

```
118  AGCTGGGGCTGCTCATGGTGGCCCCGGGCCGGTTCAACGAGGGCCAGTACCGGCGCCTGGTGTCCGTCGACGGCGTGAACATCCTCACCG  720
     E  L  G  L  L  M  V  A  P  G  R  F  N  E  G  Q  Y  R  R  L  V  S  V  D  G  V  N  I  L  T
148  ACTTCATGGTGGCGCTCCCCGAGGGCCAAGAGTGCCCGTTCGCCCGCGTGGACGACCACCGCACGTACAAGTTCGGCGCCGTGCTGGAGCG  810
     D  F  M  V  A  L  P  E  G  Q  E  C  P  F  A  R  V  D  D  H  R  T  Y  K  F  G  A  C  W  S
178  ACGACAGCTTCAAGCGGGGCGTGGACGTGATGCGATTCCTGACGCCGTTCTACCAGCAGCCCCACCGGGAGGTGGTGAACTACTGGT    900
     D  D  S  F  K  R  G  V  D  V  M  R  F  L  T  P  F  Y  Q  Q  P  P  H  R  E  V  V  N  Y  W
208  ACCGCAAGAACGGCTGGACGCTCCCGCGGGCCTACGCCGCGTACGCCATCGACCCGGCCCGGCCCTCGGCGGGCTCGCCGA         990
     Y  R  K  N  G  W  T  L  P  R  A  Y  A  A  A  T  P  Y  A  I  D  P  A  R  P  S  A  G  S  P
238  ACCGGCAAGAACGGCTGGACGCTCGGCGGCCCCGCCCCGGAGCCCGCCCCCGCCGACGCGGGCCACCCGCCTTCGCCGCCCGG       1080
     R  P  R  P  R  P  R  P  R  P  K  P  E  P  A  P  A  T  P  A  P  P  D  R  L  P
268  GGCCCCGCCGCCCCGCCGCCCGGCCCCGCCCCGGAGCCCGAAGCCCCGCCCCCGACCGCCGCCGAGCCCCGAGGCCCACCGCCCCGCCGG  1170
     R  P  R  P  R  P  R  P  R  P  K  P  E  P  A  P  A  T  P  A  P  P  D  R  L  P
298  AGCCGGCGACGGGACCACGCGCGCCCAGCCGGTGCCAGCGCGGACCGGGACCCCGGAGCCCGTTCCAGCCCGGGACCCGCCGGCCTGGGA  1260
     E  P  A  T  R  D  H  A  A  G  G  R  P  T  P  R  P  R  P  E  T  P  H  R  P  F  A  P  P
298  CCGCTCGTGCCCAGCGGGTGGCCCCAGCCGGCGGAGCCCTTCCAGCCGCGGACCCCGGCCGCCCCGGGCGTCTCGCGCCACCGCTCGGTGA 1350
     A  V  V  P  S  G  W  P  Q  P  A  E  P  F  Q  P  R  T  P  A  A  P  G  V  S  R  H  R  S  V
328  TCGTCGGCACGGCCATGGGCGCGCTCCTGGTGGGCGTGTGCGTCTACATCTTCTTCCGCCTGAGGGGCGAAGGGTATCGGC         1440
     I  V  G  T  A  M  G  A  L  L  V  G  V  C  V  Y  I  F  F  R  L  R  G  A  K  G  Y  R
358  TCCTGGGCGGTCCCGCCGACGCCGACGAGCTAAAAGCGCAGCCCGGTCCGTAGCCTCCGACTACCGGCGTCGATGATGATGGTGGGCCG
     L  L  G  G  P  A  D  A  D  E  L  K  A  Q  P  G  P
388 1449
CGACGTGAC
```

FIG. 23B

| FIG. 29A |
|---|
| FIG. 29B |
| FIG. 29C |

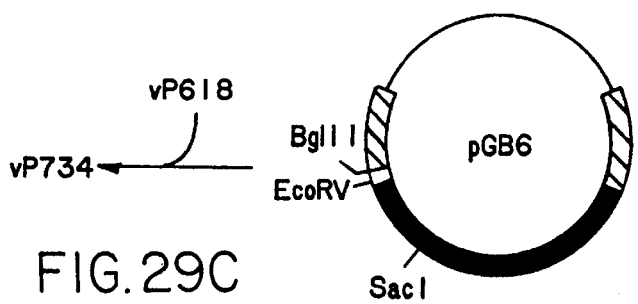
FIG.29C
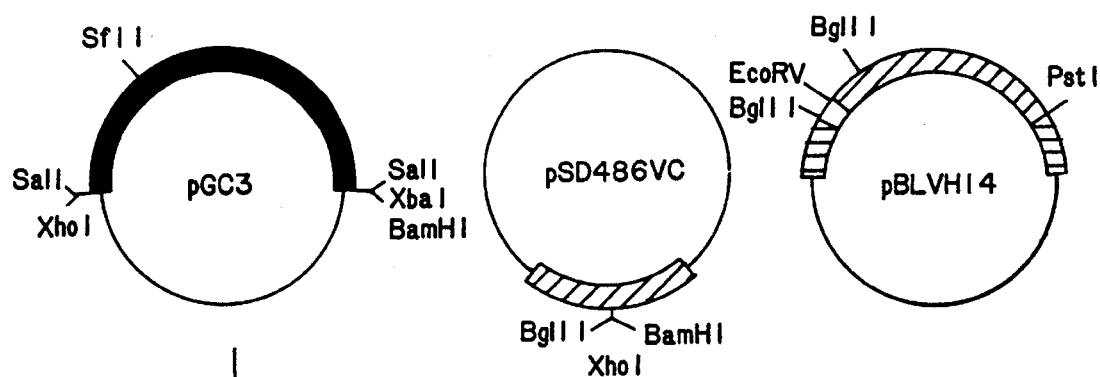
FIG.30
| FIG.30A |
| FIG.30B |
| FIG.30C |
FIG.30A
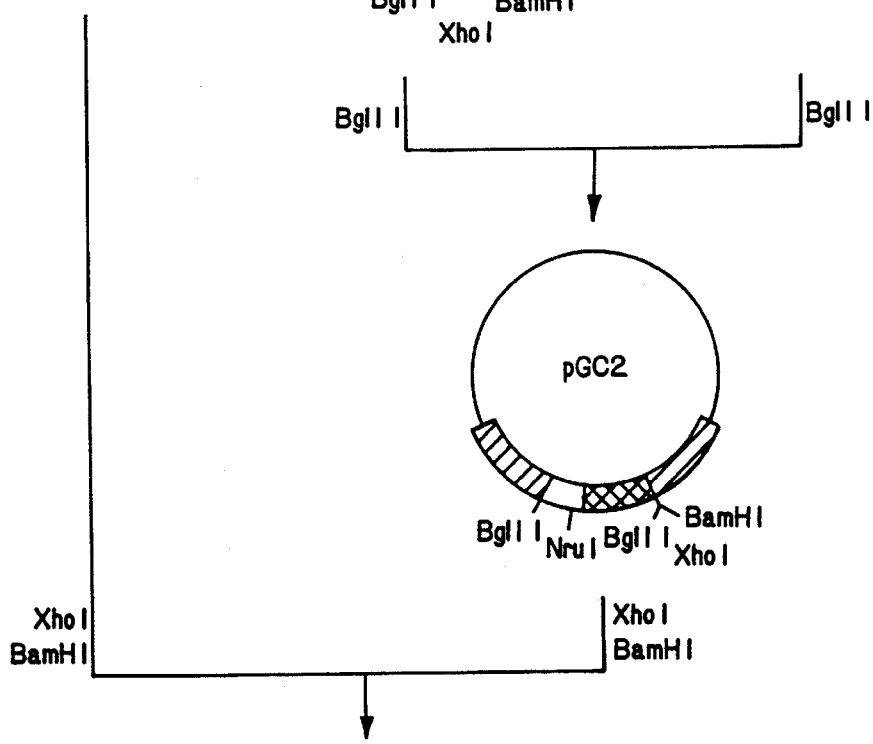

FIG. 34

| FIG.34A |
| FIG.34B |
| FIG.34C |
| FIG.34D |
| FIG.34E |
| FIG.34F |
| FIG.34G |

FIG. 34A

```
  1 CCCCCCAACACAGCGTTTATTTCAGTGTTGAGAACGTTGGTCTGCTTCCACATTTAAAGAAGAATTGG

71 CGGGATTTATGTTAACGTCCACCCGGGTGGGTGGACGGTGAGTAAATTTCAAAGATTTTACTATTTCGG

141 TGATGATACGTCTGGCGTCACAACAACTCAGCGGTTGGCTTGGAAATATATCCGTGAGCTCATTCTAGCA
                                                  Sac I
211 TCTGCCATATTTCCTCCGTGTTTCACTGCGCGTGAGGTGAAGTCTGTACGCATCTGATCGCACACGACCG
    Kpn I
281 GCTAATACAGGTACCCCAGATCTGCCACCCGGCATTTATCTAACATACGAAGAATCATGTCCACTCGTGG
                                                         M  S  T  R  G
                                                                      5

351 CGATCTTGGGAAGCGGCGACGAGGAGTCGTTGGCAGGGACACAGTGGCTATTTCGACAGAGATGTTTT
     D  L  G  K  R  R  R  G  S  R  W  Q  G  H  S  G  Y  F  R  Q  R  C  F
                                                                     28

421 TTCCCTTCTCTACTCGGTATTGCAGCGACTGGCTCCAGACATGGTAACGGATCGTCGGGATTAACCAGAC
     F  P  S  L  L  G  I  A  A  T  G  S  R  H  G  N  G  S  S  G  L  T  R
                                                                     51

491 TAGCTAGATATGTTCATTTATCTGGATCGTACTATTCTTAGTCGGTCCCCGTCCAGTAGAGGGTCAATC
     L  A  R  Y  V  S  F  I  W  I  V  L  F  L  V  G  P  R  P  V  E  G  Q  S
                                                                       75
```

```
1541 CCATATCCGCTACTTTCATCTCCAATACTTCACAATTGAAATCAATCGTATCCGTTTGGGGACTGTGC
     T  I  S  A  T  F  I  S  N  T  S  Q  F  E  I  N  R  I  R  L  G  D  C  A
                            * * * * * *                                    424

1611 CACCAAGGAGGCAGCCGAAGCCATAGACCGGATTTATAAGAGTAAATATAGTAAAACTCATATTCAGACT
     T  K  E  A  A  E  A  I  D  R  I  Y  K  S  K  Y  S  K  T  H  I  Q  T
                                                                          448

1681 GGAACCCTGGAGACCTACCTAGCCCGTGGGGATTTCTAATAGCTTTCCGTCCCATGATCAGCAACGAAC
     G  T  L  E  T  Y  L  A  R  G  G  F  L  I  A  F  R  P  M  I  S  N  E
                                                                          471

1751 TAGCAAAGTTATATATCAATGAATTAGCACGTTCCAATCGCACGGTAGATCTCAGTGCACTCCTCAATCC
     L  A  K  L  Y  I  N  E  L  A  R  S  N  R  T  V  D  L  S  A  L  L  N  P
                                * * * * * * * *                             495

1821 ATCTGGGGAAACAGTACAACGAACTAGAAGATCGGTCCCATCTAATCAACATCATAGTCGCGGCGCAGC
     S  G  E  T  V  Q  R  T  R  R  S  V  P  S  N  Q  H  H  R  S  R  R  S
                                                               # # # #  #  518
                                                                 EcoRI

1891 ACAATAGAGGGGTATAGAAACCGTGAACAATGCATCACTCCTCAAGACCACCTCATCTGTGGAATTCG
     T  I  E  G  G  I  E  T  V  N  N  A  S  L  L  K  T  T  S  S  V  E  F
                                        * * * * * * *                     541

1961 CAATGCTACAATTGCCTATGACTACATACAAGCCCATGTAAATGAAATGTTGAGTCGGATAGCCACTGC
     A  M  L  Q  F  A  Y  D  Y  I  Q  A  H  V  N  E  M  L  S  R  I  A  T  A
                                                                          565

FIG. 34D
```

```
 981  ACGGGGTATGTGCCTCTCGAAAGCTGATTACGTTCGTAACAATTATCAATTACGGCCTTTGATCGAGAC
        R  G  M  C  L  S  K  A  D  Y  V  R  N  N  Y  Q  F  T  A  F  D  R  D   238
      BamHI
1051  GAGGATCCCAGAGAGAACTGCCTCTCGAAACCCTCCAAGTTCAACACTCCAGAGTCCCGTGGATGGCACACCA
        E  D  P  R  E  L  P  L  K  P  S  K  F  N  T  P  E  S  R  G  W  H  T   261
1121  CCAATGAAACATACAAAGATCGGTGCTGCTGGATTCACCACCACTCTGGACCTCTGTAAATTGCATCGT
        T  N  E  T  Y  K  I  G  A  A  G  F  H  H  S  G  T  S  V  N  C  I  V   284
             *******
1191  AGAGGAAGTGGATGCAAGATCTGTATATCCATATGACTCATTTGCTATCTCCACTGGTGACGTGATTCAC
        E  E  V  D  A  R  S  V  Y  P  Y  D  S  F  A  I  S  T  G  D  V  I  H   308
1261  ATGTCTCCATTCTTCTTTGGGCTGAGGGATGGAGCCCATGTAGAACATACTAGTTATTCTTCAGACAGATTTC
        M  S  P  F  F  F  G  L  R  D  G  A  H  V  E  H  T  S  Y  S  S  D  R  F   331
1331  AACAAATCGAGGGATACTATCCAATAGACTTGGATACGCGATTACAACTGGGGCACCAGTTCTCGCAA
        Q  Q  I  E  G  Y  Y  P  I  D  L  D  T  R  L  Q  L  G  A  P  V  S  R  N   354
1401  TTTTTTGGAAACTCCGCATGTGACAGTGGCCTGGAACTGGACCCCAAAGTCTGGTCGGGTATGTACCTTA
        F  L  E  T  P  H  V  T  V  A  W  N  W  T  P  K  S  G  R  V  C  T  L   378
                                       *******
1471  GCCAAATGGAGGGAAATAGATGAAATGCTACGCGATGAATATCAGGGCTCCTATAGATTACAGCCAAGA
        A  K  W  R  E  I  D  E  M  L  R  D  E  Y  Q  G  S  Y  R  F  T  A  K   401
```

FIG.34C

```
1541 CCATATCCGCTACTTTCATCTCCAATACTTCACAATTGAAATCAATCGTATCCGTTTGGGGACTGTGC
      T  I  S  A  T  F  I  S  N  T  S  Q  F  E  I  N  R  I  R  L  G  D  C  A   424
                              * * * * * *

1611 CACCAAGGAGGCAGCCCGAAGCCATAGACCGGATTTATAAGAGTAAAATATAGTAAAACTCATATTCAGACT
      T  K  E  A  A  E  A  I  D  R  I  Y  K  S  K  Y  S  K  T  H  I  Q  T  448

1681 GGAACCCTGGAGACCTACCTAGCCCGTGGGGGATTTCTAATAGCTTTCCGTCCCATGATCAGCAACGAAC
      G  T  L  E  T  Y  L  A  R  G  G  F  L  I  A  F  R  P  M  I  S  N  E   471

1751 TAGCAAAGTTATATATCAATGAATTAGCACGTTCCAATCGGTAGATCTCAGTGCACTCCTCAATCC
      L  A  K  L  Y  I  N  E  L  A  R  S  N  R  T  V  D  L  S  A  L  L  N  P   495
                                   * * * * * * * *

1821 ATCTGGGGAAACAGTACAACGAACTAGAAGATCGGTCCCATCTAATCAACATCATAGGTCGCGGCCAGC
      S  G  E  T  V  Q  R  T  R  R  S  V  P  S  N  Q  H  H  R  S  R  R  S  518
                                                        # # # #     #
                                                                    EcoRI
1891 ACAATAGAGGGGGTATAGAAACCGTGAACAATGCATCACTCCTCAAGACCACCTCATCTGTGGAATTCG
      T  I  E  G  G  I  E  T  V  N  N  A  S  L  L  K  T  T  S  S  V  E  F   541
                                        * * * * * *

1961 CAATGCTACAATTGCCTATGACTACATACAAGCCCATGTAAATGAAATGTTGAGTCGGATAGCCACTGC
      A  M  L  Q  F  A  Y  D  Y  I  Q  A  H  V  N  E  M  L  S  R  I  A  T  A  565
```

FIG. 34D

```
2031  CTGGTGTACACTTCAGAACCGGAACATGTGCTGTGGACAGAGACCCTAAAACTCAATCCCGGTGGGGTG
       W  C  T  L  Q  N  R  E  H  V  L  W  T  E  T  L  K  L  N  P  G  G  V    588

2101  GTCTCGATGGCCCTAGAACGTCGTGTATCCGGCGCCAGACTTGGAGATGCCGTCGCCGTAACACAATGTG
       V  S  M  A  L  E  R  R  V  S  A  R  L  L  G  D  A  V  A  V  T  Q  C    611

2171  TTAACATTTCTAGCGGACACATGTCTATATCCAAAATTCTATGGGGTGACGGGTCATCAACGACATGTTA
       V  N  I  S  S  G  H  V  Y  I  Q  N  S  M  R  V  T  G  S  S  T  T  C  Y  635
           *******

2241  CAGCCGGCCCTCTTGTTCCTTCCGTGCCCTCAATGACTCCGAATACATAGAAGGACAACTAGGGGAAAAC
       S  R  P  L  V  S  F  R  A  L  N  D  S  E  Y  I  E  G  Q  L  G  E  N    658
                          *******

2311  AATGAACTTCTCGTGGAACGAAAACTAATTGAGCCTTGCACTGTCAATAATAAGCGGTATTTTAAGTTTG
       N  E  L  L  V  E  R  K  L  I  E  P  C  T  V  N  N  K  R  Y  F  K  F    681

2381  GGGCAGATTATGTATATTTGAGGATTATGCTATGCCGCTATCGGAGATAGAACTGAT
       G  Q  I  M  Y  I  *  G  L  C  Y  A  A  I  G  D  *  N  *
       G  A  D  Y  V  Y  F  E  D  Y  A  Y  V  R  K  V  P  L  S  E  I  E  L  I  705

2451  AAGTGGCGTATGTGAATTTAAATCTTACTCTCCTAGAGGATCGTGAATTCTCCCACTGAAGTTTATACA
       S  A  Y  V  N  L  N  L  T  L  L  E  D  R  E  F  L  P  L  E  V  Y  T    728
                      *******

2521  CGAGCTGAGCTGGAAGATACCGGCCTTTTGGACTACAGCGGAGATTCAACGCCGCAACCAACTCCACGCCT
       R  A  E  L  E  D  T  G  L  L  D  Y  S  E  I  Q  R  R  N  Q  L  H  A    751
```

FIG. 34E

```
2591 TAAAATTTTATGATATAGACAGCATAGTCAGAGTGGATAATAATCTTGTCATCATGCTGTGTATGCAAA
      L  K  F  Y  D  I  D  S  I  V  R  V  D  N  N  L  V  I  M  R  G  M  A  N   775

2661 TTTTTTCAGGGACTCGGGGATGTGGGGGCTGTGGTTCGGCAAGGTGTCTTAGGGGCTGCGAGTGCGGTA
      F  F  Q  G  L  G  D  V  G  A  G  F  G  K  V  V  L  G  A  A  S  A  V   798

2731 ATCTCAACAGTATCAGGCGTATCATCATTCTAAACAACCCATTTGGAGCATTGGCCGTGGACTGTTAA
      I  S  T  V  S  G  V  S  S  F  L  N  N  P  F  G  A  L  A  V  G  L  L   821

2801 TATTAGCTGGCATCGTCGCAGCATTCCTGGCTATATATCTAGATTACGTGCAAATCCAATGAA
      I  L  A  G  I  V  A  A  F  L  A  Y  R  Y  I  S  R  L  R  A  N  P  M  K   845

2871 AGCCTTATATCCTGTGACGACTAGGAATTTGAAACAGACGCTAAGAGCCCGCTCAACGGCTGGTGGGAT
      A  L  Y  P  V  T  T  R  N  L  K  Q  T  L  R  A  R  S  T  A  G  G  D   868

SmaI
2941 AGCGACCCGGGAGTCGATGACTTCGATGAGGAAAAGCTAATGCAGGCAAGGGAGATGATAAAATATGT
      S  D  P  G  V  D  D  F  D  E  E  K  L  M  Q  A  R  E  M  I  K  Y  M   891

3011 CCCTCGTATCGGCTATGGAGCAACAAGACATAAGGCCGATGAAAAAGAATAAGGCCCAGCGATCCTAAC
      S  L  V  S  A  M  E  Q  Q  E  H  K  A  M  K  K  N  K  G  P  A  I  L  T   914
```

FIG. 34F

```
3081 GAGTCATCTCACTAACATGGCCCTCCGTCGCCTAAATACCAACGCCCTCAATAATCTTGATAGC
      S  H  L  T  N  M  A  L  R  R  R  R  G  P  K  Y  Q  R  L  N  N  L  D  S
         938                                                              938

3151 GGTGATGATACTGAAACAAATCTTGTCTAACCAACCAGACCATCTCTAAATTTTATCCACAAAAAAGT
      G  D  D  T  E  T  N  L  V  ---
                              947

3221 TAGAGATAATAAATTTGAAGCTCAAAAATATCCTGTAATGTCATCATTCTCCGCCCATTCACGTCACGG

3291 TCTCTTTAAAATAATAACCGGTTTTGAGGGTTAGGTACACATTTCTCTCGGCCGGATCAATCCAACACAGGA

3361 AGGCTAACACTTTTTCCATCGATAACATATCATGGAGCTC
                                     Sac I
```

FIG. 34G

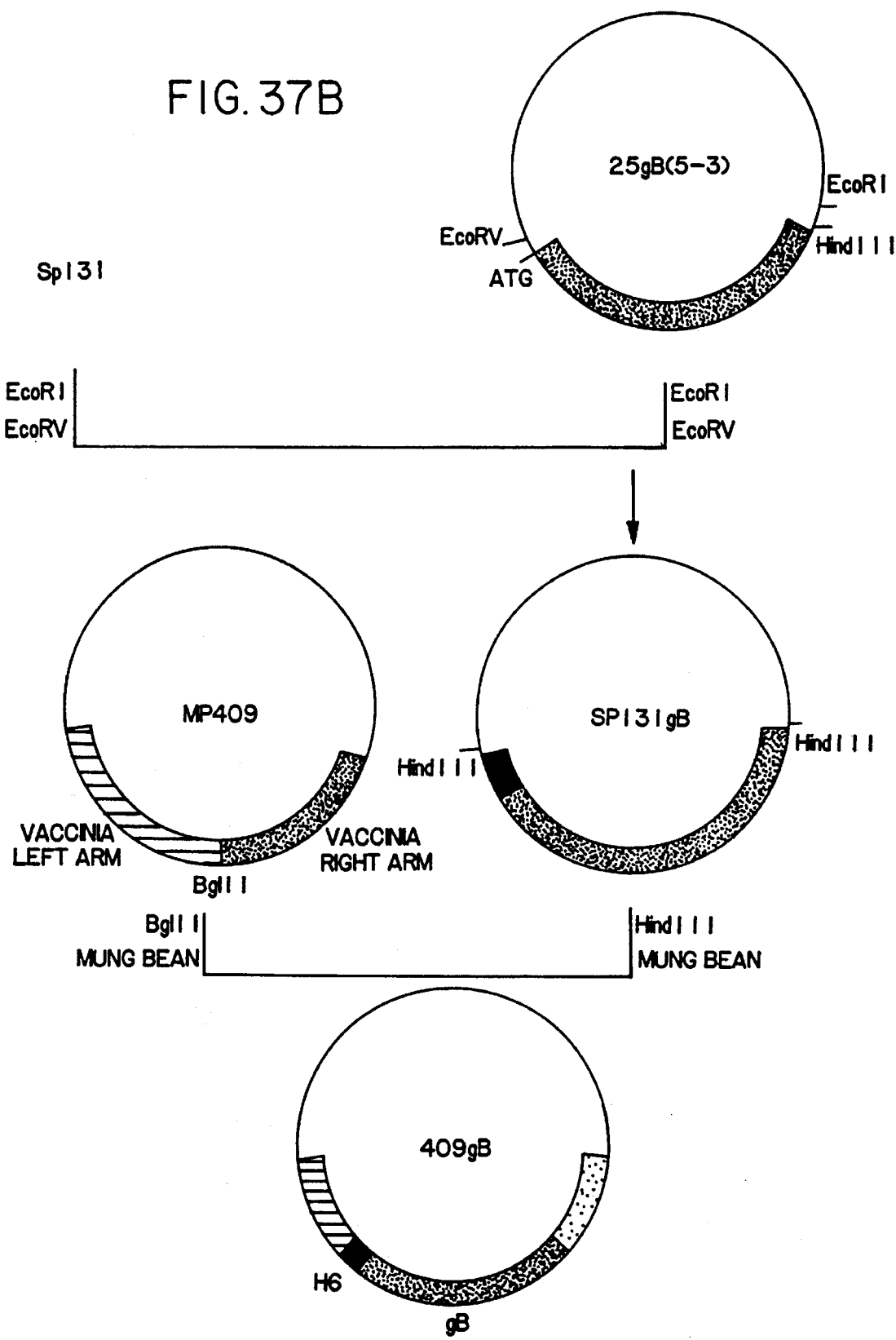

1 ATGAATCTTATAATGCTTATTCTAGCCCTCTGGGCCCCGGTCGCGGGTAGTATGCCT
   M  N  L  I  M  L  I  L  A  L  W  A  P  V  A  G  S  M  P

121 CTGCCCGATGTTTCGGAGTACCGAGTAGAGTATTCCGAGGCGCGCTGCGTGCTCCGA
    L  P  D  V  S  E  Y  R  V  E  Y  S  E  A  R  C  V  L  R

241 CCCCGGGTGTACTACCAGACGCTGGAGGGCTACGCGGATCGAGTGCCGACCCCGGTG
    P  R  V  Y  Y  Q  T  L  E  G  Y  A  D  R  V  P  T  P  V

361 CGCACAAAACTCGTGTTGTTCTACTTTTCCCCCTGCCATCAATGCCAAACTTATTAT
    R  T  K  L  V  L  F  Y  F  S  P  C  H  Q  C  Q  T  Y  Y

481 GAACGACTATTGTTCGAAGATCGCCGTCTAATGGCGTACTACGCGCTCACGATTAAG
    E  R  L  L  F  E  D  R  R  L  M  A  Y  Y  A  L  T  I  K

601 GGTTGGCTGCACCGACATTTTCCCTGGATGTTTTCGGACCAGTGGTGA
    G  W  L  H  R  H  F  P  W  M  F  S  D  Q  W>

FIG.41A

```
GAATTATCCTTGACTCTTTTCGATGAACCTCCGCCCTTGGTGGAGACGGAACCGTTACCGCCT
 E  L  S  L  T  L  F  D  E  P  P  P  L  V  E  T  E  P  L  P  P>

TCGGGCGGTCGACTGGAGGCTCTGTGGACCCTGCGCGGGAACCTGTCCGTGCCCACGCCGACA
 S  G  G  R  L  E  A  L  W  T  L  R  G  N  L  S  V  P  T  P  T>

GAGGACATCTCCGAAAGCCTCGTCGCAAAACGCTACTGGCTCCGGGACTATCGTGTTCCCCAA
 E  D  I  S  E  S  L  V  A  K  R  Y  W  L  R  D  Y  R  V  P  Q>

GTAGAGTGCGAACCCCGGTGCCTCGTGCCTTGGGTTCCCCTGTGGAGCTCGTTAGAGGACATC
 V  E  C  E  P  R  C  L  V  P  W  V  P  L  W  S  S  L  E  D  I>

TCGGCGCAGTATACGCTGATGATGGTGGCAGTGATTCAAGTGTTTTGGGGGCTGTATGTGAAA
 S  A  Q  Y  T  L  M  M  V  A  V  I  Q  V  F  W  G  L  Y  V  K>
```

1   ATGCTACGCCGGGGAAGCCTCCGGAACCCTCTCGCGACCTGCCTGTTGTGGTGGCTG
    M  L  R  R  G  S  L  R  N  P  L  A  T  C  L  L  W  W  L

121 ATTCAAAATCATGTACTGAAAGGTGCGGTGAAACTCTATGGACAATTCCCCTCGCCT
    I  Q  N  H  V  L  K  G  A  V  K  L  Y  G  Q  F  P  S  P

241 ATCCTCGTGGAAGGCACCGCGACAGCTACCGAGGCGCTCTACATTCTGCTGCCCACG
    I  L  V  E  G  T  A  T  A  T  E  A  L  Y  I  L  L  P  T

361 CGGGATTGTTATGAACGCTTCGTGTGTCCGGTATACGATTCCGGGACGCCGATGGGG
    R  D  C  Y  E  R  F  V  C  P  V  Y  D  S  G  T  P  M  G

481 TTCGGACTGTTTTGCCGGGGCTGTGTCATCACCCGATCCCTCCTCCTGATATGTGGT
    F  G  L  F  C  R  G  C  V  I  T  R  S  L  L  L  I  C  G

FIG.42A

```
GGAGTGGTGGCGGCAGCTACGGAGGAGACGAGAGAACCGACTTACTTTACGTGCGGCTGTGTT
 G   V   V   A   A   A   T   E   E   T   R   E   P   T   Y   F   T   C   G   C   V>

AAGACTTTGCGGGCCTTGGCTTGGCTACACGACGGTGAAAATCACGAAAGGCACCGGCAGCCC
 K   T   L   R   A   L   A   W   L   H   D   G   E   N   H   E   R   H   R   Q   P>

GAGCTATCGCCGCCGGAAGGAAACCGACCCCGAAACTATTCTGTTACCCTAACACTCGCCTCC
 E   L   S   P   P   E   G   N   R   P   R   N   Y   S   V   T   L   T   L   A   S>

CTTTTGATGAACTTGACGTACCTCTGGTATCTAGGCGACTACGGGGCGATACTAAAAATTTAT
 L   L   M   N   L   T   Y   L   W   Y   L   G   D   Y   G   A   I   L   K   I   Y>

TATTATCCACCTCGCGAATAA
 Y   Y   P   P   R   E>
```

FIG. 42B

EQUINE HERPESVIRUS RECOMBINANT POXVIRUS VACCINE

CROSS REFERENCE TO RELATED APPLICATIONS

This application is a division of application Ser. No. 07/502,834, filed Apr. 4, 1990, now U.S. Pat. No. 5,338,683, which is a continuation-in-part of application Ser. No. 07/394,488, filed Aug. 16, 1989, now abandoned, which in turn is a continuation-in-part of application Ser. No. 07/339,004, filed Apr. 17, 1989, now abandoned. Application Ser. No. 07/502,834 is also a continuation-in-part of U.S. application Ser. No. 07/090,209, filed Aug. 27, 1987, now abandoned, which is a division of U.S. application Ser. No. 06/622,135 filed Jun. 19, 1984, now U.S. Pat. No. 4,722,848, which in turn is a continuation-in-part of U.S. application Ser. No. 06/446,824, filed Dec. 8, 1982, now U.S. Pat. No. 4,603,112, which in turn is a continuation-in-part of U.S. application Ser. No. 06/334,456, filed Dec. 24, 1981, now U.S. Pat. No. 4,769,330.

FIELD OF THE INVENTION

The present invention relates to a modified poxvirus and to methods of making and using the same. More in particular, the invention relates to recombinant poxvirus, which virus expresses gene products of a herpesvirus gene, and to vaccines which provide protective immunity against herpesvirus infections.

Several publications are referenced in this application by arabic numerals within parentheses. Full citation to these references is found at the end of the specification immediately preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (28).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (11) and isolated (12,20).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

There are two subtypes of equine herpesvirus that, although they contain cross-neutralizing epitopes, can be distinguished by their antigenic profiles, restriction endonuclease fingerprints and their pathogenicity for horses (1). Equine herpesvirus 1 (EHV-1) is associated with respiratory tract disease, central nervous system disorders and classic herpetic abortions whereas equine herpesvirus 4 (EHV-4) is predominantly associated with respiratory tract disease (1,48). Equine herpesviruses are members of the alphaherpesvirus subfamily and display many of the typical biological and biochemical characteristics of human herpesviruses, such as genomic isomerization, regulation of gene expression, establishment of latent infections, generation of defective interfering virus particles, induction of neurological disorders, and in vitro oncogenic transformation (1,4,23). Thus, EHV advantageously can be used for studying the varied biological consequences of herpesvirus infections.

Herpesvirus glycoproteins mediate essential viral functions such as cellular attachment and penetration, cell to cell spread of the virus and, importantly, determine the pathogenicity profile of infection. Herpesvirus glycoproteins are critical components in the interaction with the host immune system (36,37).

The well characterized glycoproteins of herpes simplex virus include gB, gC, gD, gE, gG, gH and gI (36,37,49–55). A number of studies have indicated the importance of herpes simplex virus glycoproteins in eliciting immune responses.

Hence, it has been reported that gB and gD can elicit important immune responses (6,8,13,18,21,22,26,27,30,44, 46,47). gC can stimulate class I restricted cytotoxic lymphocytes (15,32) whereas gD can stimulate class II cytotoxic T cell responses (21,22,44,46,47). gG was shown to be a target for complement-dependent antibody directed virus neutralization (38,39). A number of glycoproteins from other herpesviruses have also been shown to elicit important immune responses (5,10,36,56).

Both subtypes of EHV express six abundant glycoproteins (1,3,43). The genomic portions of the DNA sequences encoding gp2, gp10, gp13, gp14, gp17/18, and gp21/22a have been determined using lambda gtII expression vectors and monoclonal antibodies (3). Glycoproteins gp13 and gp14 were located in the same locations within the L component of the genome to which the gC and gB homologs, respectively, of herpes simplex virus map (3). EHV-1 appears unique among the alphaherpesviruses whose glycoprotein genes have been mapped in that five of its six major glycoproteins are encoded from sequences within the genome L component while only one (gp17/18) is mapped to the $U_S$ region. Analyzing these data, it has been predicted that some of the low-abundance glycoproteins identified in EHV-1 virions as well as EHV-1 glycoproteins not yet identified map to the S component of the genome (3). The envelope glycoproteins are the principal immunogens of herpesviruses involved in eliciting both humoral and cellular host immune responses (5,8,73–75) and so are of the highest interest for those attempting to design vaccines.

Recently, the nucleotide sequence of the Kentucky T431 strain of the EHV-1 transcriptional unit encoding gp13 has been reported (2). An open reading frame encodes a 468 amino acid primary translation product of 51 kDa. The protein has the characteristic features of a membrane-spanning protein with nine potential N-linked glycosylation sites (Asn-X-Ser/Thr) present in the surface domain between the putative signal and transmembrane anchor portions of the protein (2). The glycoprotein was shown to be homologous to the herpes simplex virus (HSV) gC-1 and gC-2, to the pseudorabies virus (PRV) gIII and the varicella-zoster virus (VZV) gpV (2). EHV-1 gp13 is thus the structural homolog of the herpesvirus gC-like glycoproteins.

The nucleotide sequence of EHV-1 gp14 (71,72) has recently been reported. Analysis of the predicted amino acid sequence of gp14 glycoprotein revealed significant homology to the corresponding glycoprotein of HSV, gB.

Monoclonal antibodies directed against some EHV-1 glycoproteins have been shown to be neutralizing (76). Passive immunization experiments demonstrated that monoclonal antibodies directed against gp13 or gp14 (77) or against gp13, gp14 or gp17/18 (78) could protect hamsters against a lethal challenge. Other gB and gC glycoprotein analogs are also involved in protection against diseases caused by alphaherpesviruses (8,10,73). The EHV-1 gp17/18 glycoprotein, although characterized as another potential protective immunogen, had until now no known structural counterpart among the several glycoproteins encoded from the S component in the other alphaherpesviruses (66,79,80). Based on its genomic position, it has been speculated that gp17/18 could be the HSV gE analog (2).

Pseudorabies virus (PRV), an alphaherpesvirus, is the causative agent of Aujesky's disease. The disease is highly infectious causing serious economic losses in the swine industry. The disease is associated with high morbidity and mortality among piglets and is characterized by severe respiratory illness, abortions, reduced litter size and decreased growth rates of survivors. Fatal encephalitis is a frequent consequence of infection. Latent viral infections, a characteristic of herpes viruses, can be established thus allowing recovered adult swine to serve as chronic carriers of the virus. For a recent extensive review see Wittmann and Rziha (81).

The PRV genome consists of a $90\times10^6$ dalton double stranded DNA (82) separated by inverted repeat sequences into unique long ($U_L$) or unique short ($U_S$) segments (83,84). The PRV genome encodes approximately 100 polypeptides whose expression is regulated in a cascade-like fashion similar to other herpesviruses (85,86). To date, five glycoproteins gpI, gpII, gpIII, gp63 and gp50 have been shown to be associated with the viral envelope and associated with the various membranous structures of PRV infected cells (80, 86–91). A sixth PRV encoded glycoprotein (gX) is released into the culture medium (92). The physical location of these glycoproteins on the PRV genome and their DNA sequence are currently known (62,80,91–98). As with the glycoproteins of other herpesviruses, the PRV glycoproteins mediate essential viral functions such as cellular attachment and penetration into or release from cells. The PRV glycoproteins are critical in the pathogenicity profile of PRV infection and are critical components in the resolution of disease and the immune status.

PRV gpI is non-essential for virus replication in vitro and in vivo and is absent from most attenuated PRV strains (99). The attenuated nature of these gI-deleted strains also indicates a possible role for gI in virulence (99,100). Other PRV proteins, however, appear to be involved in this function since expression of gI alone is not sufficient to produce high levels of virulence (100).

The role gI plays in eliciting an immune response against PRV is unclear. Monoclonal antibodies against gI can neutralize virus in vitro (101) and passively protect immunized mice against a lethal PRV challenge (81). Kost et al. (98) have recently described the expression of PRV gpI in vaccinia virus recombinants either alone or in association with gp50 and gp63. Intracranial inoculation of the vaccinia recombinants in mice resulted in increased virulence particularly when PRV gpI was associated with coexpression of gp50 and gp63.

In swine, however, neutralizing antibodies against gI are not produced (5). In addition, a recombinant vaccinia virus expressing PRV gI-encoded polypeptides (98) does not protect mice against a lethal PRV challenge (relative to the protection afforded by the wildtype vaccinia virus control). These data, taken together, suggest that PRV gpI is more appropriate as a diagnostic probe rather than as a component in a subunit vaccine.

PRV glycoprotein gp63 is located adjacent to gp50 in the $U_S$ region of the PRV genome (80). The coding sequence for PRV gp63 starts with three consecutive ATG codons approximately 20 nucleotides downstream from the stop codon of gp50. There is no recognizable transcriptional signal motif and translation probably occurs from the same transcript as gp50. PRV gp63 is non-essential in vitro (88). PRV gp63 as a continuous DNA sequence with PRV gp50 has been expressed in vaccinia virus as reported by Kost et al. (98). The contribution of PRV gp63 to protection in mice against PRV challenge is difficult to assess since those studies did not dissect the contributions of PRV gp50 and gp63.

PRV glycoprotein gX is a non-structural glycoprotein whose end product is secreted into the extracellular fluid (85,92). No in vitro neutralization of PRV was obtained with either polyclonal or monoclonal sera to PRVgX (102,103) and subunit gX vaccines were non-protective against challenge (104).

PRV glycoprotein gp50 is the Herpes simplex virus type 1 (HSV-1) gD analog (97). The DNA open reading frame encodes 402 amino acids (95). The mature glycosylated form (50–60 kDa) contains O-linked carbohydrate without N-linked glycosylation (95). Swine serum is highly reactive with PRV gp50, suggesting its importance as an immunogen. Monoclonal antibodies to gp50 neutralize PRV in vitro with or without complement (97,105,106) and passively protect mice (102,105,106) and swine (102). Vaccinia virus recombinants expressing PRV gp50 induced serum neutralizing antibodies and protected both mice and swine against lethal PRV challenge (98,107,108).

The PRV gpIII gene is located in the $U_L$ region of the genome. The 1437 bp open reading frame encodes a protein of 479 amino acids. The 50.9 kDa deduced primary translation product has eight potential N-linked glycosylation sites (96). PRV gIII is the HSV-1 gC analog (96). Functional replacement of PRV gIII by HSVgC was not observed (109). Although PRV gIII is nonessential for replication in vitro (110,111), the mature glycosylated form (98 kDa) is an abundant constituent of the PRV envelope. Anti-gpIII monoclonal antibodies neutralize the virus in vitro with or without complement (86,106,110) and can passively protect mice and swine (102). The PRV glycoprotein gIII can protect mice and swine from lethal PRV challenge after immunization with a Cro/gIII fusion protein expressed in E. coli (Robbins, A., R. Watson, L. Enquist, European Patent application 0162738A1) or when expressed in a vaccinia recombinant (Panicali, D., L. Gritz, G. Mazzara, European Patent application 0261940A2).

One of the main constituents of the PRV envelope is a disulfide linked complex of three glycoproteins (120 kDa, 67 kDa and 58 kDa) designated as PRV gpII according to the nomenclature of Hampl (86). The DNA sequence encoding PRV gpII is located in the left end of $U_L$. The open reading frame of 2976 nucleotides encodes a primary translation product of 913 amino acids or 110 kDa. PRV gpII is the HSV-1 gB homolog (62). Monoclonal antibodies directed against PRV gpII have been shown to neutralize the virus in vitro (5) with or without complement (81). Moreover, passive immunization studies demonstrated that neutralizing monoclonal antibodies partially protected swine but failed to protect mice from virulent virus challenge (102). To date, the active immunization of swine with PRV gpII glycoprotein has not been reported.

During the past 20 years the incidence of genital infections caused by herpes simplex virus type 2 (HSV2) has increased significantly. Recent estimates indicate that in the United States, 5–20 million people have genital herpes (112). Although oral treatment with acyclovir has been shown to reduce the severity of primary infections (113) and to suppress recurrent episodes (114), the control and treatment of these infections is far from ideal. A vaccine to prevent primary and recurrent infections is therefore needed.

The herpes simplex virus type 1 (HSV1) genome encodes at least eight antigenically distinct glycoproteins: gB, gC, gD, gE, gG, gH, gI and gJ (115). Homologues for these genes appear to be present in HSV2 (116–119). Since these glycoproteins are present in both the virion envelope and the infected cell plasma membrane, they can induce humoral and cell-mediated protective immune responses (37).

The relative importance of humoral and cellular immunity in protection against herpes simplex virus infections has not been completely elucidated. Mice immunized with purified HSV1 gB, gC or gD are protected against lethal HSV1 challenge (120). Mice have also been protected against lethal HSV1 or HSV2 challenge by passive immunization with antibodies to total HSV1 (121) or HSV2 (122) virus and with antibodies to the individual HSV2 gB, gC, gD or gE glycoproteins (123). This protection, however, appears to be dependent upon a competent T-cell response since animals immunosuppressed by irradiation, cyclophosphamide or anti-thymocyte serum were not protected (124).

The contribution of the individual glycoproteins in eliciting a protective immune response is not completely understood. Expression of these glycoproteins in a heterologous system, such as vaccinia, has allowed some of these parameters to be analyzed. For example, vaccinia virus vectors expressing HSV1 gB (125) and HSV2 gC (32) have been shown to induce cytotoxic T-cell responses. In addition, it has been shown that mice immunized with recombinant vaccinia virus expressing either HSV1 gB (8), HSV1 gC (126) or HSV1 gD (26) are protected against a lethal challenge of HSV1. A recombinant vaccinia virus expressing HSV1 gD has also been shown to be protective against HSV2 in a guinea pig model system (44). It is not known, however, whether expression of multiple HSV antigens will result in a potentiation of this protective response.

Bovine herpesvirus 1 (BHV1) is responsible for a variety of diseases in cattle, including conjunctivitis, vulvovaginitis and abortion (127). It is also one of the most important agents of bovine respiratory disease, acting either directly or as a predisposing factor for bacterial infection (128).

BHV1 specifies more than 30 structural polypeptides, 11 of which are glycosylated (129). Four of these glycoproteins, gI, gII, gIII and gIV, have been characterized and found to be homologous to the herpes simplex virus (HSV) glycoproteins gB, gC, gD, and gE (130,131).

Subunit vaccines consisting of gI, gIII and/or gIV have been shown to protect cattle from disease (using a BHV1/ Pasteurella haemolytica aerosol challenge model) but not from infection (132). These results indicate the importance of these glycoproteins in eliciting a successful immune response against BHV1.

gI and gIII have also been cloned into vaccinia virus and cattle immunized with these recombinants are shown to produce neutralizing antibodies to BHV1 (56,133).

Feline rhinotracheitis is a common and worldwide disease of cats which is caused by an alphaherpesvirus designated feline herpesvirus type 1 (FHV-1). Like other herpesviruses, FHV-1 establishes a latent infection which results in periodic reactivation (134). FHV-1 infections in breeding colonies are characterized by a high rate of mortality in kittens. Secondary infections of the upper respiratory tract are quite debilitating in adults. The control of this disease is currently attempted by using modified live or inactivated vaccines which can suppress the development of clinical signs but do not prevent infection that results in shedding of virus. Thus, asymptomatic vaccinated cats can spread virulent virus and latent infections cannot be prevented by existing vaccines (135) or by the safer purified subunits vaccines under development (136,137).

Herpesvirus glycoproteins mediate attachment of the virion to the host cell and are extremely important in viral infectivity (138,139). They also determine the subtype specificity of the virus (140). Herpesvirus glycoproteins antigens are recognized by both the humoral and cellular immune systems and have been shown to evoke protective immune responses in vaccinated hosts (44,107,141,142).

FHV-1 has been shown to contain at least 23 different proteins (143,144). Of these, at least five are glycosylated (144,145) with reported molecular masses ranging from 120 kDa to 60 kDa. The FHV-1 glycoproteins have been shown to be immunogenic (143,145).

Like several other alphaherpesviruses, FHV-1 appears to have a homolog of glycoprotein B (gB) of HSV-1, and partial sequence of the FHV-1 gB gene has recently been reported (146). The HSV-1 gB is required for virus entry and for cell fusion (147–149). The HSV-1 gB and the gB analogs of other herpesviruses have been shown to elicit important circulating antibody as well as cell-mediated immune responses (8,10,37,47,73,150). The FHV-1 gB glycoprotein is a 134 kDa complex which is dissociated with B-mercaptoethanol into two glycoproteins of 66 kDa and 60 kDa. The FHV-1 DNA genome is approximately 134 Kb in size (153).

Epstein Barr Virus (EBV), a human B lymphotropic herpesvirus, is a member of the genus lymphocryptovirus which belongs to the subfamily gammaherpesvirus (115). It is the causative agent of infectious mononucleosis (154) and of B-cell lymphomas (156). EBV is associated with two human malignancies: the endemic Burkitt's lymphoma and the undifferentiated nasopharyngeal carcinoma (156).

Since the EBV genome was completely sequenced (207) as the genomes of VZV (66) and HSV1 (158) numerous homologies between these different herpesviruses have been described (159). In some cases these homologies have been used to predict the potential functions of some open reading frame (ORFs) of EBV. The EBV genes homologous to the HSV1 genes involved in immunity are of particular interest. So the EBV BALF4 gene has homologies with HSV1 gB (68) and the EBV BXLF2 gene with HSV1 gH (161). Finally, the EBV BBRF3 gene contains homologies with a CMV membrane protein (162).

Among the EBV proteins, the two major envelope glycoproteins gp340 and gp220 are the best characterized potential vaccinating antigens. They are derived from the same gene by splicing without a change in the reading frame (163,164). Monoclonal antibodies and polyclonal sera directed against gp340 neutralize EBV in vitro (165). The cottontop tamarins, the only susceptible animal, can be protected by an immunization with purified gp340 (166) and with a recombinant EBV gp340 vaccinia virus (167). In this case, the protection was achieved with a recombinant derived from the WR vaccinia strain but not with a recombinant derived from the Wyeth vaccinia strain. The Wyeth strain has been widely used as a vaccine strain.

Monoclonal antibodies directed against the gp85, the EBV homologue to HSV1 gH, have been described as in vitro neutralizing antibodies (168,169).

Human cytomegalovirus (HCMV) is a member of the betaherpesvirinae subfamily (family Herpesviridae). HCMV can produce a persistent productive infection in the face of substantial specific immunity. Even if HCMV possesses a low pathogenicity in general, intrauterine infection causes brain damages or deafness in about 0.15% of all newborns and it is the most common infectious complication of organ transplantation (170). Although the efficacy of an experimental live attenuated (Towne strain) HCMV vaccine has been demonstrated (171), concerns about live vaccine strains have directed efforts towards the identification of HCMV proteins usable as a subunit vaccine. In this prospect the identification of virion glycoproteins and their evaluation as protective agents is an important step.

Three immunologically distinct families of glycoproteins associated with the HCMV envelope have been described (172): gCI (gp55 and gp93–130); gCII (gp47–52); and gCIII (gp85–p145).

The gene coding for gCI is homologous to HSVI gB. The gCII glycoproteins are coded by a family of five genes (HXLF) arranged in tandem and sharing one or two regions of homology. More probably gCII is coded by only two of these genes (172,173). The gene coding for gCIII is homologous to HSVI gH (174).

In vitro neutralizing antibodies specifically directed against each of these families have been described (174–176).

Suitably modified poxvirus mutants carrying exogenous equine herpesvirus genes which are expressed in a host as an antigenic determinant eliciting the production by the host of antibodies to herpesvirus antigens represent novel vaccines which avoid the drawbacks of conventional vaccines employing killed or attenuated live organisms. Thus, for instance, the production of vaccines from killed organisms requires the growth of large quantities of the organisms followed by a treatment which will selectively destroy their infectivity without affecting their antigenicity. On the other hand, vaccines containing attenuated live organisms always present the possibility of a reversion of the attenuated organism to a pathogenic state. In contrast, when a recombinant poxvirus suitably modified with an equine herpesvirus gene coding for an antigenic determinant of a disease-producing herpesvirus is used as a vaccine, the possibility of reversion to a pathogenic organism is avoided since the poxvirus contains only the gene coding for the antigenic determinant of the disease-producing organism and not those genetic portions of the organism responsible for the replication of the pathogen.

PRV fatally infects many mammalian species (cattle, dogs, etc.). Adult pigs, however, usually survive infection and therefore represent an important virus reservoir. Because PRV causes severe economic losses, vaccination of pigs with attenuated or killed vaccines is performed in many countries.

Attempts to control PRV infection in swine and to reduce economic losses have been made by active immunization with modified live or inactivated vaccines. Attenuated vaccines which generally induce long lasting immunity and are cost efficient present the risk of insufficient attenuation or genetic instability. Inactivated vaccines are less efficient, require several immunizations and usually contain potent adjuvants. These latter formulations can induce post-vaccinal allergic reactions such as lack of appetite, hyperthermia or abortion in pregnant sows. These vaccine types also suffer from certain drawbacks with respect to prevention of latent infections, overcoming the effects of maternal antibodies on vaccination efficacy, and eliminating the potential use of a serological diagnostic assay to distinguish vaccinated animals from those previously infected with PRV.

Alternative vaccination strategies such as the use of recombinant poxviruses that express immunologically pertinent PRV gene products would have certain advantages: (a) eliminate live attenuated PRV vaccine strains from the field; and (b) allow the distinction of vaccinated versus infected or seropositive animals. The latter could be accomplished by the use of appropriate diagnostic reagents that would precisely distinguish vaccinated from naturally infected animals. This is an important consideration because of existing regulations controlling the movement of seropositive animals. Further, vaccination is more economical and preferable to testing and eliminating infected animals from the lots. The development of such vaccines requires a knowledge of the contributions made by appropriate PRV antigens to the induction of protective immunity. In the case of PRV, as with other members of the herpesvirus family, the glycoproteins are important candidates for antigens to be present in an effective subunit recombinant vaccine.

The technology of generating vaccinia virus recombinants has recently been extended to other members of the poxvirus family which have a more restricted host range. In particular, avipoxviruses, which replicate in avian species, have been engineered to express immunologically pertinent gene products. Inoculation of avian (42,177) and non-avian species (41) with avipoxvirus recombinants elicited protective immune responses against the corresponding pathogen.

Attenuated live vaccines and inactivated vaccines to BHV1 have been available for over 30 years and have successfully reduced the incidence of BHV1 related diseases. These vaccines, however, do not prevent latent infection or reinfection with wildtype virus. They also complicate the differentiation between infected and vaccinated animals.

Both types of vaccines have other significant drawbacks. Vaccination of pregnant cows with attenuated live vaccines can cause fetal death and subsequent abortion (127). In addition, vaccinated animals have been shown to shed virus (178). Therefore, vaccinated animals kept with pregnant cows can spread infectious virus to the pregnant animal and cause abortion of the fetus.

Inactivated vaccines do not induce abortions or provoke viral excretion. However, they necessitate the use of adjuvants and can cause fatal hypersensitivity reactions (anaphylaxis) and nonfatal inflammation and fever (179).

One of the more important issues in vaccination is overcoming or avoiding maternal immunity. In this respect, if a mother is immune to a particular pathogen, the "immunity" in the mother will be passed on to the newborn via the antibodies present in the colostrum and/or by additional pathways. Nevertheless, the newborn cannot be successfully vaccinated until the level of maternal immunity has waned sufficiently. Therefore, there is a narrow window where the newborn can be successfully vaccinated in the presence of waning maternal immunity.

It can thus be appreciated that provision of a herpesvirus recombinant poxvirus, and of vaccines which provide protective immunity against herpesvirus infections, which confer on the art the advantages of live virus inoculation but which reduce or eliminate the previously discussed problems would be a highly desirable advance over the current state of technology.

OBJECTS OF THE INVENTION

It is therefore an object of this invention to provide recombinant poxviruses, which viruses express gene products of herpesvirus, and to provide a method of making such recombinant poxviruses.

It is an additional object of this invention to provide for the cloning and expression of herpesvirus coding sequences in a poxvirus vector, particularly a vaccinia virus, fowlpox virus or canarypox virus vector.

It is another object of this invention to provide a vaccine which is capable of eliciting herpesvirus neutralizing antibodies and protective immunity against a lethal herpesvirus challenge.

These and other objects and advantages of the present invention will become more readily apparent after consideration of the following.

STATEMENT OF THE INVENTION

In one aspect, the present invention relates to a recombinant poxvirus containing therein a DNA sequence from herpesvirus in a nonessential region of the poxvirus genome. Advantageously, the herpesvirus is a member of the alphaherpesvirus, betaherpesvirus or gammaherpesvirus subfamily. In particular, the DNA sequence from herpesvirus codes for a herpesvirus glycoprotein. More in particular, the herpesvirus glycoprotein is selected from the group consisting of equine herpesvirus gp13, equine herpesvirus gp14, equine herpesvirus gD, equine herpesvirus gp63, equine herpesvirus gE, pseudorabies virus gp 50, pseudorabies virus gpII, pseudorabies virus gpIII, pseudorabies virus gpI, herpes simplex virus gB, herpes simplex virus gC, herpes simplex virus gD, bovine herpes virus gI, feline herpes virus gB, Epstein-Barr virus gp220, Epstein-Barr virus gp340, Epstein-Barr virus gB, Epstein-Barr virus gH and human cytomegalovirus gB.

According to the present invention, the recombinant poxvirus expresses gene products of the foreign herpesvirus gene. In particular, the foreign DNA sequence codes for a herpesvirus glycoprotein and the foreign DNA is expressed in a host by the production of the herpesvirus glycoprotein. Advantageously, a plurality of herpesvirus glycoproteins are coexpressed in the host by the recombinant poxvirus. The poxvirus is advantageously a vaccinia virus or an avipox virus, such as fowlpox virus or canarypox virus.

In another aspect, the present invention relates to a vaccine for inducing an immunological response in a host animal inoculated with the vaccine, said vaccine including a carrier and a recombinant poxvirus containing, in a nonessential region thereof, DNA from herpesvirus. More in particular, the DNA codes for and expresses a herpesvirus glycoprotein. Advantageously, a plurality of herpesvirus glycoproteins are coexpressed in the host by the poxvirus. The poxvirus used in the vaccine according to the present invention is advantageously a vaccinia virus or an avipox virus, such as fowlpox virus or canarypox virus.

In another aspect, the present invention relates to mechanisms to bypass the issue of maternal immunity. If the barrier is due to the presence of antibodies to a given antigen(s) then the barrier of maternal immunity may be overcome or avoided by using, selectively, vectors expressing defined subsets of antigens. For example, the pregnant animal can be vaccinated with a recombinant vaccinia virus expressing pseudorabies virus glycoprotein gp50 and the offspring can be vaccinated at birth or shortly thereafter with vaccinia recombinants expressing other pseudorabies virus glycoproteins gpII or gpIII or combinations thereof. On the other hand, if the barrier presented by maternal immunity is due to the vector then one may differentially vaccinate the mother with one vector (vaccinia or avipox) and vaccinate the offspring with the other vector. This procedure, of course, takes into consideration not only the use of different vectors but also vectors expressing a different constellation of glycoproteins. Thus, the present invention relates to a method for overcoming or avoiding maternal immunity which would otherwise prevent successful immunization in a newborn offspring. By the present invention, the newborn offspring is inoculated with a recombinant poxvirus containing therein DNA from a non-pox source in a nonessential region of the poxvirus genome, said DNA coding for a first antigen of a pathogen of the newborn offspring, and said antigen being different from a second antigen of the same pathogen used to induce an immunological response to the same pathogen in the mother of the newborn offspring. Also by the present invention, the newborn offspring is inoculated with a recombinant first poxvirus containing therein DNA from a non-pox source in a nonessential region of the first poxvirus genome, said DNA coding for an antigen of a pathogen of the newborn offspring, and said first poxvirus being different from a recombinant second poxvirus used to induce an immunological response to the same pathogen in the mother of the newborn offspring.

BRIEF DESCRIPTION OF THE DRAWINGS

A better understanding of the present invention will be had by referring to the accompanying drawings, in which:

FIG. 2 shows the DNA sequence of an EHV-1 1.88 Kb fragment containing the gp13 coding sequences;

FIG. 6 shows the DNA sequence of an EHV-1 3.35 Kb fragment containing the gp14 coding sequence;

FIG. 11 is a map of the BamHI cleavage sites of the EHV-1 Kentucky D strain indicating the inverted repeats of the genome by boxes, showing the location of the six major EHV-1 glycoprotein genes and showing an expansion of the region of the genome which includes the gD, gp63 and gE genes;

FIG. 12 shows the nucleotide sequence of an EHV-1 6402 base-pair fragment containing the gD, gp63 and gE coding sequences;

FIG. 19 shows the DNA sequence of the PRV gpII open reading frame;

FIG. 21 shows the DNA sequence of the PRV gpIII open reading frame;

FIG. 23 shows the DNA sequence of the PRV gp50 open reading frame;

FIG. 34 shows the nucleotide sequence of the 3400 bp segment of FHV-1 DNA encoding glycoprotein gB;

FIG. 41 shows the nucleotide and amino acid sequences of HCMV (Towne strain) HXLF1 gene; and FIG. 42 shows the nucleotide and amino acid sequences of HCMV (Towne strain) HXLF2 gene.

DETAILED DESCRIPTION OF THE INVENTION

A better understanding of the present invention and of its many advantages will be had from the following examples, given by way of illustration.

EXAMPLE 1

CONSTRUCTION OF VACCINIA VIRUS RECOMBINANTS EXPRESSING THE EQUINE HERPESVIRUS gp13 GLYCOPROTEIN

Replacement of the HA gene of vaccinia with the *E. coli* Beta-galactosidase gene.

The Copenhagen strain of vaccinia virus obtained from Rhone Merieux, Inc. (Athens, Ga.) was utilized in this example. The virus was propagated from a purified plaque isolate on either VERO (ATCC# CCL81) or MRC-5 (ATCC# CCL171) cells in Eagle's minimal essential medium (MEM) plus 10% fetal bovine serum (FBS). A derivative of the wildtype virus from which the entire coding sequence for the thymidine kinass gene was deleted by standard methods (25,28) was isolated and designated vP410. This thymidine kinass deletion mutant was used for further manipulations. Plasmids were constructed, screened, and grown by standard procedures (20,27,28).

Referring now to FIG. 1, the 13 Kb SalI F fragment of vaccinia virus which spans the HindIII A/B fragment junction was ligated into SalI digested pUC8 generating pSD419VC. The right arm of pSD419VC corresponding to the HindIII B portion of the SalI F fragment was removed by digestion with HindIII and religation generating pSD456VC. pSD456VC thus contains the right end of the HindIII A fragment within which is the complete coding region for the hemagglutinin (HA) gene (35) flanked by approximately 0.4 Kb additional vaccinia sequences on each side.

To generate a plasmid vector virtually devoid of HA coding sequences, pSD456VC was cut (partial digest) at the RsaI site upstream of the HA gene and at the EagI site 80 bp from the 3' end of the HA gene. The approximate 3.5 Kb RsaI/EagI fragment was isolated from an agarose gel.

Synthetic oligonucleotides MPSYN59-62 were prepared to replace the region from the RsaI site through position 2 upstream of the HA coding sequence, immediately followed by BglII, SmaI and PstI restriction sites and an EagI sticky end. The sequence of MPSYN59-62, with restriction sites as indicated, is as follows:

The annealed MPSYN59-62 mixture was ligated into the 3.5 Kb RsaI/EagI fragment from pSD456VC, generating pSD466VC. Thus, in pSD466VC the HA gene has been replaced by a polylinker region.

A 3.2 Kb BglII/BamHI (partial) fragment containing the *E. coli* Beta-galactosidase gene from pMC1871 (34) under the transcriptional control of the vaccinia 11 kDa promoter (7) was cloned into pSD466VC which had been digested with BglII. A plasmid containing the 11 kDa promoter/Beta-galactosidase gene cassette in a left to right orientation relative to flanking vaccinia arms was designated pSD466VCBGA and recombined into a thymidine kinase deletion mutant, vP410, of the Copenhagen strain of vaccinia virus generating the vaccinia recombinant vP425 expressing Beta-galactosidase. Eighty base pairs at the carboxy terminus of the HA gene were retained so not to disrupt a short potential open reading frame transcribed right to left relative to the vaccinia genome.

The recombinant vaccinia virus, vP425 (184), was identified on the basis of blue plaque formation in the presence of the chromogenic substrate, X-gal, as described by others (9,24). Substitution of the Beta-galactosidase gene by yet another foreign gene in subsequent vaccinia recombinants could be readily scored by isolating colorless plaques instead of blue plaques.

To facilitate future cloning steps, the SmaI site derived from the pUC8 multicloning region was eliminated by digestion of pSD466VC with BamHI/EcoRI, blunt ending with the Klenow fragment of *E. coli* polymerase, and religation. Thus, the single SmaI site remaining in the resulting plasmid, pSD467VC, is in the polylinker region of the HA deletion.

Identification of DNA Sequences encoding EHV-1 gp13 gene.

The DNA sequence encoding the glycoprotein EHV-1 gp13 resides in the 7.3 Kb BamHI-H fragment of EHV-1 (3). Nucleotide sequence data for both strands was obtained from the pUC (BamHI-H) region utilizing overlapping subclones using the modified T7 enzyme SEQUENASE (40) (U.S. Biochemicals, Cleveland, Ohio). Standard dideoxy chain-termination reactions (33) were performed on double stranded plasmid templates that had been denatured in alkali. The M13 forward and reverse primers were used to obtain the initial sequence of each clone. Custom 16–17-mer primers, synthesized using standard chemistries (Biosearch 8700, San Rafael, Calif.; Applied Biosystems 380B, Foster City, Calif.), were used to walk along the remaining fragment. The IBI Pustell sequence analysis program was used in all sequence data analysis (29).

DNA sequence analysis revealed an open reading frame of 1,404 bp encoding 468 amino acids with a predicted primary translation product of 50.9 kDa. Significant amino acid homology in the carboxy half of the putative gp13 open reading frame was observed to gC of herpes simplex viruses type 1 and type 2, gIII of pseudorabies virus, and gpV of varicella-zoster virus suggesting that gp13 was a member of the gC like glycoproteins of herpesviruses. Further detailed analysis of the EHV-1 gp13 open reading frame was pre- 5'-ACACGAATGATTTTCTAAAGTATTTGGAAAGTTTTATAGGTAGTTGATAGAACAA
3'-TGTGCTTACTAAAAGATTTCATAAACCTTTCAAAATATCCATCAACTATCTTGTT AATACATAATTTTGTAAAAATAAATCACTTTTTATACTAAGATCTCCCGGGCTGCAGC-3'
TTATGTATTAAAACATTTTTATTTAGTGAAAAATATGATTCTAGAGGGCCCGACGTCGCCGG5'

Figures 2, 2A, 2B:
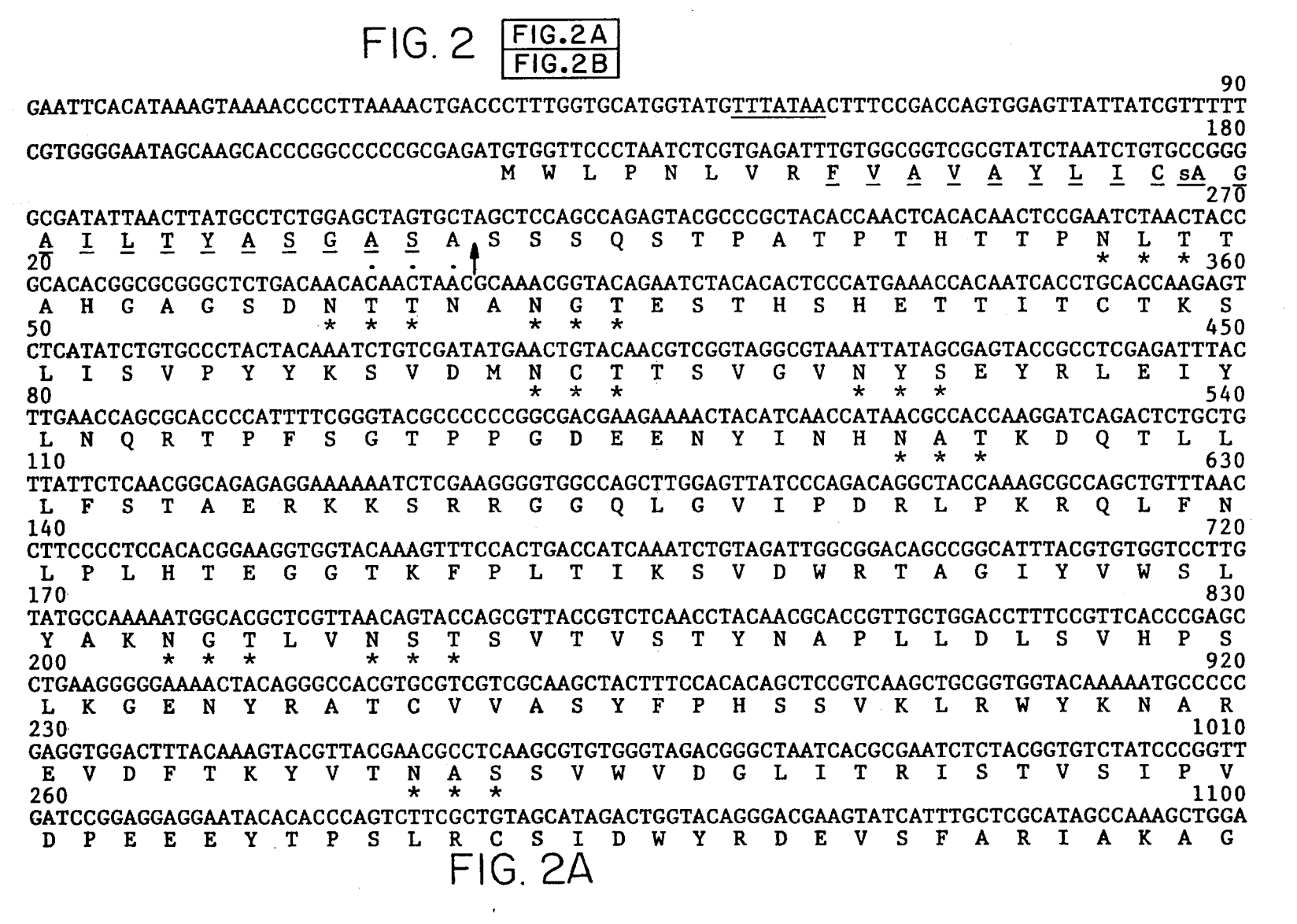

BglII SmaI PstI EagI sented in a previous publication (2). To facilitate the description of the cloning and expression of the EHV-1 gp13 in vaccinia virus vectors, the gp13 open reading frame plus additional 5' and 3' sequences are shown in FIG. 2. In FIG. 2, a presumptive TATA box and amino acids comprising

```
           NarI          gp13 3'end                              NdeI
   5'-CGCCGTACAAGAAGTCTGACTTTTAGATTTTTATCTGCAGCA-3'
   3' -GGCATGTTCTTCAGACTGAAAATCTAAAAATAGACGTCGTAT-5'
                                              PstI
``` putative signals and membrane anchor elements are underlined. The potential cleavage site of the signal sequence is noted with an arrow following the cleavage signal ASA (open circles). Potentially, nine N-linked glycosylation sites exist within the signal and anchor sequences as defined by the Asn-X-Ser/Thr motif (asterisks).

Cloning of the EHV-1 gp13 gene into a vaccinia virus donor plasmid.

An early/late vaccinia virus promoter, H6, has been used for the expression of foreign genes in fowlpox virus vectors (41,42). This promoter element corresponds to the DNA sequences immediately upstream of the H6 open reading frame in vaccinia HindIII-H fragment (31).

Figure 1:
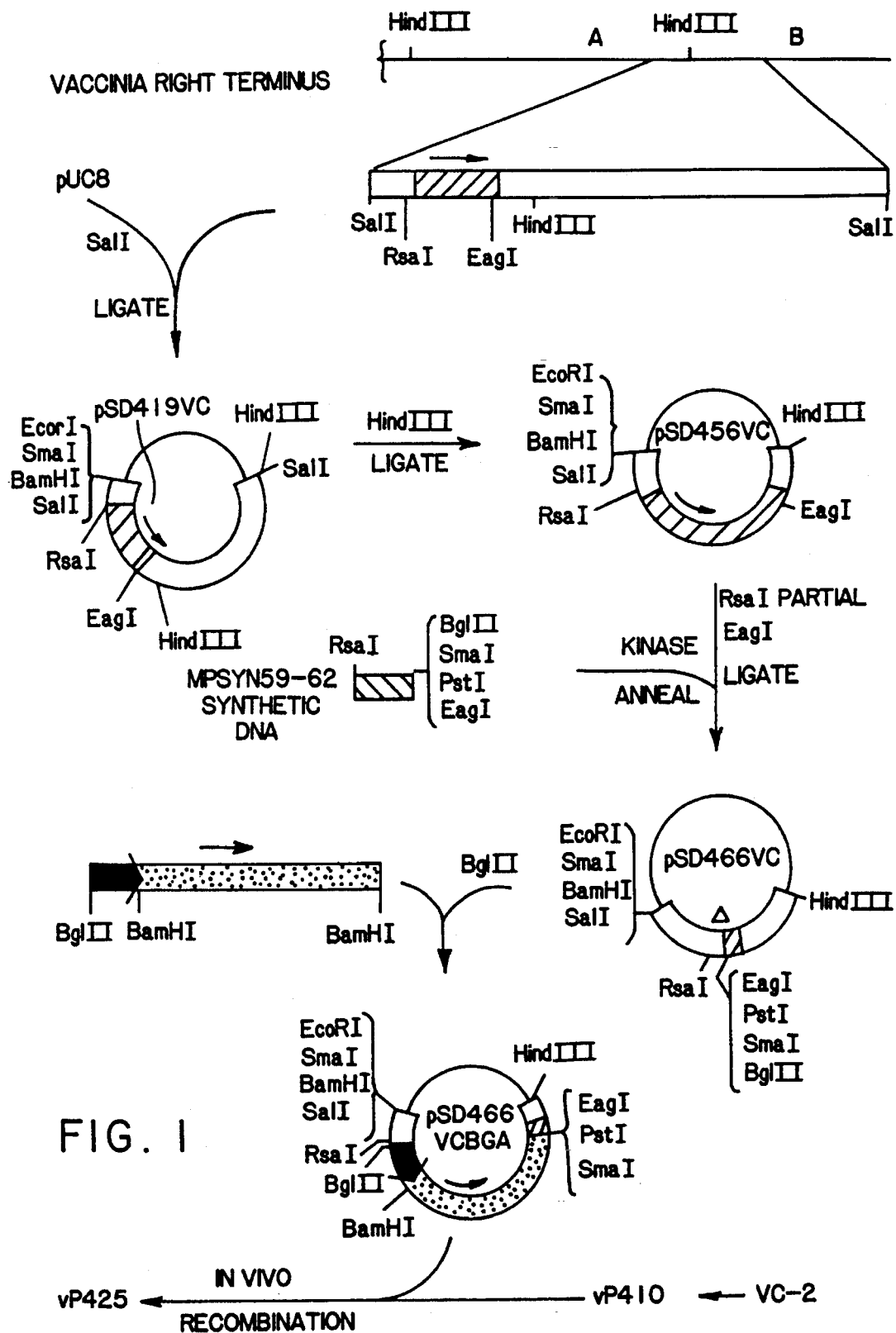
FIG. 1 schematically shows a method for the construction of the recombinant vaccinia virus vP425.
Figure 3:
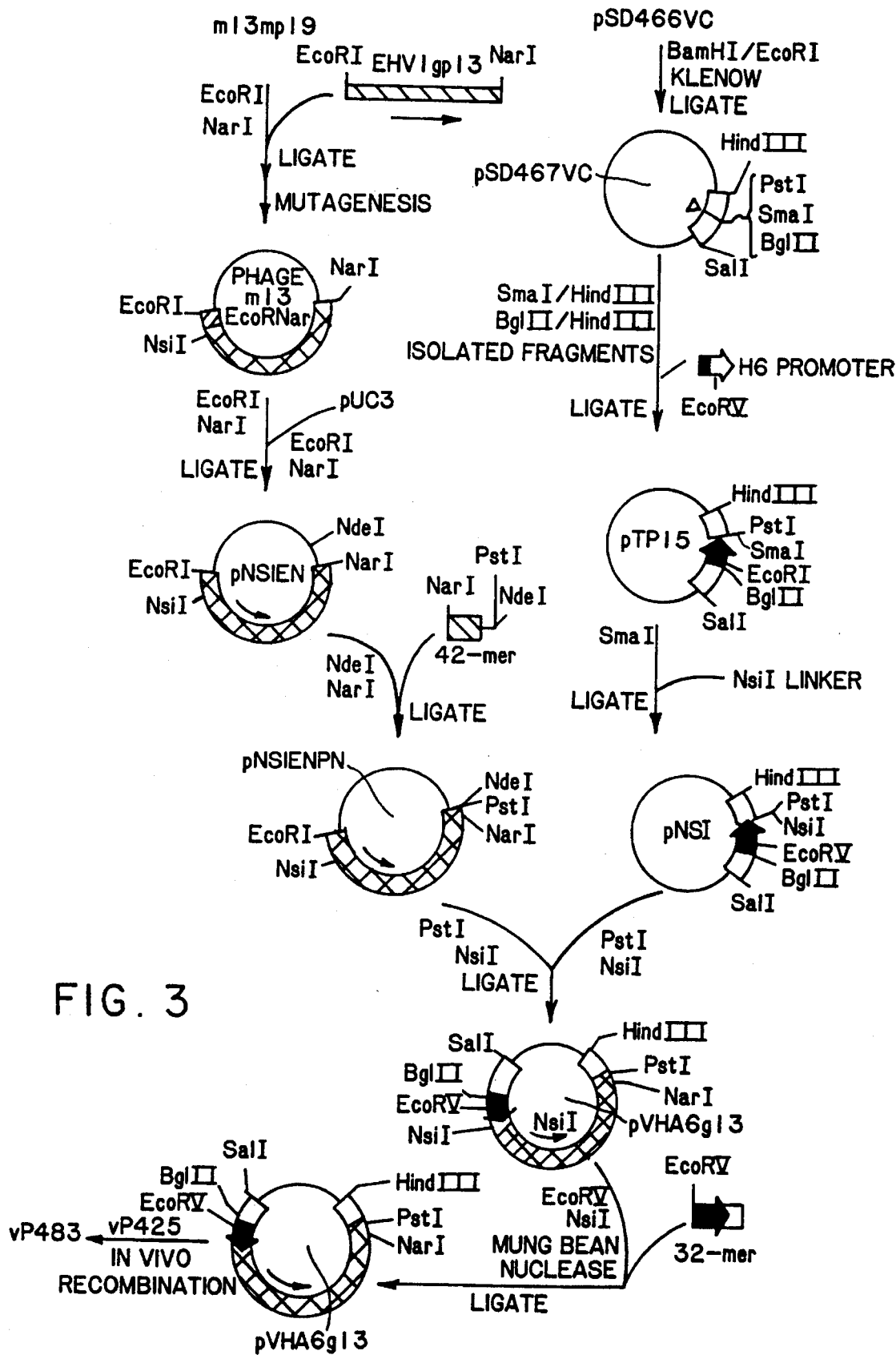
FIG. 3 schematically shows a method for the construction of the recombinant vaccinia virus vP483 containing the EHV-1 gp13 gene.

Referring now to FIG. 3, to mutate and insert the H6 promoter into pSD467VC, oligonucleotides H6SYN oligos A-D were synthesized. The sequence of H6SYN oligos A-D, with modified base as underlined and restriction sites as indicated, is as follows:

In this oligonucleotide, the termination codon (TAG) is immediately followed by a vaccinia early transcription terminator (ATTTTTAT). The double stranded DNA fragment obtained by annealing the pair of 42-mers contains an NarI sticky end, followed by the 3' end of the coding sequence for the EHV-1 gp13 gene, as well as a vaccinia early transcription termination signal (45), a PstI site, and an NdeI sticky end. This fragment was inserted between the NarI/NdeI sites of pNSIEN generating pNSIENPN (FIG. 3).

The NsiI/PstI fragment from pNSIENPN was isolated and cloned into the NsiI/PstI sites of plasmid pNSI, generating plasmid pVHA6g13NsiI (FIG. 3). pVHA6g13NsiI was cut at the EcoRV site in the H6 promoter and the NsiI site which had been introduced near the beginning of the EHV-1 gp13 gene. This vector fragment was blunt ended with Mung

```
    BglII
5'-GATCTCTTTATTCTATACTTAAAAAGTGAAAATAAATACAAAGGTTCTTGAGGGTT
3'     -AGAAATAAGATATGAATTTTTCACTTTTATTTATGTTTCCAAGAACTCCCAA

GTGTTAAATTGAAAGCGAGAAATAATCATAAATTATTTCATTATCGCGATATCCGTTAA
CACAATTTAACTTTCGCTCTTTATTAGTATTTAATAAAGTAATAGCGCTATAGGCAATT

GTTTGTATCGTACCC-3'
CAAACATAGCATGGG-5'
              SmaI
```

The underlined bases denote modification from the native H6 promoter sequence.

The 130 bp full length, double stranded DNA formed by the annealing of H6SYN oligos A-D was purified by electroelution from an agarose gel and ligated to 0.5 Kb SmaI/HindIII and 3.1 Kb BglII/HindIII fragments derived from pSD467VC. The resulting plasmid, pTP15 (184), has the ATG initiation codon modified to CCC as part of the SmaI site which is immediately followed by a PstI site. An NsiI linker, 5'-TGCATGCATGCA-3' (New England Biolabs, Beverly, Mass.) was inserted into the SmaI site of pTP15 to generate the plasmid pNSI.

An EHV-1 EcoRI/NarI fragment in which the EcoRI site is bp upstream of the ATG initiation codon and where the NarI site is 23 bp upstream from the TAG termination codon of EHV-1 gp13 was cloned into phage M13mp19 generating the recombinant phage M13EcoRNar. Using oligonucleotide-directed mutagenesis (17) an NsiI site was introduced by changing the sequence TTGCCT (bases 130–135 in FIG. 2) in the EHV-1 gp13 gene to ATGCAT. The EcoRI/NarI fragment from mutant phage M13EcoRNar was cloned into pUC8 at EcoRI/NarI sites generating plasmid pNSIEN.

Two 42-mer oligonucleotides were synthesized having the sequence, with restriction sites as indicated, as follows:

Bean nuclease. Two complementary 32-mer oligonucleotides were synthesized having the sequence, with restriction site as indicated, as follows:

```
     EcoRV
5'-ATCCGTTAAGTTTGTATCGTAATGTGGTTGCC-3'
3'-TAGGCAATTCAAACATAGCATTACACCAACGG-5'
    H6 promoter           gp13  5' end.
```

These oligonucleotides were annealed and ligated into the pVHA6g13NsiI vector fragment, producing plasmid pVHA6g13, which contains a precise junction at the ATG initiation codon (underlined in the 32-mer sequence) of the H6 promoter and EHV-1 gp13 gene (FIG. 3).

pVHA6g13 was transfected into vP425 infected cells to generate the vaccinia recombinant vP483 containing the EHV-1 gp13 gene (FIG. 3).

Construction of vaccinia virus recombinants.

Procedures for transfection of recombinant donor plasmids into tissue culture cells infected with a rescuing vaccinia virus and identification of recombinants by in situ hybridization on nitrocellulose filters were as previously described (25,28). To construct vP425 where the *E. coli*

Beta-galactosidase gene replaces the vaccinia HA coding sequences, plasmid DNA (25 ug of pSD466VCBGA in HeBS (16)) was electroporated (BioRad Gene Pulser, capacitance 960, 200 volts) into VERO cells. Subconfluent monolayers of cells were infected at 10 pfu/cell with vP410 one hour prior to use. The infected cells were harvested with trypsin and washed with HeBS before electroporation. Cells were incubated in MEM+5% fetal bovine serum at 37° C. for 24 hours, harvested and progeny virus plated on VERO monolayers. Recombinant virus expressing Beta-galactosidase was detected as blue plaques in the presence of X-gal substrate (9,24). To generate recombinant vaccinia virus where the EHV-1 gp13 gene replaced the Beta-galactosidase gene in vP425, a similar protocol was followed except that the donor plasmid was pVHA6g13 and rescuing virus was vP425. The vaccinia recombinant vP483, containing EHV-1 gp13 was detected as a colorless plaque in the presence of X-gal and confirmed as a true recombinant by DNA hybridization after 3 cycles of plaque purification.

Expression of the EHV-1 gp13 gene on the surface of cells infected with the recombinant vaccinia virus vP483.

BSC-40 cells were seeded on 22 mm glass coverslips in 35 mm dishes at $5 \times 10^5$ cells/dish. At approximately 80% confluency the cells were infected at 2 pfu/cell. After a 1 hour adsorption period the virus inoculum was removed and MEM plus 2% fetal bovine serum added. At 20 hours post infection the coverslips were washed with phosphate buffered saline (PBS) containing 0.2% BSA and 0.1% NaN3 (PBS+) and exposed to 0.1 ml of anti-gp13 monoclonal antibody, 14H7 (3) diluted one to a thousand in PBS+. After 1 hour in a humidified chamber at room temperature the cells were washed 3 times in PBS+. This procedure was repeated with fluorescein isothiocyanate-conjugated goat anti-mouse IgG. Finally, the cells were fixed for 20 minutes in 2% paraformaldehyde in PBS. The coverslips were mounted in 80% glycerol in PBS containing 3% n-propyl gallate and fluorescence was observed with a microscope.

The protein predicted from the DNA sequence has the typical features characteristic of a membrane spanning glycoprotein (14). In a productive EHV-1 infection that gp13 glycoprotein is incorporated into the various membrane systems of the cell and is transported into the cytoplasmic membrane and detectable on the external surface of the infected cell. EHV-1 gp13 is additionally a component of the EHV-1 virion. Therefore, immunofluorescence studies were performed to determine whether EHV-1 gp13 expressed by the vaccinia virus recombinant, vP483, was similarly presented on the cytoplasmic membrane of infected cells. Anti-gp13 specific monoclonal antibody followed by fluorescein-conjugated goat anti-mouse IgG revealed a strong membrane immunofluorescence in vP483 infected cells but not in vaccinia virus vP410 infected cells. This suggests that the EHV-1 gp13 expressed by the recombinant vaccinia virus vP483 is presented on the cytoplasmic membrane as expected for authentic synthesis of a membrane spanning glycoprotein.

Immunoprecipitation of EHV-1 gp13 products synthesized from recombinant vaccinia virus vP483 infected cells.

Two million cells forming a confluent monolayer in a 60 mm dish were infected at 10 pfu/cell. The inoculation was performed in methionine-free medium. After the adsorption period, the inoculum was removed and 2 ml of methionine-free medium containing 20 μCi/ml of $^{35}$S-methionine added. The infection was allowed to proceed for 24 hours when cells were lysed by the addition of 1 ml of 3× Buffer A containing 3% NP-40, 30 mM Tris pH 7.4, 450 mM NaCl, 3 mM EDTA, 0.03% sodium azide, and 0.6 mg/ml PMSF. The lysed cells and supernatant were harvested, vortexed, and clarified by centrifugation at 10,000 g for 15 minutes.

Protein A-Sepharose CL-4B (Pharmacia, Cat. No. 17.0780.01) was prepared as a 1:1 slurry in 1× Buffer A. A rat anti-mouse conjugate (Boehringer Mannheim, Cat. No. 605 500) was diluted to 1:100 in the slurry and bound to the beads at room temperature for 4 hours with rocking. The beads were then washed thoroughly with 6 one ml washes in Buffer A to remove unbound conjugate. A monoclonal antibody specific to gp13 was then bound to the beads at room temperature for 4 hours. Excess antibody was removed by thorough washing. One ml of clarified infected cell lysate was precleared by incubation with Protein A-Sepharose beads to which normal mouse serum had been bound. These beads were removed by centrifugation. One ml of the clarified precleared lysate was then mixed with 100 ul of the beads to which the specific monoclonal antibody had been bound. This mixture was rocked at room temperature for 4 hours. The beads were then removed by centrifugation and washed thoroughly by four washes in 1× Buffer A and two washes in 10 mM Tris pH 7.4 containing 0.2M LiCl and 2M urea. The antibody-antigen complex was then removed from the beads and disrupted by the addition of 50 ul of 2× Laemmli Disrupting Solution (60,195). The sample was then boiled for 5 min before electrophoresis.

There are two products of approximately 44 and 47 kDa detectable which are somewhat smaller than the predicted primary translation product (51 kDa) and a larger product of approximately 90 kDa which is consistent with a fully glycosylated form of the EHV-1 gp13 gene product. No equivalent polypeptides were precipitated from control vaccinia virus infected cells.

EXAMPLE 2

CONSTRUCTION OF VACCINIA VIRUS RECOMBINANTS EXPRESSING THE EQUINE HERPESVIRUS gp14 GLYCOPROTEIN

Replacement of the M2L gene in vaccinia virus by the *E. coli* Beta-galactosidase gene.

In order to insert the EHV-1 gp14 coding sequences into a vaccinia virus vector, a recombinant vaccinia virus, vP458, expressing the *E. coli* LacZ gene was constructed. Substitution of the LacZ coding sequences in the recombinant virus, vP458, with sequences encoding EHV-1 gp14 allows a blue to colorless plaque screening system for identifying EHV-1 gp14 containing recombinant viruses (9,24) in the presence of X-gal, a chromogenic Beta-galactosidase substrate. Furthermore, with the intention of constructing vaccinia virus recombinants expressing both EHV-1 gp14 and EH-1 gp13, an insertion locus for EHV-1 gp14 unique from the hemagglutinin deleted locus used for the insertion of EHV-1 gp13 in Example 1 was prepared at the M2L locus of HindIII M. The entire coding sequence of the M2L gene in the vaccinia HindIII M fragment was eliminated and replaced with the *E. coli* LacZ gene encoding Beta-galactosidase. The cloning steps for the construction of vP458 are schematically presented in FIG. 4.

Figure 4:
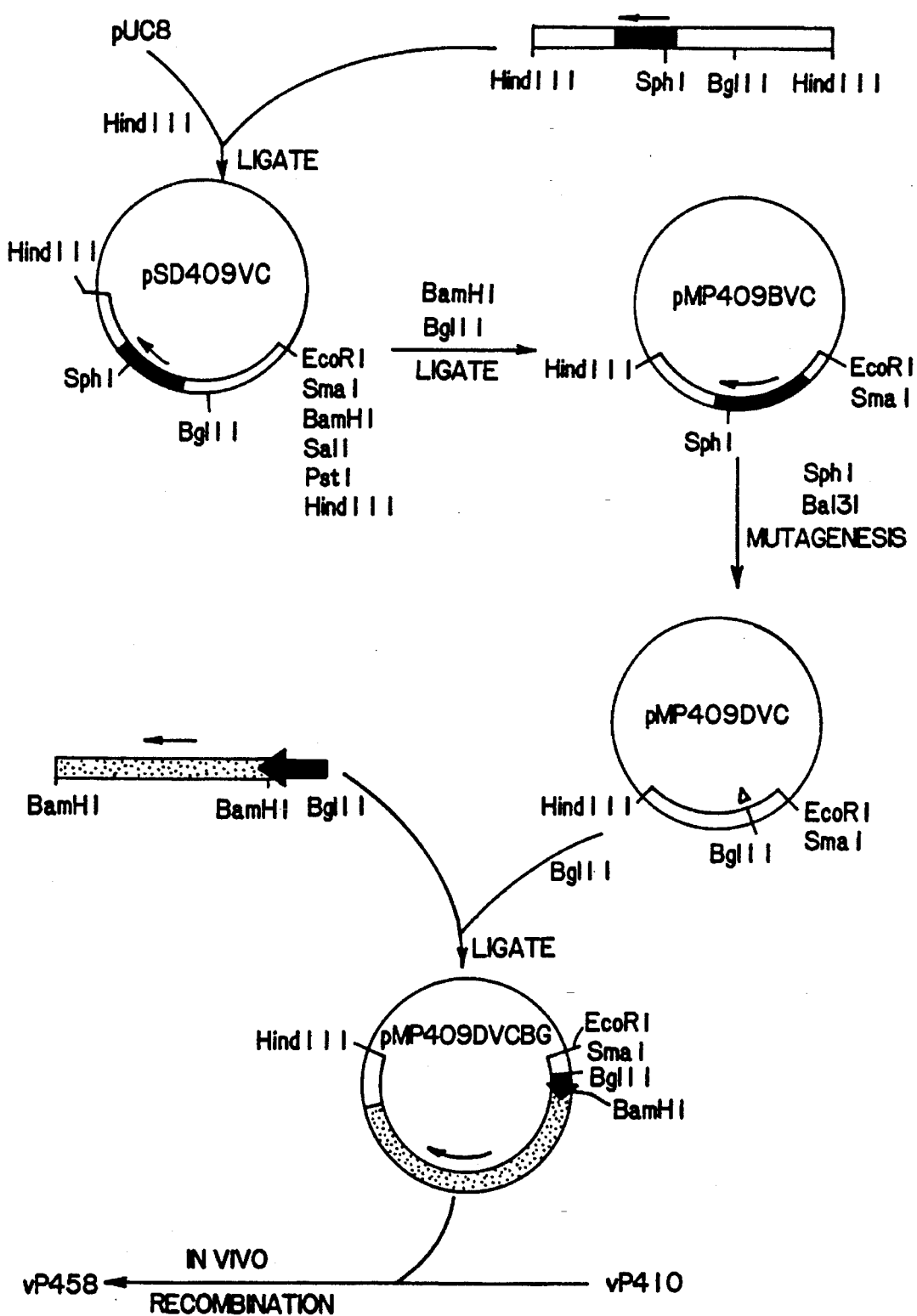
FIG. 4 schematically shows a method for the construction of the recombinant vaccinia virus vP458.

Referring now to FIG. 4, an open reading frame reading right to left relative to the vaccinia genome and encoding a putative protein of 220 amino acids is located entirely within the HindIII M fragment from the Copenhagen strain of vaccinia virus to the left of the unique BglII site. According to convention (31), this gene, which is located immediately to the right of M1L (58), was designated M2L. Deletion studies directed to the vaccinia (WR) genome extending leftward from the unique BglII site in HindIII fragment M (57) indicate that vaccinia coding sequences contained in HindIII M to the left of the BglII site are not essential for replication of the virus in tissue culture.

To facilitate use of the M2L region as an insertion locus for foreign genes, a plasmid vector, pMP409DVC, was created in which the entire M2L coding sequence was replaced by a BglII site as follows. pSD409VC, which consists of the Copenhagen vaccinia HindIII M fragment cloned into the HindIII site of pUC8, was digested with BamHI/BglII and self-ligated, thus removing the right end of HindIII M and destroying the BglII site. The resulting plasmid, pMP409BVC, was linearized with SphI, which cuts within the M2L open reading frame, and was subjected to Bal-31 exonuclease digestion for two minutes. Mutagenesis was performed on the resulting DNA (19) using a synthetic 49 mer (5'-TTTCTGTATATTTGCAACAATTTA-GATCTTACTCAAAATATGTAACAAT-3'; BglII site underlined). In the mutagenized plasmid, pMP409DVC, the M2L coding sequences have been deleted from position ≠ through the end of the open reading frame. The G of the initiation codon ATG was changed to a C to create a unique BglII site (AGATCT) at the deletion junction.

A 3.2 Kb BglII/BamHI partial fragment containing 3.1 Kb of the E. coli Beta-galactosidase gene between the BamHI sites of pMC1871 (34) under the transcriptional control of the 0.1 Kb vaccinia 11 kDa late promoter (7) was cloned into the unique BglII site of pMP409DVC. A recombinant plasmid containing the 11 kDa promoter/Beta-galactosidase gene cassette in a right to left orientation relative to flanking vaccinia arms and genome was designated pMP409DVCBG. pMP409DVCBG was used as donor plasmid for recombination with rescuing vaccinia virus, vP410, described in Example 1. The novel vaccinia recombinant, designated vP458, expressing the Beta-galactosidase gene inserted into the M2L deletion locus was detected using the chromogenic X-gal substrate (9,24) and purified by repeated plaque cloning.

Cloning of the EHV-1 gp14 gene.

Figure 5:
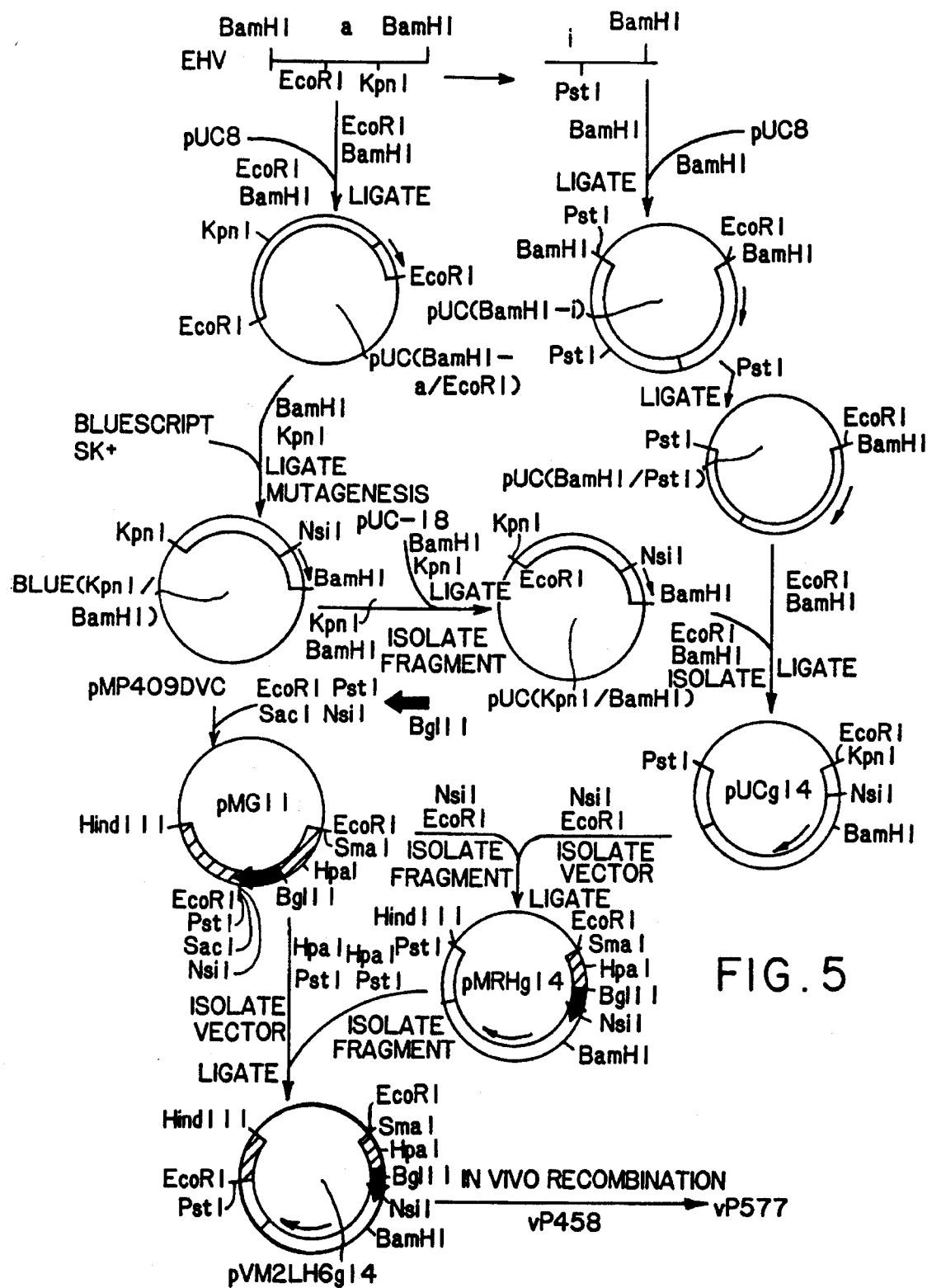
FIG. 5 schematically shows a method for the construction of the recombinant vaccinia virus vP577 containing the EHV-1 gp14 gene.

Referring now to FIG. 5, the EHV-1 gp14 coding sequence spans the junction between the BamHI restriction fragments a and i (3). The EHV-1 DNA fragments BamHI-a (21.3 Kb) and i (7.1 Kb) (59) were isolated from agarose gels. Plasmid pUC (DamHI-i) was constructed by inserting the EHV-1 BamHI-i fragment into plasmid pUC8 at the BamHI site. The EHV-1 BamHI-a fragment was digested with EcoRI and ligated into EcoRI/BamHI digested pUCS. Plasmid pUC (BamHI-a/EcoRI) contains a 10 Kb EHV-1 BamHI/EcoRI insert. Based on the fragment size determinations reported (59), DNA sequences in this insert are contiguous with those of the BamHI-i fragment in the EHV-1 genome.

Nucleotide sequence analysis.

Nucleotide sequence analysis was obtained utilizing different subclones from the pUC (BamHI-a/EcoRI) and pUC (BamHI-i) plasmids. Sequencing of the plasmid pUC (BamHI-a/EcORI) was started at the BamHI site because the EHV-1 gp14 gene spans the DamHI-a/i junction (3). The orientation of the pUC (BamHI-i) plasmid was determined by restriction enzyme digestion. Since the EHV-1 BamHI terminus closest to the EcoRI site in pUC (BamHI-i) was found to be the BamHi site at the BamHI-a/i junction, sequencing of the fragment was initiated from this BamHI end.

Sequence data for both strands was obtained as described in Example 1. The nucleotide sequence of the 3,351 bp fragment containing the EHV-1 gp14 coding sequence is shown in FIG. 6. Numbering in the left and right hand margins pertains to the amino acid and nucleic acid sequence, respectively. The putative CAT and TATA boxes are underlined. Amino acids in the signal and membrane spanning region are also underlined with the arrow indicating a potential signal peptide cleavage site. The thirteen potential glycosylation sites using the consensus sequence (Asn-X-Ser/Thr) are indicated by an asterisk.

DNA sequence analysis revealed an open reading frame extending from nucleotide positions 300 to 3239 reading from left to right relative to the EHV-1 genome, i.e. the ATG start codon was contained in the BamHI-a/EcoRI fragment and the stop codon TAA was contained in the BamHI-i fragment (3,59).

Putative transcriptional regulatory signals were found in the region 5' to the ATG initiation codon at position 300. A TATA box having the sequence AAATATAT (nucleotides 148 to 155) was located 70 nucleotides downstream from a putative CAT box at positions 71 to 77 having the sequence GGTCAAT. A polyadenylation signal AATAAA (nucleotides 3251 to 3256) was located 8 nucleotides downstream from the TAA termination codon (nucleotides 3240 to 3242). Nine out of eleven nucleotides in the sequence 5'-TCCT-GCGCGCA-3' (nucleotides 218 to 228) are complementary to the 18S ribosomal RNA sequence 3'-AGGAAGGCGT-5' (61) and may serve as the ribosome binding site.

Analysis of the EHV-1 gp14 structure.

The EHV-1 gp14 open reading frame encodes 980 amino acids with a calculated molecular weight of 109.8 kDa. Analysis of the amino acid sequence revealed a number of features common to membrane-associated glycoproteins. A region extending from amino acids 58 to 99 had a characteristic hydrophobicity profile and is proposed to be the signal sequence (FIG. 6). An unusual feature of the EHV-1 gp14 gene product is that the long hydrophobic signal sequence is preceded by a long hydrophilic sequence. This characteristic has also been noted for the pseudorabies virus (PRV) gII (62) and for the bovine herpesvirus 1 (BHV-1) gI gene (63), both of which are also HSV gB homologs. A hydrophobic region consisting of 45 amino acids (amino acids 826 to 870) is predicted to function as a transmembrane anchor domain. The hydrophilic cytoplasmic domain contains 110 amino acids.

There are eleven Asn-X-Thr/Ser (where X can be any amino acid except proline) sites for potential N-linked glycosylation (64). An unusual feature is that there are also two potential glycosylation sites in the cytoplasmic domain (FIG. 6).

Figure 7:
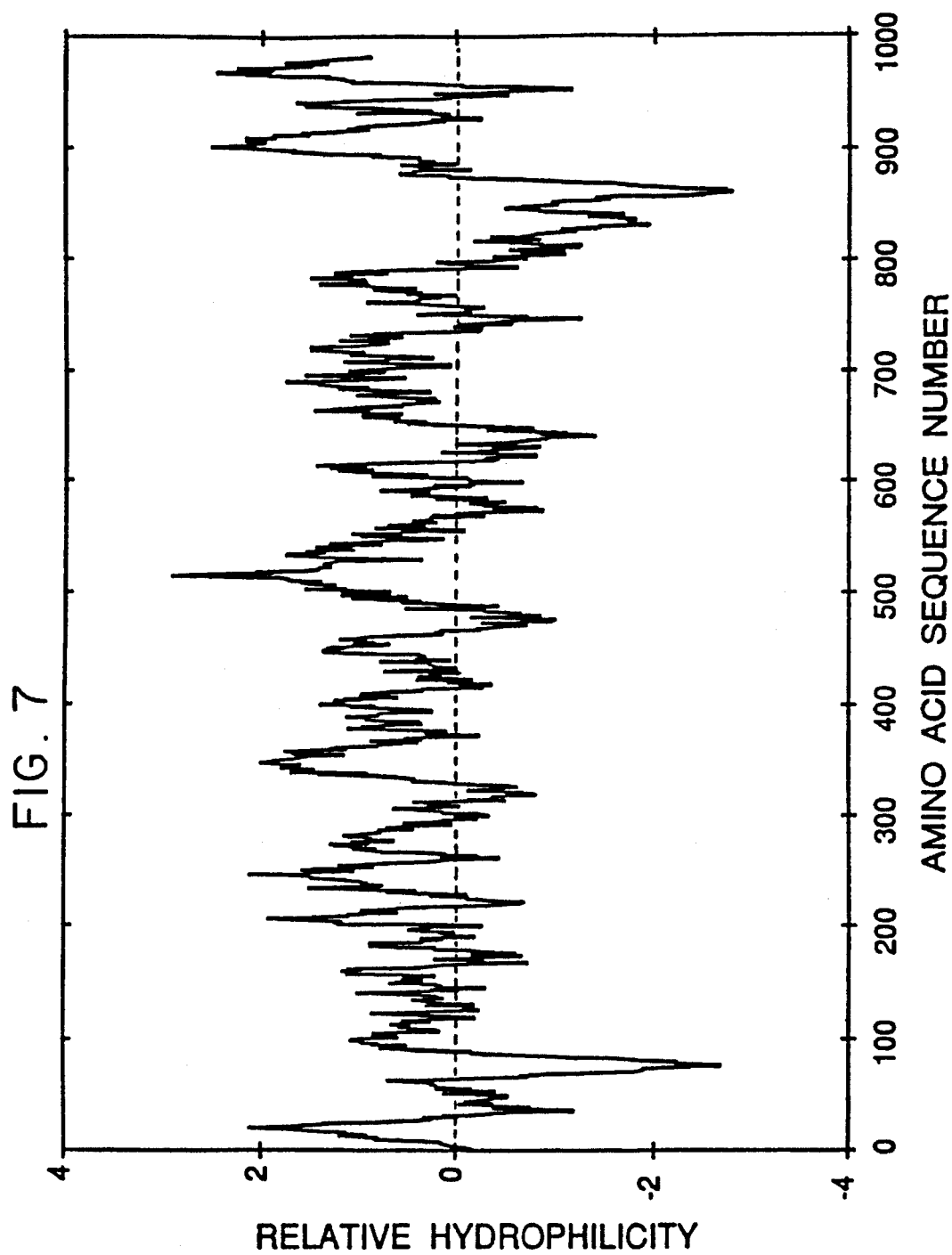
FIG. 7 is a plot of relative hydrophilicity for the EHV-1 gp14 coding sequences.
Figure 8:
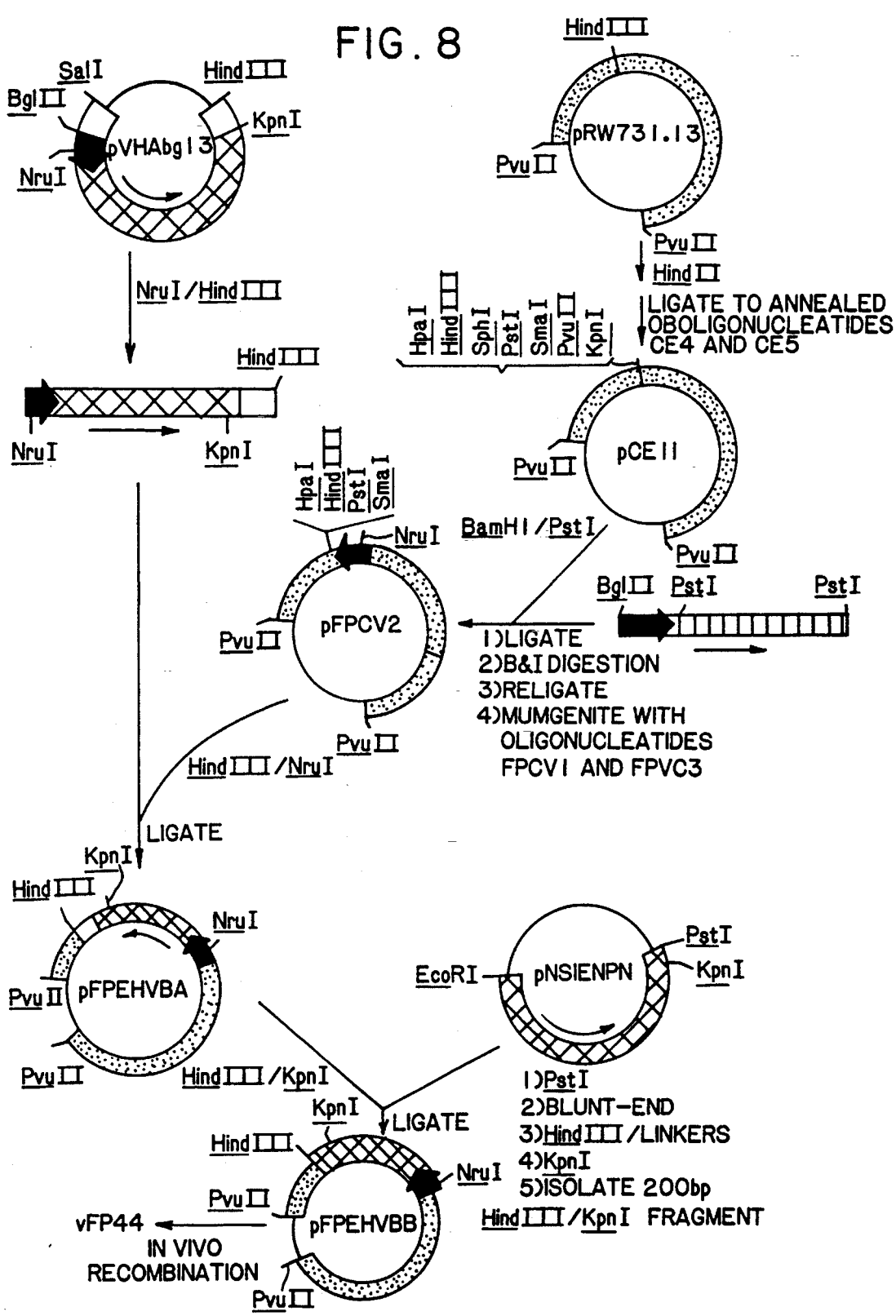
FIG. 8 schematically shows a method for the construction of the fowlpox virus vFP44 containing the EHV-1 gp13 gene.
Figure 9:
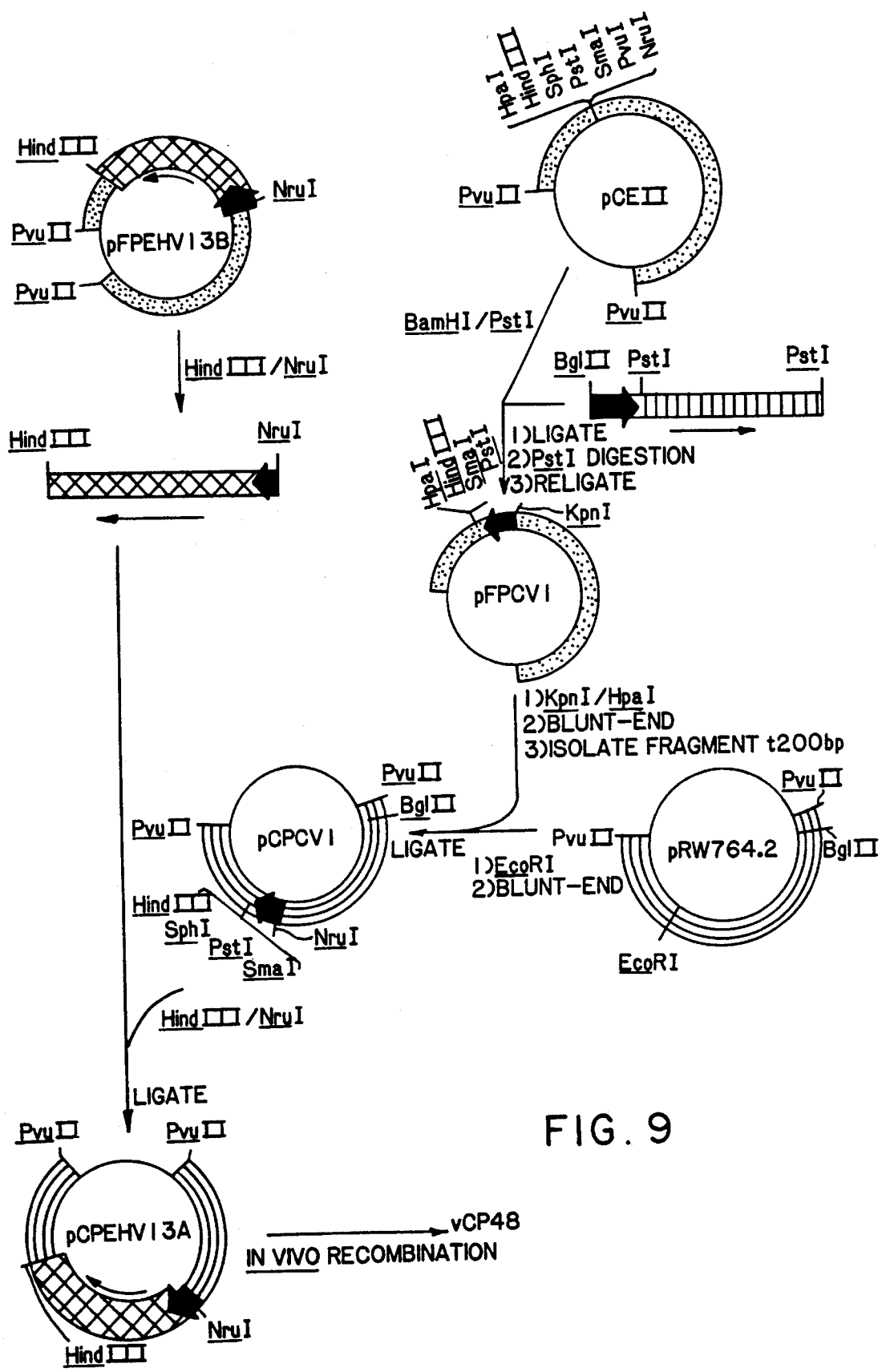
FIG. 9 schematically shows a method for the construction of the recombinant canarypox virus vCP48 containing the EHV-1 gp13 gene.

A hydrophilicity plot of the EHV-1 gp14 coding sequence is shown in FIG. 7. The hydropathic index of EHV-1 gp14 is computed by the method of Kyte and Doolittle (65) with a window of seven amino acids and no smoothing. Points below the horizontal line represent areas of higher hydrophobicity, therefore indicating potential signal and/or membrane spanning regions. The characteristics of a membrane spanning glycoprotein including signal and anchor elements and the long hydrophilic region preceding the signal sequence are found for the EHV-1 gp14 coding sequence. Localization of the antigenic determinant recognized by the anti-EHV-1 gp14 monoclonal antibody, 3F6.

Lambda gt11 expression vectors and monoclonal antibodies have been useful in identifying the EHV-1 DNA sequences encoding the major EHV-1 glycoproteins (3). A lambda gt11 recombinant, 4a1, was shown to express an EHV-1 gp14 epitope recognized by the specific monoclonal antibody 3F6 (3). In order to determine the identity of this epitope, the EHV-1 DNA contained within 4a1 was sequenced and compared with the DNA sequence of the EHV-1 gp14 coding sequence (FIG. 6). To sequence the DNA fragment corresponding to the EHV-1 gp14 epitope in the lambda gt11 recombinant 4a1 recognized by anti-EHV-1 gp14 monoclonal 3F6 (3), 4a1 was digested with EcoRI, the EHV-1 fragment isolated on agarose gels and ligated into the EcORI site of pUC8. DNA sequencing was performed as described above with the M13 universal forward and reverse primers.

The nucleotide sequence alignment indicated that this epitope was contained within the 66 amino acid region corresponding to 107 (Thr) through 172 (Val) of the deduced primary translation product. The epitope is therefore located within the amino-terminal region of the deduced EHV-1 gp14 surface domain.

Comparison of the EHV-1 gp14 amino acid sequence to other herpesvirus glycoproteins.

Comparison of the amino acid composition of the EHV-1 gp14 gene revealed extensive homology with glycoproteins of other herpesviruses. Thus, the EHV-1 gp14 is homologous to gII of PRV (62), gI of BHV-1 (63), gII of varicella-zoster virus (VZV) (66), gB of herpes simplex virus (HSV) (67,71,72) as well as to glycoproteins in Epstein-Barr virus (EBV) (68) and human cytomegalovirus (HCMV) (10).

Oligonucleotide-directed mutagenesis of the 5' terminus of the EHV-1 gp14 coding sequence.

Referring now again to FIG. 5, plasmid Blue (KpnI/BamHI) was generated by inserting a KpnI/BamHI fragment from pUC (BamHI-a/EcoRI) into plasmid Bluescript SK+ digested with KpnII/BamHI. Oligonucleotide directed mutagenesis was performed by a modification of the procedure of Kunkel (17) using uracil-containing DNA templates from plasmid Blue (KpnI/BamHI) produced in the dut⁻ ung⁻ host *E. coli* strain CJ236. In the mutagenized plasmid an NsiI site was created at codons 1 and 2 of the EHV-1 gp14 gene, changing the sequence ATG/TCC (Met/Ser) to ATG/CAT (Met/His). The mutated sequence was verified by DNA sequence analysis. The KpnI/BamHI fragment from the mutant was transferred to KpnI/BamHI digested pUC18 generating the plasmid pUC (KpnI/DamHI).

A plasmid, pUCg14, containing the complete EHV-1 gp14 gene with the NsiI site mutation was constructed by inserting the EcoRI/BamHI fragment from pUC (KpnI/BamHI) into EcORI/BamHI digested pUC (BamHI/PstI), a 3.9 Kb subclone of pUC (BamHI-i).

Construction of chimeric donor plasmid pVM2LH6al14.

pMP409DVC was cut with BglII and ligated with synthetic double-stranded DNA containing the modified vaccinia H6 (early/late) promoter, described in Example 1, flanked by restriction sites. Restriction sites for NsiI, SacI, PstI and EcoRI were created immediately downstream from the endogenous initiation codon in the H6 promoter. In pMG11, the polylinker sequence downstream from the H6 promoter is ATG CAT GAG CTC TGC AGA ATT CGG ATC T. The unique NsiI site, containing the H6 initiation codon (underlined), is immediately followed by unique SacI, PstI and EcoRI sites.

The EcoRI/NsiI DNA fragment from pUCg14 containing the EHV-1 DNA region upstream from the EHV-1 gp14 initiation codon was replaced by the EcoRI/NsiI fragment from plasmid pMG11, thus generating plasmid pMRHg14 which contains the right arm of vaccinia HindIII M, the H6 promoter, and the entire length of the EHV-1 gp14 gene. The HpaI/PstI EHV-1 gp14 containing fragment from plasmid pMRHg14 was transferred to the vector plasmid pMG11 cut with HDaI/PStI, creating plasmid pVM2LH6g14. pVM2LH6g14 contains the entire EHV-1 gp14 coding sequence (with codon 2 changed from TCC (Ser) to CAT (His) as indicated, and approximately 1.2 Kb of EHV-1 DNA downstream from the EHV-1 gp14 gene) under the control of the H6 promoter, inserted in a right to left orientation with respect to flanking vaccinia sequences relative to the vaccinia genome targeting the insertion of the EHV-1 gp14 gene to the M2L locus.

Recombination was performed using vP458 as rescuing virus and pVM2LH6g14 as donor plasmid. Colorless plaques were picked and analyzed for the presence of EHV-1 gp14 coding sequences using a specific EHV-1 gp14 probe labeled with $^{32}$P. After repeated plaque cloning the vaccinia recombinant was designated vP577.

Truncation of the EHV-1 gp14 hydrophilic leader sequences.

Using variations of the mutagenesis and cloning manipulations described above, chimeric donor plasmid pVM2LH6g14-1 was constructed. To create pVM2LH6g14-14 1, which contains a deletion of codons 2 through 34 of EHV-1 gp14 with the substitution of 4 codons, in vitro mutagenesis (17) was performed on plasmid Blue (KpnI/BamHI), creating an NsiI site in codons 32 through 34 rather than codons 1 and 2. The NsiI/BamHI fragment from the newly mutagenized Blue (KpnI/BamHI) plasmid was substituted for the NsiI/BamHI fragment in pVM2LH6g14. Multiple NsiI linkers (New England BioLabs, Beverly, Mass.) were ligated into the NsiI site to bring the initial ATG in frame with the remainder of the EHV-1 gp14 coding sequence. The final plasmid, pVM2LH6g14-1, contains the sequence ATG/CAT/GCA/TGC/ATT/GCT . . . encoding Met/His/Ala/Cys/Ile/Ala . . . where GCT (Ala) is codon 35 of EHV-1 gp14. The remainder of pVM2LH6g14-1 is identical to that in pVM2LH6g14.

The vaccinia recombinant vP613 was obtained by recombination with rescuing virus vP458 and donor plasmid pVM2LH6g14-1.

EXAMPLE 3

CONSTRUCTION OF VACCINIA VIRUS RECOMBINANTS vP633 AND vP634 EXPRESSING EACH OF THE EQUINE HERPESVIRUS gp13 AND gp14 GLYCOPROTEINS

In order to construct vaccinia recombinants expressing both gp13 and gp14 EHV-1 glycoproteins, recombination was performed with either vP577 or vP613 as rescuing virus and the donor plasmid pVHA6g13 (described in Example 1) which contains the EHV-1 gp13 gene under the control of the vaccinia H6 promoter inserted at the HA deletion locus of vaccinia. Insertion of the EHV-1 gp13 sequences into recombinant viruses was identified by in situ DNA hybridization (25,28). Recombination of pVHA6g13 with vaccinia virus recombinant vP577 (containing full length EHV-1 gp14) generated the double vaccinia virus recombinant vP633; recombination with vP613 (containing truncated EHV-1 gp14) generated the double vaccinia recombinant vP634. The vaccinia virus double recombinants vP633 and vP634 were plaque cloned and the presence of both EHV-1 gp13 and gp14 coding sequences confirmed by DNA hybridization analysis and by expression assays (see below).

Immunoprecipitation of EHV-1 gp13 and gp14 glycoproteins expressed in vaccinia virus recombinants.

In order to assess the EHV-1 gp13 and gp14 glycoproteins expressed by vaccinia virus recombinants, VERO cells were infected with the recombinants and proteins were metabolically labeled with $^{35}$S-methionine and immunoprecipitated as described in Example 1. The specific monoclonal antibody to EHV-1 gp13 (14H7) (3) or to EHV-1 gp14 (3F6) (3) were bound at a 1:1000 dilution for 4 hours at room temperature. Samples were analyzed by SDS polyacrylamide gel electrophoresis on a 10% polymer gel at 30 mA (constant current) for approximately 6 hours. Autoradiograms were prepared.

No significant products were immunoprecipitated by the specific anti-EHV-1 gp13 monoclonal 14H7 (3) or by the specific anti-EHV-1 gp14 monoclonal 3F6 (3) from either uninfected VERO cells or VERO cells infected with the control hemagglutinin minus vaccinia virus, vP452 (184). EHV-1 gp13 radiolabeled products were precipitated by monoclonal 14H7 from VERO cells infected with vP483, a vaccinia recombinant expressing only the EHV-1 gp13, or the vaccinia virus double recombinants expressing both EHV-1 gp13 with either intact gp14, vP633, or truncated gp14, vP634. There are two products of approximately 44 and 47 kDa detectable which are somewhat smaller than the predicted primary translation product (51 kDa) and a larger product of approximately 90 kDa which is consistent with a fully glycosylated form of the EHV-1 gp13 gene product. Significantly, the quality and quantity of expression of EHV-1 gp13 is unaffected by coexpression of either form of EHV-1 gp14 in the vaccinia double recombinants, vP633 and vP634.

VERO cells were infected with vP633, vP634, vP613, and vP577, respectively, and immunoprecipitated with the specific anti-EHV-1 gp14 monoclonal 3F6 (3). With vP633 (containing full length gp14 plus gp13) and with vP577 (containing full length gp14), major bands at approximately 34, 47, 60–64 and 90 kDa were observed; whereas with vP634 (containing truncated gp14 plus gp13) and with vP613 (containing truncated gp14), major bands at 34, 47, 57, 72–82 and 116 kDa were observed. Again no significant differences in the synthesis of EHV-1 gp14 of either form is observed during coexpression with EHV-1 gp13.

Immunofluorscence analysis of EHV-1 gp13 and gp14 products synthesized by recombinant vaccinia viruses.

Immunofluorescence of recombinant vaccinia virus infected VERO cells was performed as described in Example 1 using either EHV-1 gp13 or gp14 specific monoclonal antibody.

EHV-1 gp13 was readily detectable on the surface of VERO cells infected with vaccinia recombinants vP483, vP633 and vP634 as well as internally after acetone fixation. No significant internal or surface immunoreactivity toward gp13-specific antibody was seen in vP410, vP577 or vP613 infected cells. Expression of EHV-1 gp14 was readily detectable in acetone fixed VERO cells infected with vaccinia recombinants vP577, vP613, vP633 and vP634. No significant internal immunofluorescence toward gp14-specific antibody was seen in vP410 or vP483 infected cells. Using gp14-specific monoclonal antibody, 3F6, a weak surface immunofluorescence was observed in cells infected with vP613 or vP634, which express the truncated form of EHV-1 gp14 and no significant surface response above control viruses vP410 and vP483 was obtained with recombinant vaccinia viruses vP577 and vP633 which express the full length EHV-1 gp14 gene (see also Example 8).

EXAMPLE 4

IMMUNIZATION OF GUINEA PIGS WITH THE VACCINIA RECOMBINANT vP483

In order to determine the immunogenicity of the gp13 equine herpes virus gene product expressed by the vaccinia recombinant vP483, guinea pigs were inoculated with the virus and the presence of serum neutralizing antibodies against both vaccinia virus and equine herpes virus was assayed.

Fifteen guinea pigs weighing approximately 450 grams were divided into groups of five. One group received 1 ml of the vaccinia recombinant ($10^8$ TCID$_{50}$/ml) on day 0 followed by a 1 ml booster on day 21 by subcutaneous inoculation. The second group received similar inoculations but with vaccinia vP452 ($10^8$ CID$_{50}$/ml). The third group remained unvaccinated. All the guinea pigs were bled prior to the primary vaccination and on days 21 and 35. Sera were prepared and tested for the presence of neutralizing antibodies to both vaccinia and EHV-1 (strain Kentucky) using 50 TCID$_{50}$ of virus assayed on swine testicular cells.

As shown in Table 1, the EHV-1 gp13 vaccinia recombinant vP483 elicits an obvious seroconversion in guinea pigs. Serum neutralizing titers obtained with vaccinia virus are shown in parenthesis in Table 1. Both vaccinia and EHV-1 serum neutralizing antibodies are detectable 21 days after the primary inoculation and a significant increase in the titer of serum neutralizing antibodies is obtained by 2 weeks after a second inoculation of virus on day 21. It should be noted that the serum vaccinia neutralizing titers obtained in guinea pigs inoculated with the recombinant virus expressing EHV-1 gp13 are significantly higher (t=7.2) than the titers obtained from guinea pigs inoculated with the vaccinia vP452 virus.

TABLE 1

Serum neutralizing antibodies present in guinea pigs inoculated with either a vaccinia recombinant expressing EHV-1 gp13 or a control vaccinia virus, vP452.

| Inoculum Virus | Animal No. | Serum Neutralizing Titer ($\log_{10}$) on Days | | |
|---|---|---|---|---|
| | | 0 | 21 | 35 |
| Unvaccinated Controls | 26 | 0.24 (0.35) | — | 0.24 (0.70) |
| | 27 | 0.24 (0.35) | — | 0.56 (1.05) |
| | 28 | 0.24 (0.35) | — | 0.80 (0.70) |
| | 29 | 0.24 (0.35) | — | 0.40 (0.70) |
| | 30 | 0.24 (0.35) | —· | 0.32 (0.35) |
| Control Vaccinia Virus vP452 | 191 | 0.24 (0.35) | 0.36 (0.47) | 0.72 (1.75) |
| | 192 | 0.24 (0.35) | 0.21 (0.93) | 0.24 (2.30) |
| | 193 | 0.24 (0.35) | 0.48 (0.58) | — — |
| | 194 | 0.24 (0.35) | 0.24 (0.82) | 0.24 (2.10) |
| | 195 | 0.24 (0.35) | — — | — — |
| Recombinant Vaccinia Virus vP483 | 186 | 0.24 (0.35) | 0.48 (1.28) | 1.20 (2.57) |
| | 187 | 0.24 (0.35) | 0.72 (1.63) | 1.68 (2.57) |
| | 188 | 0.24 (0.35) | 0.24 (1.52) | 1.68 (2.57) |
| | 189 | 0.24 (0.35) | 0.36 (1.40) | 1.56 (2.22) |
| | 190 | 0.24 (0.35) | 0.48 (1.63) | 1.56 (3.00) |

EXAMPLE 5

IMMUNIZATION OF GUINEA PIGS WITH THE VACCINIA RECOMBINANT vP577 AND vP613

Guinea pigs were immunized to evaluate their response against EHV-1 gp14 expressed by vaccinia recombinants vP577 and vP613. Guinea pigs weighing approximately 450 g received $10^5$ TCID$_{50}$ of either vP577 or vP613 vaccinia recombinant by the subcutaneous route, one ml on each of day 0 and day 21. Guinea pigs were bled on days 0, 21 and 35, sera prepared and assayed for EHV-1 antibodies. Neutralization tests were performed on swine testicular cells against 50 TCID$_{50}$ of EHV-1 virus, strain Kentucky. Vaccinia antibodies were titrated by ELISA using an anti IgG (H&L) peroxidase conjugate.

The results are shown in Table 2. No serum neutralizing activity against EHV-1 was obtained in guinea pigs immunized with the vaccinia recombinant, vP577, containing the full length EHV-1 gp14 gene (data not shown). On the other hand, guinea pigs inoculated with the recombinant vaccinia virus, vP613, expressing a truncated EHV-1 gp14 gene induced similar levels of EHV-1 serum neutralizing antibodies (Table 2) as did the vaccinia recombinant, vP483, expressing EHV-1 gp13 (Table 1). Although EHV-1 serum neutralizing antibodies are detectable at three weeks after the primary vaccination, a more significant level is observed two weeks after the secondary immunization (Table 2). In all immunized animals, responses were obtained when vaccinia antibodies were assayed by ELISA.

TABLE 2

Serum neutralizing antibodies present in guinea pigs inoculated with a vaccinia recombinant expressing ERV-1 gp14.

| Inoculum Virus | Serum Neutralizing Titer ($\log_{10}$) on Days | | |
|---|---|---|---|
| | 0 | 21 | 35 |
| Recombinant Vaccinia Virus vP613 | 0.4 | 0.7 | 1.3 |
| | 0.2 | 0.7 | 1.2 |
| | 0.2 | 0.7 | 1.7 |
| | 0.2 | 1.1 | 1.6 |
| | 0.2 | 1.0 | 1.6 |
| Unvaccinated Controls | 0.2 | — | 0.4 |
| | 0.6 | — | 0.4 |
| | 0.7 | — | 0.8 |
| | 0.6 | — | 0.2 |
| | 0.4 | — | 0.4 |

EXAMPLE 6

PROTECTION OF VACCINATED HAMSTERS FROM CHALLENGE WITH EHV-1

In order to assess the efficacy of the vaccinia recombinant vP483 expressing EHV-1 gp13, hamsters were given either a primary or primary plus booster vaccination and they, along with an uninoculated control group or a group inoculated twice with a control vaccinia virus, vP452, were challenged intraperitoneally with a hamster adapted Kentucky strain of EHV-1.

Forty syrian hamsters (forty day old weighing between 55 and 65 g) were separated into four groups. Group A received a single subcutaneous (1 ml) inoculation of either $10^8$, $10^6$, or $10^4$ TCID$_{50}$ of the vaccinia recombinant vP483, five animals per dose. Group B was vaccinated with vP483 on day 0 followed by a booster on day 14. The (1 ml) primary and booster doses were administered subcutaneously to groups of 5 animals using $10^8$, $10^6$, or $10^4$ TCID$_{50}$. Group C consisted of 5 hamsters and received 2 subcutaneous injections ($10^8$ TCID$_{50}$ per injection) on days 0 and 14 of vaccinia vP452. Five hamsters in group D were left as unvaccinated controls. All the hamsters received 200 LD$_{50}$ of a hamster adapted Kentucky strain of EHV-1 by the intraperitoneal route 14 days after the last immunization. Survivors were counted 7 days after challenge.

The results are shown in Table 3. All unvaccinated and vaccinia vP452 virus vaccinated hamsters died within 5 days of

TABLE 3

Protection of hamsters vaccinated with the vaccinia recombinant, expressing EHV-1 gp13, against EVH-1 challenge.

| Vaccinating virus | | | | |
|---|---|---|---|---|
| | Recombinant Vaccinia vP483 | | Control Vaccinia vP452 | |
| | Primary | Booster | Booster | No Virus |
| Vaccinating Dose log$^{10}$ TCID$_{50}$ | 8 6 4 | 8 6 4 | 8 | |
| Proportion Surviving | 4 1 2<br>5 5 5 | 5 2 0<br>5 5 5 | 0<br>5 | 0<br>5 | challenge. Significant levels of protection against EHV-1 challenge were observed in hamsters vaccinated with the vaccinia recombinant vP483 expressing EHV-1 gp13. No significant differences in protection levels were observed in hamsters immunized with either primary or primary plus booster doses. The protective dose (PD$_{50}$) was similar PD$_{50}$=6.32 log$_{10}$ primary and 6.12 log$_{10}$ primary plus booster. Nevertheless, 100% protection was only observed in the group receiving two doses of $10^8$ TCID$_{50}$ recombinant virus.

In order to determine the protective efficacy of a vaccinia virus recombinant expressing EHV-1 gp14 alone or in combination with EHV-1 gp13, challenge studies were performed on vaccinated hamsters. Twenty one-day-old syrian hamsters weighing approximately 60 g each were inoculated subcutaneously with 1 ml of control vaccinia virus or with recombinant vaccinia viruses vP483, vP577, vP613, vP633 and vP634 expressing EHV-1 gp13 and/or gp14. Primary vaccination was followed by an identical vaccinating dose (pfu/ml (log$_{10}$)) on day 14. All hamsters, including non-inoculated controls, were challenged 14 days after the last immunization with an intraperitoneal injection of 200 LD$_{50}$ of EHV-1 hamster adapted Kentucky strain. Survivors from groups of five were calculated 14 days post-challenge at which point the experiment was terminated. The dose of inoculum giving 50% protection of the hamsters is evaluated as log$_{10}$ TCID$_{50}$/ml inoculant.

As shown in Table 4, the vaccinia virus recombinant, vP577, expressing the full length EHV-1 gp14 gene failed to protect hamsters against challenge with a PD$_{50}$ calculated ≦9.0 log$_{10}$. On the other hand, the truncated EHV-1 gp14 gene as expressed by the vaccinia recombinant, vP613, gave good protection on challenge (Table 4). The calculated PD$_{50}$ is somewhat better (5.2) than that obtained with the EHV-1 gp13 expressing vaccinia recombinant, vP483 (6.1). Surprisingly, the coexpression of EHV-1 gp13 and gp14, whether the full length gp14 gene or the truncated gp14 gene in vaccinia virus recombinants vP633 and vP634, respectively, gave significantly enhanced protective efficacy compared with efficacy for the EHV-1 glycoproteins expressed singly. Hence, the amount of virus inoculum to achieve a 50% protection of the vaccinated hamsters was significantly decreased when EHV-1 gp13 and gp14 were coexpressed in the same vaccinia virus recombinant.

TABLE 4

Protection of hamsters vaccinated with the vaccinia recombinants, expressing EHV-1 gp13 and/or gp14, against EHV-1 challenge.

| Inoculum | EHV-1 proteins | Vaccination dose/Survivors | | | $PD_{50}$ |
|---|---|---|---|---|---|
| vP483 | gp13 | 8/5 | 6/2 | 4/0 | 6.1 |
| None | — | 0/0 | — | — | — |
| vP577 | gp14 | 8/1 | 6/0 | 4/0 | ≧9.0 |
| None | — | 0/0 | — | — | — |
| vP613 | gp14* | 8.4/5 | 6.4/5 | 4.4/1 | 5.2 |
| vP633 | gp13 + gp14 | 8/5 | 6/3 | 4/4 | 4.3 |
| vP634 | gp13 + gp14 | 7.6/5 | 5.6/5 | 3.6/5 | ≦3.6 |
| Vaccinia | — | 8/0 | — | — | ≧9.0 |
| None | — | 0/1 | — | — | — |

*vP613 and vP634 express the truncated version of EHV-1 gp14.

EXAMPLE 7

CONSTRUCTION OF AVIPOXVIRUS RECOMBINANTS EXPRESSING THE EQUINE HERPESVIRUS gp13 GLYCOPROTEIN

Referring now to FIG. 8, pVHA6913 was utilized as the source of the EHV-1 gp13 gene. To isolate the DNA segment containing the entire EHV-1 gp13 gene, pVHA6g13 was digested with NruI and HindIII. A fragment of approximately 1.8 Kb containing 28 bp of the 3' end of the vaccinia virus H6 promoter, the entire EHV-1 gp13 gene, and approximately 410 bp of vaccinia virus sequences was generated by this digestion. The 1.8 Kb NruI/HindIII fragment was isolated for insertion into the avipoxvirus insertion vectors pFPCV2 and pCPCV1.

The fowlpox virus (FP) insertion vector pFPCV2 provides a vehicle for generating recombinants which harbor foreign genes in a non-essential region of the FP genome designated the f7 locus. pFPCV2 was derived from pRW731.13. The plasmid pRW731.13 contains an FP genomic PvuII fragment of approximately 5.5 Kb inserted between the two PvuII sites of pUC9. Initially, a multiple cloning sequence (MCS) was ligated into the unique HincII insertion site within this 5.5 Kb pvuII FP genomic fragment. The MCS was derived by annealing oligonucleotides CE4 (5'-TCGC GAGAATTCGAGCTCGGTACCGGGGATC-CTCTGAGT-CGACCTGCAGGCATGCAAGCTTGTT-3') and CE5 (5'-AACAAGCTTGCATGCCTGCAGGTCGACTCTTAGA-GGATCCCCGGTACCGA GCTCGAATTCTCGCGA-3'). The plasmid containing the MCS was designated as pCE11.

pFeLV1A is a derivative of vaccinia insertion vector pTP15 (184) (FIG. 3) in which the feline leukemia virus (FeLV) env gene (192), is inserted into the PstI site downstream from the H6 promoter. To transfer the 2.4 kb expression cassette to a FP vector, (FIG. 8) the H6/FeLV env sequences were excised from pFeLV1A by digestion with BglII and partial digestion with PstI. The BglII site is at the 5' border of the H6 promoter sequence. The PstI site is located 420 bp downstream from the translation termination signal for the FeLV envelope glycoprotein open reading frame.

The 2.4 Kb H6/FeLV env sequence was inserted into pCE11 digested with BamHI and pstI. This plasmid was designated as pFeLVF1. The pFeLVF1 plasmid was then digested with pstI to remove the FeLV env sequences. The resultant plasmid containing the vaccinia virus H6 promoter within pCE11 was designated pFPCV1. The sequences 5' to the promoter were mutagenized (19) to remove extraneous sequences using oligonucleotide FPCV1 (5' -CAGTAATA-CACGTTATTGCAGAGAGGACCATTCTT-TATTCTATACTTAAAAAGT-3') to produce pFPCV1. The region 3' to the promoter (multiple cloning site) was mutagenized with oligonucleotide FPCV3 (5'-TAGAGT CGACCTGCAGGCATCCAAGCTTGTTAACGAC-3') to remove the SphI site, which contains an ATG. The resultant plasmid was designated pFPCV2.

The 1.8 Kb NruI/HindIII EHV-1 gp13 fragment, defined above, was inserted into the 8.0 Kb NruI/HindIII fragment derived by digestion of pFPCV2. This 8.0 Kb NruI/HindIII fragment contained the 5' portion of the vaccinia virus H6 promoter (100 bp), the FP flanking sequences (4.8 Kb upstream and 1.5 Kb downstream from the insertion site) and 2.4 Kb of pUC (BRL, Bethesda, Md.). Ligation of these two fragments resulted in the formation of a 9.8 Kb plasmid designated as pFPEHV13A.

The plasmid pFPEHV13A was then digested with KpnI and HindIII to remove an approximately 600 bp fragment. This fragment contained the 3' most region of the EHV-1 gp13 gene (200 bp) and the 410 bp vaccinia virus DNA segment. The 600 bp KpnI/HindIII fragment was replaced by a 200 bp fragment derived from pNSIENPN (FIG. 3) as follows. A PstI digestion of pNSIENPN linearized the plasmid. The PstI termini were blunt-ended by the T4 DNA polymerase (New England Biolabs, Beverly, Mass.) in the presence of dNTPs (0.5 mM each). HindIII linkers (BRL, Bethesda, Md.) were then ligated to the blunt-ended fragment. Following digestion with HindIII the linearized plasmid was digested with KpnI to yield a 200 bp fragment containing the 3' portion of the EHV-1 gp13 gene, the sequence corresponding to the termination codon (TAG), and the TTTTTNT sequence motif known to be a vaccinia virus early transcription termination signal (45). The recombinant plasmid was designated as pFPEHV13B and was used in in vitro recombination for insertion of the H6 promoted EHV gp13 gene into the f7 locus of the FP genome. The recombinant fowlpox virus was designated vFP44.

Referring now to FIG. 9, pFPEHV13B was also utilized to generate a 1.4 Kb NruI/HindIII fragment for insertion into pCPCV1. The pCPCV1 plasmid contains the vaccinia virus H6 promoter in the unique EcoRI site within the 3.3 Kb PvuII canarypox virus (CP) genomic fragment. This insertion plasmid enables the insertion of foreign genes into the C3 locus of the CP genome. pCPCV1 was derived from pRW764.2, which contains a 3.3 Kb PvuII CP genomic fragment inserted into a pUC vector. pRW764.2 was linearized by digestion with EcoRI. This fragment was blunt-ended using the Klenow fragment of the *E. coli* DNA polymerase (Boehringer Mannheim Biochemicals, Indianapolis, Ind.) in the presence of dNTPs (0.5 mM each). Vaccinia virus H6 promoter sequences and a multiple cloning region situated 3' to the promoter were excised from pFPCV1 by digestion with KpnI/HpaI. This 200 bp fragment was blunt-ended with T4 DNA polymerase in the presence of dNTPs (0.5 mM each) and inserted into the linearized blunt-ended plasmid pRW764.2. The resultant plasmid was designated pCPCV1. The plasmid pCPCV1 was digested with NruI and HindIII and the 5.8 Kb fragment was isolated for ligation to the 1.4 Kb EHV gp13 containing fragment described above. The resultant plasmid was designated pCPEHV13A. This plasmid was used in in vitro recombination experiments for insertion of the H6 promoted EHV gp13 gene into the C3 locus of the CP genome. The recombinant canarypox virus was designated vCP48.

Following the in vitro recombination, recombinant avipoxvirus containing the EHV-1 gp13 gene were identified by a standard plaque hybridization assay. Positive plaques were purified by 3 cycles of plaque isolation followed by hybridization analyses. Recombinants were designated as vFP44 and vCP48 for FP and CP recombinants, respectively. Both recombinants were analyzed using a Protein A-B-galactosidase immunoscreen assay with a monoclonal antiserum to EHV-1 gp13. The results demonstrated that CEF and VERO cell monolayers infected with either vFP44 or vCP48 express the EHV-1 gp13 on the surface of virus infected cells.

EXAMPLE 8

EVALUATION OF ADDITIONAL VACCINIA VIRUS RECOMBINANTS EXPRESSING UNMODIFIED AND MODIFIED VERSIONS OF THE GENE FROM EQUINE HERPES VIRUS-1 ENCODING GLYCOPROTEIN gp14

Construction and evaluation of additional recombinant vaccinia virus expressing EHV-1 gp14. The EHV-1 gp14 containing constructs (Example 2) were modified in three ways: (a) varying the length of the EHV-1 gp14 leader sequence; (b) removing excess EHV-1 DNA 3' from the gene; and (c) inserting the modified versions of the EHV-1 gp14 gene into a vaccinia virus vP293 host range selection system (69) for evaluation.

The EHV-1 gp14 gene product contains an unusually long leader sequence. A long hydrophobic sequence extending from amino acids 58 through 99 is proposed to be the signal sequence. This region is preceded by a long hydrophilic sequence. A similar long leader sequence has also been noted for two other gB homologs, pseudorabies virus gII (62) and bovine herpesvirus 1 gI (63).
Modification of the 5' end of EHV-1 gp14.

To study the effect of the length of the leader sequence of EHV-1 gp14 on processing, presentation and immunological efficacy of the gp14 product expressed in recombinant vaccinia virus, plasmids containing the EHV-1 gp14 gene with three different lengths of leader sequence were constructed by modifying the previous EHV-1 gp14 containing constructs in the following ways.

Figure 10:
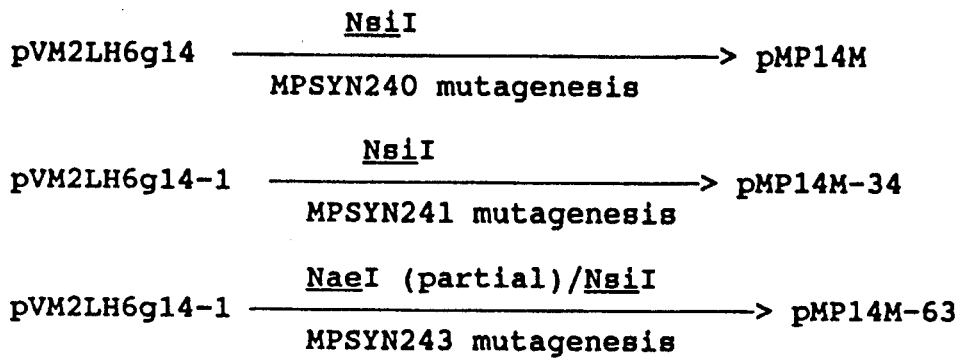
FIG. 10 schematically shows a method for the construction of donor plasmids pHES-MP63, pHES-MP1 and pHES-MP34 containing modified versions of the EHV-1 gp14 gene.

Referring now to FIG. 10, plasmid pVM2LH6g14 (Example 2) contains the entire EHV-1 gp14 coding sequence under the control of the H6 promoter inserted into the Copenhagen vaccinia M2L deletion locus. In pVM2LH6g14, amino acid number 2 of the EHV-1 gp14 gene is present as His rather than the native Ser. To change amino acid 2 to Ser, pVM2LH6g14 was cut with NsiI (recognition sequence ATGCAT) at codons 1-2 (Met/His). Mutagenesis was performed (19) using synthetic oligonucleotide MPSYN240 (5' ATCCGTTAAGTTTGTATCGTAATGTCCTCTGGTTGCCGTTCTGTC 3'). The resulting plasmid, pMP14M, contains the entire EHV-1 gp14 gene with the native codon (Ser) at position 2.

Plasmid pVM2LH6g14-1 (Example 2) is identical to pVM2LH6g14 except for a truncation of the leader sequence and introduction of four codons derived from synthetic NsiI linkers. In pVM2LH6g14-1, the sequence of the 5' truncated end of the EHV-1 gp14 gene is ATG/CAT/GCA/TGC/ATT/GCT . . . encoding Met/His/Ala/Cys/Ile/Ala . . . where GCT (Ala) is codon 35 of EHV-1 gp14. pVM2LH6g14-1 was modified by mutagenesis (19) in two ways. To produce a version of the gp14 gene truncated to approximately the same degree as pVM2LH6g14-1 but more closely approximating the native gp14 sequence, pVM2LH6g14-1 was cut with NsiI at codons 1–2. Mutagenesis was performed using synthetic oligonucleotide MPSYN241 (5' ATCCGTTAAGTTTGTATCGTAATGAGTGTCCCAGCAGCTGGCTCCTGGATC 3'). In the resulting plasmid, pMP14M-34, the EHV-1 gp14 coding sequence begins with ATG/AGT/GTC/CCA . . . Met/Ser/Val/Pro . . . where CCA (Pro) is amino acid 36 of EHV-1 gp14. The EHV-1 gp14 gene contains an NaeI site (GCCGGC) at codons 61–63 (Lys/Pro/Ala). To produce a more severely truncated version of the EHV-1 gp14 gene, pVM2LH6g14-1 was linearized with NaeI, followed by digestion with NsiI and isolation of vector fragment from an agarose gel. Mutagenesis was performed using synthetic oligonucleotide MPSYN243 (5' ATCCGTTAAGTTTGTATCGTAATGGCATCATCGAGGGTGGGCACAATAGTT 3'). In the resulting plasmid, pMP14M-63, the EHV-1 gp14 coding sequence begins with ATG/GCA . . . Met/Ala . . . where GCA (Ala) is amino acid 63 of the native EHV-1 gp14.
Removal of extraneous EHV-1 DNA.

In all EHV-1 gp14 containing plasmids discussed above, the EHV-gp14 coding sequences are followed by approximately 1200 bp of EHV-1 DNA. The termination codon (TAA) for the gp14 gene occurs within a DraI site (TTTAAA). To remove excess EHV-1 DNA, pMP14M-63 was subjected to partial DraI digestion followed by isolation of linear DNA from an agarose gel, and digestion with PstI which cuts at the junction of EHV-1 DNA and the downstream vaccinia flanking arm. A 6.5 Kb DraI/PstI DNA band was isolated from an agarose gel. Synthetic oligonucleotides MPSYN247 (5' AAATTTTTGTTAACTCGAGCTGCA 3') and MPSYN248 (5' GCTCGAGTTAACAAAAATTT 3') were annealed and ligated with the 6.5 Kb fragment. In the resulting plasmid, pMP14M-63P, the EHV-1 gp14 coding sequences are followed immediately by a sequence specifying termination of early vaccinia transcription (45) followed by a polylinker region (containing HpaI, XhoI, PstI restriction sites) and the left vaccinia flanking arm derived from HindIII M.
Insertion of the H6 promoter/EHV-1 gp14 gene into a pHES/vP293 selection system.

In all EHV-1 gp14 containing plasmids discussed above, the EHV-1 gp14 gene is under the control of the vaccinia H6 promoter inserted into the M2L deletion locus of Copenhagen strain vaccinia virus. Since the M2L insertion locus is located within a larger region of the genome that can be deleted (69), the relocation of the H6 promoter/EHV-1 gp14 expression cassette to a potentially more stable insertion site was investigated. As a preliminary step, EHV-1 gp14 gene constructs containing different lengths of the leader sequence were moved to the WR pHES/vP293-based host range selection system (69) to allow rapid generation of vaccinia recombinants for comparative evaluation.

Plasmid pHES-4 contains the vaccinia H6 promoter, followed by a polylinker region and the K1L human host range gene (70), all inserted between WR vaccinia arms flanking a 21.7 Kb deletion (69). pHES-4 contains two NruI sites, one within the H6 promoter and one within flanking vaccinia sequences. pHES-4 was linearized by partial digestion with NruI and the band containing full length linear DNA was isolated from an agarose gel. This linear DNA was cut at the XhoI site in the polylinker region. pMP14M-63P contains two NruI sites, one within the H6 promoter and the other within EHV-1 gp14 coding sequences, 0.2 Kb from the 3' end of the gene. pMP14M-63P was linearized with NruI, followed by digestion with XhoI. A 2.8 Kb NruI (partial)/XhoI fragment was isolated from an agarose gel. This fragment contains part of the H6 promoter, followed by the form of the modified EHV-1 gp14 gene containing the shortest version of the leader sequence. The 2.8 Kb H6 promoter/EHV-1 gp14-containing fragment derived from pMP14-63P was ligated with the NruI(partial)/XhoI vector fragment derived from pHES-4. The resulting plasmid, pHES-MP63, contains the H6 promoter/EHV-1 gp14 gene cassette with no extraneous EHV-1 DNA. To transfer the H6 promoter/EHV-1 gp14 5' ends containing full length or moderately truncated leader sequences, plasmids pMP14M and pMP14M-34 were cut with NruI and the 2.8 Kb and 2.7 Kb bands, respectively, isolated from agarose gels. pHES-MP63 was subjected to partial NruI digestion and a 7.2 Kb fragment isolated from an agarose gel. The 7.2 Kb vector fragment corresponds to pHES-MP63 from which the 2.6 Kb NruI fragment containing the H6 promoter/EHV-1 gp14 5' end has been removed. The 7.2 Kb NruI (partial) vector fragment derived from pHES-MP63 was ligated with the 2.8 Kb NruI fragment from pMP14M, generating pHES-MP1. The 7.2 Kb NruI (partial) vector fragment derived from pHES-MP63 was also ligated with the 2.7 Kb NruI fragment from pMP14M-34, generating pHES-MP34. The cloning steps leading to the generation of plasmids pHES-MP63, pHES-MP1 and pHES-MP34 are presented schematically in FIG. 10.

Plasmids pHES-MP1, pHES-MP34 and pHES-MP63 were used as donor plasmids for recombination with vP293 (69), generating recombinant vaccinia viruses vP753, vP765 and vP721, respectively. Recombinant progeny were selected on human MRC-5 cells.

Evaluation of vP293-based vaccinia virus recombinants expressing the EHV-1 gp14 gene.

To determine whether the three forms of the EHV-1 gp14 gene product expressed in recombinant vaccinia virus vP753, vP765 and vP721 were present on the surface of infected cells, VERO cell monolayers were infected with the three EHV-1 gp14-containing recombinant vaccinia viruses. Infected cell monolayers were analyzed for surface immunofluorescence using the EHV-1 gp14-specific monoclonal antibody 3F6. Surface immunofluorescence was positive for cells infected with all three vaccinia viral recombinants, vP753, vP765 and vP721. This indicates that proper trafficking of the EHV-1 gp14 gene product in vaccinia infected cells is not affected by varying the length of the leader sequence.

To compare the EHV-1 gp14 gene products expressed by the three EHV-1 gp14-containing vaccinia virus recombinants, MRC-5 cells were infected by vP753, vP765 and vP721 and proteins were metabolically labeled with $^{35}$S-methionine. Immunoprecipitations were performed with the radiolabeled cell lysates using EHV-1 gp14-specific monoclonal antibody 3F6.

Immunoprecipitated proteins from cells infected with vP753, vP765 and vP721 are indistinguishable from each other, and are equivalent to the proteins immunoprecipitated from vP613, the EHV-1 gp14-containing vaccinia recombinant produced from plasmid pVM2LH6g14-1. These results indicate that the variations in length of the EHV-1 gp14 leader sequence tested in these recombinants neither enhance nor interfere with proper processing of the gene product.

To evaluate the protective efficacy of recombinant vaccinia virus expressing the different forms of EHV-1 gp14, hamsters were inoculated with varying doses of vP753, vP765 and vP721 and challenged with EHV-1 hamster adapted Kentucky strain. All three EHV-1 gp14-containing vaccinia recombinants are protective, with a $\log_{10}$ PD$_{50}$ of 6.2 or better. Differences in protection among the three vaccinia virus recombinants are not statistically significant.

In contrast with vP577, a subsequent vaccinia virus recombinant which was also generated by recombination between pVM2LH6g14 and vP458 shows an identical EHV-1 gp14 immunoprecipitation pattern to the one seen with vP613, vP753, vP765 and vP721 and, like these EHV-1 gp14 expressing recombinant vaccinia virus, expressed the EHV-1 gp14 protein on the surface of infected cells.

The above data suggest that the EHV-1 gp14 expressed in vaccinia virus recombinant vP577 is defective and the defect probably arose during recombination between the donor plasmid pVM2LH6g14 and vaccinia virus vP458.

EXAMPLE 9

NUCLEOTIDE SEQUENCE OF THREE NOVEL GENES FROM EQUINE HERPESVIRUS TYPE 1 AND EXPRESSION IN VACCINIA VIRUS RECOMBINANTS

To identify and isolate the EHV-1 gene encoding gp17/18 prior to expressing it in a vaccinia recombinant virus, most of the $U_S$ region of the EHV-1 genome was sequenced and the different open reading frames found on this DNA fragment were expressed. Three new EHV-1 genes encoded by the S component were identified and analyzed: EHV-1 gD which on sequencing showed homology with the products of the HSV gD and PRV gp50 genes, EHV-1 gp63 which showed homology with the products of the HSV US7 and PRV gp63 genes, and EHV-1 gE which showed homology with the products of the HSV gE and PRV gI genes. All three genes, either individually or in association, were cloned in a host range selection system of the Copenhagen vaccinia strain for rapid expression studies. Immunofluorescence obtained with an anti-EHV-1 rabbit serum revealed the expression of EHV-1 specific products.

Cloning of the EHV-1 BamHI D fragment.

As the EHV-1 gp17/18 gene was located on the S component of the EHV-1 genome (3), the BamHI D fragment which represents most of the $U_S$ region (59) was isolated and cloned. EHV-1 genomic DNA of Kentucky D strain was digested with BamHI. The 11.0 Kb BamHI D fragment was isolated from agarose gel (Geneclean, Bio101, Inc., La Jolla, Calif.) and cloned in plasmid pIBI24 as plasmid pEHVBamHID. A restriction map of this fragment was derived (FIG. 11).

Identification of DNA sequences encoding EHV-1 gD, gp63 and gE.

Nucleotide sequence data for both strands were obtained from several subclones of the BamHI D fragment subcloned in pIBI24, as described in Example 1. Sequences of the junctions between consecutive fragments were checked on the initial clone pEHVBamHID. The PC/GENE software package (Intelligenetics Inc., Mountain View, Calif.) was used in all sequence data analyses.

DNA sequence analysis of the EHV-1 gD, gp63 and gE genes.

The DNA sequence analysis of the 6402 bp region sequenced from the BamHI D fragment (representing most of the unique short region) revealed the existence of at least three complete open reading frames reading all from the same strand. This sequence is presented in FIG. 12 as the rightward 5' to 3' strand. The base composition is 50.44% G+C.

The first open reading frame (ORF1) extended from nucleotide positions 971 to 2176. Putative transcriptional regulatory signals were found in the region 5' to the most probable ATG initiation codon at position 971. A TATA box having the sequence TATATTAA (nucleotides 871 to 878) was located 60 nucleotides downstream from a putative CAT box at positions 811 to 817 having the sequence TGACAAT. No polyadenylation signal (AATAAA) was found downstream of the TAA termination codon (nucleotides 2177 to 2179). Seven out of ten nucleotides in the sequence 5' TCCCTTCGCC 3' (nucleotides 890 to 899) are complementary to the 18S ribosomal RNA sequence 3' AGGAAGGCGT 5' (61) and may serve as the ribosome binding site. A scanning model has been proposed by which eukaryotic mRNAs initiate translation (151). The cardinal rule of this model is that ribosomes bind to the 5' end of the mRNA and linearly scan the mRNA molecule. Commitment to the translation initiation is usually at the first 5' proximal ATG codon although exceptions have been noted (152). A purine in position −3 is essential for translation initiation and translation is stimulated by C in positions −1 and −2 when the rest of the sequence is suboptimal (155). The sequence context around the proposed initiation codon AGCATGT (nucleotides 968 to 974) qualifies as a functional sequence context for translation initiation of eukaryotic mRNA. There are two other possible ATG initiation codons located respectively at positions 989 to 991 and 992 to 994. The context of these two codons CTTATGATGG does not qualify as functional for translation initiation. The EHV-1ORF1 encodes 402 amino acids with a calculated molecular mass of 45239 daltons.

Analysis of the EHV-1 ORF1 protein structure.

Figure 13:
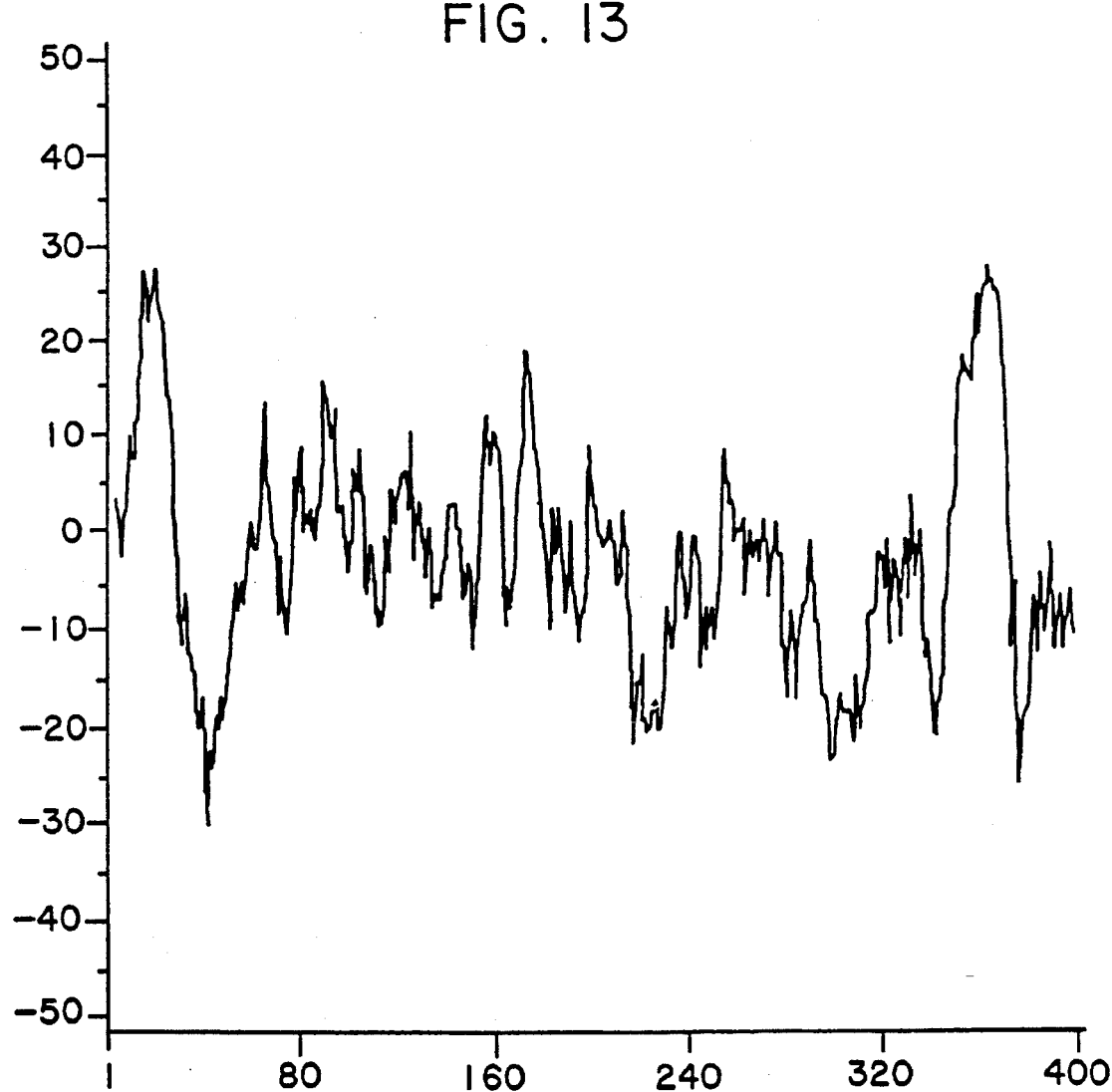
FIG. 13 is a hydropathy plot of the sequence of 402 amino acids composing EHV-1 gD.

Analysis of the amino acid sequence revealed a number of features common to membrane-associated glycoproteins. A region extending from amino acids 1 to 26 had a characteristic hydrophobicity profile and is proposed to be the signal sequence. A hydrophobic region consisting of 24 amino acids (amino acids 351 to 374) is predicted to function as a transmembrane anchor domain. There are four Asn-X-Thr/Ser (where X can be any amino acid except proline) sites for potential N-linked glycosylation (157). The hydrophobicity profile of the EHV-1ORF1 amino acid sequence is shown in FIG. 13. The characteristics of a membrane spanning glycoprotein including signal and anchor elements are clearly defined. The two most hydrophobic regions at the N- and near the C-termini are predicted to represent the signal sequence and transmembrane spanning region, respectively, of the glycoprotein molecule.

Comparison of the EHV-1ORF1 amino acid sequence to other herpesvirus glycoproteins.

Comparison of the amino acid composition of the putative EHV-1ORF1 protein revealed significant homology with glycoproteins of other herpesviruses. Thus, the EHV-1ORF1 protein is similar to PRV gp50 (95) and HSV-1 gD (79,160).

The second open reading frame (ORF2) extended from nucleotide positions 2287 to 3525. No putative transcriptional regulatory signals were found in the region 5' to the ATG initiation codon at position 2287. No AATAAA polyadenylation signal was found downstream of the TGA termination codon (nucleotides 3526 to 3528) but two potential YGTGTTYY polyadenylation signals (180) are located downstream of this termination codon at approximately 40 and 70 bp. The sequence context around the proposed initiation codon GCTATGG is consistent with Kozak's rules (151,155). There are at least two other possible ATG initiation codons at positions 2305 to 2307 and 2332 to 2334 but the sequence context of these two codons (GGGATGT and TCTATGG) does not qualify as functional for translation initiation. The EHV-1ORF2 encodes a 413 amino acid polypeptide with a calculated molecular mass of 45431 daltons.

Analysis of the EHV-1ORF2 protein structure.

Figure 14:
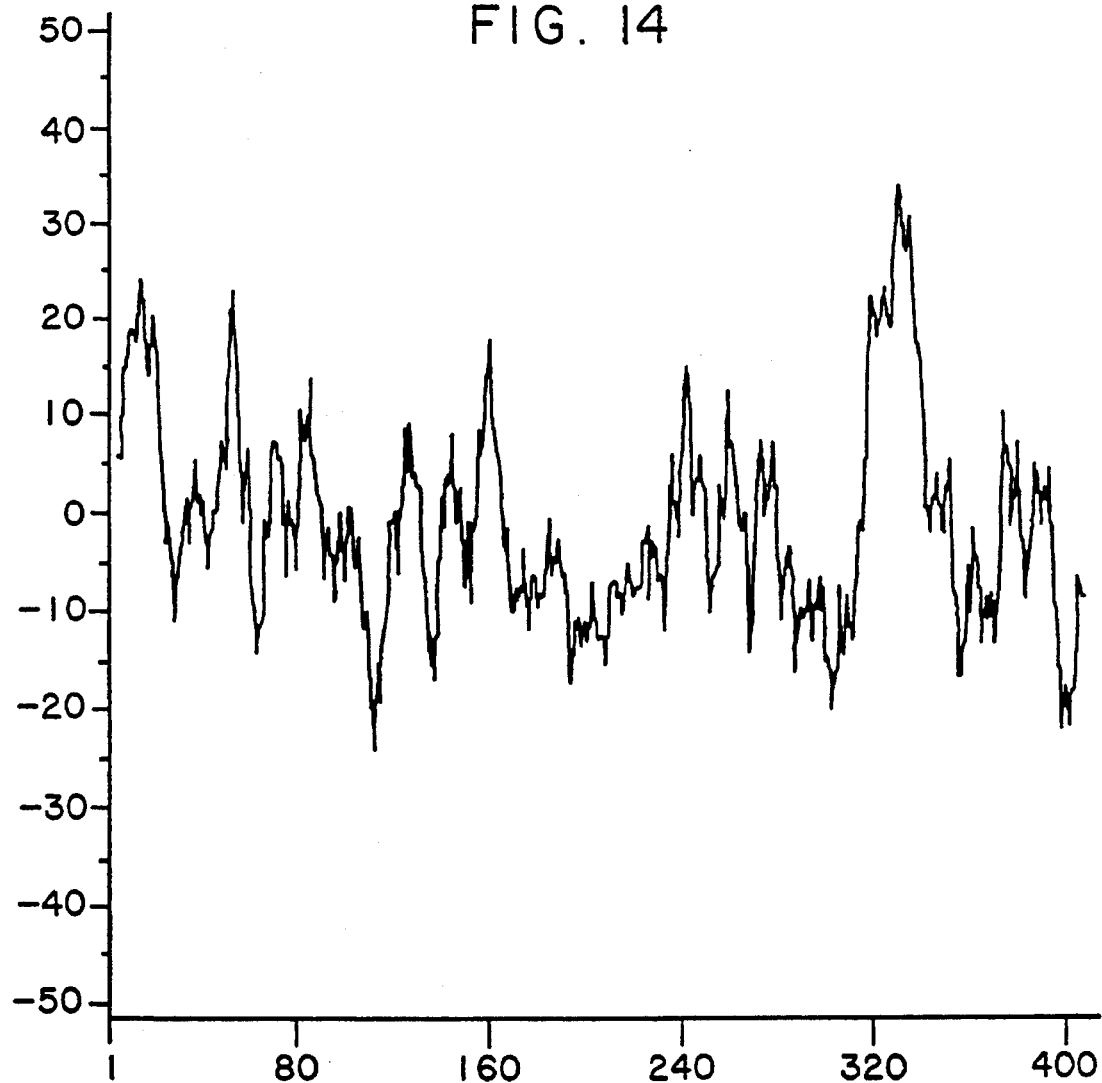
FIG. 14 is a hydropathy plot of the sequence of 413 amino acids composing EHV-1 gp63.

Analysis of the amino acid sequence revealed a number of features common to membrane-associated glycoproteins. A region extending from amino acids 1 to 22 had a characteristic hydrophobicity profile and is proposed to be the signal sequence (although the computer score for the putative cleavage site was low). A hydrophobic region consisting of 32 amino acids (positions 315 to 346) is predicted to function as a transmembrane anchor domain. There are seven Asn-X-Thr/Ser sites for potential N-linked glycosylation. A hydrophobicity plot of the EHV-1ORF2 amino acid sequence is shown in FIG. 14. The characteristics of a membrane spanning glycoprotein including signal and anchor elements are clearly defined. The two most hydrophobic regions at the N- and near the C-termini are predicted to represent the signal sequence and transmembrane spanning region, respectively, of the glycoprotein molecule.

Comparison of the EHV-1ORF2 amino acid sequence to other herpesvirus glycoproteins.

Comparison of the amino acid composition of the EHV-1ORF2 revealed significant homology with glycoproteins of other herpesviruses. Thus, the EHV-1ORF2 protein is homologous to PRV gp63 (80), VZV gpIV (181) and HSV-1 US7 (79).

The third open reading frame (ORF3) extended from nucleotide positions 3796 to 5451. Putative transcriptional regulatory signals were found in the region 5' to the ATG initiation codon at position 3796. A TATA box having the sequence GTTTAAA (nucleotides 3705 to 3711) was located 50 nucleotides downstream of a putative CAT box at positions 3649 to 3654 having the sequence GCAATG. No evident polyadenylation signal was found downstream of the TGA termination codon (nucleotides 5452 to 5454). The sequence context around the proposed initiation codon ACAATGG is consistent with Kozak's rules (151,155). The EHV-1ORF3 encodes a 552 amino acid polypeptide with a calculated molecular mass of 61493 daltons.

Analysis of the EHV-1ORF3 protein structure.

Figure 15:
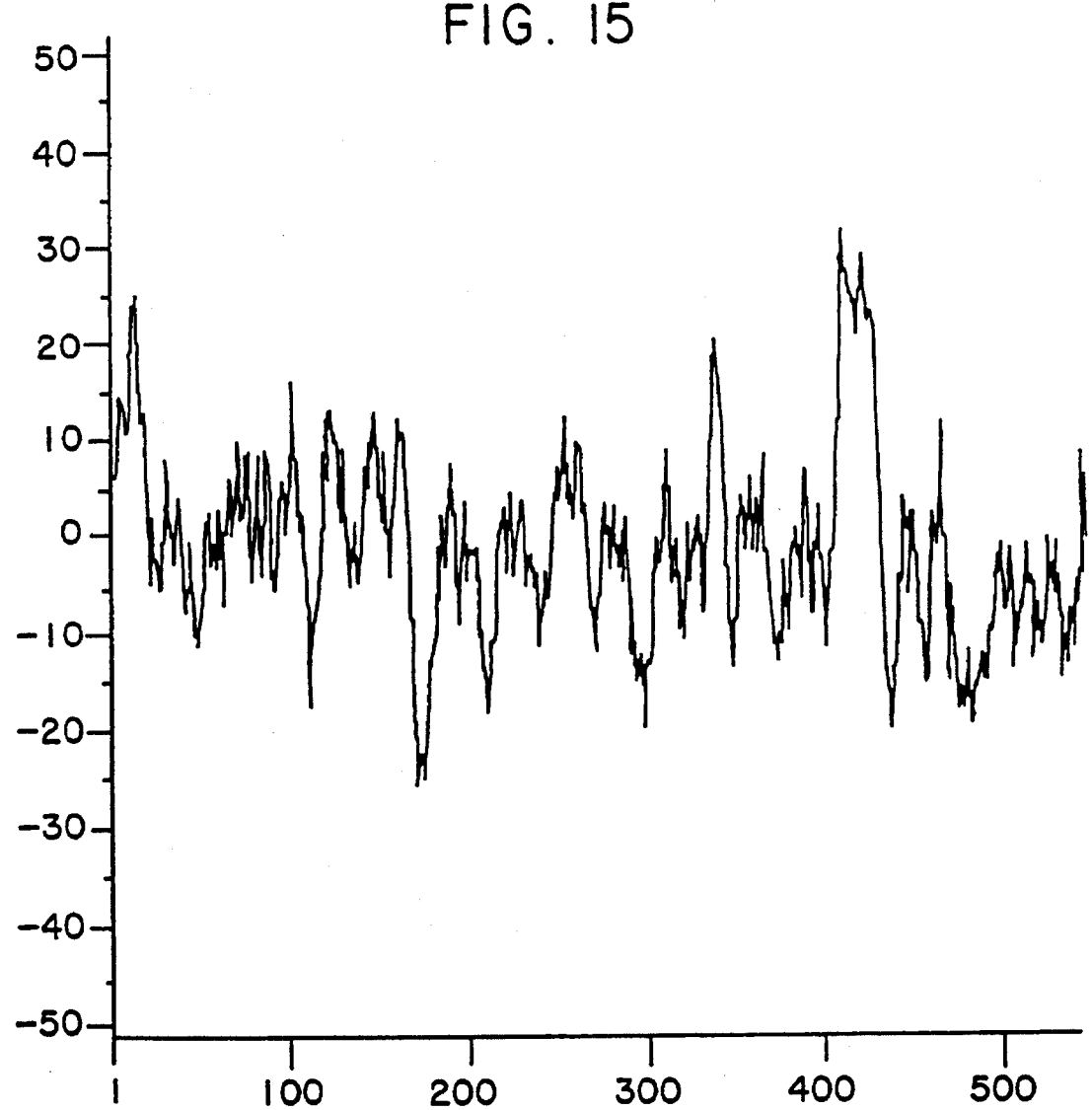
FIG. 15 is a hydropathy plot of the sequence of 552 amino acids composing EHV-1 gE.

Analysis of the amino acid sequence revealed a number of features common to membrane-associated glycoproteins. A region extending from amino acids 1 to 23 had a characteristic hydrophobicity profile and is proposed to be the signal sequence. A hydrophobic region consisting of 38 amino acids (positions 404 to 437) is predicted to function as a transmembrane anchor domain. There are five Asn-X-Thr/Ser sites for potential N-linked glycosylation. A hydrophobicity plot of the EHV-1ORF3 amino acid sequence is shown in FIG. 15. The characteristics of a membrane spanning glycoprotein including signal and anchor elements are clearly defined. The two most hydrophobic regions at the N- and near the C-termini are predicted to represent the signal sequence and transmembrane spanning region, respectively, of the glycoprotein molecule.

Comparison of the EHV-1ORF3 amino acid sequence to other herpesvirus glycoproteins.

Comparison of the amino acid composition of the EHV-1ORF3 protein revealed significant homology with glycoproteins of other herpesviruses. Thus, the EHV-1ORF3 protein is homologous to PRV gI (80), VZV gE (181) and HSV-1 gE (79).

Construction of a Copenhagen vaccinia virus based host range selection system.

A Copenhagen vaccinia virus based host range selection system similar to the WR pHES/vP293 host range selection system (69) was constructed.

Copenhagen vaccinia virus deletion mutant vP668 is deleted for 12 genes from the HindIII C through HindIII K region, including both human host range genes KIL (70) and C7L, a gene which maps to HindIII C. vP668 is unable to grow on human MRC-5 cells. Members of the COPCS plasmid series contain the C7L gene within flanking vaccinia arms, allowing recombination with vP668 and restoration of the ability of the virus to grow on MRC-5 cells. The ability of recombinant vaccinia progeny generated by recombination using the vP668/COPCS host range selection system to plaque on human MRC-5 cells provides a means of rapid identification of these recombinants. Plasmid pCOPCS657 contains the synthetic H6 vaccinia promoter followed by a polylinker cloning region for the insertion of foreign genes. The polylinker region is followed by stop codons and a vaccinia transcriptional termination signal (45).

Cloning of the EHV-1 gD gene into pCOPCS657.

Figure 16:
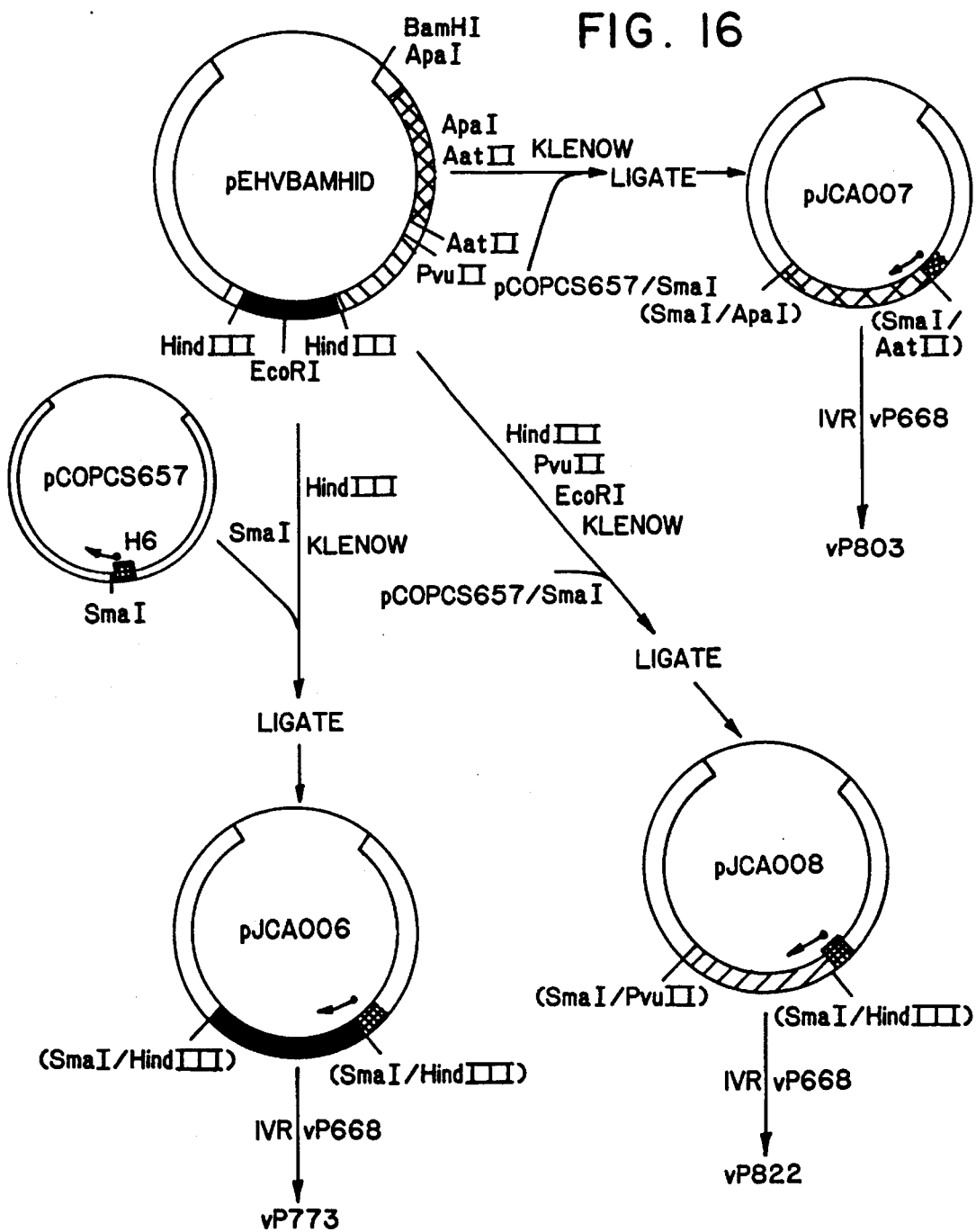
FIG. 16 schematically shows a method for the construction of donor plasmids pJCA006, pJCA007 and pJCA008 containing the EHV-1 gD gene, the EHV-1 gE gene and the EHV-1 gp63 gene, respectively, and generation of recombinant vaccinia virus containing these genes.

Referring now to FIG. 16, plasmid pEHVBamHID was digested with HindIII and a 1240 bp HindIII DNA fragment containing EHV-1 gD was isolated from an agarose gel (Geneclean, Bio10, Inc., La Jolla, Calif.) and repaired using the Klenow fragment of DNA polymerase. The repaired fragment was then ligated into plasmid pCOPCS657 digested with SmaI. The resulting plasmid, pJCA006, has the ATG initiation codon approximately 10 bp from the H6 promoter (FIG. 16).

Cloning of the EHV-1 gp63 gene into pCOPCS657.

Plasmid pEHVBamHID was digested with HindIII, EcoRI and PvuII and the 1300 bp HindIII-PvuII DNA fragment containing EHV-1 gp63 was isolated from an agarose gel and repaired with Klenow. The repaired fragment was then ligated into plasmid pCOPCS657 digested with SmaI. The resulting plasmid with EHV-1 gp63 in the proper orientation relative to the H6 promoter was designated pJCA008 (FIG. 16).

Cloning of the EHV-1 gE gene into pCOPCS657.

Plasmid pEHVBamHID was digested with AatII and ApaI and a 2630 bp AatII-ApaI DNA fragment containing EHV-1 gE was isolated from an agarose gel and repaired with Klenow. The repaired fragment was then inserted into plasmid pCOPCS657 digested with SmaI. The resulting plasmid with the EHV-1 gE gene in the right orientation relative to the H6 promoter was designated pJCA007 (FIG. 16).

Cloning of the EHV-1 gD-gp63 fragment into pCOPCS657.

Figure 17:
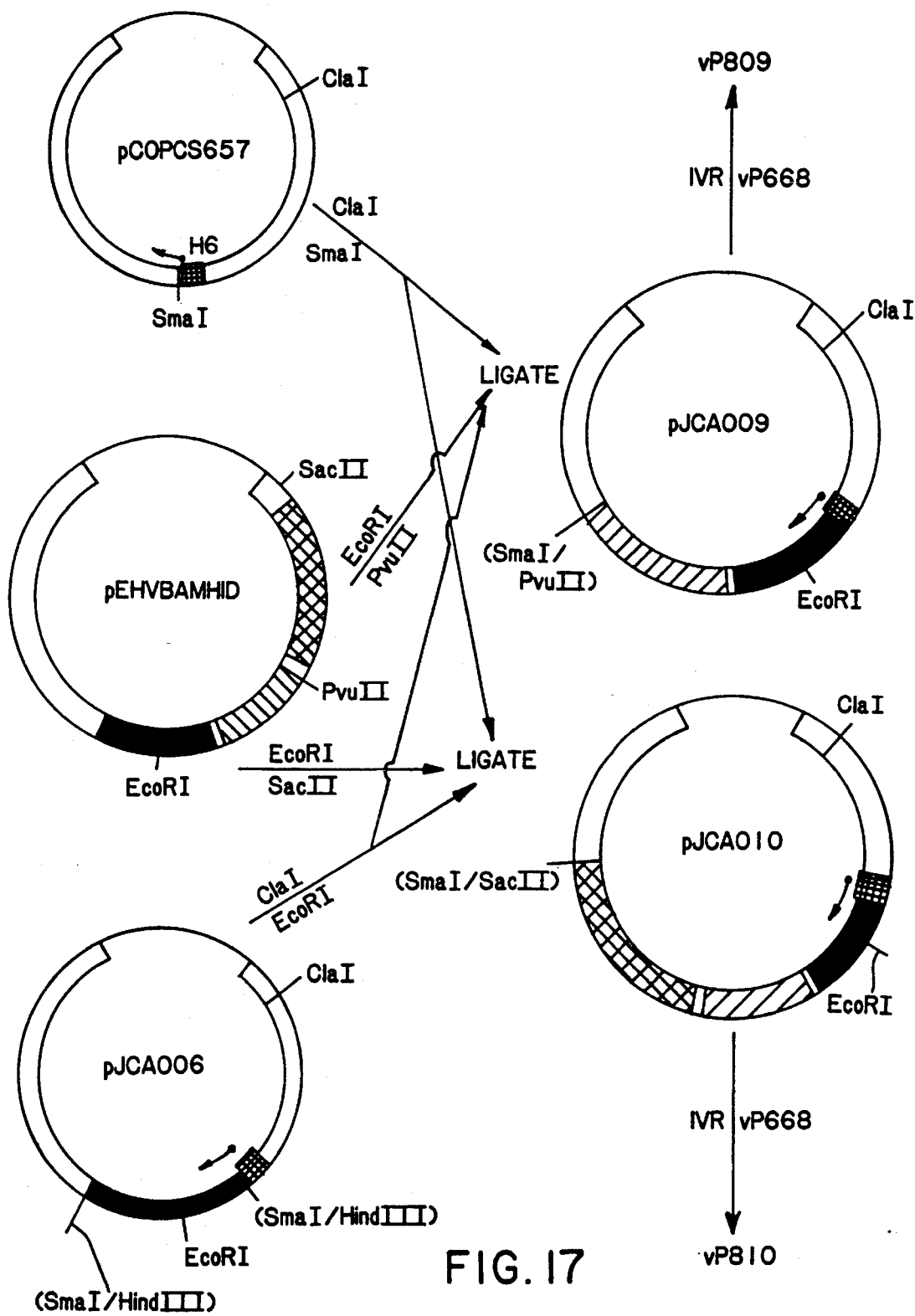
FIG. 17 schematically shows a method for the construction of donor plasmids pJCA009 (containing the EHV-1 gD and gp63 genes) and pJCA010 (containing the EHV-1 gD, gp63 and gE genes), and generation of recombinant vaccinia virus containing these genes.

Referring now to FIG. 17, plasmid pEHVBamHID was digested with EcoRI and pvuII and the 1832 bp EcoRI-PvuII DNA fragment (A) was isolated from an agarose gel. Plasmid pJCA006 was digested with ClaI and EcoRI and the 1450 bp ClaI-EcoRI DNA fragment (B) was isolated from an agarose gel. Plasmid pCOPCS657 was digested with ClaI and SmaI and the 3700 bp ClaI-SmaI DNA fragment (C) was isolated from an agarose gel. Fragments A, B and C were then ligated together and the resulting plasmid was designated pJCA009 (FIG. 17).

Cloning of the EHV-1 gp-gp63-gE fragment into pCOPCS657.

Plasmid pEHVBamHID was digested with EcoRI and SacII and the 4240 bp EcQRI-SacII DNA fragment (D) was isolated from an agarose gel. Fragment D was then ligated with fragments B and C (see above) with addition of dNTPs to ensure the repair of the junction SacII-SmaI. The resulting plasmid was designated pJCA010 (FIG. 17).

Construction of recombinant vaccinia viruses vP773, vP803, vP809, vP810 and vP822 expressing the EHV-1 $U_S$ open reading frames.

In order to check quickly the expression of the EHV-1 open reading frames described above, a number of vaccinia recombinant viruses were constructed using the COPCS host range selection system. The three open reading frames identified from the sequence analysis were cloned either individually or in association ("double" and "triple") in plasmid pCOPCS657 (FIGS. 16,17). The resulting plasmids were then used for recombination with vaccinia recombinant vP668 as rescuing virus. The different recombinant vaccinia viruses issued from these recombinations are presented in Table 5.

Vaccinia recombinant vP773 was obtained from recombination performed with donor plasmid pJCA006 containing the EHV-1 gD gene. Vaccinia recombinant vP822 was obtained from recombination performed with donor plasmid pJCA008 containing the EHV-1 gp63 gene. Vaccinia recombinant vP803 was obtained from recombination performed with donor plasmid pJCA007 containing the EHV-1 gE gene. Vaccinia recombinant vP809 was obtained from recombination performed with donor plasmid pJCA009 containing the EHV-1 gD-gp63 fragment and vaccinia recombinant vP810 was obtained from recombination performed with donor plasmid pJCA010 containing the EHV-1 gD-gp63-gE fragment (Table 5).

Immunofluorescence analysis of EHV-1ORF1 (gD), ORF2 (gp63) and ORF3 (gE) products synthesized by single or multiple recombinant vaccinia viruses.

Immunofluorescence of recombinant vaccinia virus infected VERO and MRC-5 cells was performed as described in Example 1 using anti-EHV-1 specific polyclonal rabbit serum R5935 (1:200) (Table 6).

TABLE 5

Designation of vaccinia virus recombinants expressing EHV-1 gD, gE and gp63 genes.

| Donor plasmid | EHV-1 insert | Rescuing virus | Recombinant |
| --- | --- | --- | --- |
| pJCA006 | gD | vP668 | vP773 |
| pJCA007 | gE | vP668 | vPBO3 |
| pJCA008 | gp63 | vP668 | vP822 |
| pJCA009 | gD-gp63 | vP668 | vP809 |
| pJCA010 | gD-gp63-gE | vP668 | vP810 |

TABLE 6

Immunofluorescence of recombinant vaccinia virus infected cells performed using anti-EHV-1 rabbit serum R5935.

| | R5935 | |
| --- | --- | --- |
| EHV-1 recombinant | internal | surface |
| gD | positive | negative |
| gp63 | positive | negative |
| gE | negative | negative |
| gD-gp63 | positive | negative |
| gD-gp63-gE | positive | negative |

EXAMPLE 10

IMMUNOLOGICAL EVALUATION IN MICE AND SWINE OF PSEUDORABIES VIRUS GLYCOPROTEINS gpII, gpIII AND gp50 EXPRESSED INDIVIDUALLY OR IN COMBINATION BY VACCINIA VIRUS RECOMBINANTS

The Copenhagen strain of vaccinia virus and its derivatives vP410, vP425 and vP458 were utilized in this example. Cloning of the PRV genes encoding gpII, gpIII and gp50.

PRV NIA$_3$ virus (182) was propagated on NIL$_2$ cell culture (183). Cellular debris was removed from the supernatant by centrifugation at 3,000×g for 30 minutes. The virions were purified by centrifugation through a 40% (wt/vol) sucrose cushion at 40,000 rpm for 60 minutes in a 45 Ti Beckman rotor followed by a discontinuous 30–50% (wt/vol) sucrose gradient (SW25 Beckman rotor at 23,000 rpm for 5 hours). Banded virions were collected, diluted with TNE buffer (50 mM Tris-HCl, pH7.8, 150 mM NaCl and 10 mM EDTA) and pelleted at 30,000 rpm for 1 hour in an SW40 Beckman rotor. The viral pellet was resuspended in TE buffer (50 mM Tris-HCl pH7.8, 10 mM EDTA) and lysed by addition of sodium dodecyl sulfate to a final concentration of 0.5% (wt/vol) and proteinase K to 100 mg/ml. After incubation at 37° C. for 2 hours the lysate was extracted once with phenol:chloroform (1:1) and once with chloroform:isoamylalcohol (24:1). The DNA was precipitated with ethanol and redissolved in H$_2$O. After complete digestion with BamHI the fragments were cloned into the BamHI site of pBR322 previously treated with calf intestine alkaline phosphatase (CIAP). The ligation mixture was used to transform competent E. coli strain NM522 (20).

Figure 18B:
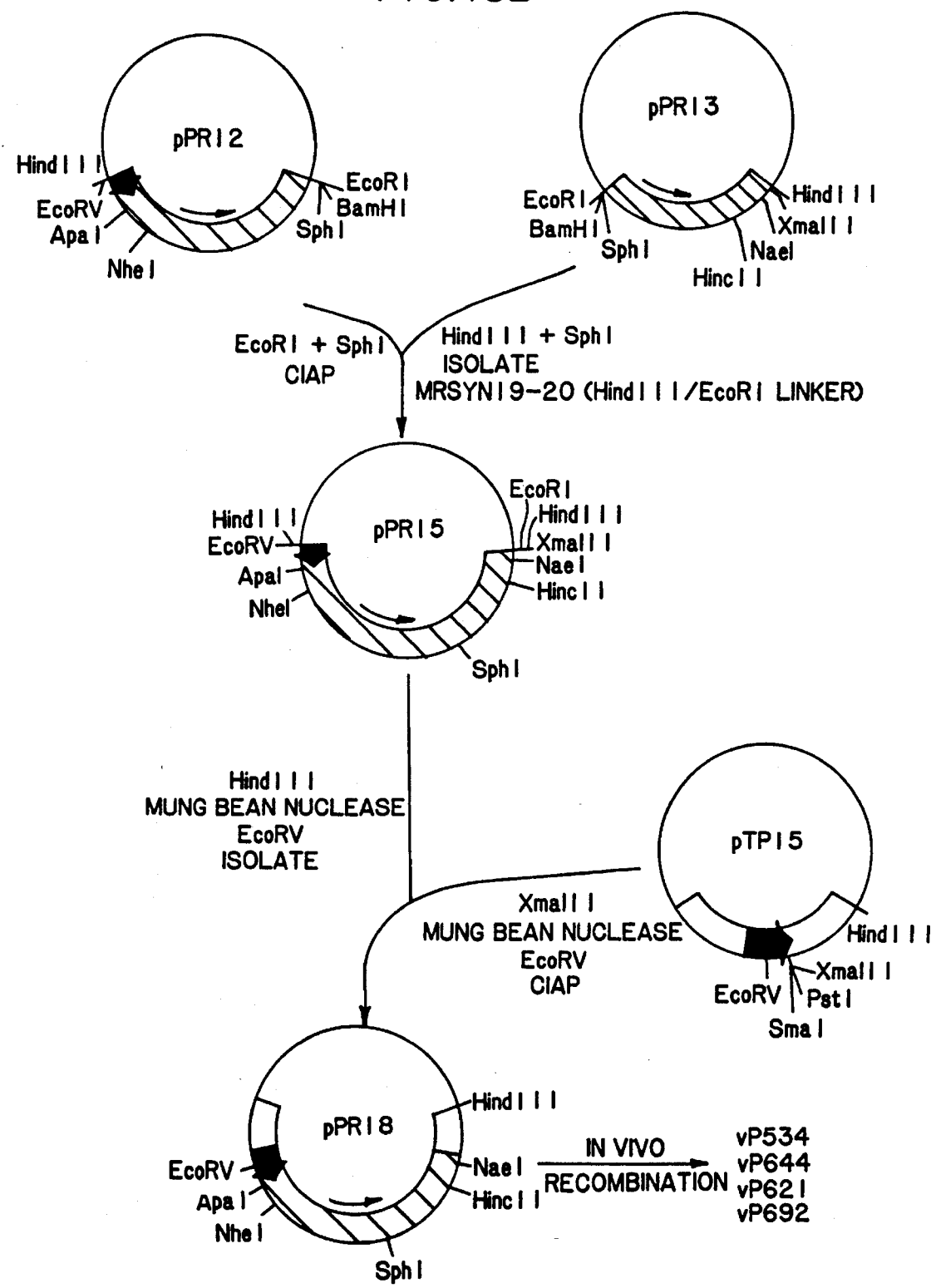
FIG. 18 schematically shows a method for the construction of donor plasmid PR18 containing the PRV gpII gene, and generation of recombinant vaccinia virus expressing the PRV gpII gene.

Referring now to FIGS. 18 and 19, the DNA sequence encoding the gpII gene resides in the BamHI fragment 1 and SalI subfragments 1A and 1B of the PRV genome (62,94). The plasmid designated pPR9.25 containing the PRV BamHI fragment 1 inserted into the BamHI site of pBR322 was digested with NcoI. The resulting DNA digest was fractionated on a 0.8% agarose gel and a 6.2 Kb NcoI DNA fragment was purified using Gene Clean™ procedure (Bio101, Inc. La Jolla, Calif.) and subsequently inserted into the NcoI site of pBR328 (Boehringer Mannheim Biochemicals, Indianapolis, Ind.) treated with CIAP. The resulting plasmid pPR2.15 was digested with SphI and fractionated on an agarose gel. The 2.7 and 1.8 Kb fragments were purified and inserted into the SphI site of phosphatased pUC18 to create plasmids pPR1 and pPR2 (FIG. 18) and into M13 phage. Nucleotide sequence was determined as described above. The DNA sequence analysis revealed an open reading frame of 2742 bp encoding 913 amino acids. Significant amino acid homology to the HSV-1 gB was observed as expected (62). To facilitate the description of the cloning manipulations for expression of PRV gpII in vaccinia virus vectors, the DNA sequence of the PRV gpII open reading frame plus additional 5' and 3' non-coding sequences is shown in FIG. 19.

Figure 20:
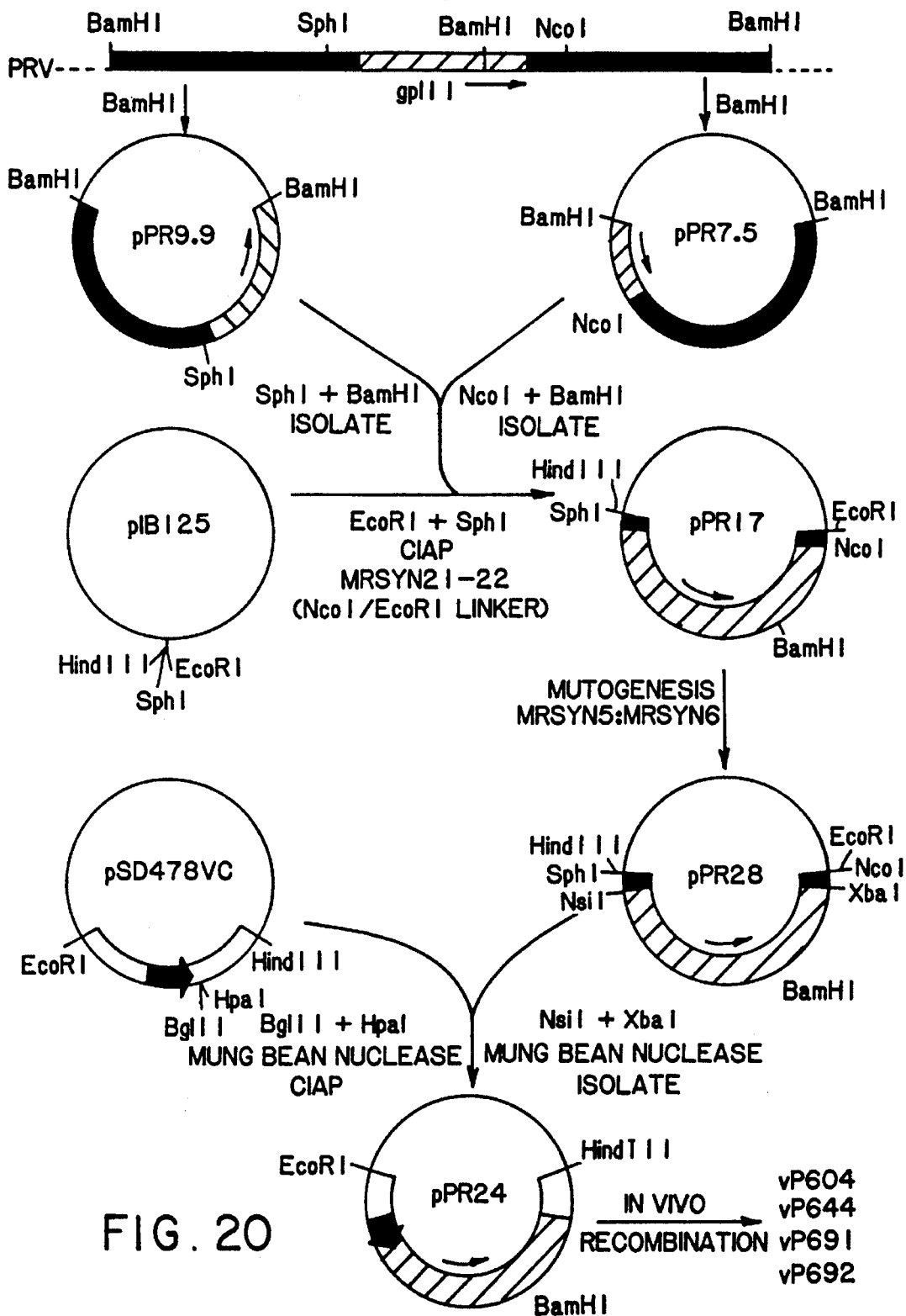
FIG. 20 schematically shows a method for the construction of donor plasmid pPR24 containing the PRV gpIII gene, and generation of recombinant vaccinia virus expressing the PRV gpIII gene.

Referring now to FIGS. 20 and 21, the DNA sequence encoding the PRV glycoprotein gpIII resides in the BamHI fragments 2 and 9 of the PRV genome (96). The plasmid pPR9.9 containing the BamHI fragment 2 inserted into the BamHI site of pBR322 (FIG. 20) was digested with BamHI and SphI. The plasmid pPR7.5 containing the BamHI fragment 9 inserted into the BamHI site of pBR322 was digested with NcoI and BamHI. The DNA resulting from both digestions was fractionated on an agarose gel. The 2.35 Kb SphI-BamHI fragment and the 1.1 Kb NcoI-BamHI fragment were purified and ligated into the EcoRI-SphI sites of phosphatased IBI25 (FIG. 20) using an NcoI-EcoRI phosphorylated linker MRSYN21/MRSYN22

```
              NcoI                EcoRI
MRSYN21  5'  CATGGGTCTGCAGTCG           3'
MRSYN22  3'            CCAGACGTCAGCTTAA 5'.
```

A plasmid designated pPR17 was isolated which contained a 3450 bp SphI-NcoI fragment including the complete PRV gpIII gene (FIG. 20). The nucleotide sequence was obtained from double stranded plasmid templates denatured with alkali and from single stranded templates after cloning into M13 phage. The DNA sequence analysis revealed an open reading frame of 1440 bp encoding 479 amino acids (FIG. 21). Significant homology to HSV gC was observed as previously reported (96).

Figure 22:
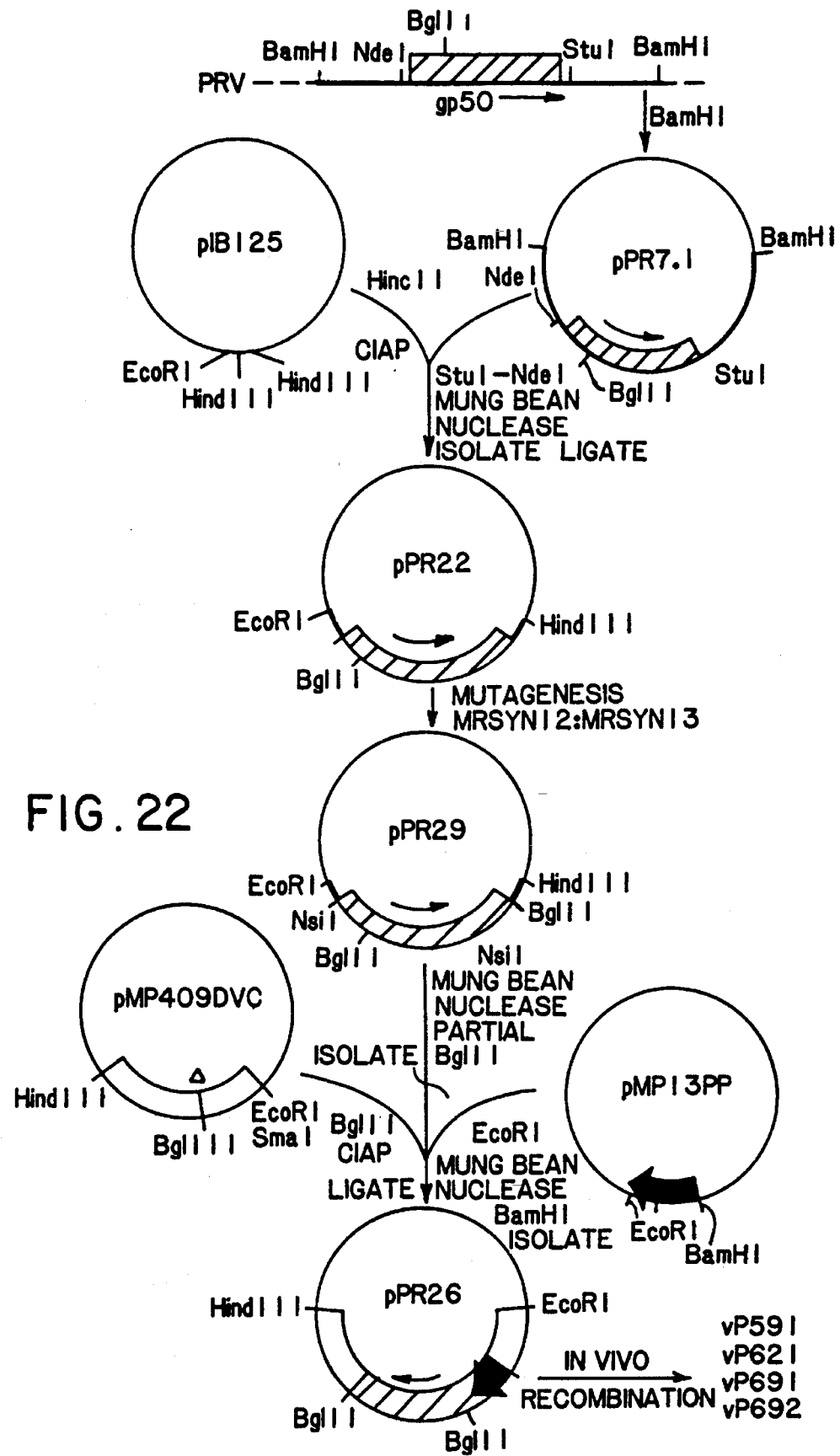
FIG. 22 schematically shows a method for the construction of donor plasmid pPR26 containing the PRV gp50 gene, and generation of recombinant vaccinia virus expressing the PRV gp50 gene.

Referring now to FIGS. 22 and 23, the DNA sequence encoding the PRV glycoprotein gp50 resides in the BamHI fragment 7 of the PRV genome (95). Plasmid pPR7.1 (FIG. 22) containing the PRV BamHI fragment 7 inserted into the BamHI site of pBR322 was digested with StuI and NdeI and treated with Mung bean nuclease. The 1.7 Kb fragment was purified from an agarose gel, inserted into the HincII site of phosphatased IBI25. This plasmid, pPR22, (FIG. 22) contains the entire PRV gp50 gene. Determination of the nucleotide sequence revealed a 1215 bp open reading frame encoding 404 amino acids (FIG. 23). Significant homology to the HSV-1 gD was observed as previously reported (95). Cloning of the PRV genes encoding gpII, gpIII and gp50 into vaccinia virus insertion donor plasmids.

The 1060 bp PRV SphI-NheI fragment from pPR1 (FIG. 18) was isolated from an agarose gel and inserted into the BamHI-SphI sites of pIBI25 after treatment with CIAP using a BamHI-NheI phosphorylated linker MRSYN1/MRSYN2

```
             BamHI              NheI
MRSYN1  5'  GATCCATTCCATGGTTG            3'
MRSYN2  3'          GTAAGGTACCAACGATC    5'
``` to generate plasmid pPR6 (FIG. 18).

pPR6 was digested with HindIII and ApaI and treated with CIAP. The ApaI site is located 32 bp downstream from the ATG initiation codon of PRV gpII (FIG. 19). A double stranded DNA fragment was obtained by annealing the pair of synthetic phosphorylated oligonucleotides MRSYN3/MRSYN4. This fragment contains DNA specifying the vaccinia H6 promoter from the EcoRV site through the ATG (underlined), followed immediately by PRV gpII coding sequences.

```
         HindIIIEcoRV                                                          ApaI
MRSYN3 5' AGCTTGATATCCGTTAAGTTTGTATCGTAATGCCCGCTGGTGGCGGTCTTTGGCGCGGGCC 3'
MYSYN4   3'    ACTATAGGCAATTCAAACATAGCATTACGGGCGACCACCGCCAGAAACCGCGC          5'
```

The synthetic DNA was ligated to the 3920 bp HindIII-ApaI fragment derived from pPR6 to generate plasmid pPR9 (FIG. 18).

Plasmid pPR9 was digested with BamHi and NheI, treated with CIAP and ligated using a phosphorylated BamHI-SphI linker

```
             SphI                BamHI
MRSYN7  5'        CCCAGATCTCCTTG        3'
MRSYN8  3'  GTACGGGTCTAGAGGAACCTAG      5'
``` to a 1640 bp SphI-NheI fragment obtained from pPR1 generating plasmid pPR12 (FIG. 18).

The 1030 bp HincII-SphI fragment from pPR2 (FIG. 18) was isolated from an agarose gel and inserted into the HincII-SphI sites of phosphatased pUC18. The resulting plasmid pPR10 was digested with HindIII and NaeI and treated with CIAP. The NaeI site is located 44 bp upstream of the TAG termination codon (FIG. 19). A double stranded DNA fragment obtained by annealing the pair of phosphorylated synthetic oligonucleotides MRSYN9/MRSYN10

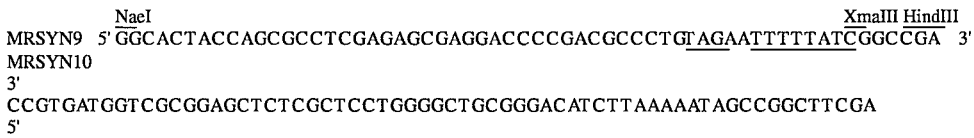

```
              NaeI                                                    XmaIII HindIII
MRSYN9  5' GGCACTACCAGCGCCTCGAGAGCGAGGACCCCGACGCCCTGTAGAATTTTTATCGGCCGA  3'
MRSYN10
3'
CCGTGATGGTCGCGGAGCTCTCGCTCCTGGGGCTGCGGGACATCTTAAAAATAGCCGGCTTCGA
5'
``` was ligated to the 3720 bp NaeI-HindIII fragment derived from pPR10 to generate the plasmid pPR11.

The underlined sequences correspond to the PRV gpII termination codon and to a vaccinia early transcription termination signal (45). The 770 bp SphI-HincII fragment from pPR2 was purified from an agarose gel and inserted

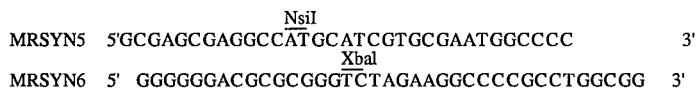

```
                                  NsiI
         MRSYN5  5'GCGAGCGAGGCCATGCATCGTGCGAATGGCCCC                3'
                                        XbaI
         MRSYN6  5' GGGGGGACGCGCGGGTCTAGAAGGCCCCGCCTGGCGG            3'
``` using a BamHI-SphI phosphorylated linker (MRSYN7/MRSYN8) into the BamHI-HincII sites of CIAP-treated pPR11 to generate pPR13 (FIG. 18). Plasmid pPR12 digested with EcoRI and SphI and treated with CIAP was ligated using a phosphorylated HindIII-EcoRI linker (MRSYN19/MRSYN20)

```
                 HindIII                      EcoRI
MRSYN19   5'  AGCTTCTGCAGCCATGGCGATCGG              3'
MRSYN20   3'            AGACGTCGGTACCGCTAGCCTTAA    5'
``` to a 990 bp HindIII-SphI isolated fragment derived from pPR13 to generate plasmid pPR15 (FIG. 18).

The HindIII-EcoRV digested 2780 bp fragment from pPR15 was treated with Mung bean nuclease, purified from an agarose gel and inserted into plasmid pTP15 (184) (FIG. 3) which had been digested with XmaIII-EcoRV, Mung bean nuclease and CIAP to generate plasmid pPR18 (FIG. 18). In pPR18, PRV gpII is linked with the synthetic vaccinia H6 promoter in the vaccinia hemagglutinin deletion locus. This plasmid was transfected into vaccinia virus infected cells to generate vaccinia recombinants vP534, vP644, v621 and vP692 containing the PRV gpII gene (see below).

The PRV gpIII gene was manipulated to be expressed under the control of the early vaccinia virus promoter, μ, (see below) located in the vaccinia HindIII B fragment. Using site-specific mutagenesis, an NsiI site was introduced by changing the sequence CGC (bases 192–194) (FIG. 21) in PRV gpIII to ATG and an XbaI site was introduced by changing the sequence GTGACGT to TTCTAGA (bases 1632–1638) (FIG. 21). To do this single stranded DNA was generated from plasmid pPR17 using a helper phage R408 (Stratagene, La Jolla, Calif.) (185). The site directed mutagenesis was performed using two purified phosphorylated synthetic oligonucleotides MRSYN5 and MRSYN6.

and selection on E. coli dut⁻ ung⁻ strain CJ236 (IBI, New Haven, Conn.) (17,186).

These mutations generated plasmid pPR28. Plasmid pPR28 was digested with NsiI and XbaI and treated with Mung bean nuclease. A 1440 bp fragment was purified from an agarose gel and inserted into the BglII-HpaI sites of pSD478VC (FIGS. 20,24) after treatment with Mung bean nuclease and CIAP. Plasmid pPR24 was transfected into vaccinia virus infected cells to generate vaccinia virus recombinants vP604, vP644, vP691 and vP692 containing the PRV gpIII gene (see below).

PRV gp50 was manipulated to be expressed under the control of an early/intermediate vaccinia virus promoter, I3L (187). Using site-specific mutagenesis, an NsiI site was introduced by changing the sequence, CCTGCCAGCGC (bases 177–187) (FIG. 23) in gp50 to ATGCATTTAAT and a BglII site was introduced by changing the sequence CCTCCGCAGTACCGG at bases 1404–1418 (FIG. 23) to AATTTTTATAGATCT. Previously described procedures (17,185,186) of mutagenesis were employed to generate plasmid pPR29 from pPR22 using purified, phosphorylated synthetic oligonucleotides MRSYN12 and MRSYN13 (FIG. 22).

```
                     NsiI
MRSYN12  5'GGTTCCCATACACTCAATGCATTTAATCATGCTGCTCGCAGCGC         3'
                     BglII
MRSYN13  5'GCAGCCCGGTCCGTAGAATTTTTATAGATCTCGTCGATGATGATGGT       3'
``` pPR29 was digested with NsiI, treated with Mung bean nuclease and partially digested with BglII to generate a 1290 bp fragment. Plasmid pMP13PP (FIGS. 22,25) was digested with EcoRI, treated with Mung bean nuclease and then with BamHI to generate a 140 bp fragment containing the vaccinia I3L promoter. The 1290 and 140 bp fragments were purified from agarose gels and ligated into the phosphatased BglII site of pMP409DVC (FIGS. 4,22). The resulting plasmid, pPR26, was used in recombination to produce vaccinia virus recombinants vP591, vP621, vP691 and vP692 containing the gp50 gene (see below).

Construction of vaccinia recombants epressing PRV glycoproteins gpII, gpIII and gp50 individually or in combinations.

In order to assess the immunogenicity and relative contribution of the three PRV glycoproteins (gpII, gpIII and gp50) to protection of immunized animals against virulent PRV challenge, a series of vaccinia recombinants were constructed expressing the three PRV glycoproteins alone or in combination.

```
              ClaI                    HpaI
22mer  5' CGATTACTATGAAGGATCCGTT    3'
20mer  3'    TAATGATACTTCCTAGGCAA   5'
```

Figure 24:
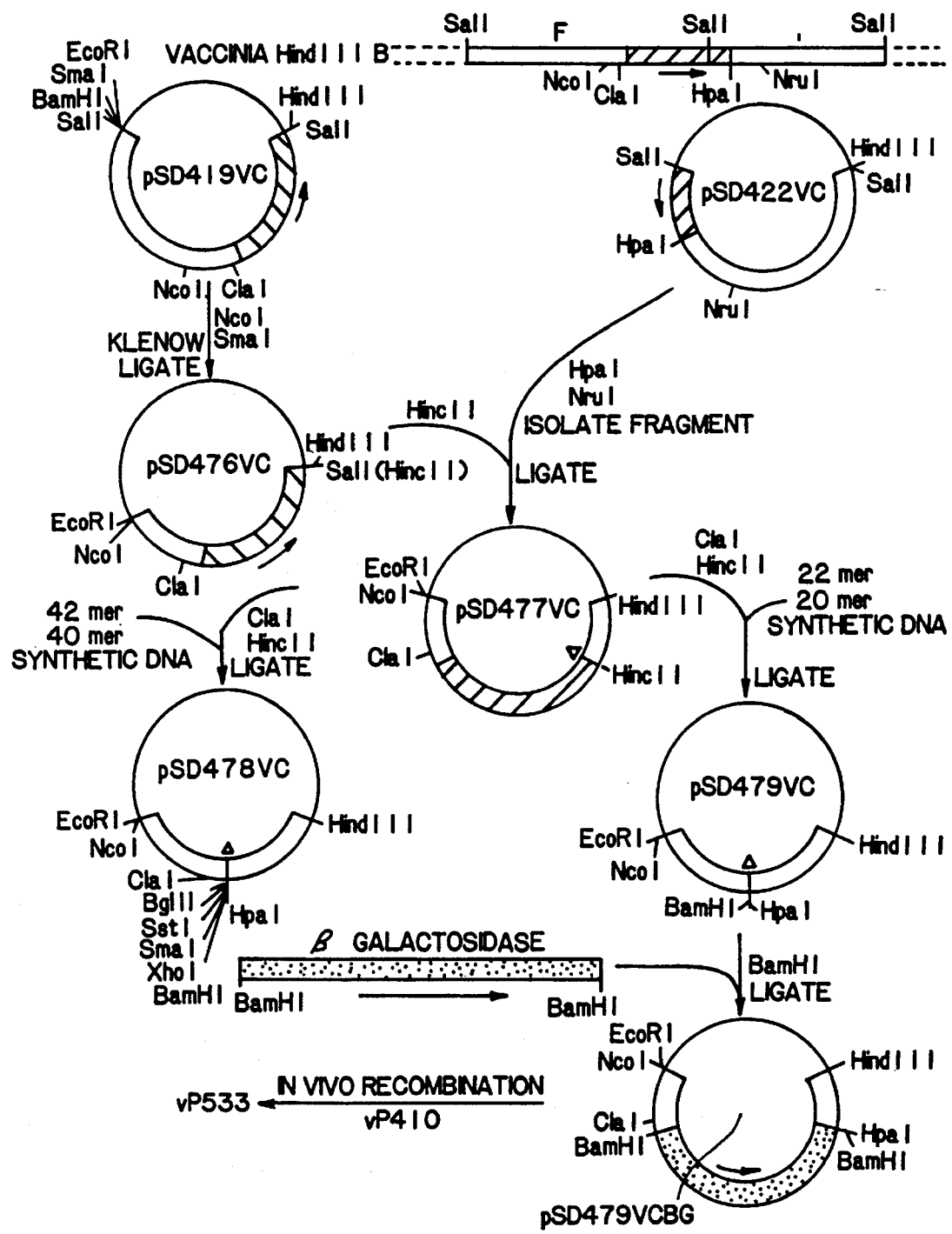
FIG. 24 schematically shows a method for the construction of plasmid pSD478VC, and pSD479VCBG and insertion of Beta-galactoside into vaccinia virus.

The annealed 22mer/20mer mixture was ligated into pSD477VC digested with ClaI and HincII resulting in the novel plasmid pSD479VC (FIG. 24). A 3.1 Kb BamHI fragment containing the E. coli Beta-galactosidase coding sequences from pMC1871 (34) devoid of initiation codon and promoter was ligated into pSD479VC cut with BamI. The resulting plasmid containing the lacZ gene in the proper orientation under the control of the Copenhagen μ promoter was designated pSD479VCBG. This insertion donor plasmid was recombined into vaccinia virus vP410 (184). A recombinant vaccinia virus was identified on the basis of blue plaque formation in the presence of the chromogenic substrate, X-gal (9,24), plaque cloned and designated vP533 (FIG. 24).

To construct a vector plasmid for the insertion of foreign genes, synthetic oligonucleotides 42mer/40mer were prepared.

```
              ClaI     BglII   SacI    SmaI   XhoI   BamHI  HpaI
42mer  5'  CGATTACTAGATCTGAGCTCCCCGGGCTCGAGGGGATCCGTT    3'
40mer  3'     TAATGATCTAGACTCGAGGGGCCCGAGCTCCCCTAGGCAA   5'
```

Referring now to FIG. 24, recombinant vaccinia virus, vP533, expressing the Beta-galactosidase gene was constructed as follows: A 1 Kb region within vaccinia HindIII fragment B spanning the SalI F/I junction of the Copenhagen genome contains DNA homology with the hemorrhagic (μ) gene of cowpox virus (188) as determined by Southern blot analysis (189). The μ gene encodes a polypeptide with similarity to serine protease inhibitors and biologically is responsible for hemorrhagic pock formation by virus on the chorioallantoic membrane. The DNA sequence of the Copenhagen genome revealed that the μ gene equivalent contained multiple frameshift mutations and was biologically non-functional. Plasmid pSD419VC (184) (FIG. 24) contains the left portion of the μ region. Plasmid pSD422VC, which contains the Copenhagen SalI fragment I cloned into pUC8, contains the remainder of the μ region. To remove unwanted vaccinia sequences to the left, pSD419VC was digested with NcoI and SmaI, blunt-ended with the Klenow fragment of E. coli polymerase and religated resulting in plasmid pSD476VC (FIG. 24). Plasmid pSD422VC was digested with HpaI and NruI and an approximately 0.3 Kb fragment located immediately to the right of the μ region was isolated from an agarose gel. This fragment was ligated into pSD476VC cut with HincII (which recognizes SalI sites) resulting in plasmid pSD477VC. To express Beta-galactosidase under the control of the Copenhagen vaccinia μ promoter region, synthetic oligonucleotides 22mer/20mer were prepared. The sequence of 22mer/20mer with restriction sites indicated and ATG initiation codon underlined is as follows:

The annealed 42mer/40mer mixture was ligated into pSD477VC cut with ClaI and HincII resulting in the novel plasmid pSD478VC (FIG. 24). This plasmid contains approximately 0.3 Kb of vaccinia sequences on each side of the multicloning region which completely replaces the μ coding region of the Copenhagen strain of vaccinia. pSD478VC was used to generate pPR24 (FIG. 20) containing PRV gpIII coding sequences and vaccinia recombinants vP604, vP644, vP691 and vP692.

Figure 25:
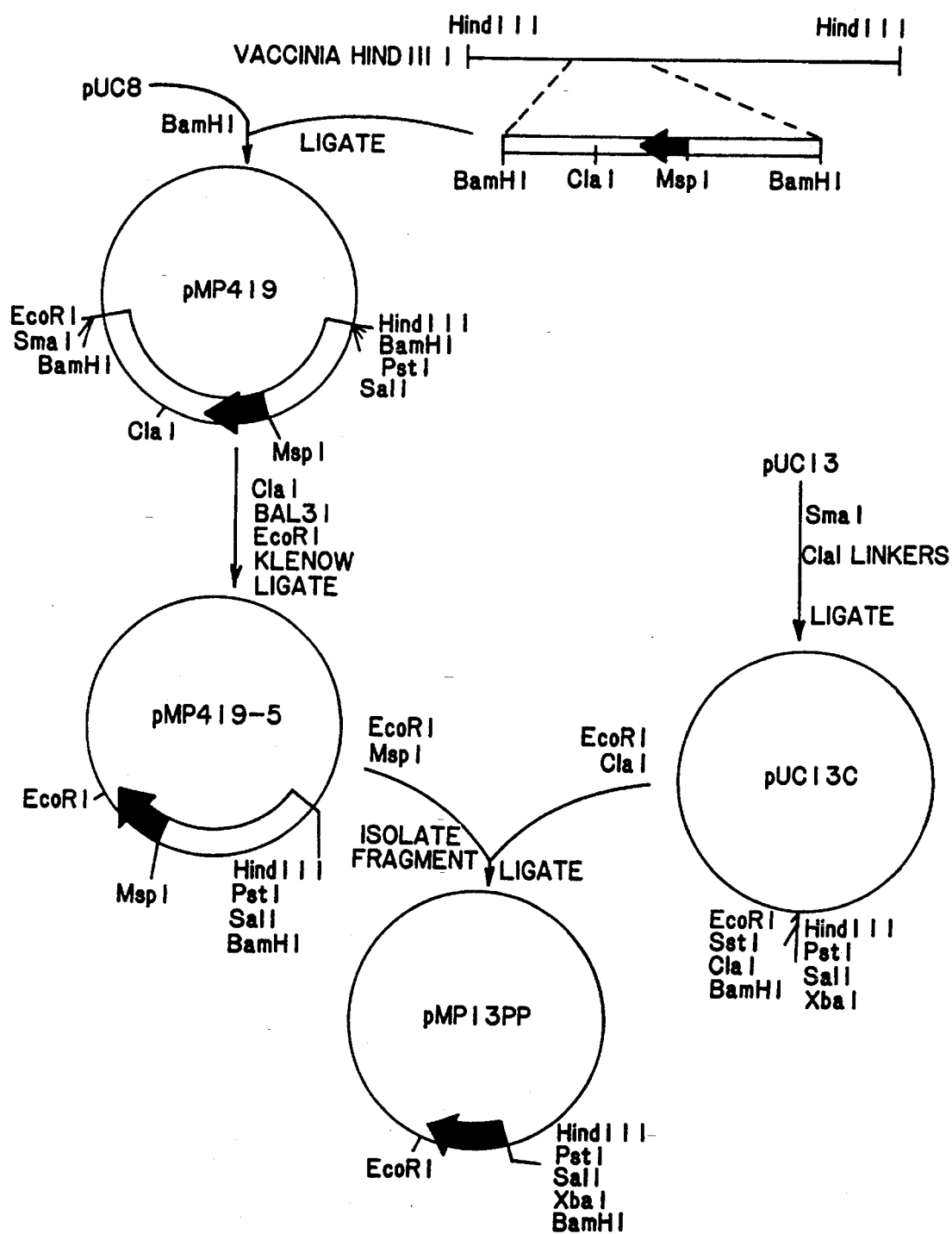
FIG. 25 schematically shows a method for the construction of plasmid pMP13PP.
Figure 26:
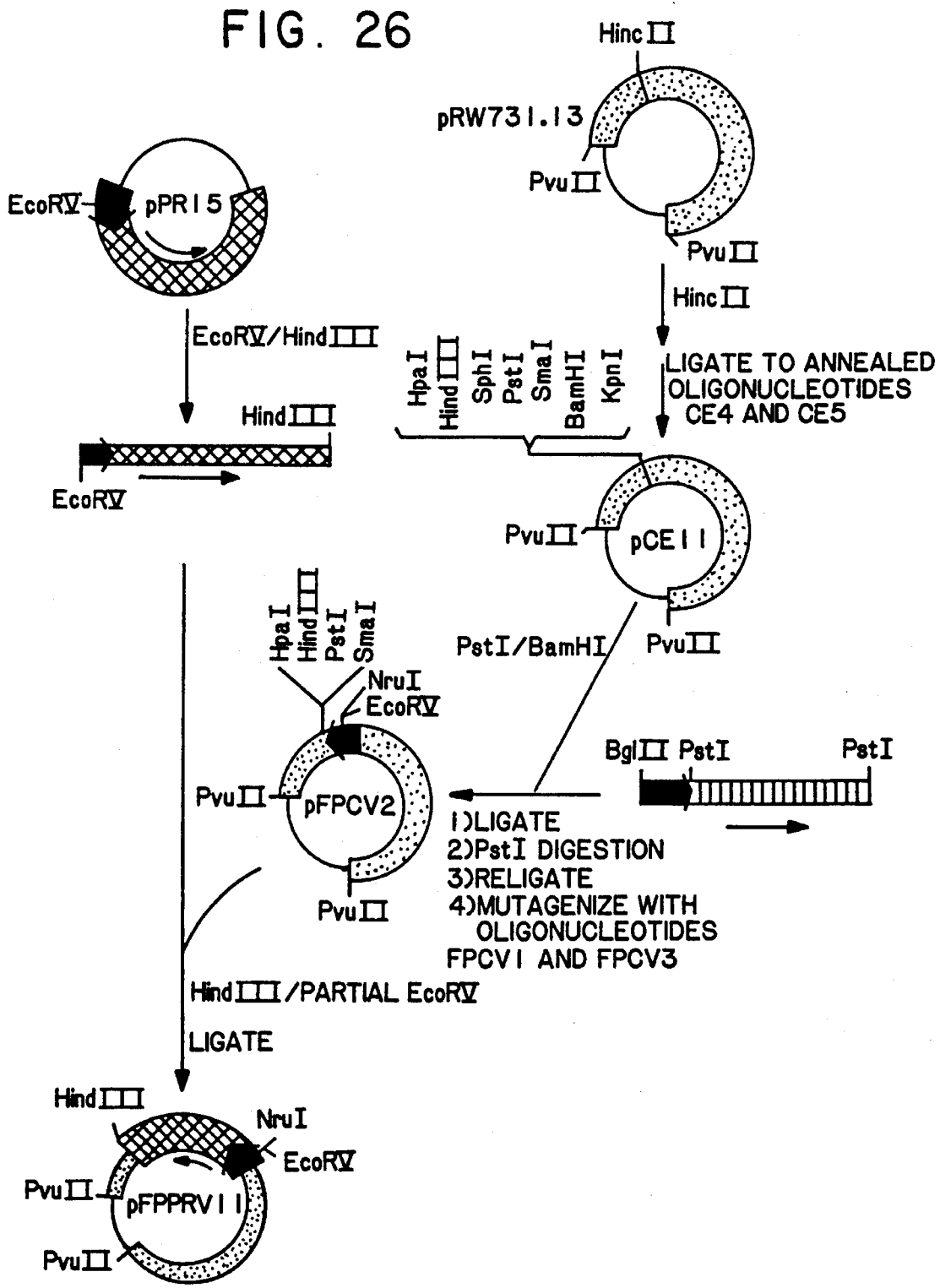
FIG. 26 schematically shows a method for the construction of plasmid pFPPRVII containing the PRV gpII gene.
Figure 27:
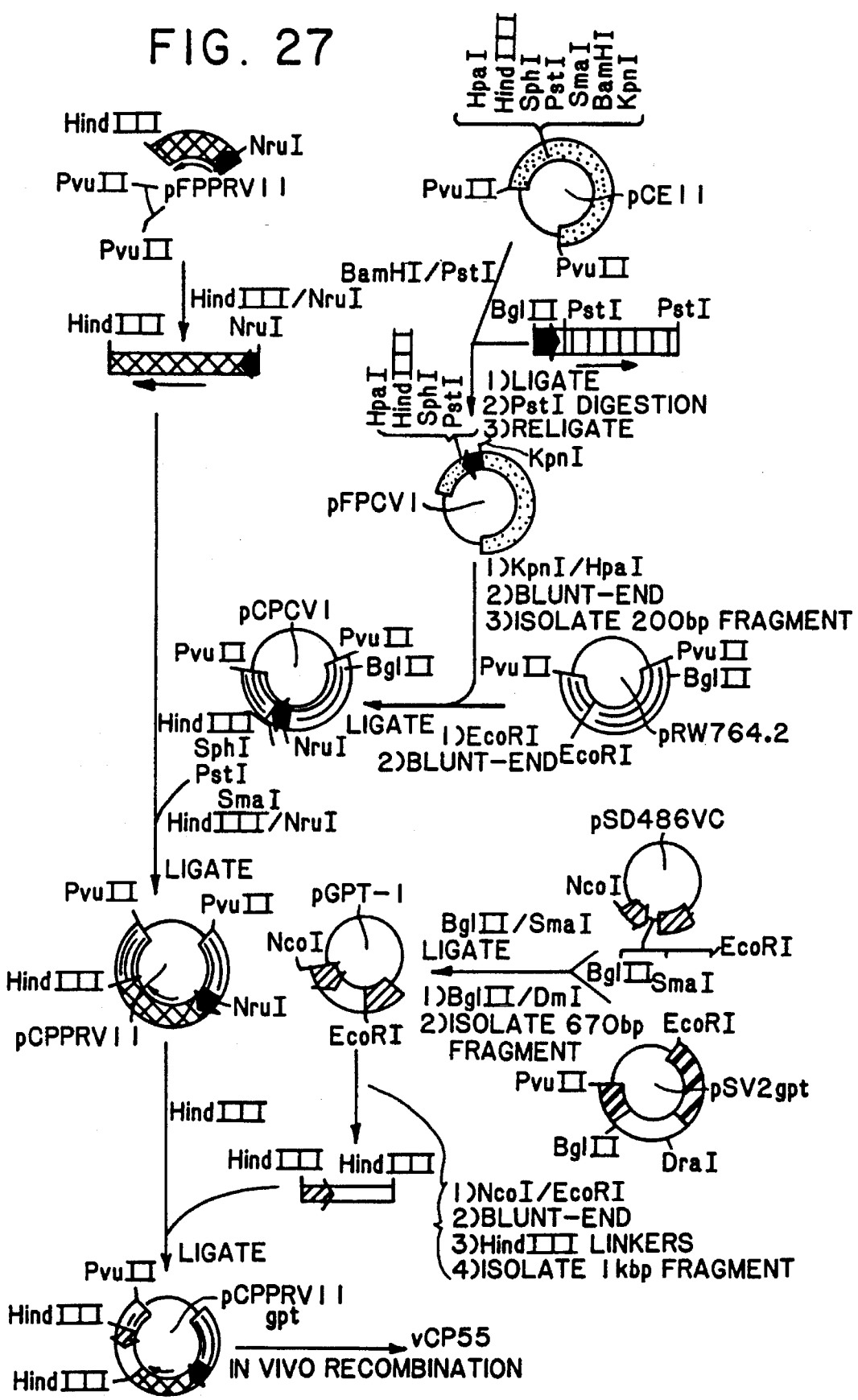
FIG. 27 schematically shows a method for the construction of the recombinant canarypox virus vCP55 expressing the PRV gpII gene.

Referring now to FIG. 25, plasmid pMP419 contains an 850 bp BamHI fragment from vaccinia HindIII fragment I containing the I3L promoter inserted into the BamHI site of pUC8 (FIG. 25). The I3L promoter element corresponds to DNA sequences upstream of the I3L open reading frame in the vaccinia HindIII fragment I (187) and has been used previously to express foreign genes in vaccinia virus recombinants (27,190). pMP419 was linearized at the unique ClaI site within I3L coding sequences and subjected to Bal 31 digestion followed by digestion with EcoRI and bluntending by treatment with the Klenow fragment of E. coli polymerase. The resulting plasmid, pMP419-5, (FIG. 25) contains the I3L promoter sequences upstream of nucleotide −8 linked to an EcoRI site. The promoter element was isolated as an EcoRI-MspI fragment from pMP419-5 and inserted into ECORI-ClaI digested pUC13C, a pUC13 derivative containing a ClaI linker at the SmaI site. The resulting plasmid, pMP13PP, (FIGS. 22,25) contains the I3L promoter sequences from position −126 through position −8 followed by an EcoRI site at position −8.

PRV gp50 driven by the vaccinia I3L promoter was inserted into the M2L deletion plasmid vector pMP409DVC (FIG. 4) resulting in pPR26 (FIG. 22). pPR26 was used to generate vaccinia recombinants vP591, vP621 and vP691 and vP692.

Isolation of recombinant vaccinia viruses.

Recombinant vaccinia viruses containing the PRV genes were identified and purified as described above. Recombinant vaccinia viruses expressing the three PRV glycoproteins gpII, gpIII, and gp50 alone or in combination are listed in Table 7.

TABLE 7

Designation of vaccinia virus recombinants expressing PRV glycoproteins gpII, gpIII and gp50.

| Recombinant | Parent | Donor Plasmid | PRV Glycoproteins |
| --- | --- | --- | --- |
| vP534 | vP425 | pPR18 | gII |
| vP591 | vP458 | pPR26 | gp50 |
| vP604 | vP533 | pPR24 | GIII |
| vP621 | vPS34 | pPR26 | gII + gp50 |
| vP644 | vP604 | pPR18 | gII + gIII |
| vP691 | vP604 | pPR26 | gIII + gp50 |
| vP692 | vP644 | pPR26 | gII + gIII + gp50 |

In vitro evaluation of the PRV glycoproteins expressed by vaccinia virus recombinants.

The PRV glycoproteins gpII, gpIII and gp50 are typical glycoproteins associated with the membranous structure of PRV infected cells and are additionally components of the virus. Anti-gpII, anti-gpIII and anti-gp50 specific monoclonal antibodies followed by fluorescein conjugated goat anti-mouse IgG gave a strong surface immunofluorescence on cells infected with the recombinant vaccinia viruses but not in wildtype vaccinia virus infected cells.

In vivo evaluation of the immunogenic potential of PRV glycoproteins gpII, gpIII and gp50 expressed by vaccinia virus recombinants in mice and swine.

In order to assess the relative immunogenicity of the three PRV glycoproteins expressed by vaccinia virus recombinants, mice were inoculated in the footpad with 50 to 100 ul of different doses of the recombinant viruses. Fourteen days after the immunization the mice were challenged with 10 $LD_{50}$ of the virulent Kojnock strain of PRV by the intraperitoneal route. In preliminary experiments each of the PRV glycoproteins were shown to be efficacious in protecting inoculated mice against a virulent PRV challenge. In a more extended series of experiments utilizing over 500 mice, the efficacy of vaccinia recombinants expressing PRV glycoproteins was assessed. The vaccination dose able to protect 50% of the challenged mice ($PD_{50}$) was calculated and the results of these studies are shown in Table 8. Recombinant vaccinia virus expressing individually PRV glycoproteins gpII, gp50 and gpIII generate calculated $PD_{50}$ values of 6.4, 5.4 and 5.8 ($log_{10}$), respectively. When the glycoproteins are expressed in combination significantly better $PD_{50}$ values are calculated. The vaccinia recombinant expressing PRV gpII plus gp50 generated a PDso value of 3.3, whereas the vaccinia recombinant expressing PRV gp50 plus gpIII results in an essentially similar $PD_{50}$ value (3.6). Apparently more efficacious is the recombinant expressing PRV glycoproteins gpII plus gpIII where a $PD_{50}$ of 1.5 is obtained. Coexpression of all three PRV glycoproteins gpII, gpIII and gp50 in a recombinant vaccinia virus does not provide a $PD_{50}$ value significantly lower than those obtained with the recombinant viruses expressing the three PRV glycoproteins individually. The potentiated efficacy obtained with the vaccinia recombinant expressing gpII and gpIII compared to vaccinia recombinant virus expressing the genes individually is similar to the results reported in Example 6 for the coexpression of equine herpesvirus glycoproteins gp13 and gp14.

TABLE 8

Potency of vaccinia virus recombinants expressing pseudorabies virus glycoproteins gp50, gpII and gpIII.

| Recombinant Virus | PRV genes expressed | $PD_{50}$ |
| --- | --- | --- |
| vP534 | gpII | 6.4 |
| vP591 | gp50 | 5.4 |
| vP604 | gpIII | 5.8 |
| vP621 | gpII + gp50 | 3.3 |
| vP644 | gpII + gpIII | 1.5 |
| vP691 | gp50 + gpIII | 3.6 |
| vP692 | gp50 + gpII + gpIII | 5.1 |

Although the mouse can provide an interesting model system for evaluation of PRV glycoprotein immunogenicity, the major target species of a PRV vaccine is swine. Therefore, in order to assess the validity of the recombinant vaccinia virus approach in swine the following experiment was performed. Piglets of approximately 25 kg were inoculated intramuscularly with 2 ml of the vaccinia recombinants expressing combinations of the PRV glycoproteins gpII, gpIII and gp50. Virus inoculum was diluted in PBS. Thirty five days after this inoculation, the piglets were challenged by an intranasal injection (1 ml into each nostril) of a virulent PRV isolate NIA3 suspension. The effectiveness of vaccination was evaluated by measuring comparative weight gain of vaccinated and control piglets for seven days after challenge. Relative weight gain is calculated as the daily mean percentage weight gain observed in vaccinated pigs minus the daily mean percentage weight gain of unvaccinated control pigs. Normal weight gain of pigs in unperturbed conditions is greater than 1.1 kg. As demonstrated by the data in Table 9, weight evolution during the seven day period after PRV challenge is greatly enhanced in the vaccinated piglets over the wildtype virus inoculated control set. A single inoculation with the vaccinia virus recombinants gives significant protection against weight loss after virulent PRV challenge.

TABLE 9

Evaluation of vaccinia recombinants expressing combinations of PRV-glycoproteins gp50, gpII and gpIII in piglets.

| Inoculum Virus | PRV Genes Expressed | Vaccinating Dose $log_{10}$ $TCID_{50}$/ml | Relative Weight Gain |
| --- | --- | --- | --- |
| vP452 | None | $10^{7.7}$ | −0.31 |
| vP621 | gpII + gp50 | $10^{7.7}$ | 2.89 |
| vP644 | gpII + gpIII | $10^{7.7}$ | 2.15 |
| vP691 | gp50 + gpIII | $10^{7.3}$ | 1.21 |
| vP692 | gP50 + gpII + gpIII | $10^{7.3}$ | 2.67 |

The availability of vaccinia virus recombinants expressing the three dominant PRV glycoproteins individually or in combination offer a number of advantages to the control of PRV infections in the field: (a) one significant advantage is that the recombinant vaccinia viruses as vaccinating agents express only a limited number of PRV genes and, therefore, there is no attendant risk of reversion of an attenuated PRV vaccine strain to a virulent form and, therefore, there is no continued introduction of PRV virus into the environment; (b) since only a limited number of PRV antigens are expressed by the vaccinia virus recombinant PRV vaccine candidates, this allows the discrimination of vaccinated versus naturally infected animals since diagnostic reagents consisting of other PRV antigens could be assembled to discriminate between vaccinated and naturally infected animals; and (c) such recombinant vaccines could be useful in disrupting the natural vertical transmission of PRV from sow to offspring. This could be accomplished by the vaccination of the pregnant sow by a vaccinia virus recombinant expressing a discrete set of PRV glycoproteins. Maternal immunity should protect the offspring from PRV infection. In turn, the offspring then could be vaccinated with a vaccinia virus recombinant expressing yet a different configuration of PRV antigens distinct from those used to vaccinate the sow. This is one potential way to break through maternal immunity. Another approach to address the issue of maternal immunity would be to express the PRV glycoproteins in whatever combination in a completely heterologous vector. This is achieved by the construction of avipox virus recombinants expressing PRV glycoproteins. The utility of avipox virus recombinants whose natural host range is restricted to avian species, in the vaccination of non-avian species has been demonstrated (41). Thus, two approaches are available for addressing the issue of the barrier provided by maternal immunity: (1) the vectors and (2) the constellation of the antigens expressed by those vectors.

EXAMPLE 11

AVIPOX VECTORS EXPRESSING THE PSEUDORABIES VIRUS GLYCOPROTEIN gpII

Canarypoxvirus was propagated on primary chick embryo fibroblasts (CEF) derived from 10 to 11 day old embryonated eggs obtained from SPAFAS, Inc. (Norwich, Conn.) using conditions described previously (41,42). Virus was purified from host cell contaminants by sucrose gradient centrifugation using the method described by Joklik (191). Pig kidney (PK-1) cells were obtained from American Type Culture Collection, Rockville, Md. (ATCC #CL101).

Construction of a canarypoxvirus recombinant expressing the pseudorabies virus gpII glycoprotein.

Referring now to FIG. 26, the plasmid pPR15 (FIG. 18) was utilized as the source of the PRVgpII gene. To isolate the DNA segment containing the entire PRVgpII gene, pPR15 was digested with EcoRV and HindIII. A fragment of approximately 2.8 Kb containing 21 bp of the 3' end of the vaccinia virus (VV) H6 promoter and the entire PRVgpII gene was generated by this digestion. The 2.8 Kb EcoRV/HindIII fragment was isolated for insertion in pFPCV2 (FIGS. 8,26).

The 2.8 Kb EcoRV/HindIII fragment (defined above) was inserted into the 8.0 Kb pFPCV2 fragment derived by complete digest with HindIII and partial digestion with EcoRV. Ligation of these two fragments resulted in the formation of a 10.8 Kb plasmid designated as pFPPRVII.

Referring now to FIG. 27, plasmid pFPPRVII was utilized to generate a 2.8 Kb NruI/HindIII fragment for insertion into pCPCV1 (FIG. 9). The pCPCV1 plasmid contains the W H6 promoter in the unique ECoRI site within the 3.3 Kb PvuII CP genomic fragment. This insertion plasmid enables the insertion of foreign genes into the C3 locus of the CP genome. The plasmid pCPCV1 was digested with NruI and HindIII and the 5.8 Kb fragment was isolated for ligation to the 2.8 Kb fragment defined above. The resultant plasmid was designated pCPPRVII.

The dominant selectable marker *E. coli* xanthine-guanine phosphoribosyl transferase (Eco gpt) was inserted into pCPPRVII as a means of growth selection for CP/PRVgpII recombinants. Previous reports have described the use of Eco gpt as a selectable marker in the generation of poxvirus recombinants (193,194). The Eco gpt gene was obtained from the plasmid pSV2gpt (ATCC #37145). The 670 bp BglII/DraI fragment, containing the Eco gpt gene, was isolated from this plasmid and inserted into the BglII/SmaI site of pSD486VC. The resulting plasmid, pGPT-1, contains the Eco gpt gene between the VV μ gene flanking arms and under the transcriptional regulation of the μ promoter. The plasmid pSD486VC was derived from pSD478VC (FIG. 24) in the following manner. pSD478VC was digested with EcoRI in the MCR, filled in by Klenow standard reaction in the presence of dNTP (0.5 mM each) and religated to produce pSD478E$^-$ VC. This plasmid was digested with HDaI and BamHI and annealed oligonucleotide HEM 5 (5'-GATCCGATTCTAGCT-3') and HEM 6 (5' -AGCTAGAATCG-3') were inserted to produce pSD486VC.

Digestion of pGPT-1 with NcoI and EcoRI liberated a 1.0 Kb fragment containing the Eco gpt gene (670 bp) and the VV μ promoter (330 bp). The NCOI and EcoRI ends were blunted using the Klenow fragment from the *E. coli* DNA polymerase in the presence of 0.5 mM dNTPs. HindIII linkers (Bethesda Research Laboratories, Bethesda, Md.) were added to the blunt-ended fragment. The DNA was digested with HindIII and the 1.0 Kb fragment recovered from an agarose gel. This 1.0 Kb HindIII fragment was then inserted into the HindIII site of pCPPRVII. The resultant plasmid containing the Eco gpt and PRVgpII genes linked in a tail to tail configuration was designated as pCPPRVII gpt. This plasmid was used in in vitro recombination experiments for insertion into the C3 locus of the CP genome. Selection of recombinants containing the Eco gpt gene were done in the presence of 100 μg/ml mycophenolic acid and the Eco gpt-positive recombinants were subsequently screened for the presence of the PRVgpII gene by plaque hybridization analyses. Eco gpt and PRV gpII positive plaques were purified by three cycles of plaque isolation and pure populations grown to high titer and designated as pCP55. Southern blot analyses confirmed that these two genes were indeed genetically linked in these CP recombinants. The CP recombinant was designated as vCP55.

Immunofluorescence of vCP55 infected cells.

Immunofluorescence studies were performed to demonstrate the cellular localization of the expressed PRV gpII in vCP55 infected cells. CEF or PK-1 cells were seeded on 22 mm glass coverslips in 35 mm dishes at $5\times10^5$ cells/dish. CEF and PK-1 cells were infected with either vCP55 or the CP parental virus. Infections and incubations for the immunofluorescence assay were performed as described in Example 1, using monoclonal antibody 75N10, diluted 1 to 100 in PBS+.

The infected cells were analyzed for both internal and surface expression. No significant surface expression of gpII was observed in either cell system infected with vCP55. Internal expression of the gpII gene product was, however, demonstrated in both vCP55 infected CEF cells and PK-1 cells. The internal fluorescence signals in both cell types were localized to granules in the perinuclear region of the infected cells. These results suggest that the PRVgpII expressed by CP is trafficked to the golgi complex but not to the plasma membrane. This result differs from the results with vaccinia virus expressed gpII which was detected on the surface of infected cells.

Immunoprecipitation of PRVgpII from CEF and PK-1 infected cells.

Expression of the PRVgpII gene product by vCP55 was analyzed by immunoprecipitation from infected cell lysates. Cell monolayers were infected at 5 PFU/cell. The immunoprecipitation assay was performed as described in Example 1.

The predominant polypeptide species precipitated with rabbit anti-PRV serum from CEF and PK-1 infected cells migrated with apparent molecular weights of approximately 120 kDa, 67 kDa, and 58 kDa. These polypeptides represent the precursor and proteolytically processed forms, respectively, of the PRVgpII detected in PRV infected cells that are complexed via disulfide linkages (86,101,196). Minor species with apparent molecular weights of approximately 26 kDa were also observed and may reflect further proteolytic processing events of gpII in these CP/PRV recombinant infected cells. No equivalent polypeptides were precipitated from control CP virus infected cell and uninfected cell lysates.

Protection studies.

The ability for vCP55 to elicit a protective immune response against live PRV challenge was analyzed in the mouse system. Mice were inoculated in the footpad with 50 ul to 100 ul samples containing various doses of vCP55 shown in Table 10. Fourteen days following immunization the mice received 16 LD50 of the Kojnock strain of PRV by the intraperitoneal route. Survivors were counted 14 days after challenge at which point the experiment was concluded. As demonstrated in Table 10, inoculation of mice with a single dose of $10^{6.85}$ TCID$_{50}$ protected eight out of ten mice from a lethal challenge of PRV. The lower doses of VCP55 tested did not afford any level of protection. Challenge with live PRV killed seven out of eight unvaccinated mice. From the results presented in Table 10, a PD$_{50}$ (protective dose 50%) was calculated to be $10^{6.16}$ for the vCP55 recombinant.

The efficacy of vCP55 as an immunizing agent against live PRV challenge was also evaluated in the target species, the piglet. Fifteen piglets weighing nearly 25 kg were separated into three groups. The vCP55 group and the CP parental virus group each received two inoculations (2 ml equaling $2\times10^8$ TCID$_{50}$) on days 0 and 28 by the intramuscular route. Five piglets were left as unvaccinated controls. All piglets were administered the pathogenic NIA3 strain of PRV by the intranasal route on day 35. Efficacy was monitored by comparing the weight evolution of vCP55 vaccinated and control pigs during the seven days post challenge. Weight evolution is calculated as Delta GMQR Values (in kilograms)=mean GMQR % vaccinated piglets–mean GMQR % unvaccinated piglets.

In the unvaccinated group, all piglets succumbed to the PRV virus challenge (two on day five, two on day six, and one on day seven). In the wildtype virus (CP) inoculated groups four of the five piglets succumbed to challenge (three on day six, one on day seven). All the piglets in the vCP55 vaccinated group survived PRV challenge and thrived.

Significant levels of protection for piglets inoculated with vCP55 expressing the PRVgpII glycoprotein against live PRV challenge was observed (Table 11). vCP55 vaccinated animals had a significant net weight gain over the experimental period, whereas the two control groups had a significant weight loss over the period following PRV challenge. Additionally, no deaths were observed in the vCP55 vaccinated group, while an 80% to 100% mortality rate was noted in the control groups following live PRV challenge.

TABLE 10

Efficacy of vCP55 in mice.

| Dose log$_{10}$ TCID$_{50}$ | Protection |
|---|---|
| 6.85 | 8/10 |
| 4.85 | 0/10 |
| 2.80 | 0/10 |
| 0.85 | 0/10 |

TABLE 11

Protection of vaccinated (cCP55) piglets from PRV challenge as determined by death and weight gain.

| Treatment | Mortality | Weight Gain |
|---|---|---|
| Unvaccinated | 5/5 | −2.12 |
| Wildtype (CP) | 4/5 | +0.61 |
| Recombinant (vCP55) | 0/5 | +2.51 |

EXAMPLE 12

VACCINIA RECOMBINANTS EXPRESSING PRV gI GLYCOPROTEINS

The Copenhagen strain of vaccinia virus and recombinants derived therefrom were utilized in this example.

Cloning of the PRVgI gene into canary pox and vaccinia virus donor plasmids.

Figure 28A:
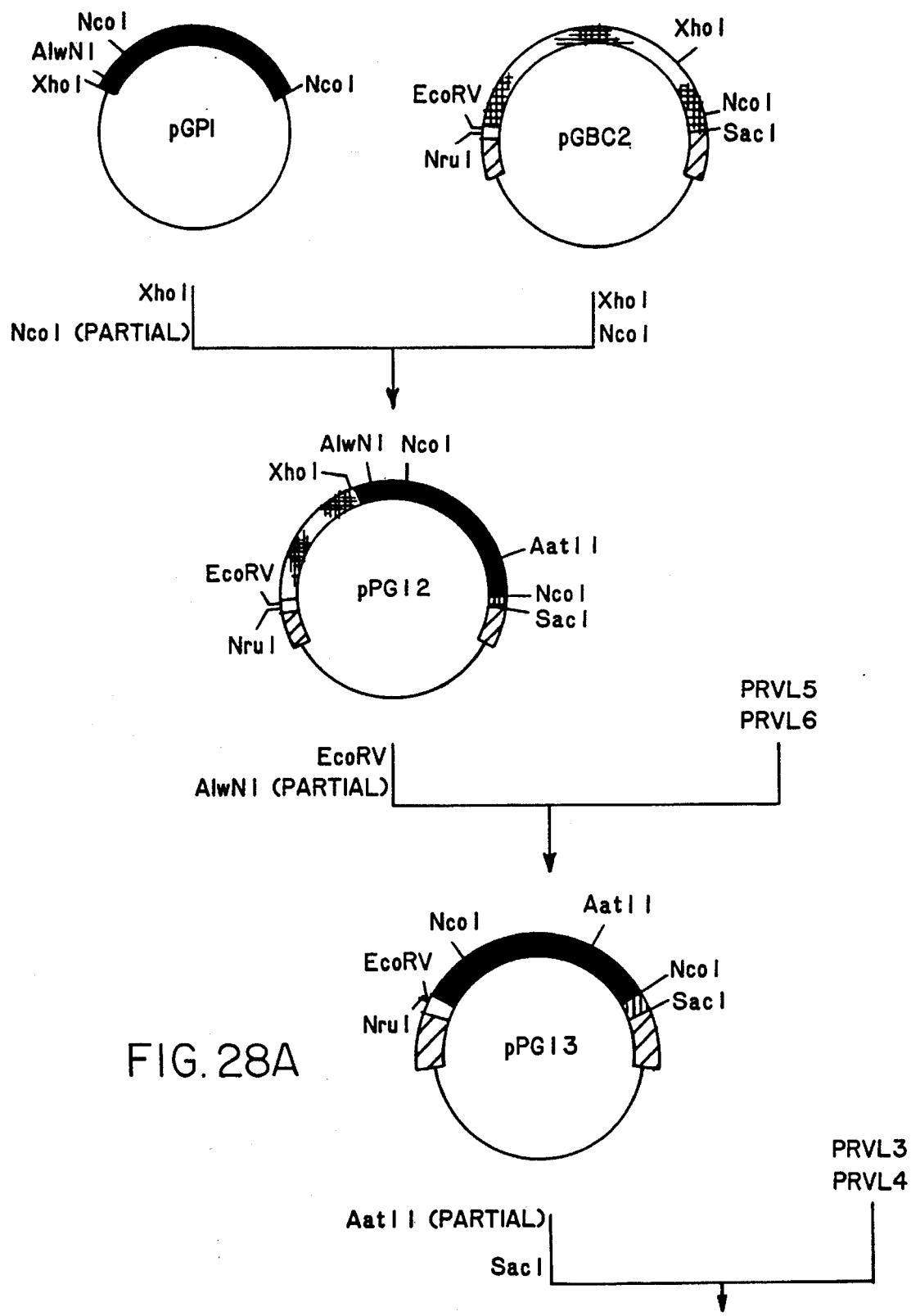
FIG. 28 schematically shows a method for the construction of the recombinant vaccinia virus vP717 expressing the PRV gI gene.
Figure 28B:
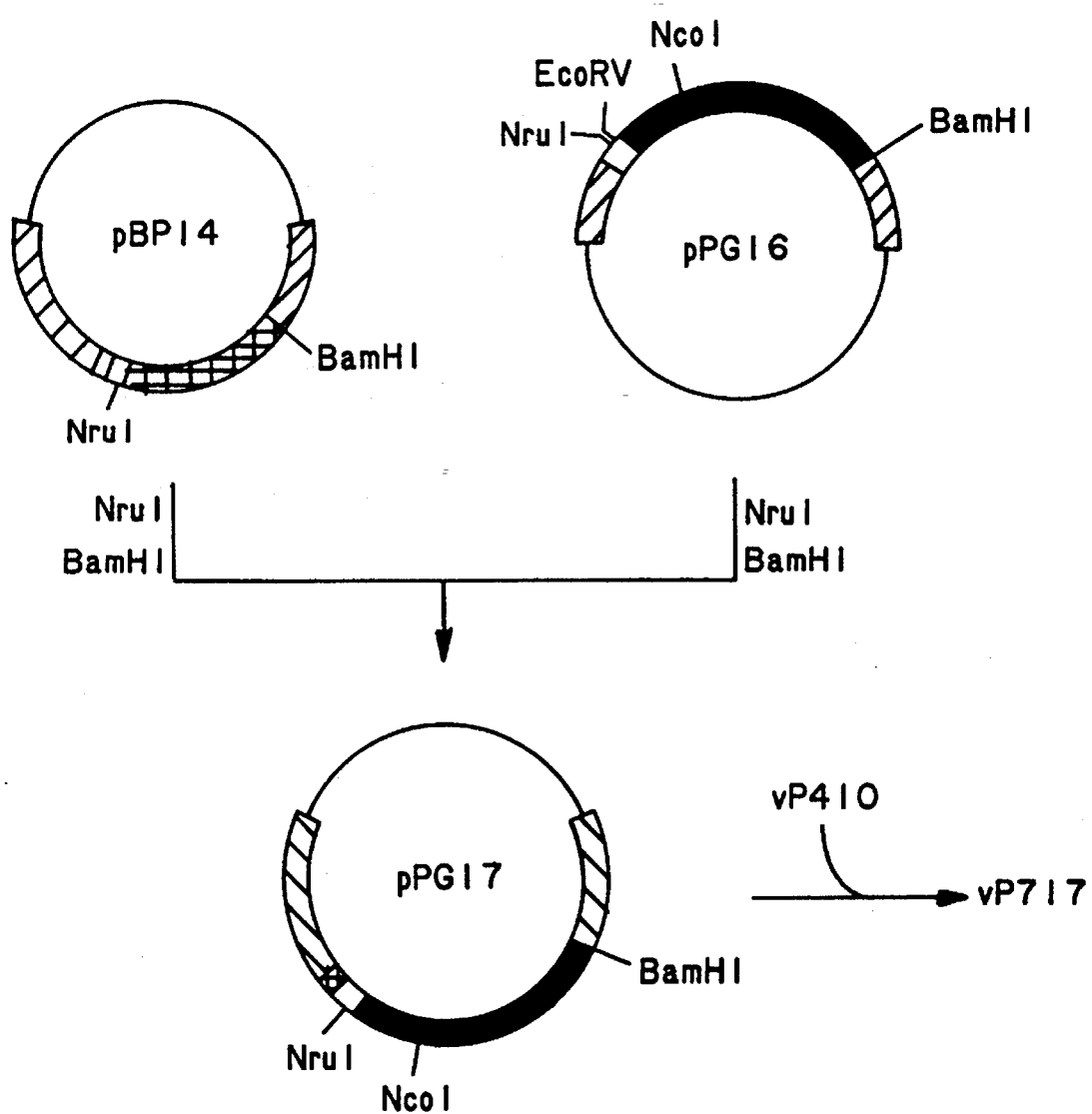

Referring now to FIG. 28, a plasmid pGPI containing the PRVgI gene (NIA3 strain) was obtained from Rhone Merieux, Lyon, France. The gI gene (sequence reference (80)) was isolated from this plasmid and cloned downstream of the vaccinia synthetic H6 promoter (69). This was accomplished by cloning the 2,330 bp XhoI-NcoI (partial) fragment of pGPI into the 6,400 bp XhoI-NcoI fragment of pGBC2. (pGBC2 was generated by cloning the HSV2 gB gene into the 3,200 bp BglII fragment of pRW764.5. pRW764.5 was constructed by cloning a 0.8 Kb pvuII fragment from canarypox DNA into the 2,360 bp pvuII fragment of pUC18.) The plasmid generated by this manipulation is designated pPGI2.

The initiation codon of the H6 promoter was then aligned with the initiation codon of the gI gene. This was accomplished by cloning the oligonucleotides, PRVL5 5' -ATC- CGTTAAGTTTGTATCGTAATGCGGC- CCTTTCTGCTGCGCGCCGCGCAGCTC-3' and PRVL6 5'-CTGCGCGGCGCGCAGCAGAAAGGGCCG- CATTACGATACAAACTTAACGGAT-3', into the 5,900 bp EcoRV-AlwNI (partial) fragment of pPGI2. The plasmid generated by this manipulation is designated pPGI3.

Extraneous PRV gI 3'-noncoding sequences were then eliminated. This was accomplished by cloning the oligonucleotides, PRVL3 5'-CTGGTTCCGCGATCCG- GAGAAACCGGAAGTGACGA ATGGGCCCAACTATG- GCGTGACCGCCAGCCGCCTGTTGAATGCCCGCCCC- GCTTAACTGCAG AATTCGGATCCGAGCT-3' and PRVL4 5'-CGGATCCGAATTCTGCAGTTAAGCGGGGC GGGCATTCAACAGGCGGCTGGCGGT- CACGCCATAGTTGGGCCCATTCGTCACT- TCCGGTTTC TCCGGATCGCGGAACCAGACGT-3', into the 5,200 bp SacI-AatII (partial) fragment of pPGI3. The plasmid generated by this manipulation is designated pPGI6.

The H6 promoted gI gene was then cloned into a vaccinia virus donor plasmid. This was accomplished by cloning the 1,750 bp NruI-BamHI fragment of pPGI6 into the 5,000 bp NruI-BamHI fragment of pBP14. (pBP14 contains the Bovine leukemia virus gag gene under the control of the synthetic vaccinia H6 promoter in vaccinia vector plasmid pSD494VC. pSD494VC is a subclone of the Copenhagen vaccinia virus HindIII A fragment in which the coding sequence of the vaccinia gene containing homology to the cowpox ATI gene (210) is replaced by a polylinker region.) This places the H6 promoted gI gene between the vaccinia virus (Copenhagen) sequences flanking the ATI gene. The plasmid generated by this manipulation is designated pPGI7.

The recombinant vaccinia virus vP717 was generated by transfecting pPGI7 into vP410 infected cells.

Construction of vP717.

The gI gene of PRV was cloned into a vaccinia virus vector. The strategy used to construct this vaccinia virus recombinant, vP717, is outlined in FIG. 28. The PRVgI gene contained in vP717 is cloned between the vaccinia virus sequences flanking the ATI gene and utilizes the vaccinia virus early-late promoter, H6 (41,42,69).

Immunofluorescence of the PRV-encoded polypeptide on vP717 infected cells.

In PRV infected cells, gI is expressed on the plasma membrane. Immunofluorescence analyses of vP717 infected cells with the PRV gI-specific monoclonal antibody, 42M17, indicate that the PRV encoded polypeptide produced in these cells is also expressed on the plasma membrane.

Evaluation of vP717 in mice.

In vivo evaluation of vP717 in mice indicated some protection against PRV challenge (Table 12) using standard procedures.

TABLE 12

Evaluation of vaccinia virus recombinant vP717 expressing PRV gpI in mice.

| vP717 Inoculation Dose $\log_{10}$ $TCID_{50}$ | Survival Against PRV Challenge |
|---|---|
| 7.3 | 4/10 |
| 5.3 | 5/10 |
| 3.3 | 0/10 |
| 1.3 | 2/10 |

EXAMPLE 13

EXPRESSION OF HERPES SIMPLEX VIRUS TYPE 2 GLYCOPROTEINS gB, gC AND gD IN VACCINIA VIRUS RECOMBINANTS EITHER INDIVIDUALLY OR IN COMBINATIONS

HSV2 (strain G) (American Type Culture Collection, Bethesda, Md.) (ATCC #VR734) utilized in this example was propagated in VERO cells (ATCC #CCL81) and purified by centrifugation on a sucrose gradient (197).

Cloning of the HSV2 gB gene into vaccinia virus donor plasmids.

The nucleotide sequence of the HSV2 gB gene has been previously published (116). Referring now to FIG. 29, a 12 Kb BglII fragment containing the HSV2 gB gene was isolated from HSV2 (strain G) genomic DNA and inserted into the BamHI site of pUC19 generating the plasmid pJ4.

The gB gene was then cloned between vaccinia virus (Copenhagen) flanking arms. This was accomplished by cloning the 2,700 bp SstII-SacI (partial) fragment of pJ4 into the SstII-SacI fragment of pMP409DVC3. (pMP409DVC3 is a derivative of pMP409DVC (FIG. 4) in which the BglII site is replaced by a polylinker region). This places the gB gene between the vaccinia sequences flanking the M2L gene. The plasmid generated by this manipulation is designated pGB1.

An in-frame termination codon was then added to the 3' end of the gB gene. This was accomplished by cloning the oligonucleotides GBL3 5'-CTAATAG-3' and GBL4 5'-GATCCTATTAGAGCT-3' into the 6,300 bp DamHI-SacI (partial) fragment of pGB1. The plasmid generated by this manipulation is designated pGB2.

The H6 promoter was then cloned upstream of the gB gene. This was accomplished by cloning the 370 bp BglII fragment of pBLVH14 containing the H6 promoter into the BglII site of pGB2 (pBLVH14 contains the H6 promoted bovine leukemia virus envelope gene in the vaccinia HA deletion locus). The plasmid generated by this manipulation is designated pGB3.

The initiation codon of the H6 promoter was then aligned with the initiation codon of the gB gene. This was accomplished by cloning the oligonucleotides, GBL1 5'-ATCCGT-TAAGTTTGTATCGTAATGCGCGGGGGGG-GCTTGATTTGCGCGCTGGTCGTGGGGGCGCT GGTGGCCGC-3' and GBL2 5'-GGCCACCAGCGC-CCCCACGACCAGCGCGCAAATCA AGC-CCCCCCCGCGCATTACGATACAAACTTAACGGAT-3, into the 6,300 bp SstII-EcoRV (partial) fragment of pGB3. The plasmid generated by this manipulation is designated pGB5. In plasmid pGB5 the HSV gB gene is under the control of the vaccinia H6 promoter inserted into the M2L deletion locus of vaccinia. Since the M2L insertion locus is located within a larger region of the genome which can be deleted, the H6-promoted gB gene was cloned into a different insertion site in a different vaccinia virus donor plasmid. This was accomplished by cloning the 2,800 bp BglII-BamHI fragment of pGB5 into the BglII site of pSD513VCVQ. (pSD513VCVQ is a subclone of the Copenhagen vaccinia virus HindIII J fragment in which the coding sequence for the thymidine kinase (TK) gene is replaced by a polylinker region). This places the H6-promoted gB gene between the vaccinia virus sequences flanking the TK gene. The plasmid generated by this manipulation is designated pGB6.

Cloning of the HSV2 gC gene into vaccinia virus donor plasmids.

The nucleotide sequence of the HSV2 gC gene has been previously determined (117). Referring now to FIG. 30, a 2,900 bp SalI fragment containing the HSV2 gC gene was isolated from HSV2 (strain G) genomic DNA and inserted into the SalI site of pIBI25 generating the plasmid pGC3.

The gC gene was then cloned between vaccinia virus (Copenhagen) flanking arms. This was accomplished by cloning the 2,900 bp XhoI-BamHI fragment of pGC3 into the XhoI-BamHI site of pGC2. pGC2 was generated by cloning the 370 bp BglII fragment of pBLVH14, containing the vaccinia virus H6 promoter into the BglII site of pSD486VC. pSD486VC is a subclone of the Copenhagen vaccinia virus HindIII B fragment in which the coding sequence of the μ gene is replaced by a polylinker region. This places the gC gene between the vaccinia virus sequence flanking the μ gene. The plasmid generated by this manipulation is designated pGC5.

The initiation codon of the H6 promoter was then aligned with the initiation codon of the gC gene. This was accomplished by cloning the oligonucleotides, GCL1 5'-ATCCGT-TAAGTTTGTATCGTAATGGCCCTTGGAC- GGGTGGGCCTAGCCGTGGGCCTGTG-3' and GCL2 5'-AGGCCCACGGCTAGGCCCACCCGTCCAAGGGC-CATTACGATACAAACTTAACGGAT-3, into the 5,400 bp NruI-SfiI fragment of pGC5. The plasmid generated by this manipulation is designated pGC10.

Extraneous 3'-noncoding sequence was then eliminated from pGC10. This was accomplished by recircularizing the E. coli DNA polymerase I (Klenow fragment) treated 4,900 bp SalI-SmaI (partial) fragment of pGC10. The plasmid generated by this manipulation is designated pGC11.

Additional 3'-noncoding sequence was then eliminated from pGC11. This was accomplished by cloning the oligonucleotide, GCL3 5'-CTAGGGCC-3', into the 4,900 bp XbaI-ApaI (partial) fragment of pGC11. The plasmid generated by this manipulation is designated pGC12. In plasmid pGC12 the HSV gC gene is under the control of the H6 promoter inserted into the μ deletion locus of vaccinia. Since the μ insertion locus is located within a larger region of the genome which can be deleted, the H6-promoted gC gene was then cloned into the ATI insertion site in a vaccinia virus donor plasmid. This was accomplished by cloning the 1,550 bp NruI-BamHI fragment of pGC12 into the 5,000 bp NruI-DamHI fragment of pBP14. This places the H6-promoted gC gene between the vaccinia virus (Copenhagen) sequences flanking the ATI gene. The plasmid generated by this manipulation is designated pGC13.

Cloning of the HSV2 gD gene into vaccinia virus donor plasmids.

Figures 31, 31A:
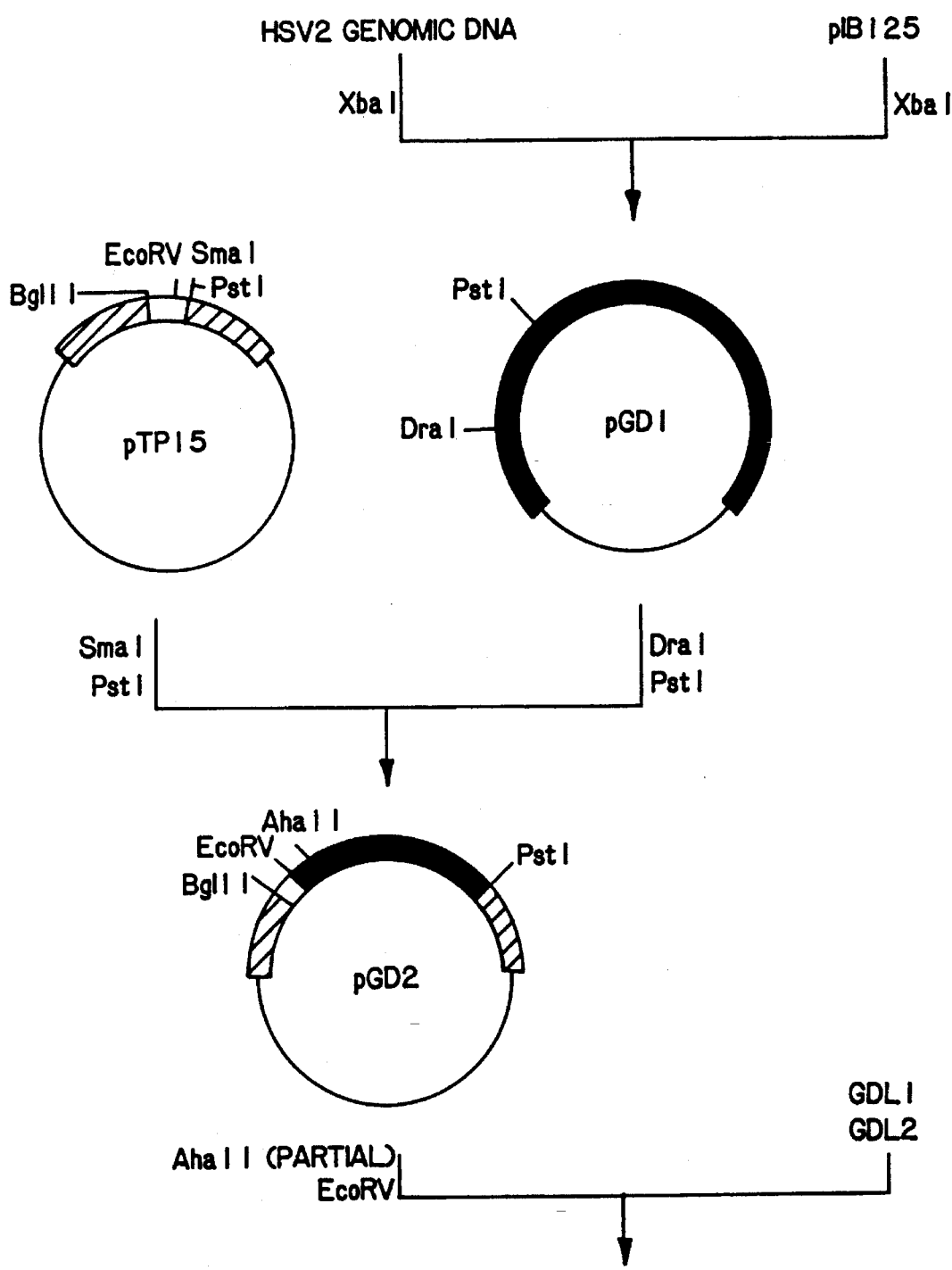
FIG. 31 schematically shows a method for the construction of recombinant vaccinia viruses vP570, vP761, vP775 and vP777 expressing the HSV-2 gD gene.
Figure 31B:
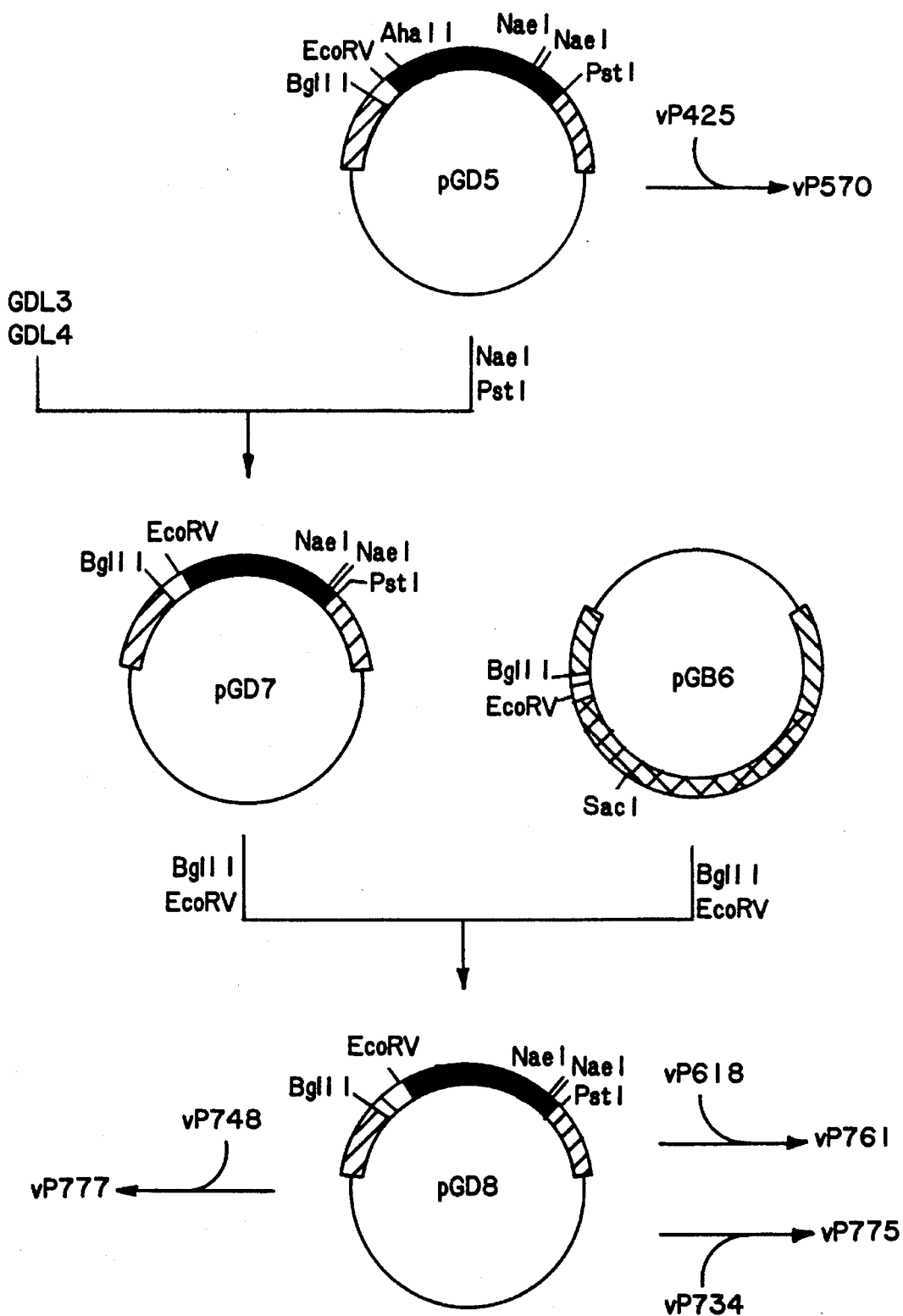

The nucleotide sequence for the HSV2 gD gene has been previously determined (118). Referring now to FIG. 31, a 7.5 Kb XbaI fragment containing the HSV2 gD gene was isolated from HSV2 (strain G) genomic DNA and inserted into the XbaI site of pIBI25 generating the plasmid pGD1.

The gD gene was then cloned downstream of the H6 promoter and between vaccinia virus (Copenhagen) flanking arms. This was accomplished by cloning the 1,500 bp DraI-PstI fragment of pGD1 into the SmaI-pstI site of pTP15 (184) (FIG. 3). This places the gD gene downstream of the H6 promoter and between the vaccinia virus sequences flanking the HA gene. The plasmid generated by this manipulation is designated pGD2.

The initiation codon of the H6 promoter was then aligned with the initiation codon of the gD gene. This was accomplished by cloning the oligonucleotides, GDL1 5'-ATCCGT-TAAGTTTGTATCG-TAATGGGGCGTTTGACCTCCGG-3' and GDL2 5'-CGCCGGAGGTCAAACGCCCCATTAC-GATACAAACTTAACGGAT-3', into the 5,100 bp EcoRV-AhaII (partial) fragment of pGD2. The plasmid generated by this manipulation is designated pGD5.

Extraneous 3'-noncoding sequence was then eliminated. This was accomplished by cloning the oligonucleotides, GDL3 5'-GGCAGTACCCTGGCGGCGCTGGTCATCG-GCGGTATTGCGTTTTGGGTACGCCGCCG-GCGCTCAGT GGCCCCCAAGCGCCTACGTCTC-CCCCACATCCGGGATGACGACGCGCCCCCCTCGCA-CCAGCCATT TGTTTTACTAGCTGCA-3' and GDL4 5'-GCTAGTAAAACAATGGCTGGTGC-GAGGGGGGCGCGTCGTCATCCCGGAT-GTGGGGGAGACGTAGG CGCTTGGGGGCCACT-GAGCGCCGGCGGCGTACCCAAAACGCAATACCGC-CGATGACCAGCGCCGC CAGGGTACTGCC-3', into the 4,800 bp NaeI-PstI fragment of pGD5 The plasmid generated by this manipulation is designated pGD7.

Additional sequence was then added 5' to the H6 promoter. This was accomplished by cloning the 150 bp BglII-EcoRV fragment of pGB6 (FIG. 29) into the 4,800 bp DglII-EcoRV fragment of pGD7. The plasmid generated by this manipulation is designated pGD8.

Construction of recombinant vaccinia viruses.

Figures 29, 29A:
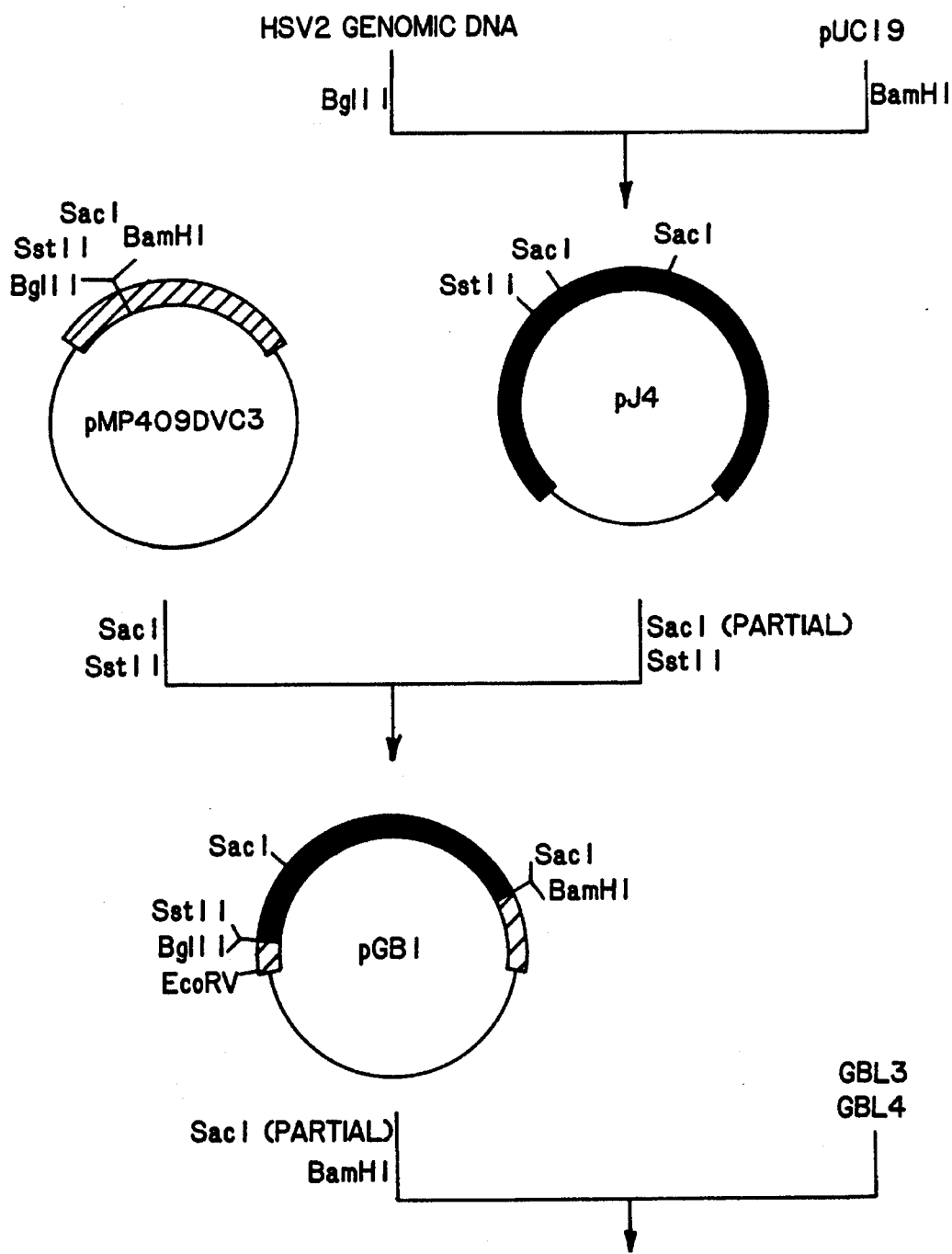
FIG. 29 schematically shows a method for the construction of recombinant vaccinia viruses vP569 and vP734 expressing the HSV-2 gB gene.
Figure 29B:
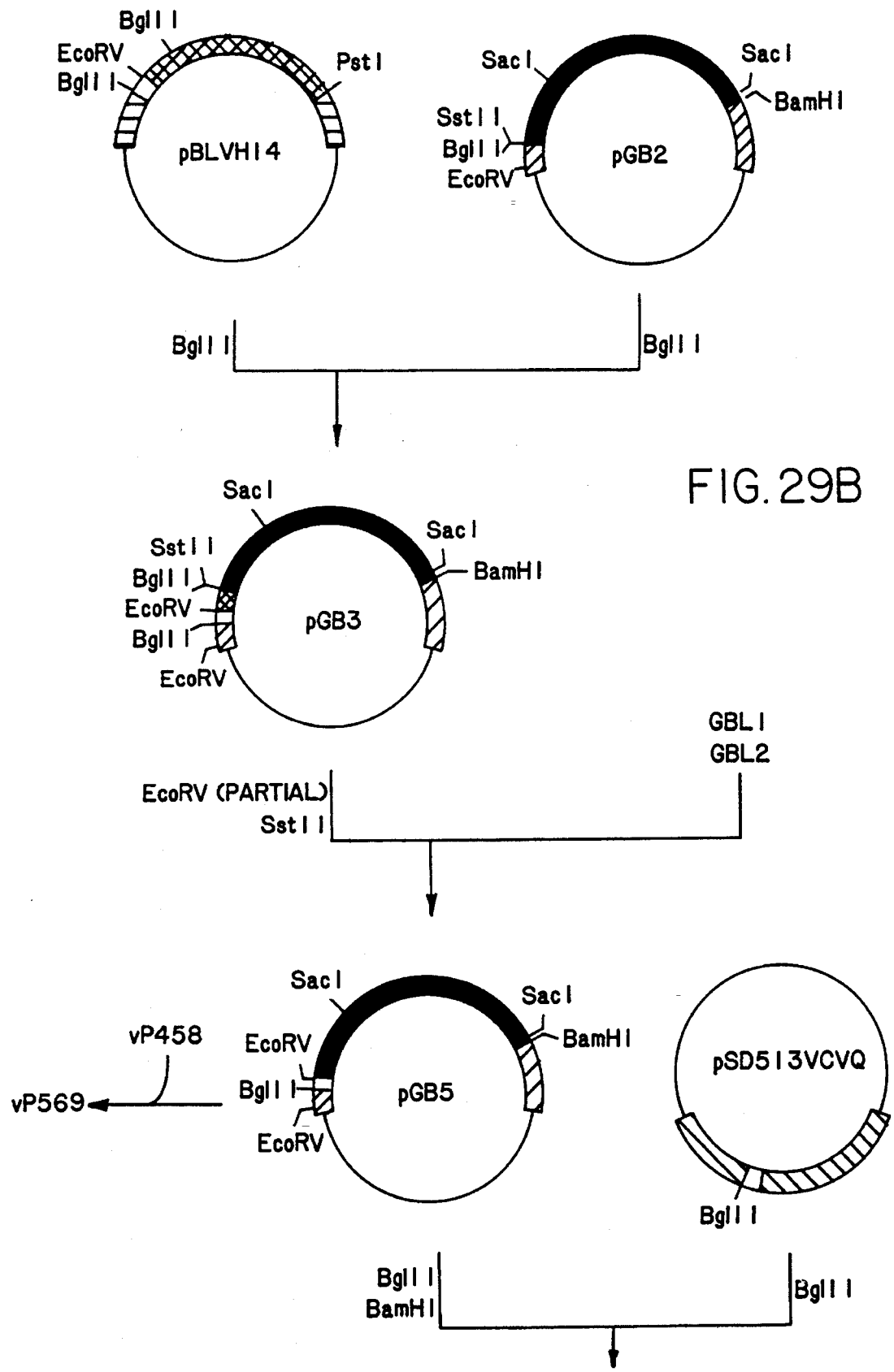
Figure 30B:
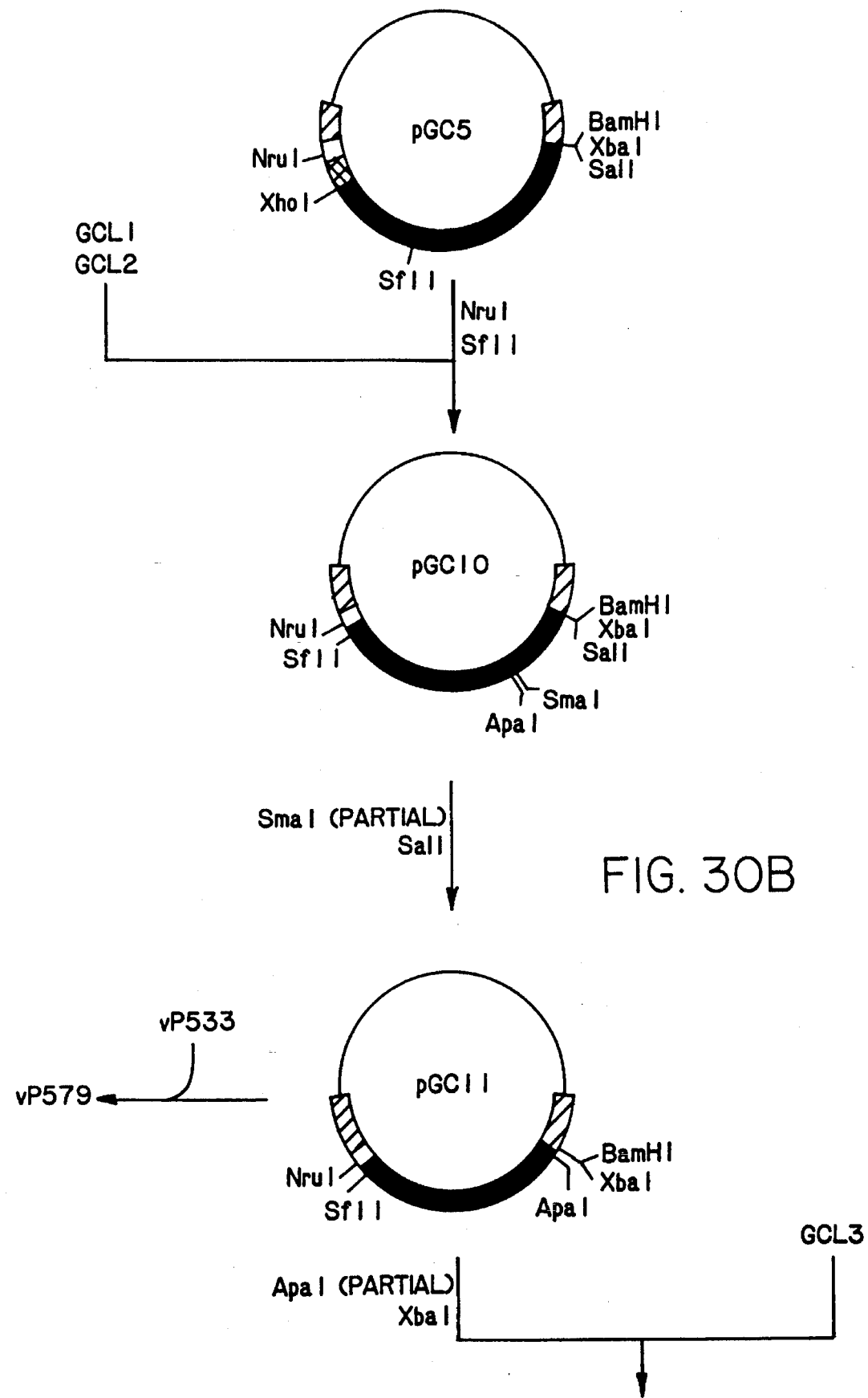
FIG. 30 schematically shows a method for the construction of recombinant vaccinia viruses vP579, vP748 and vP776 expressing the HSV-2 gC gene.
Figure 30C:
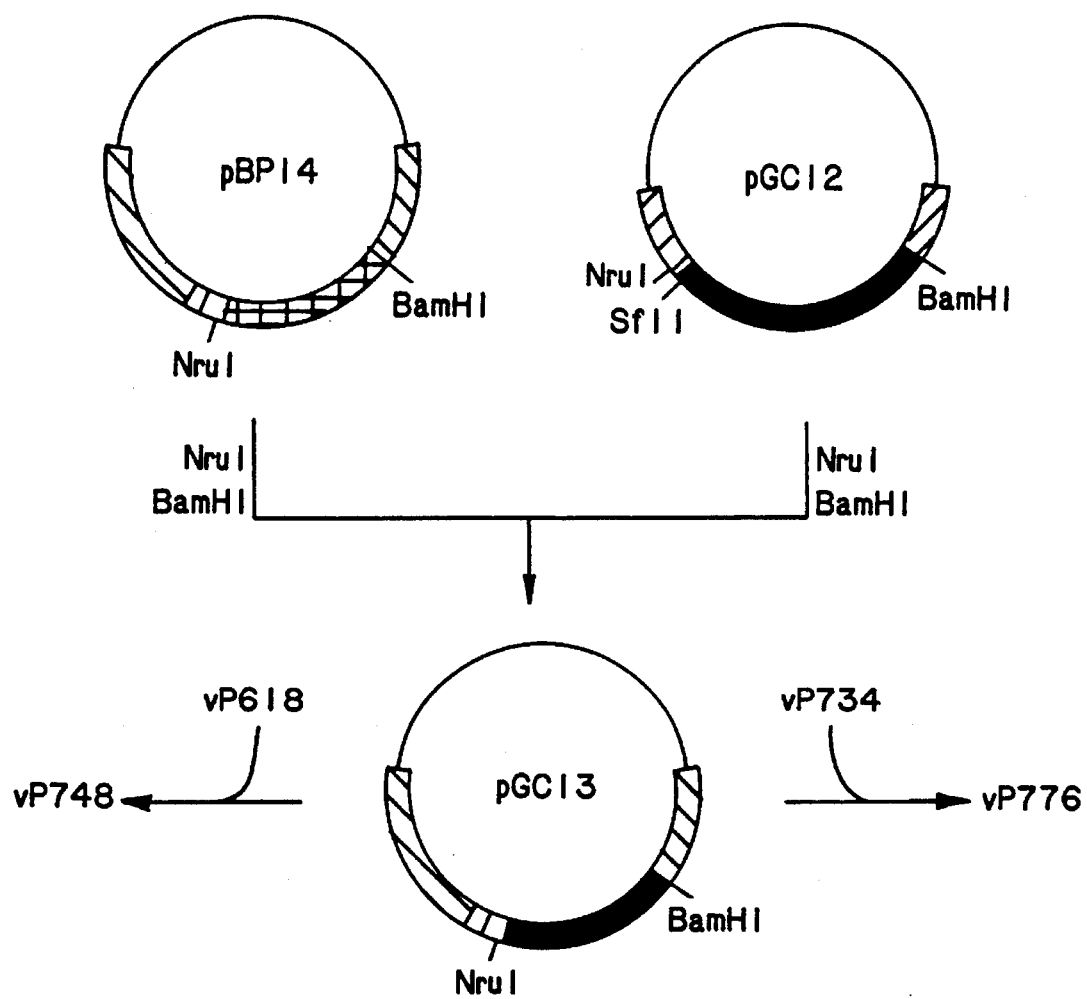

The strategy used to clone the HSV2 gB, gC and gD genes into vaccinia virus is outlined in FIGS. 29, 30 and 31, respectively. All constructs utilize the vaccinia virus early-late promoter, H6 (41,42,184). Each HSV2 gene, however, is cloned into a different site in the vaccinia virus genome. The H6-promoted gB gene is cloned between the sequence flanking the M2L gene (vP569) or the sequence flanking the TK gene (vP734, vP775 and vP776). The H6promoted gC gene is cloned between the sequence flanking the μ gene (vP579) or the sequence flanking the ATI gene (vP748, vP776 and vP777). The H6-promoted gD gene is cloned between the sequence flanking the HA gene (vP570, vP761, vP775, and vP777). The recombinant vaccinia virus vP569 was generated by transfecting pGB5 into vP458 infected cells. vP734 was generated by transfecting pGB6 into vP618 infected cells. vP579 was generated by transfecting pGC11 into vP533 infected cells. vP748 was generated by transfecting pGC13 into vP618 infected cells. vP570 was generated by transfecting pGD5 into vP425 infected cells. vP761 was generated by transfecting pGD8 into vP618 infected cells.

vP425 is a variant of wildtype vaccinia virus (Copenhagen) from which the TK gene has been deleted and the HA gene has been replaced by Beta-galactosidase (Example 1) (184). vP458 is a variant of wildtype vaccinia virus from which the TK gene has been deleted and the M2L gene has been replaced by Beta-galactosidase (Example 2). vP533 is a variant of wildtype vaccinia virus from which the TK gene has been deleted and the μ gene has been replaced by Beta-galactosidase. vP618 is a variant of wildtype vaccinia virus from which the TK, μ and ATI genes have been deleted.

Recombinant vaccinia virus containing two HSV2 glycoprotein genes were also constructed. vP775 contains the gB and gD genes, vP776 contains the gB and gC genes and vP777 contains the gC and gD genes. vP775 was generated by transfecting pGD8 into vP734 infected cells. vP776 was generated by transfecting pGC13 into vP734 infected cells. vP777 was generated by transfecting pGD8 into vP748 infected cells.

A recombinant vaccinia virus containing three HSV2 glycoprotein genes was also constructed. vP812 contains the gB, gC and gD genes of HSV-2. vP812 was generated by transfecting pGD8 into vP776 infected cells.

Immunofluorescence of HSV2 glycoproteins in recombinant vaccinia virus infected cells.

In HSV2 infected cells, gB, gC and gD (as well as other HSV2 encoded glycoproteins) are expressed on the plasma membrane. Immunofluorescence studies performed on cells infected with the recombinant vaccinia viruses containing HSV2 genes indicate that the HSV2 polypeptides produced in cells infected with these recombinant vaccinia viruses are also expressed on the plasma membrane.

Immunoprecipitation of HSV2 glycoproteins in recombinant vaccinia virus infected cells.

The HSV2 gB glycoprotein produced in HSV2 infected cells has a molecular weight of approximately 117 kDa (198,199). Cells infected with recombinant vaccinia viruses containing the HSV2 gB gene (vP569, vP734, vP775 and vP776) also produce a HSV2 encoded polypeptide with a molecular weight of approximately 117 kDa. Immunoprecipitation of vP569 infected cells with antisera to whole HSV2 virus precipitates two major proteins with molecular weights of approximately 117 kDa and 110 kDa and three minor proteins with molecular weights of 50 kDa, 45 kDa and 30 kDa. Immunoprecipitation of vP734, vP775 and vP776 infected cells precipitates two major proteins with molecular weights of approximately 110 kDa and 90 kDa and five minor proteins with molecular weights of approximately 117 kDa, 100 kDa, 50 kDa, 45 kDa and 30 kDa.

The HSV2 gC glycoprotein produced in HSV2 infected cells has a molecular weight of approximately 63 kDa (199,200). Cells infected with recombinant vaccinia viruses containing the HSV2 gC gene (vP579, vP748, vP776 and vP777) also produce a HSV2 encoded polypeptide with a molecular weight of approximately 63 kDa. Immunoprecipitation of vP579, vP748, vP776 and vP777 infected cells with antisera to whole HSV2 virus precipitates a major protein with a molecular weight of approximately 65 kDa and a minor protein with a molecular weight of approximately 85 kDa. Rabbit antisera against whole HSV2 virus was obtained from DAKO Corporation (Santa Barbara, Calif.; code no. B116) and used at a dilution of 1:100.

The HSV2 gD glycoprotein produced in HSV2 infected cells has a molecular weight of approximately 51 kDa (198,199). Cells infected with recombinant vaccinia viruses containing the HSV2 gD gene (vP570, vP761, vP775 and vP777) also produce a HSV2 encoded polypeptide with a molecular weight of approximately 51 kDa. Immunoprecipitation of vP570, vP761, vP775 and vP777 infected cells with antisera to whole HSV2 virus precipitates a major protein with a molecular weight of approximately 48 kDa and two minor proteins with molecular weights of approximately 40 kDa and 31 kDa.

In vivo evaluation.

All the recombinant vaccinia viruses expressing the various constructions of HSV2 glycoproteins protected immunized mice from subsequent lethal HSV challenge in experiments similar to those described by Paoletti et al. (26).

EXAMPLE 14

EXPRESSION OF THE BOVINE HERPES VIRUS 1 GLYCOPROTEIN gI IN VACCINIA VIRUS RECOMBINANTS

Cloning of the BHV1 gI gene into vaccinia virus donor plasmids.

Figures 32, 32A:
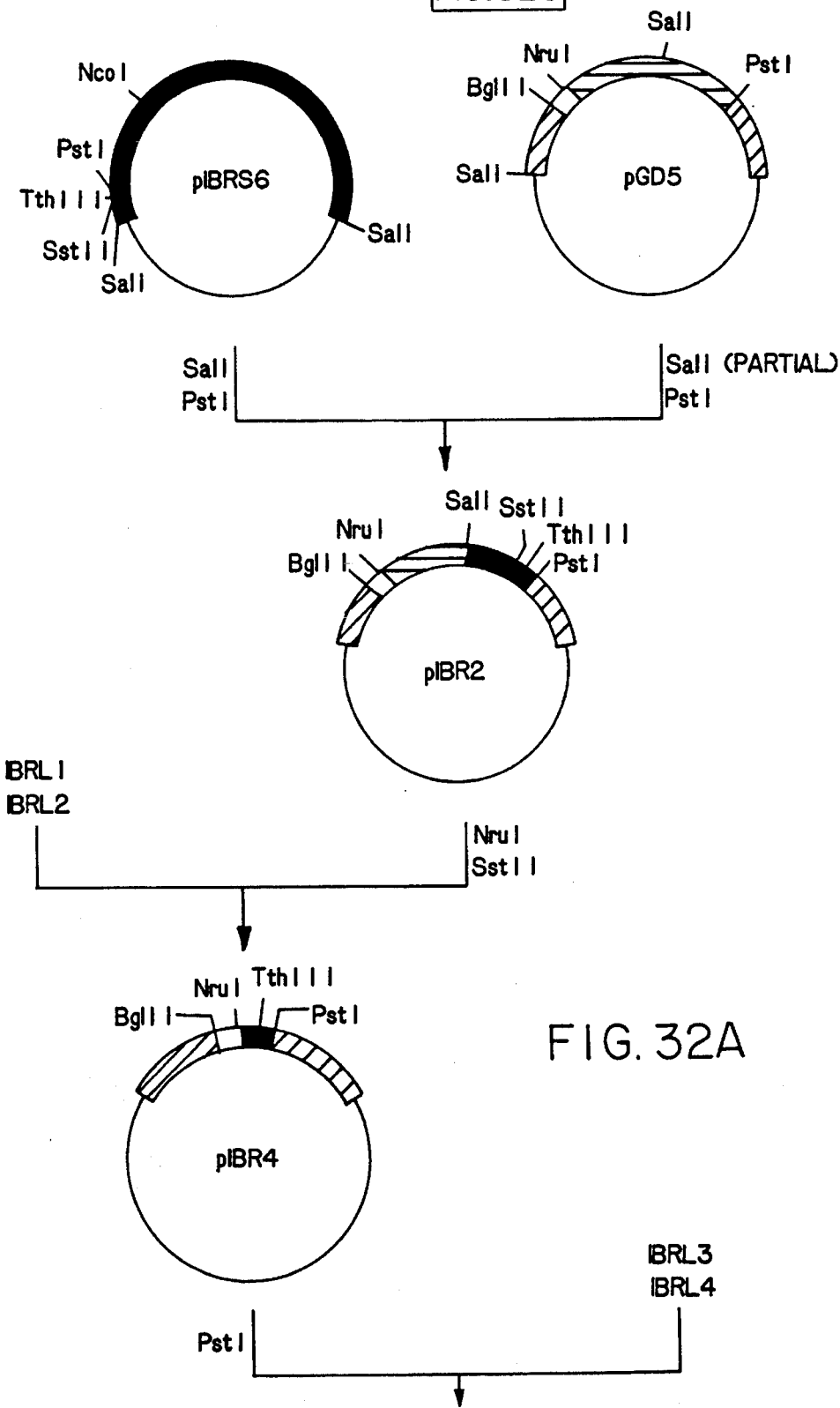
FIG. 32 schematically shows a method for the construction of recombinant vaccinia viruses vP637 and vP724 expressing the BHV-1 gI gene.
Figure 32B:
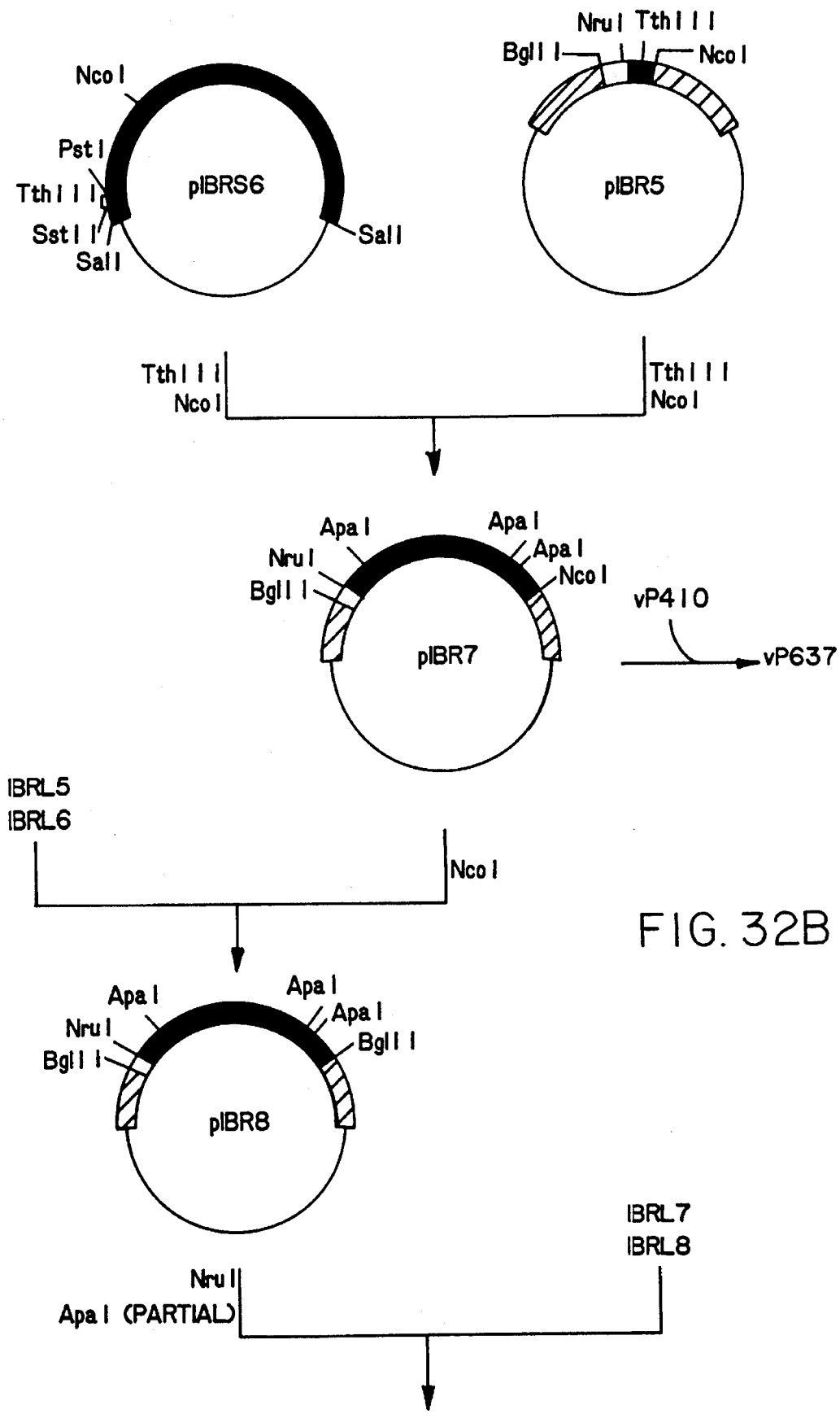
Figure 33:
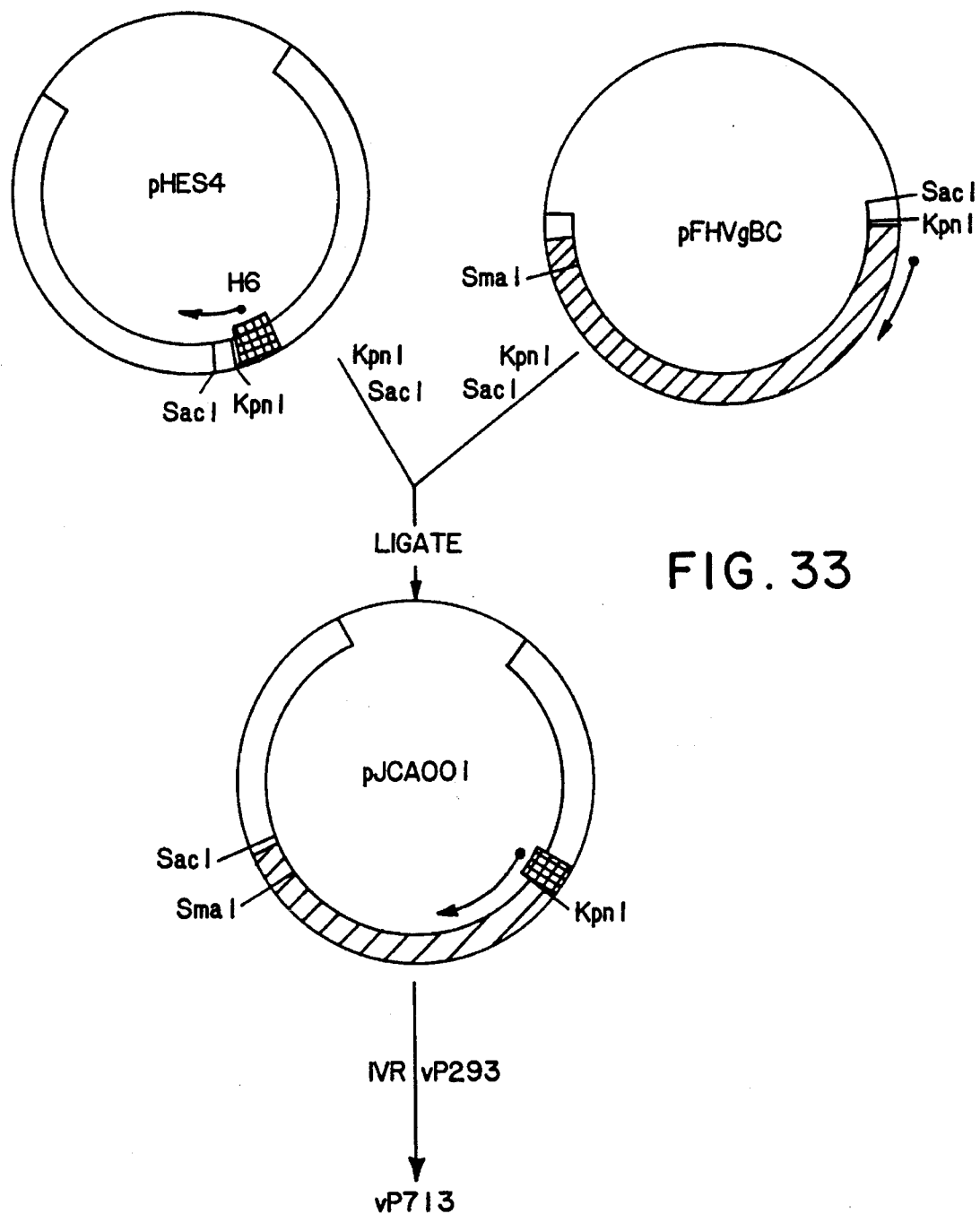
FIG. 33 schematically shows a method for the construction of donor plasmid pJCA001 containing the FHV-1 gB gene and for the construction of the recombinant vaccinia virus vP713 expressing the FHV-1 gB gene.
Figure 32C:
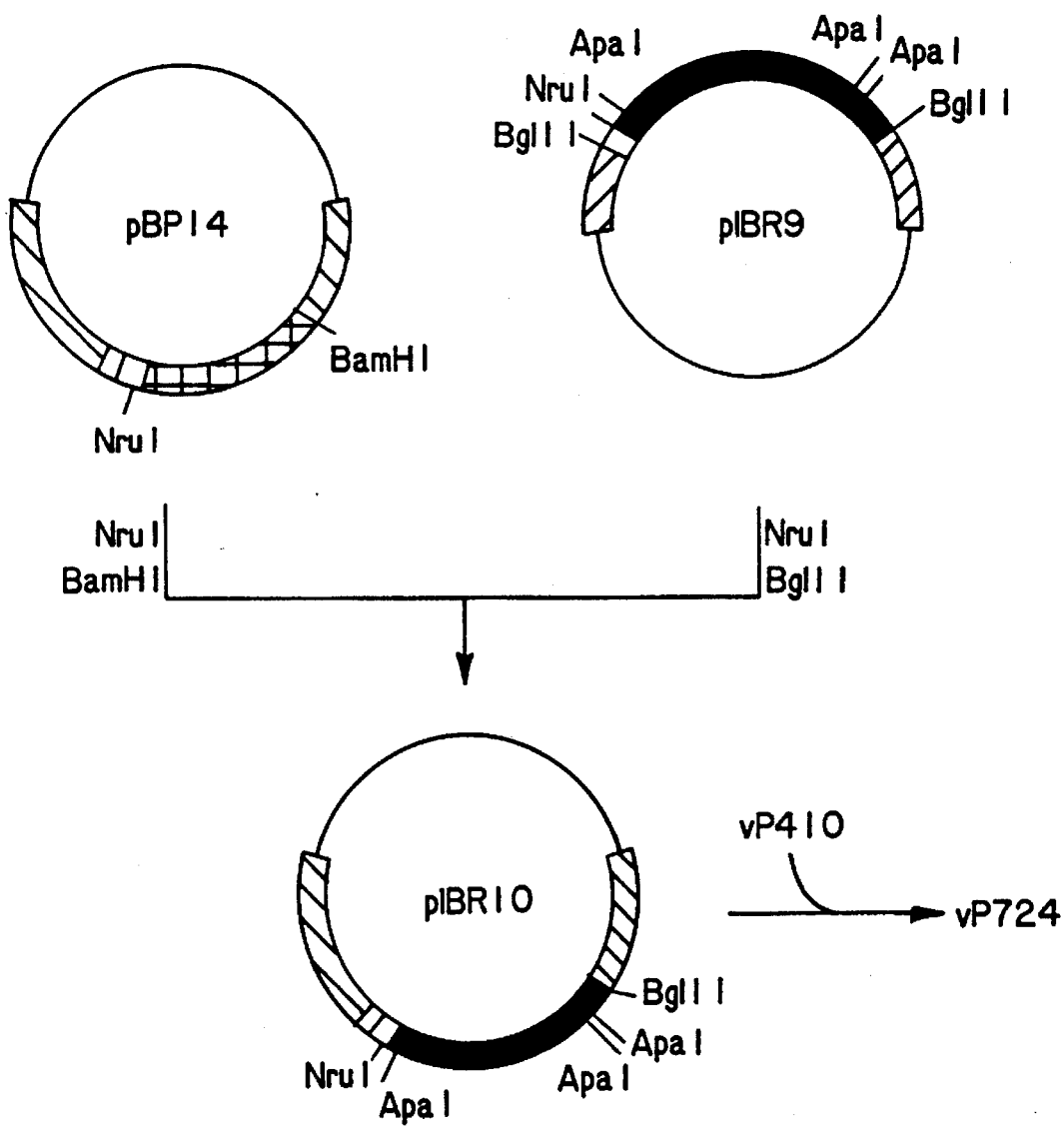
Figure 35:
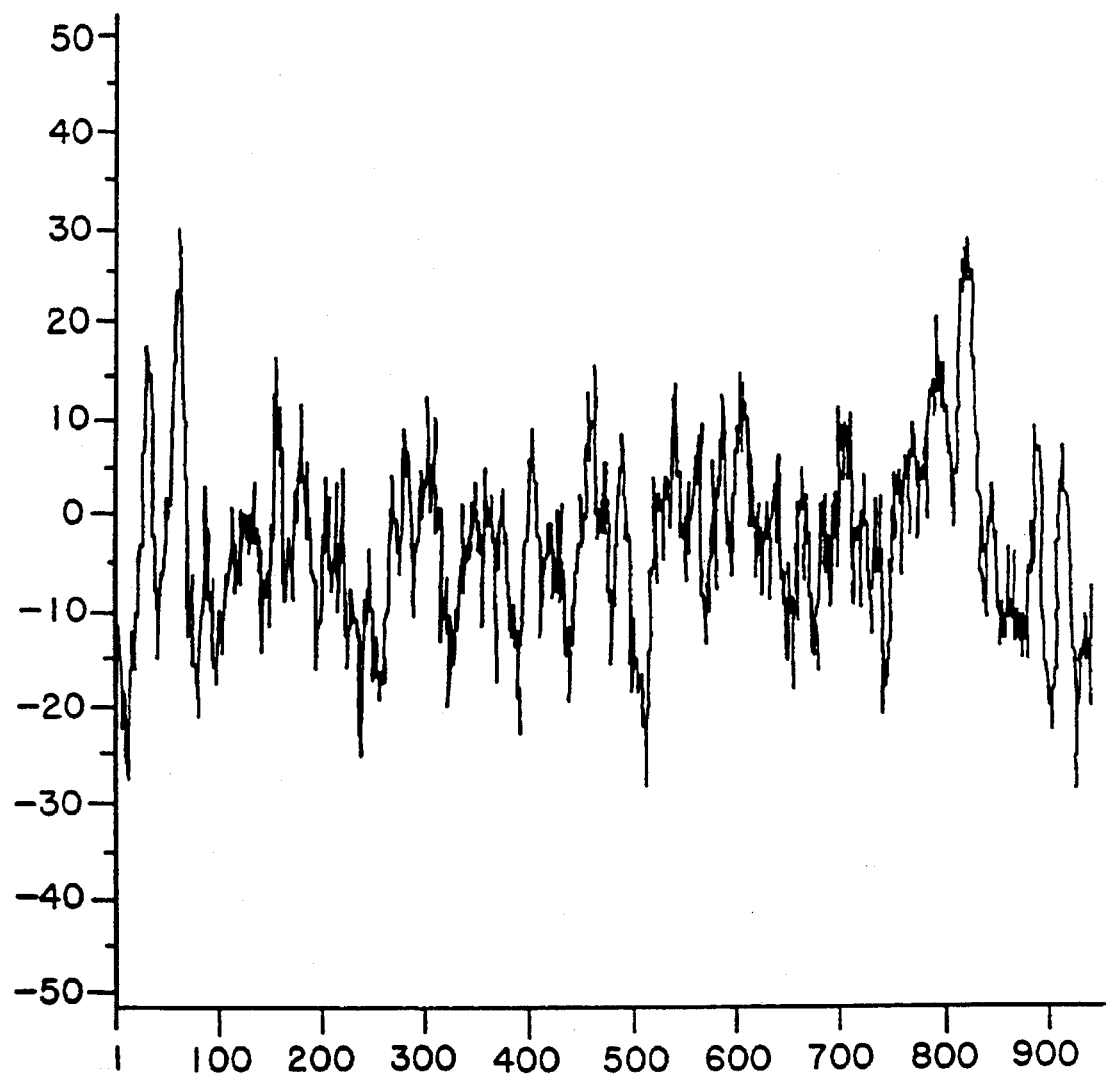
FIG. 35 is a hydropathy plot of the sequence of 947 amino acids composing FHV-1 gB.
Figure 36A:
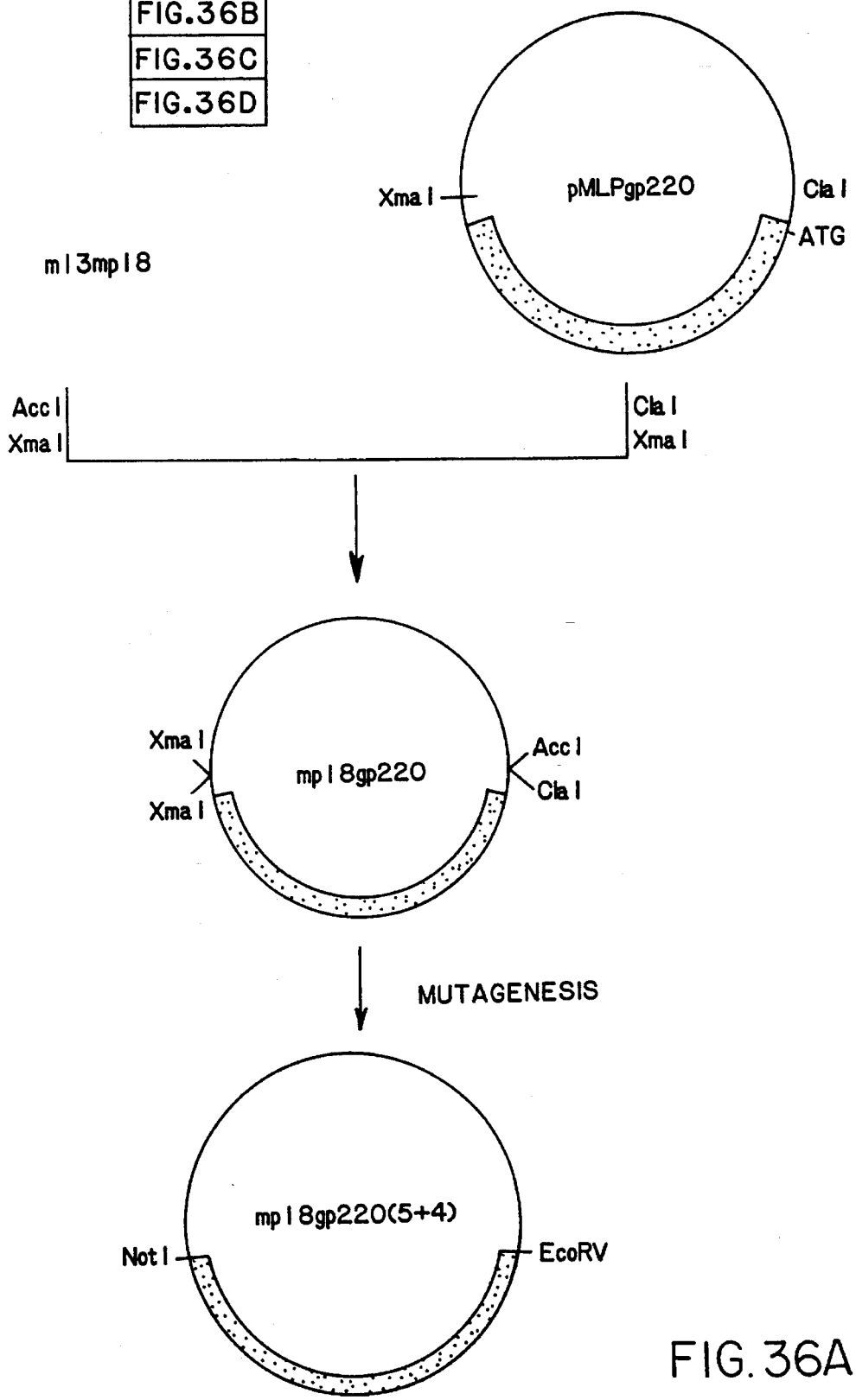
FIG. 36 schematically shows a method for the construction of donor plasmids 409gp220 containing the EBV gp220 gene and 409gp340 containing the EBV gp340 gene.
Figure 36B:
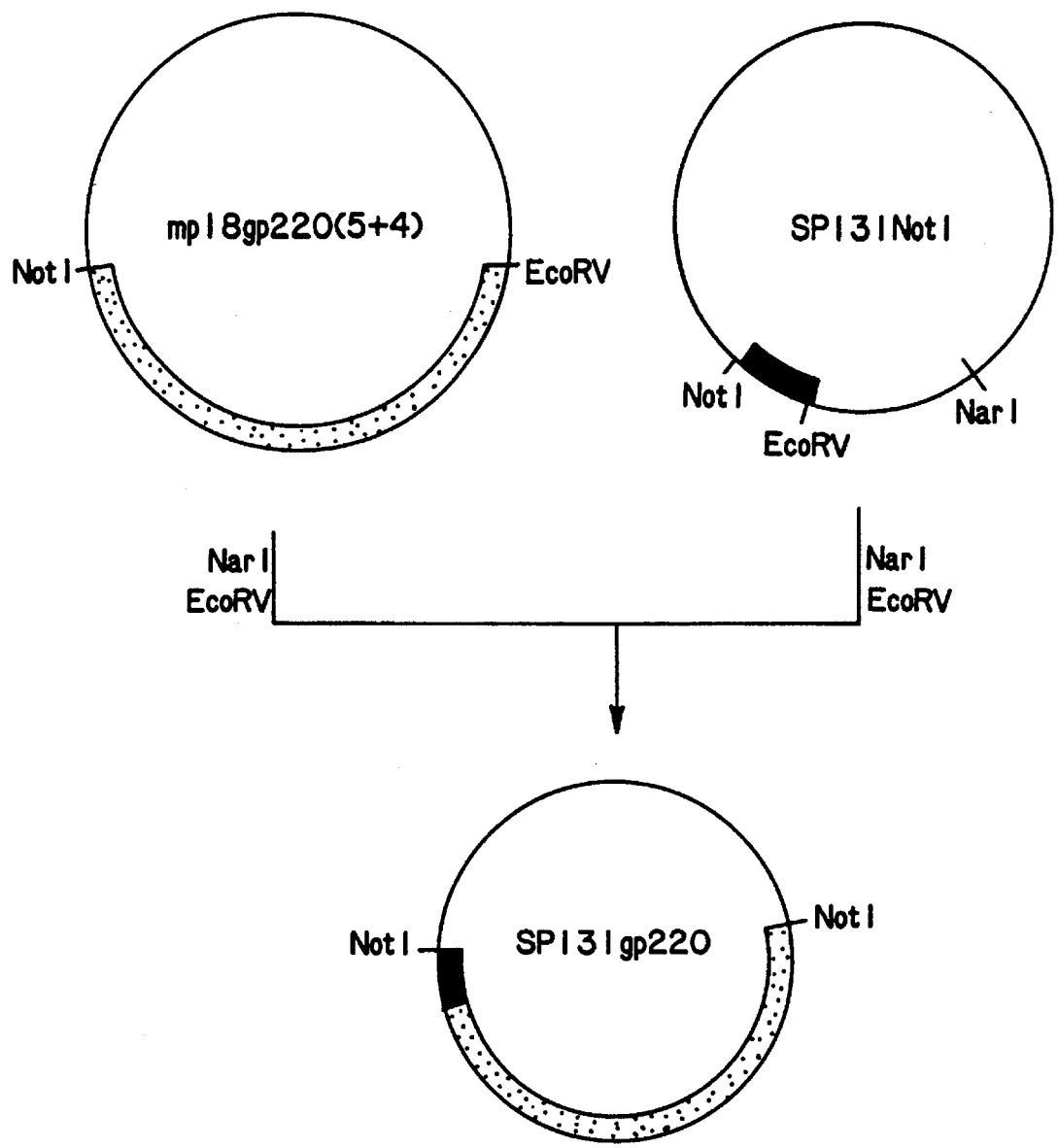
Figure 36C:
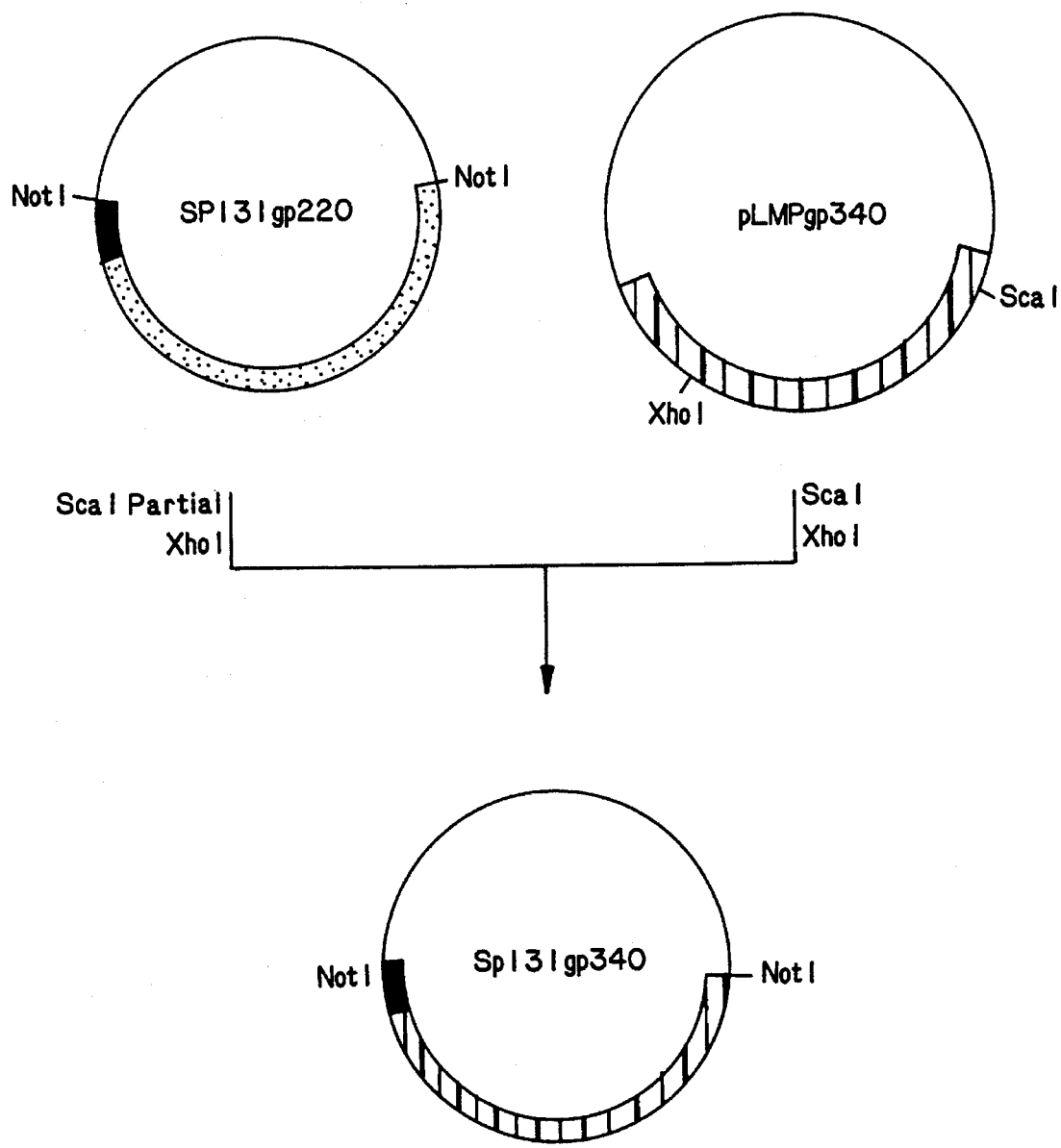
Figure 36D:
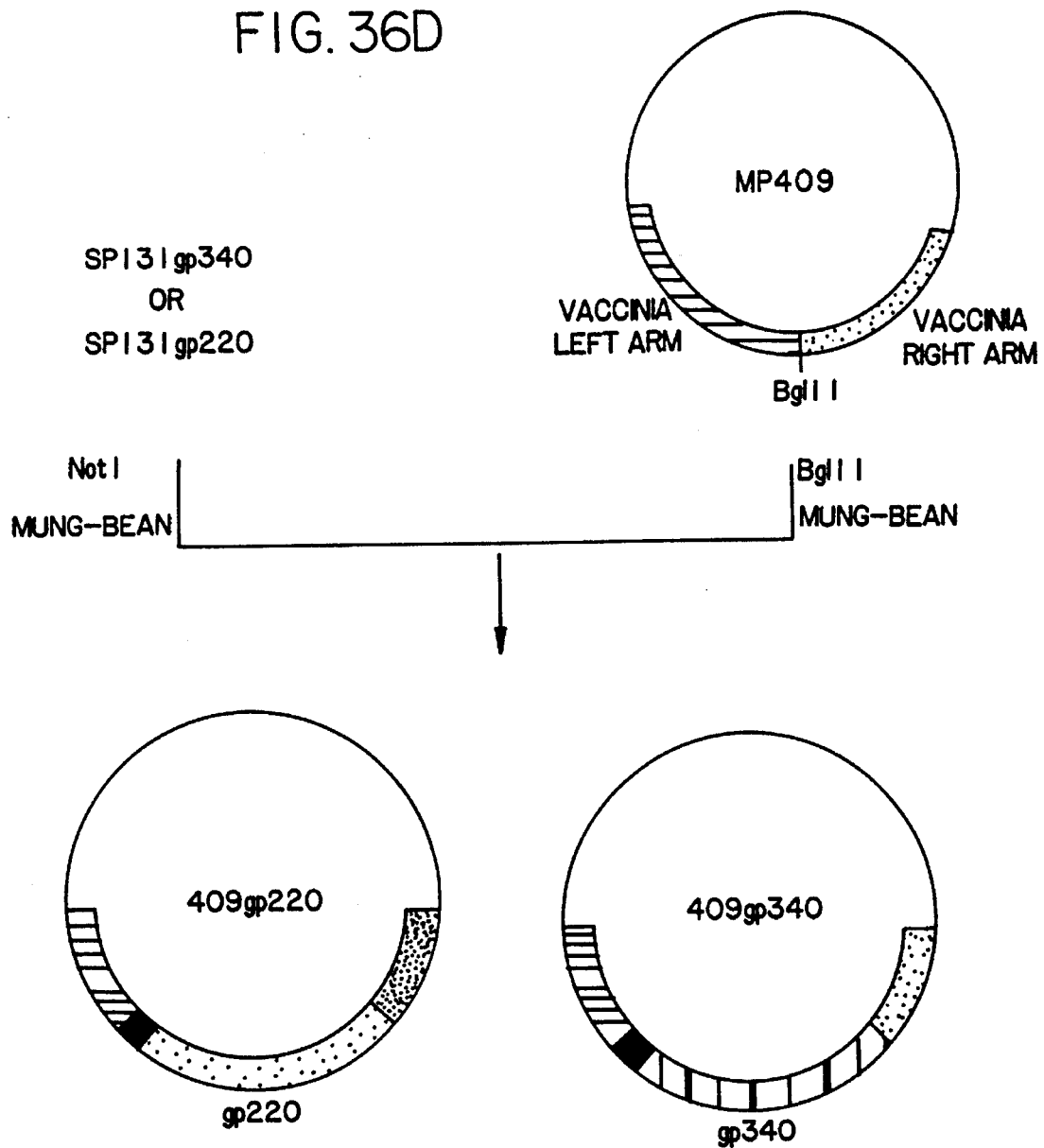

The nucleotide sequence of the BHV1 gI gene has been previously published (63). Referring now to FIG. 32 a plasmid pIBRS6 containing the BHV1 gI gene (Straub strain) was obtained from Rhone Merieux, Lyon, France. The 5' end of the gI gene was cloned downstream of the H6 promoter (41,42,69) and between vaccinia virus (Copenhagen) flanking arms. This was accomplished by cloning the 540 bp SalI-pstI fragment of pIBRS6 into the 4,400 bp SalI-PstI fragment of pGD5 (pGD5 was generated by cloning the HSV2 gD gene into pTP15 (184) (FIG. 3). This places the gI gene downstream of the H6 promoter and between vaccinia virus HA flanking arms. The plasmid generated by this manipulation is designated pIBR2.

The initiation codon of the H6 promoter was then aligned with the initiation codon of the gI gene. This was accomplished by cloning the oligonucleotides, IBRL1 5'-ATCCGTTAAGTTTGTATCGTAATGGC-CGCTCGCGGCGGTGCTGAACGCGCCGC-3' and IBRL2 5'-GGCGCGTTCAGCACCGCCGCGAGCGGC-CATTACGATACAAACTTAACGGAT-3', into the 3,800 bp NruI-SstII fragment of pIBR2. The plasmid generated by this manipulation is designated pIBR4.

An NcoI site, necessary for future manipulations, was then generated. This was accomplished by cloning the oligonucleotides IBRL3 5'-CCATGGTTTAATGCA-3' and IBRL4 5'-TTAAACCATGGTGCA-3' into the PstI site of pIBR4. The plasmid generated by this manipulation is designated pIBR5.

The 3' end of the gI gene was then cloned into pIBR5. This was accomplished by cloning the 1,740 bp Tth111I-NcoI fragment of pIBRS6 into the 3,700 bp Tth111I-NcoI fragment of pIBR5. The plasmid generated by this manipulation is designated pIBR7.

A BglII site necessary for future manipulations was then generated. This was accomplished by cloning the oligonucleotides IBRL5 5'-CATGGTTTAAGATCTC-3' and IBRL6 5'-CATGGAGATCTTAAAC-3', into the NcoI site of pIBR7. The plasmid generated by this manipulation is designated pIBR8.

A portion of the long hydrophilic leader sequence of the gI gene was then deleted (63). This was accomplished by cloning the oligonucleotides, IBRL7 5'-ATCCGTTAAGTTTGTATCGTAATGGC-CGCGCTAGCCGCTGCCCTGCTATGGGC-GACGTGGGCC-3' and IBRL8 5'-CACGTCGCCCATAGCAGGGCAGCG-GCTAGCGCGGCCATTACGATACAAACTTAACGGAT-3', into the 4,400 bp NrUI-ADaI (partial) fragment of pIBR8. This eliminates 132 bp of the hydrophilic leader sequence. The plasmid generated by this manipulation is designated pIBR9.

The H6 promoted truncated gI gene was then cloned into a different vaccinia virus donor plasmid. This was accomplished by cloning the 1,700 bp NruI-BglII fragment of pIBR9 into the 4,900 bp NruI-BamHI fragment of pBP14. The plasmid generated by this manipulation is designated pIBR10.

Construction of recombinant vaccinia viruses.

The strategy used to clone the BHV1 gI gene into vaccinia virus is outlined in FIG. 32. The recombinant vaccinia virus vP637 was generated by transfecting pIBR7 into vP410 infected cells. vP724 was generated by transfecting pIBR10 into vP410 infected cells. vP637 contains the entire BHV1 gI gene. vP724 contains a gI gene deleted of 132 bp of 5' signal sequence (63). Both constructs utilize the vaccinia virus early-late promoter, H6 (41,42,184). The gI gene in vP637 is cloned between the sequences flanking the HA gene. The gI gene in vP724 is cloned between the sequences flanking the ATI gene.

Immunofluorescence and detection of a BHV1-encoded polypeptide in recombinant vaccinia virus infected cells.

In BHV1 infected cells gI is expressed on the plasma membrane. Immunofluorescence studies of cells infected with vP637 or vP724 indicate that the BHV1 encoded polypeptide produced in these cells is also expressed on the plasma membrane. Immunofluorescence was performed as described in Example 1. The BHV1 gI-specific monoclonal antibodies, 4203 and 5106, were used (201).

EXAMPLE 15

EXPRESSION OF FELINE HERPESVIRUS GLYCOPROTEIN gB IN A VACCINIA VIRUS RECOMBINANT

The WR strain of vaccinia virus (202) was utilized in this example. The WR strain derived recombinant vaccinia virus vP293 was used as a rescuing virus (69).

Extraction of FHV-1 DNA and cloning of the FPFV-1 SacI-SacI 3.2 Kb fragment.

FHV-1 DNA was extracted and purified from the C O strain. The FHV-1 DNA genome was digested with EcORI and ligated in plasmid pBR322 using standard procedures (20). This FHV-1 bank was screened with DNA probes derived from the PRVgII (62) and BHV-1 gB (203) genes. Subsequent hybridizations with subclones derived from the two EcoRI clones found positive by hybridization allowed more accurate mapping of the FHV-1 gB gene. A 3.2 Kb SacI-SacI fragment containing the FHV-1 gB gene was cloned into pUCl8, thus generating plasmid pFHVgBC.

Sequencing of the SacI-SacI fragment encoding FHV-1 gB.

Nucleotide sequence data for both strands were obtained from pFHVgBC and pFHVgBC-derived subclones using modified T7 Sequenase as described above.

Cloning of the FHV-1 gB gene into a vaccinia virus donor plasmid.

Referring now to FIG. 33, the FHV-1 gB gene was cloned in pHES4, one of the plasmids designed for the host range selection system in WR vaccinia virus strain (69) (FIG. 10). This plasmid bears the host range gene K1L which allows the deletion mutant vP293 to replicate on human cells. The FHV-1 gB gene was inserted immediately downstream from the vaccinia synthetic H6 promoter (69). Plasmid pFHVgBC was digested with KpnI and SacI and the 3150 bp restriction fragment containing FHV-1 gB was isolated from an agarose gel and then ligated into plasmid pHES4 previously digested with KpnI and SacI. The resulting plasmid was designated pJCA001 (FIG. 33).

DNA sequence analysis of the FHV-1 gB gene.

Referring now to FIG. 34, DNA sequence analysis revealed an open reading frame extending from nucleotide positions 337 to 3177. Putative transcriptional regulatory signals were found in the region 5' to the ATG initiation codon at position 337. A TATA box having the sequence AAATATAT (nucleotides 184 to 191) was located 80 nucleotides downstream from a putative CAT box having the sequence GGTGAGTA. A polyadenylation signal AATAAA (nucleotides 3251 to 3256) was located 50 nucleotides downstream from the TAA termination codon (nucleotides 3178 to 3180). Eight out of 11 nucleotides in the sequence 5' TCATTCTAGCA 3' (nucleotides 200 to 210) are complementary to the 18S ribosomal RNA sequence 3' AGGAAGGCGT 5' (61) and may serve as the ribosome binding site. A scanning model has been proposed by which eukaryotic mRNAs initiate translation (151,155). The sequence context around the proposed initiation codon ATCATGT (nucleotides 334 to 340) qualifies as a functional sequence context for translation initiation of eukaryotic mRNA. The FHV-1 gB open reading frame encodes 947 amino acids with a calculated molecular mass of 106.2 kDa. The G+C content is 45.8%.

Analysis of the FHV-1 gB protein structure.

Analysis of the amino acid sequence revealed a number of features common to membrane associated glycoproteins. A region extending from amino acids 23 to 73 had a characteristic hydrophobicity profile and is proposed to be the signal sequence (FIG. 34). Referring now to FIG. 35, there is a 22 amino acids long hydrophilic sequence preceding the long hydrophobic signal sequence. This characteristic has also been noted for the pseudorabies (PRV) gII gene (62), for the bovine herpesvirus-1 (BHV-1) gI gene (63) and for the equine herpesvirus-1 (EHV-1) (71) and equine herpesvirus-4 (EHV-4) (72) gp14 genes, all of which are also HSV gB homologs. A hydrophobic region consisting of 42 amino acids (amino acids 789 to 831) is predicted to function as a transmembrane anchor domain. The hydrophilic cytoplasmic domain contains 116 amino acids. There are ten Asn-X-Thr/Ser (where X can be any amino acid except proline) sites for potential N-linked glycosylation (64), one site being located in the signal sequence. There are two consecutive and close potential proteolytic cleavage sites (Arg-Arg-Ser) (positions 504 to 506 and 516 to 518) identical to those present in PRVgII (94), VZV gpII and HCMV gB (71) and EHV-1 gp14 (71,72). The hydrophobicity profile of the FHV-1 gB amino acid sequence is shown in FIG. 35.

Comparison of the FHV-1 gB amino acid sequence to other herpesvirus glycoproteins.

Comparison of the amino acid composition of the FHV-1 gB gene revealed extensive homology with glycoproteins of other herpesviruses. Thus the FHV-1 gB is homologous to PRVgII (62), BHV-1 gI (63), varicella zoster virus (VZV) gII (66,204), HSV-1 gB (67), HSV-2 gB (205), EHV-1 gp14 (71), as well as to glycoproteins in Epstein-Barr virus (EBV) (68,206) and human cytomegalovirus (HCMV) (10).

Construction of the vaccinia recombinant vP713 expressing the FHV-1 gB glycoprotein.

The FHV-1 gB coding sequences were inserted into a vaccinia virus vector using the WR vaccinia virus host range selection system pHES4/vP293 (69). The ability of recombinant vaccinia progeny generated by recombination using the WR vaccinia virus vP293/pHES host range selection system to plaque on human MRC-5 cells permits rapid identification of these recombinants (69). Vaccinia virus recombinant vP713 was obtained by recombination performed with plasmid pJCA001 as donor plasmid and vP293 as rescuing virus (FIG. 33).

Immunofluorescence of FHV-1 gB glycoprotein synthesized by vP713.

Immunofluorescence of recombinant vaccinia virus vP713 infected VERO and MRC-5 cells was performed as described in Example 1, using anti-FHV-1 gB specific sheep serum #2854. A multiplicity of infection of two pfu per cell was used. FITC donkey anti-sheep IgG was used as the second antibody.

FHV-1 gB was detectable on the surface of VERO cells infected with vaccinia recombinant vP713 as well as internally after acetone fixation. No significant internal or surface immunoreactivity toward FHV-1 gB was seen in vP410 infected control cells.

Immunoprecipitation of FHV-1 gB glycoprotein synthesized by vP713.

In order to assess the FHV-1 gB glycoprotein expressed by vP713, VERO cells were infected with vP713 and proteins were metabolically labeled with $^{35}S$ methionine. Immunoprecipitations were performed with the radiolabeled cell lysates using anti-FHV-1 gB specific sheep serum #2854.

VERO cell monolayers seeded at $2\times10^6$ cells per 60 mm dishes were infected at a low multiplicity of infection of 0.1 pfu per cell with control (vP410) or recombinant vaccinia virus vP713. Immunoprecipitations were performed as described in Example 1.

No significant products are immunoprecipitated by the specific anti-FHV-1 gB serum from either uninfected VERO cells or VERO cells infected with the control vaccinia virus vP410. FHV-1 gB radiolabeled products were precipitated by serum #2854 from VERO cells infected with vP713. Five dominant metabolically radiolabeled polypeptides are specifically precipitated. The two larger polypeptides of apparent molecular sizes 115 kDa and 110 kDa, could correspond to the non-glycosylated precursor and mature proteins (theoretical sizes respectively of 106 kDa and 98 kDa). A large band at 68 kDa could represent the two glycosylated subunits (69 kDa+66 kDa) resulting from the proteolytic cleavage of a glycosylated precursor (136 kDa) which is lacking here. Three smaller precipitated products (59, 53 and 48 kDa) do not correspond to any known FHV-1 gB products and may represent degradation products.

EXAMPLE 16

CLONING AND EXPRESSION OF EPSTEIN-BARR VIRUS GLYCOPROTEIN IN POXVIRUS VECTORS

Cloning of the EBV gp340 and gp220 genes into the vaccinia donor plasmid pMP409DVC.

In this example, the EBV genes were isolated from the B95-8 EBV strain (207), the gp340 and gp220 genes were cDNA clones (plasmids pMLPgp340 and pMLPgp220, respectively), and the gB, gH and BBRF3 genes were isolated from a BamH1 genebank. Referring now to FIG. 36, a 2100 bp XmaI-ClaI fragment of pMLPgp220 plasmid was cloned into M13mp18 digested with XmaI-AccI. The phage obtained by this manipulation was designated mp18gp220 (FIG. 36). By in vitro mutagenesis (17) using the oligonucleotides CM4 (TAAAGTCAATAAATTTTTATTGCGGCCGCTACCGAGCTCGAATTCG) and CM5 (GCTTGCATGCCTGCAGATATCCGTTAAGTTTGTATCGTAATGGAGGCAGCCTTGC) the gp220 gene was modified to be expressed under the control of the vaccinia H6 promoter. The plasmid containing the modified gp220 gene was designated mp18gp220(5+4) (FIG. 36).

The modified gp220 gene was cloned into the plasmid SP131NotI which contains the complete H6 synthetic promoter (69). This was accomplished by cloning the 2300 bp NarI-EcoRV fragment of mp18gp220(5+4) into the 2940 bp EcoRV-NarI fragment of SP131NotI plasmid. The resulting plasmid was designated SP131gp220 (FIG. 36).

The gp340 gene under the control of the H6 promoter was obtained by cloning a 2360 bp ScaI-XhoI fragment of pMLPgp340 into the XhoI-ScaI (partial) digested SP131gp220 plasmid. The resulting plasmid was designated SP131gp340 (FIG. 36).

Figure 40A:
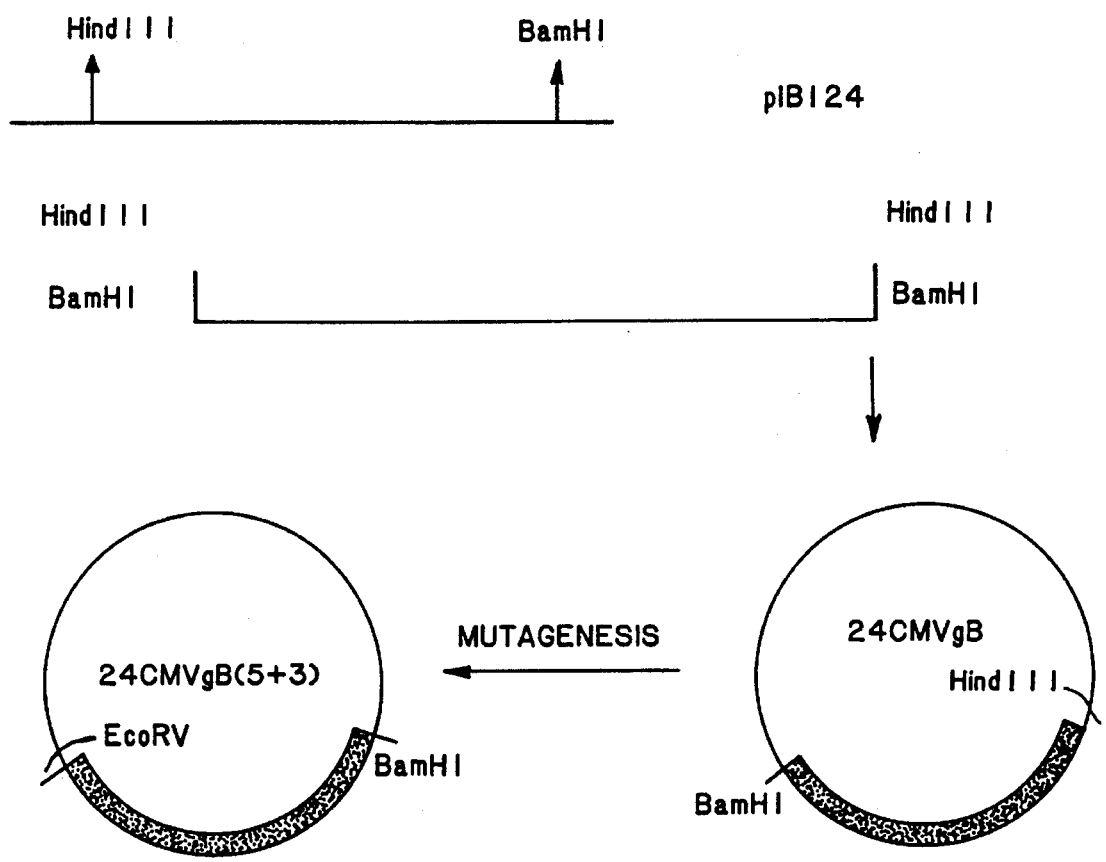
FIG. 40 schematically shows a method for the construction of vaccinia donor plasmid 409CMVgB containing the CMV gB gene.
Figure 40B:
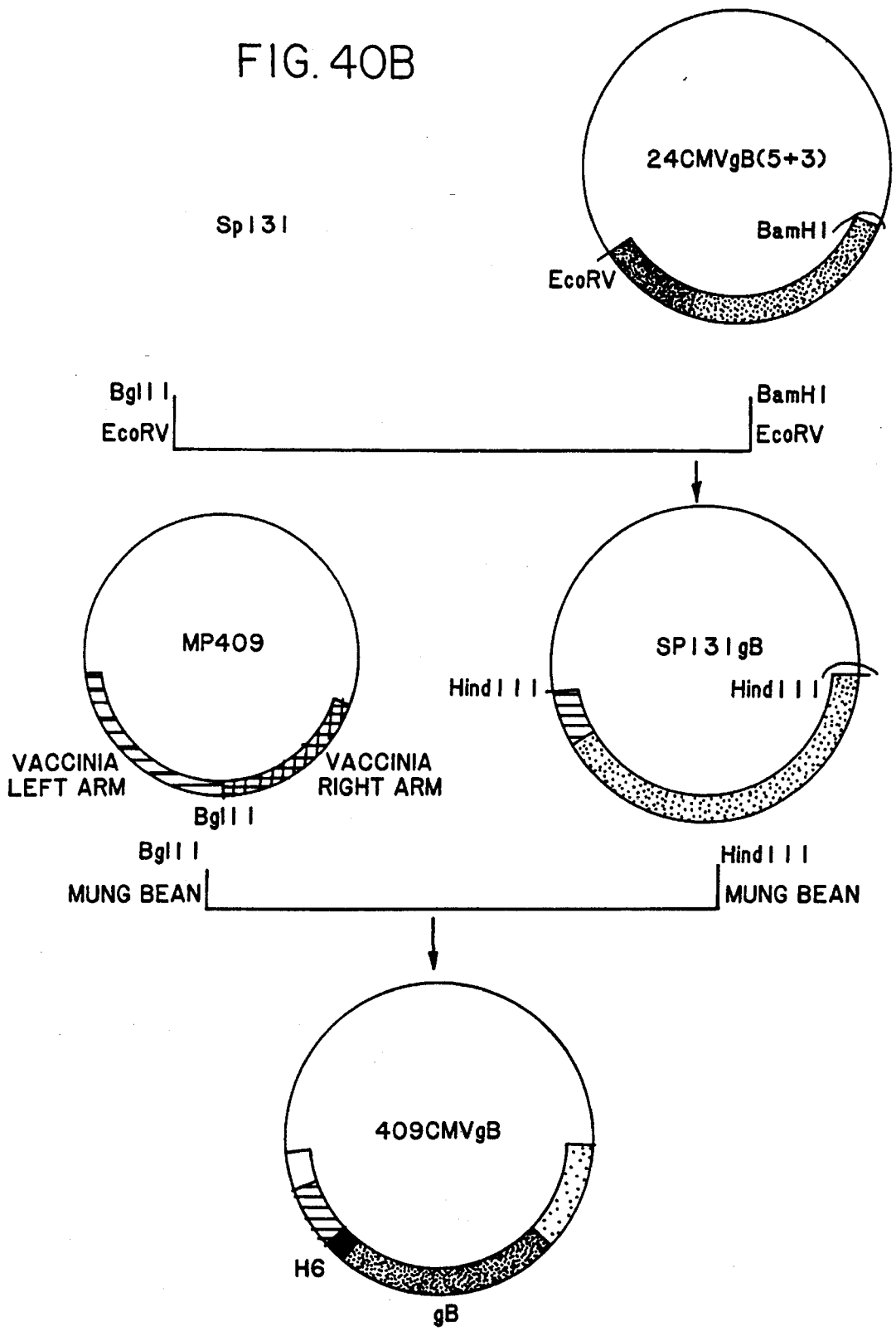

The H6 promoted gp340 and gp220 genes were cloned into the vaccinia virus M2L insertion locus plasmid pMP409DVC (FIG. 4; in FIGS. 36, 40 this plasmid is designated MP409). This was accomplished by cloning the 2800 bp Mung-Bean nuclease treated NotI fragment of the plasmid SP131gp340 and the 2100 bp Mung-Bean nuclease treated NotI fragment of the plasmid SP131gp220 into the BglII Mung-Bean nuclease treated site of the plasmid pMP409DVC. The resulting plasmids were designated 409gp340 and 409gp220 respectively (FIG. 36).

Cloning of the EBV gB gene into the vaccinia virus donor plasmid pMP409DVC.

Figures 37, 37A:
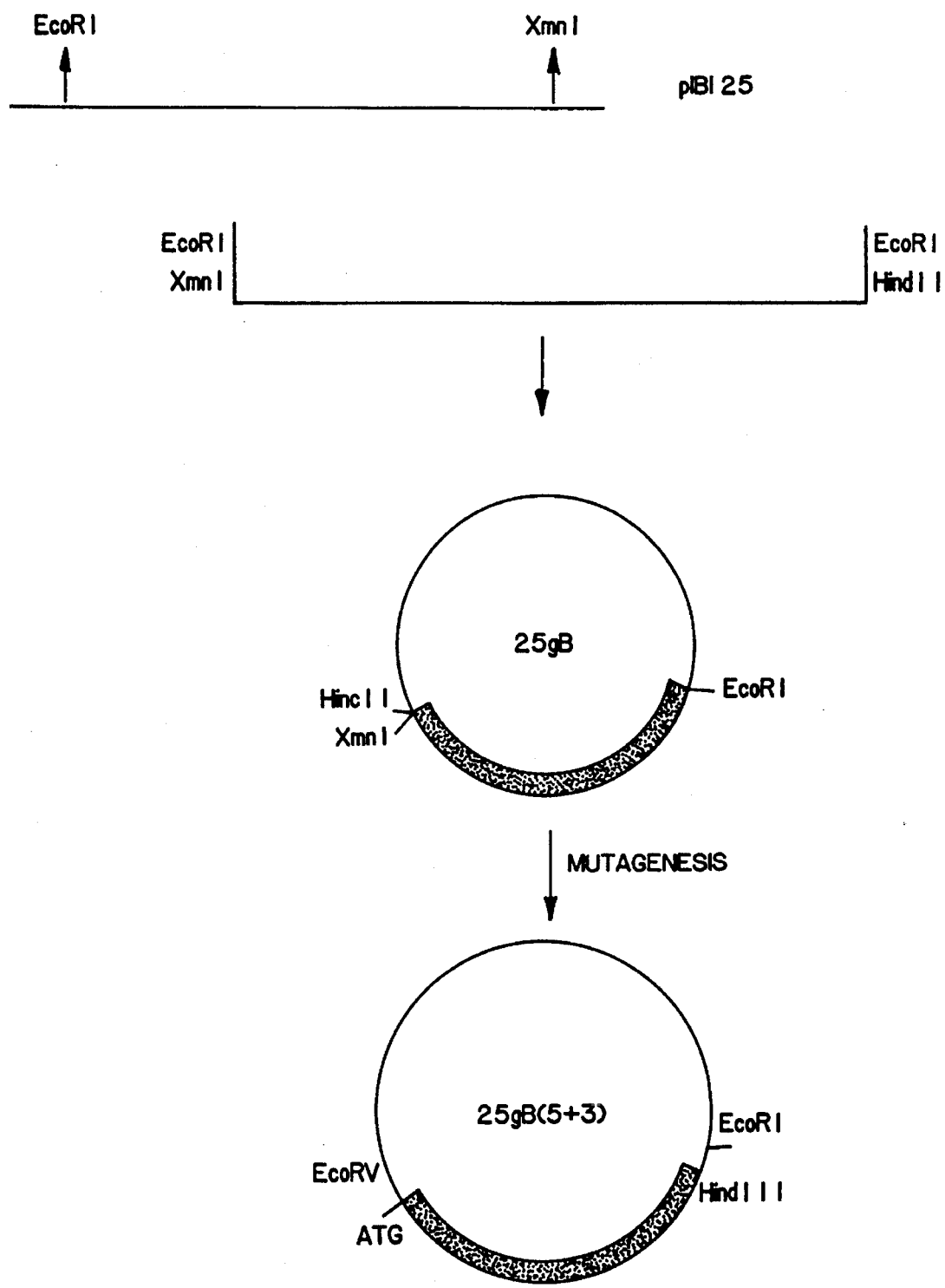
FIG. 37 schematically shows a method for the construction of vaccinia donor plasmid 409gB containing the EBV gB gene.

Referring now to FIG. 37, a 3500 bp EcoRI-XmnI fragment of the EBV DNA BamI A fragment (207), containing the EBV gB gene, was isolated from the EBV genomic library and cloned into the 2837 bp HincII-EcoRI fragment of pIBI25. The resulting plasmid was designated p25gB (FIG. 37).

By in vitro mutagenesis (17,185) using the oligonucleotides EBVBM5 (CCCTACGCCGAGTCATTACGATACAAACTTAACGGATATCAGAGTCGTACGTAGG) and EBVBM3 (CTGGAAACACTTGGGAATTCAAGCTTCATAAAAAGGGTTATAGAAGAGTCC), the gB gene was adapted to be expressed under the control of the vaccinia H6 promoter. The resulting plasmid was designated p25gB(5+3).

The 2600 bp EcoRV-EcoRI fragment of p25gB(5+3) was cloned into the 3300 bp EcoRV-EcoRI fragment of SP131. The resulting plasmid was designated SP131gB (FIG. 37).

The H6 promoter gB gene was then cloned into the vaccinia virus donor plasmid pMP409DVC. This was accomplished by cloning the 2700 bp HindIII Mung-Bean nuclease treated fragment of SP131gB into the GglII Mung-Bean nuclease treated site of pMP409DVC. The resulting plasmid was designated 409gB (FIG. 37).

Cloning of the EBV gM gene into the vaccinia donor plasmid pSD486VC.

Figures 38, 38A, 38B:
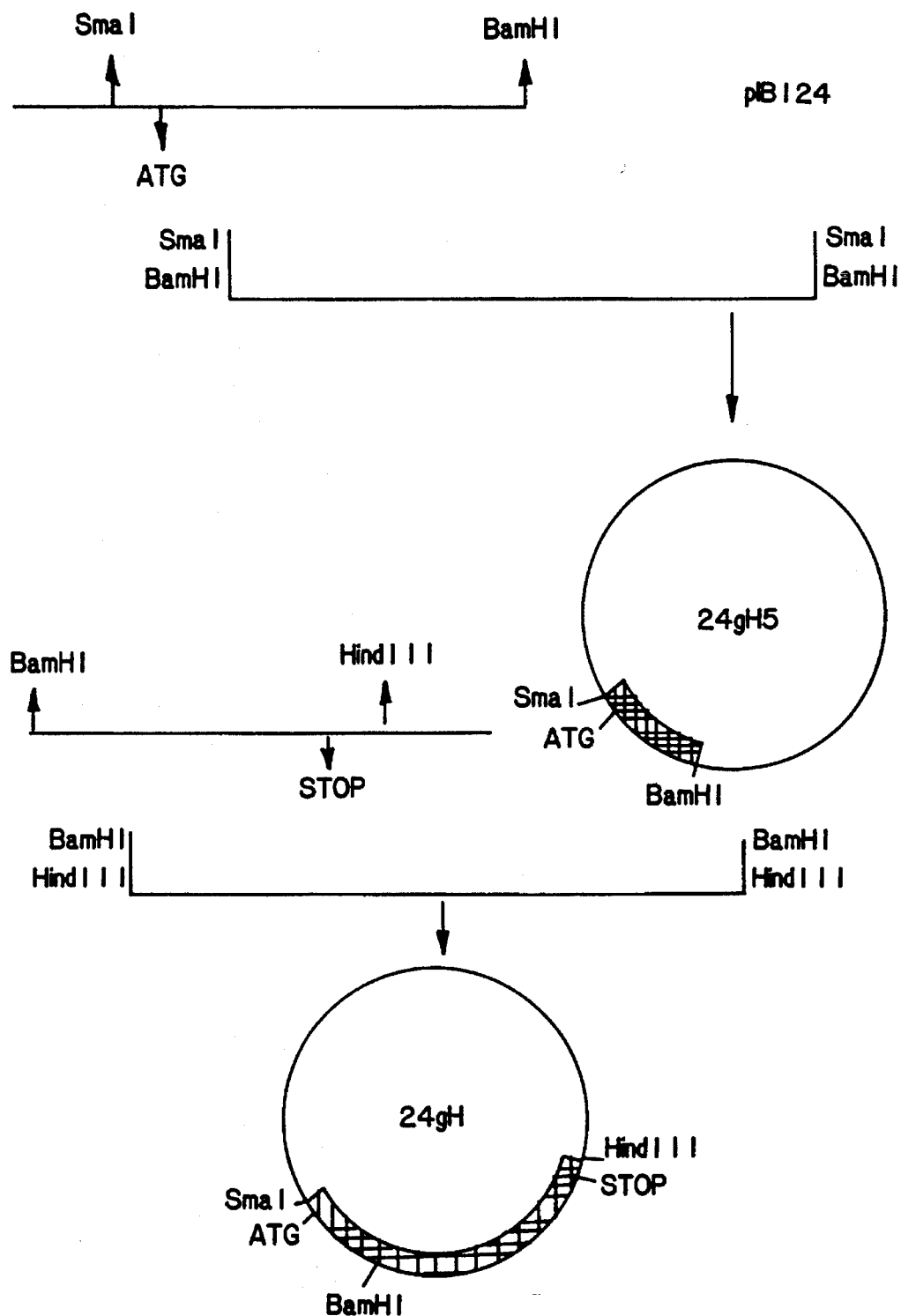
FIG. 38 schematically shows a method for the construction vaccinia donor plasmid 486gH containing the EBV gH gene.
Figure 38B:
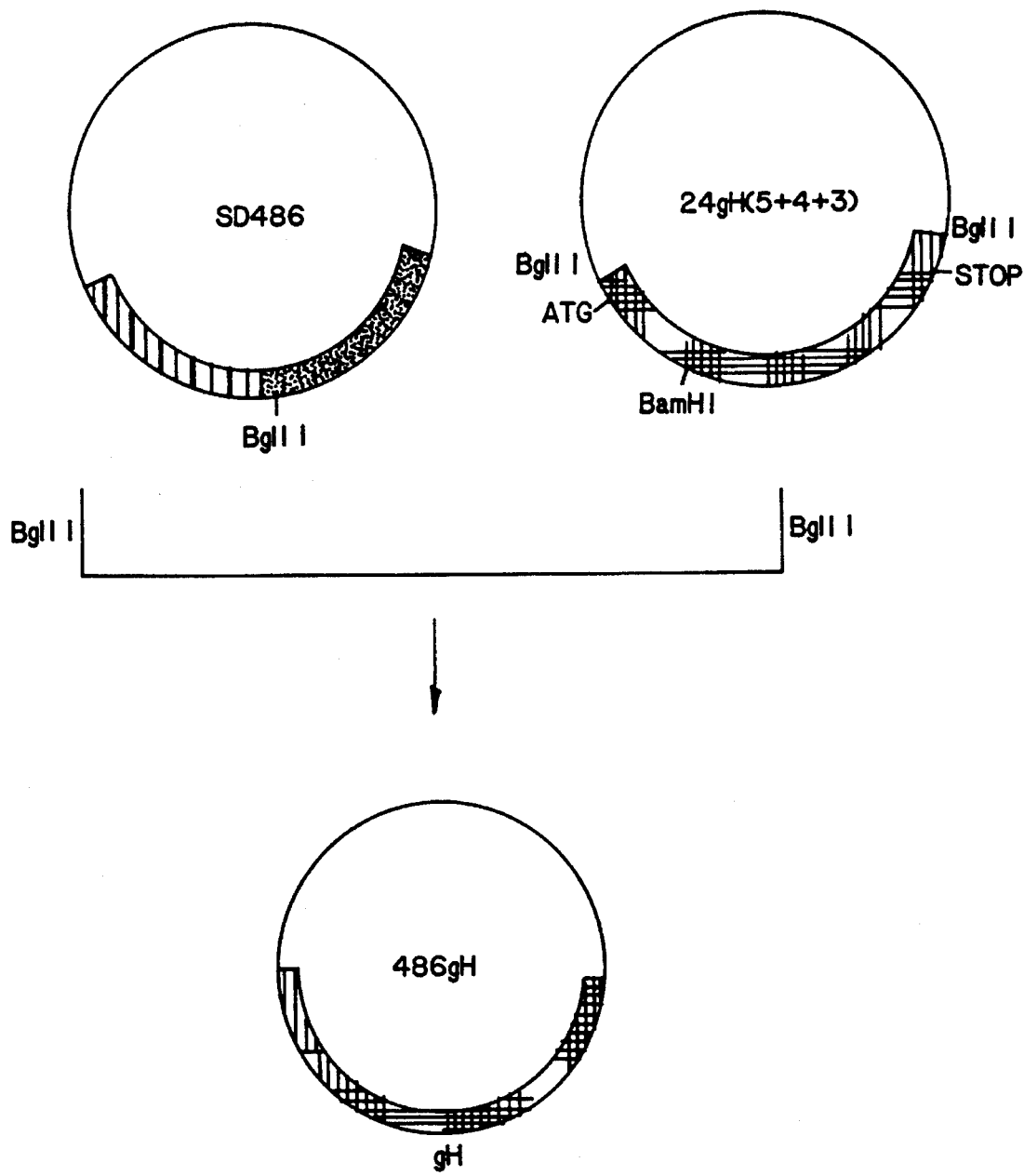

In the EBV BamHI cloned restriction fragments library, the open reading frame BXLF2 is contained in the BamHI X and BamHI T fragments (207). As shown in FIG. 38, the complete BXLF2 open reading frame was reconstituted by cloning the 830 bp SmaI-BamHI fragment of BamHI X into the 2880 bp SmaI-BamHI fragment of pIBI24; the resulting plasmid was designated 24gH5. The 1850 bp BamHI-HindIII fragment of BamHI T was cloned in the 3660 bp DamHI-HindIII fragment of 24gH5. The resulting plasmid containing the complete gH gene was designated 24gH (FIG. 38).

By in vitro mutagenesis (17,185) using the oligonucleotides HM5 (ACACAGAGCAACTGCAGATCTCCCGATTTCCCCTCT), HM4 (GGGCAAAGCCACAAAATATGCAGGATTTCTGCG) and HM3 (GCCAGGGTTTTCCCAGAGATCTGATAAAAACGACGGCCAGTG) the gH gene was modified to be expressed under the control of the vaccinia hemorrhagic (µ) early promoter. The oligonucleotide HM4 was used to remove a vaccinia early transcription stop signal contained into the gH gene (45). The plasmid containing the modified gH gene was designated 24gH(5+4+3).

Referring now to FIG. 38, the vaccinia µ promoter is contained into the plasmid, pSD486 VC (FIG. 30). (In FIG. 38, this plasmid is designated SD486). The 2130 bp BglII Mung Bean nuclease treated fragment of 24gH(5+4+3) was cloned into the BglII Mung-Bean nuclease treated pSD486VC. This last cloning step put the gH gene under the control of the vaccinia µ promoter. The plasmid generated by this manipulation was designated 486gH (FIG. 38).

Cloning of the open reading frame BBRF3 into the vaccinia virus donor plasmid pCOPSc-5H.

The complete BBRF3 open reading frame is contained in the BamHI B fragment of the EBV DNA. This fragment was digested by BspHI, treated by the *E. coli* DNA polymerase I (Klenow fragment) and digested by BglII. The BglII site within the BamHI A fragment is located 10 bases before the stop codon of BBRF3. The 1230 bp BspHI-BglII fragment was isolated and cloned into the 4200 bp SmaI-BglII fragment of the plasmid pCOPSC-5H. (Plasmid pCOPCS-5H is identical to plasmid pCOPCS657 (FIG. 16)). The plasmid generated by this manipulation was designated COPSCEBVX.

Cloning of the EBV gp340, gB and gH genes into vaccinia virus donor plasmid pSD513VCVQ.

The vaccinia virus donor plasmid used to generate the triple EBV recombinant was the plasmid, pSD513VCVQ (FIG. 29). This plasmid contains a subclone of the Copenhagen vaccinia virus HindIII J fragment in which the coding sequence for the thymidine kinase gene is replaced by a polylinker region.

In a first step, the µ promoted EBV gH gene was cloned into pSD513VCVQ. In particular, the 2300 bp SnaBI-BglII fragment of 486gH was cloned into the 4000 bp SmaI-BglII fragment of pSD513VCVQ. The plasmid generated by this manipulation was designated 513UgH.

Next, the H6 promoted EBV gp340 gene was cloned into 513gH. In particular, the 2800 bp NotI Mung-Bean treated fragment of SP131gp340 was cloned into the 6300 bp XhoI-PstI Mung-Bean nuclease treated fragment of 513UgH. The plasmid generated by this manipulation was designated 513UgH340H6.

Figure 39:
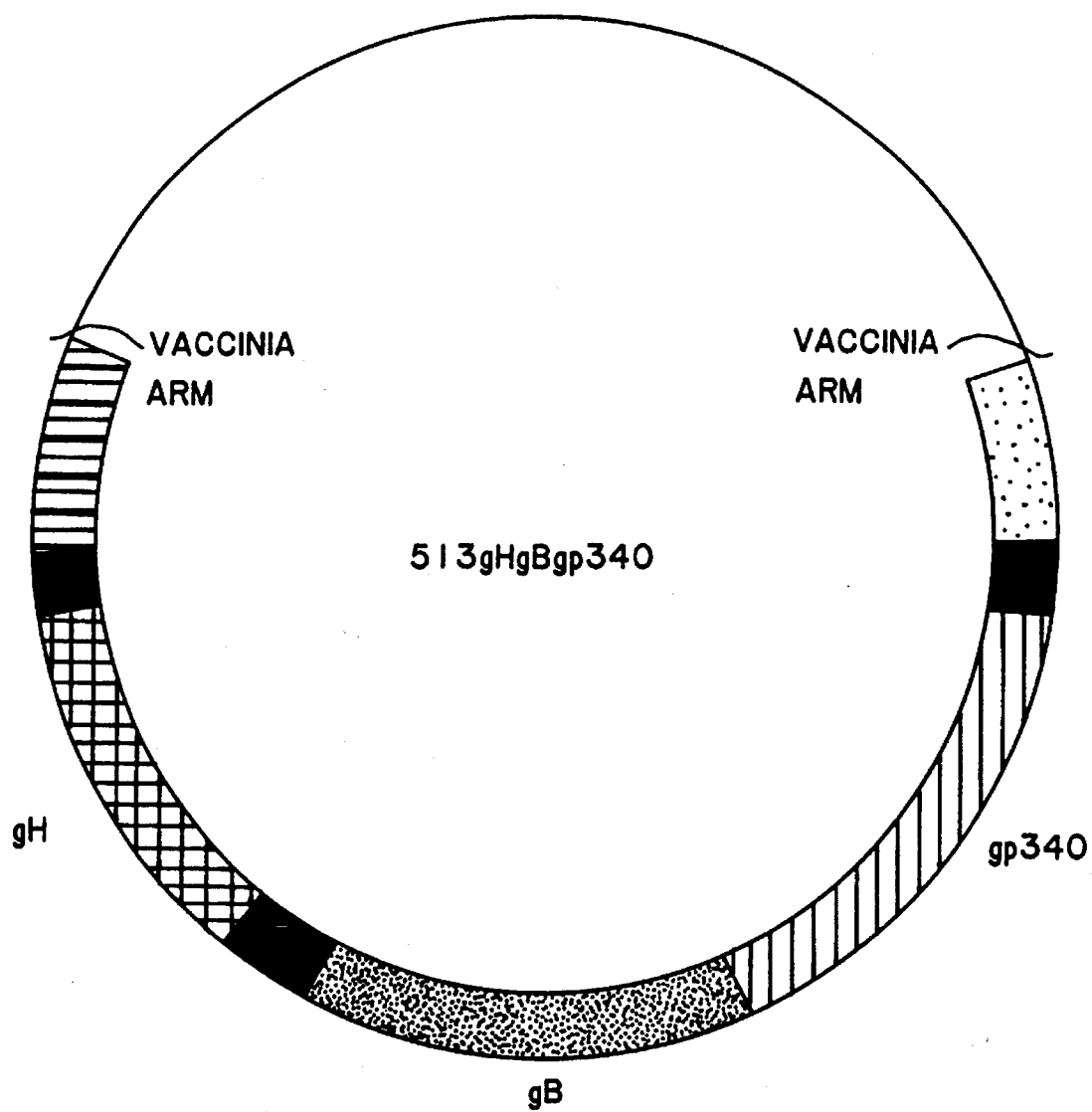
FIG. 39 schematically shows the structure of the vaccinia donor plasmid 513gHgBgp340 containing the EBV genes gp340, gB and gH.

Then, the H6 promoted EBV gB gene was cloned into 513UgH340H6. In particular, the 2700 bp HindIII Mung-Bean nuclease treated fragment of SP131gp340 was cloned into the 9100 bp BglII Mung-bean nuclease treated fragment of 513UgH340H6. The resulting plasmid was designated 513gHgBgp340 (FIG. 39).

Construction of recombinant vaccinia virus.

EBV gp340 (donor plasmid 409gp340), EBV gp220 (donor plasmid 409gp220), and EBV gB (donor plasmid 409gpgB) were recombined into the vaccinia virus vP458 (M2L site): these single vaccinia virus recombinants are designated vP474, vP480 and vP561, respectively. EBV gH (donor plasmid 486gH) was recombined into the vaccinia virus vP533 (μ insertion site): this single vaccinia virus recombinant is designated vP611.

Finally the triple vaccinia virus recombinant containing gp340, gB and gH was obtained by recombining the donor plasmid 513gHgBgp340 into the vaccinia virus vP617 at the thymidine kinase insertion site. This recombinant virus is designated vP712. vP617 is a Copenhagen vaccinia virus deleted for TK, HA and ATI genes.

Immunofluorescence of EBV proteins in recombinant vaccinia virus infected cells.

Immunofluorescence studies performed on cells infected with vP474 (gp340) and vP480 (gp220) using the monoclonal antibody F29-89 (165) showed EBV gp340 and EBV gp220 proteins expressed on the plasma membrane.

Cells infected with vP611 (gH), using a human serum, showed a weak positive signal on the plasma membrane.

Finally, the same experiment was performed with cells infected with vP712 (triple EBV vaccinia recombinant): a positive signal on the plasma membrane was obtained with the monoclonal antibodies F29-89 and NEA 9247 (gB specificity obtained from DuPont).

Immunoprecipitation of EBV proteins in recombinant vaccinia virus infected cells.

The EBV gp340 glycoprotein produced in EBV infected cells has a molecular weight of approximately 340 kDa (165). Cells infected with the recombinant vaccinia viruses vP474 or vP712 also produce an EBV encoded protein of approximately 340 kDa (immunoprecipitation performed with the monoclonal antibody F29-89). The EBV gp220 glycoprotein has a molecular weight of 220 kDa (165). Cells infected with the vaccinia recombinant virus vP480 produce an EBV encoded protein of approximately 220 kDa.

The EBV gB glycoprotein produced in EBV infected cells has a molecular weight of 110 kDa to 125 kDa with a precursor form of 93 kDa (206,208). Cells infected with the recombinant vaccinia viruses vP561 or vP712 produce an EBV major protein with a molecular weight of approximately 125 kDa and four minor proteins with molecular weights of approximately 80 kDa, 60 kDa, 50 kDa and 45 kDa.

The EBV gH glycoprotein produced in EBV infected cells has a molecular weight of 85 kDa with a precursor form of 70 kDa (209). Cells infected with the recombinant virus vP611 produce an EBV encoded protein of approximately 85 kDa.

Immunization of rabbits with vaccinia recombinants expressing EBV glycoproteins.

Rabbits were immunized with vP474 (gp340) or vP480 (gp220) or vP561 (gB) or vP611 (gH) or vP712 (triple). After one boost the sera were tested by immunofluorescence on TPA treated B95-8 cells. Positive signals were obtained in each case. In Vitro neutralizing activity was demonstrated using the sera raised against vP474 (gp340).

EXAMPLE 17

CLONING AND EXPRESSION OF HUMAN CYTOMEGALOVIRUS GLYCOPROTEIN ANTIGENS IN POXVIRUS VECTORS

Cloning of the HCMV gB gene into the vaccinia donor plasmid pMP409DVC.

Referring now to FIG. 40, the 4800 bp HindIII-BamHI fragment of the HindIII D fragment of the HCMV DNA was cloned into the 2800 bp HindIII-BamHI fragment of the plasmid pIBI24. By in vitro mutagenesis (17,185) using the oligonucleotides CMVM5 (GCCTCATCGCTGCTG-GATATCCGTTAAGTTTGTATCGTAATG-GAATCCAGGATCTG) and CMVM3 (GACAGATTGT-GATTTTTATAAGCATCGTAAGCTGTCA), the HCMV gB gene was modified to be expressed under the control of the vaccinia H6 promoter. The plasmid containing the modified HCMV gB gene was designated 24CMVgB(5+3) (FIG. 40).

Next, the 2900 bp EcoRV-BamHI fragment of 24CMVgB(5+3) was cloned into the 3100 bp EcoRV-BglII fragment of plasmid pSP131 which contains the synthetic H6 promoter (69). This cloning step put the HCMV gB gene under the control of the vaccinia H6 promoter. The resulting plasmid was designated SP131gB.

Finally, the H6 promoted HCMV gB gene was cloned into the vaccinia donor plasmid pMP409DVC. The 3000 bp HindIII Mung Bean nuclease treated fragment of SP131gB was cloned into the BglII Mung Bean nuclease treated site of pMP409DVC. The resulting plasmid was designated 409CMVgB (FIG. 40).

Construction of recombinant vaccinia virus.

The H6 promoted CMV gB gene in plasmid 409CMVgB was inserted into the M2L site of the rescue virus vP458. The recombinant vaccinia virus was designated vP525.

Immunofluorescence of CMV gB protein in recombinant vaccinia virus infected cells.

Immunofluorescence studies on cells infected with vP525 using a monoclonal antibody or a guinea pig polyclonal serum showed HCMV gB expressed on the plasma membrane.

Immunoprecipitation of CMV gB in recombinant vaccinia infected cells.

The CMV gB glycoprotein produced in CMV infected cells has a molecular weight of 55 kDa with a precursor form of 130 kDa (172). Cells infected with vP525 produce two CMV gB encoded proteins of approximately 130 kDa and 55 kDa.

Nucleotide sequences of HXLF1 and HXLF2.

The HXLF gene family is localized in the HindIII X fragment of the HCMV genomic DNA (172). Using specific oligonucleotide primers the nucleotide sequence of HXLF1 and HXLF2 have been determined (FIGS. 41, 42). HXLF1 is 648 nucleotides long and codes for a 215 amino acid protein. HXLF2 is 558 nucleotides long and codes for a 185 amino acid protein. The nucleotide sequences of the same genes (AD169 HCMV strain) have been published (173) and comparison studies show a 99% homology for HXLF1 and a 96% homology for HXLF2.

Immunization Of guinea pigs with vaccinia recombinants expressing HCMV antigens.

Three guinea pigs were immunized with vP525. After one boost, the animals developed HCMV neutralizing antibodies (mean titer: 518). Interestingly 50 to 87% of the neutralizing activity of HCMV seropositive human sera can be absorbed out by vP525 infected cells. This result indicates the potential importance of HCMV gB as a subunit vaccine.

REFERENCES

1. Allen, G. P. and J. T. Bryans, In: Progress in Veterinary Microbiology and Immunology, Vol. 2, ed. R. Pandey (Basel), pp. 78–144 (1986).
2. Allen, G. P., and L. D. Coogle, J. Virol. 62, 2850–2858 (1988).
3. Allen, G. P. and M. R. Yeargan, J. Virol. 61, 2454–2461 (1987).
4. Baumann, R. P., D. C. Sulivan, J. Staczek, and D. J. O'Callaghan, J. Virol. 57, 816–825 (1986).
5. Ben-Porat, T., J. DeMarchi, B. Lomniczi, and A. Kaplan, Virology 154, 325–334 (1986).
6. Berman, P. W., D. Dowbenko, L. A. Lasky, and C. C. Simonsen, Science 222, 524–527 (1983).
7. Bertholet, C., R. Drillien, and R. Wittek, Proc. Natl. Acad. Sci. USA 82, 2096–2100 (1985).
8. Cantin, E. M., R. Eberle, J. L. Baldick, B. Moss, D. E. Willey, A. L. Notkins, and H. Openshaw, Proc. Natl. Acad. Sci. USA 84, 5908–5912 (1987).
8. Chakrabarti, S., K. Brechling, and B. Moss, Mol. Cell. Biol. 5, 3403–3409 (1985).
10. Cranage, M. P., T. Kouzarides, A. T. Bankier, S. Satchwell, K. Weston, P. Tomlinson, B. Barrell, H. Hart, S. E. Bell, A. C. Minson, and G. L. Smith, EMBO J. 5, 3057–3063 (1986).
11. Clewell, D. B., J. Bacteriol. 110, 667–676 (1972).
12. Clewell, D. B. and D. R. Helinski, Proc. Natl. Acad. Sci. USA 62, 1159–1166 (1969).
13. Cremer, K. J., M. Mackett, C. Wohlenberg, A. L. Notkins, and B. Moss, Science 228, 737–740 (1985).
14. Eisenberg, D., Annu. Rev. Biochem. 53, 595–623 (1984).
15. Glorioso, J., U. Kees, G. Kumel, H. Kirchner, and P. Krammer, J. Immunol. 135, 575–582 (1985).
16. Graham, F. L. and A. J. Van der Eb., Virology 54, 536–539 (1973).
17. Kunkel, T. A., Proc. Natl. Acad. Sci. USA 82, 488–492 (1985). 18. Lasky, L. A., D. Dowbenko, C. C. Simonsen, and P. W. Berman, Bio-Technology 2, 527–532 (1984).
19. Mandecki, W., Proc. Natl. Acad. Sci. USA 83, 7177–7181 (1986).
20. Maniatis, T., E. F. Fritsch, and J. Sambrook, Molecular Cloning: A Laboratory Manual, (Cold Spring Harbor Laboratory, New York) (1982).
21. Martin, S. and B. T. Rouse, J. Immunol. 138, 3431–3437 (1987).
22. Martin, S., B. Moss, P. W. Berman, L. A. Lasky, and B. T. Rouse, J. Virol. 61, 726–734 (1987).
23. O'Callaghan, D. J., B. E. Henry, J. H. Wharton, S. A. Dauenhauer, R. B. Vance, J. Staczek, and R. A. Robinson, In: Developments in Molecular Virology, Vol. 1, ed. Y. Decker, pp. 387–418 (1981).
24. Panicali, D., A. Grzelecki, and C. Huang, Gene 47, 193–199 (1986).
25. Panicali, D., and E. Paoletti, Proc. Natl. Acad. Sci. USA 79, 4927–4931 (1982).
26. Paoletti, E., B. R. Lipinskas, C. Samsonoff, S. Mercer, and D. Panicall, Proc. Natl. Acad. Sci. USA 81, 193–197 (1984).
27. Perkus, M. E., A. Piccini, B. R. Lipinskas, and E. Paoletti, Science 229, 981–984 (1985).
28. Piccini, A., M. E. Perkus, and E. Paoletti, In: Methods in Enzymology, Vol. 153, eds. Wu, R., and L. Grossman (Academic Press) pp. 545–563 (1987).
29. Pustell, J., and F. C. Kafatos, Nucleic Acids Res. 12, 643–655 (1984).
30. Rooney, J. F., C. Wohlenberg, K. J. Cremer, B. Moss, and A. L. Notkins, J. Virol. 62, 1530–1534 (1988).
31. Rosel, J. L., P. L. Earl, J. P. Weir, and B. Moss, J. Virol. 60, 436–449 (1986).
32. Rosenthal, K. L., J. R. Smiley, S. South, and D. C. Johnson, J. Virol. 61, 2438–2447 (1987).
33. Sanger, F., S. Nicklen, and A. Coulson, Proc. Natl. Acad. Sci. USA .74, 5463–5467 (1977).
34. Shapira, S. K., J. Chou, F. V. Richaud, and M. J. Casadaban, Gene 25, 71–82 (1983).
35. Shida, H., Virology 150, 451–462 (1986).
36. Spear, P. G., In: The Basis for Serodiagnosis and Vaccines, Immunochemistry of Viruses, Vol. 2, eds. M. H. V. Van Regenmortel and A.R. Neurath (New York), pp. 425–443 (1985).
37. Spear, P. G., .In: The Herpesvirus, Vol. 3, ed. B. Roizman (New York), pp. 315–356 (1985).
38. Sullivan, V. and G. L. Smith, J. gen. Virol. 68, 2587–2598 (1987).
39. Sullivan, V. and G. L. Smith, J. gen. Virol. 69, 859–867 (1988).
40. Tabor, S., and C. C. Richardson, Proc. Natl. Acad. Sci. USA 84, 4767–4771 (1987).
41. Taylor, J., R. Weinberg, B. Lanquet, P. Desmettre, and E. Paoletti, Vaccine 6, 497–503 (1988).
42. Taylor, J., R. Weinberg, Y. Kawaoka, R. Webster, and E. Paoletti, Vaccine 6, 504–508 (1988).
43. Turtinen, L. W., and G. P. Allen, J. gen. Virol. 63, 481–485 (1982).
44. Wachsman, M., L. Aurelian, C. C. Smith, B. R. Lipinskas, M. E. Perkus, and E. Paoletti, J. Infect. Dis. 155, 1188–1197 (1987).
45. Yuen, L. and B. Moss, Proc. Natl. Acad. Sci. USA 84, 6417–6421 (1987).
46. Zarling, J. M., P. A. Moran, L. A. Lasky, and B. Moss, J. Virol. 59, 506–509 (1986).
47. Zarling, J. M., P. A. Moran, R. L. Burke, C. Pachl, P. W. Berman, and L. A. Lasky, J. Immunol. 136, 4669–4673 (1986).
48. O'Callaghan, D. J., G. A. Gentry, and C. C. Randall, In: The Herpesviruses, Vol. 2, ed. B. Roizman (New York), pp. 215–318 (1983).
49. Ackermann, M., R. Longnecker, B. Roizman, and L. Pereira, Virology 950, 207–220 (1986).
50. Frink, R. J., M. R. Eisenberg, G. Cohen, and E. K. Wagner, J. Virol. 45, 634–647 (1983).
51. Frame, M. C., H. S. Marsden, and D. J. McGeoch, J. gen. Virol. 67, 745–751 (1986).
52. Longnecker, R., S. Chatterjee, R. Whitley, and B. Roizman, Proc. Natl. Acad. Sci. USA 84, 4303–4307 (1987).
53. Richman, D. D., A. Buckmaster, S. Bell, C. Hodgman and A. C. Minson, J. Virol. 57, 647–655 (1986).
54. Swain, M. A., R. W. Peet, and D. A. Galloway, J. Virol, 53, 561–569 (1985).
55. Zezulak, K. M., and P. G. Spear, J. Virol. 49, 741–747 (1984).

56. van Drunen Littel-van der Hurk, S., T. Zamb, and L. A. Babrick, J. Virol. 63, 2159–2168 (1989).
57. Perkus, M. E., D. Panicall, S. Mercer, and E. Paoletti, Virology 152, 285–297 (1986).
58. Tamin, A., E. C. Villarreal, S. L. Weinrich, and D. E. Hruby, Virology 165, 141–150 (1988).
59. Whalley, J. M., G. R. Robertson, and A. J. Davidson, J. gen. Virol. 57, 307–323 (1981).
60. Laemmli, U. K., Nature (London) 227, 680–685 (1970).
61. Hagenbuchle, O., M. Santer, J. A. Steitz, and R. J. Mans, Cell 13, 551–563 (1978).
62. Robbins, A. K., D. J. Dorney, M. W. Wathen, M. E. Whealey, C. Gold, R. J. Watson, L. E. Holland, S. D. Weed, M. Levine, J. C. Glorioso, and L. W. Enquist, J. Virol. 61, 2691–2701 (1987).
63. Whitbeck, J. C., L. Z. Bello, and W. C. Lawrence, J. Virol. 62, 3319–3327 (1988).
64. Montreuil, J., J. Biol. Cell. 51, 115–132 (1984).
65. Kyte, J., and R. F Doolittle, J. Mol. Biol. 157, 105–132 (1982).
66. Davison, A. J., and J. E. Scott, J. gen. Virol. 67, 1759–1816 (1986).
67. Bzik, D. J., B. A. Fox, N. A. DeLuca, and S. Person, Virology 133, 301–307 (1984).
68. Pellett, P. E., M. D. Biggin, B. L. Barrell, and B. Roizman, J. Virol. 56, 807–813 (1985).
69. Perkus, M. E., K. Limbach, and E. Paoletti, J. Virol. 63, 3829–3836 (1989).
70. Gillard, S., D. Spehner, R. Drillien, and A. Kirn, Proc. Natl. Acad. Sci. USA 83, 5573–5577 (1986).
71. Whalley, J. M., G. R. Robertson, N. A. Scott, G. C. Hudson, C. W. Bell, and L. M. Woodworth, J. gen. Virol. 70, 383–394 (1989).
72. Riggio, M. P., A. A. Cullinane, and D. E. Onions, J. Virol. 63, 1123–1133 (1989).
73. Glorioso, J., C. H. Schroder, G. Kumel, M. Szczesiul, and M. Levine, J. Virol. 5:0, 805–812 (1984).
74. Wachsman, M., L. Aurelian, J. C. R. Hunter, M. E. Perkus, and E. Paoletti, Bioscience Reports 8, 323–334 (1988).
75. Wachsman, M., J. H. Luo, L. Aurelian, M. E. Perkus, and E. Paoletti, J. gen. Virol. 70, 2513–2520 (1989).
76. Sinclair, R., R. F. Cook, and J. A. Mumford, J. gen. Virol. 70, 455–459 (1989).
77. Shimizu, M., K. Satou, and N. Nishioka, Arch. Virol. 104, 169–174 (1989).
78. Stokes, A., G. P. Allen, L. A. Pullen, and P. K. Murray, J. gen. Virol. 70, 1173–1183 (1989).
79. McGeoch, D. J., A. Dolan, S. Donald, and F. J. Rixon, J. Mol. Biol. 181, 1–13 (1985).
80. Petrovskis, E. A., J. G. Timmins, and L. E. Post, J. Virol. 60, 185–193 (1986).
81. Wittmann, G. and H.-J. Rziha, In: Herpesvirus Diseases of Cattle, Horses and Pigs, ed. G. Wittmann (Kluwer Academic Publishers) pp. 230–325 (1989).
82. Rubenstein, A. S. and A. S. Kaplan, Virology 66, 385–392 (1975).
83. Stevely, W. S., J. Virol. 22, 232–234 (1977).
84. Ben-Porat, T., F. J. Rixon, and M. L. Blankenship, Virology 95, 285–294 (1979).
85. Ben-Porat, T. and A. S. Kaplan, In: The Herpesviruses, vol. 3, ed. B. Roizman (Plenum Publishing Corp., New York) pp. 105–173 (1985).
86. Hampl, H., T. Ben-Porat, L. Ehrlicher, K.-O. Habermehl, and A. S. Kaplan, J. Virol. 52, 583–590 (1984).
87. Ben-Porat, T. In: Organization and replication of viral DNA, ed. A. S. Kaplan (CRC Press, Inc., Boca Raton, Fla.) pp. 147–172 (1982).
88. Ben-Porat, T., J. DeMarchi, J. Pendrys, R. A. Veach, and A. S. Kaplan, J. Virol. 57, 191–196 (1986).
89. Ben-Porat, T. and A. S. Kaplan, Virology 41, 265–273 (1970).
90. Killington, R. A., J. Yeo, R. W. Honess, D. H. Watson, B. E. Duncan, I. W. Halliburton, and J. Mumford, J. gen. Virol. 297–310 (1977).
91. Robbins, A. K., J. H. Weis, L. W. Enquist, and R. J. Watson, J. Mol. Appl. Genet. 2, 485–496 (1984).
92. Rea, T. J., J. G. Timmins, G. W. Long, and L. E. Post, J. Virol. 54, 21–29 (1985).
93. Mettenleiter, T. C., N. Lukacs, and H.-J. Rziha, J. Virol. 53, 52–57 (1985).
94. Mettenleiter, T. C., N. Lukacs, H.-J. Thiel, C. Schreurs, and H.-J. Rziha, Virology 152, 66–75 (1986).
95. Petrovskis, E. A., J. G. Timmins, M. A. Armentrout, C. C. Marchioli, R. J. Yancey, Jr., and L. E. Post, J. Virol. 59, 216–223 (1986).
96. Robbins, A. K., R. J. Watson, M. E. Whealy, W. W. Hays, and L. W. Enquist, J. Virol. 58, 339–347 (1986).
97. Wathen, M. W. and L. M. K. Wathen, J. Virol. 51, 57–62 (1984).
98. Kost, T. A., E. V. Jones, K. M. Smith, A. P. Reed, A. L. Brown, and T. J. Miller, Virology 171, 365–376 (1989).
99. Mettenleiter, T. C., N. Lukacs, and H.-J. Rziha, J. Virol. 56, 307–311 (1985).
100. Lomniczi, B., S. Watanabe, T. Ben-Porat, and A. S. Kaplan, J. Virol. 52, 198–205 (1984).
101. Lukacs, N., H.-J. Thiel, T. C. Mettenleiter, and H.-J. Rziha, J. Virol. 53, 166–173 (1985).
102. Marchioli, C., R. J. Yancey, Jr., J. G. Timmins, L. E. Post, B. R. Young, and D. A. Povendo, Am. J. Vet. Res. 49, 860–864 (1988).
103. Marchioli, C. C., R. J. Yancey, Jr., R. C. Wardley, D. R. Thomsen and L. E. Post, Am. J. Vet. Res. 48, 1577–1583 (1987).
104. Thomsen, D. R., C. C. Marchloll, R. J. Yancey, Jr. and L. E. Post, J. Virol. 61, 229–232 (1987).
105. Wathen, L. M. K., K. B. Platt, M. W. Wathen, R. A. Van Deusen, C. A. Whetstone, and E. C. Pirtle, Virus Res. 4, 19–29 (1985).
106. Eloit, M., D. Fargeaud, R. L'Haridon and B. Toma, Arch. Virol. 99, 45–46 (1988).
107. Marchioli, C. C., R. J. Yancey, Jr., E. A. Petrovskis, J. G. Timmins, and L. E. Post, J. Virol. 61, 3977–3982 (1987).
108. Ishii, H., Y. Kobayashi, M. Kuroki and Y. Kodama, J. gen. Virol.69, 1411–1414 (1988).
109. Whealy, M. E., A. K. Robbins and L. W. Enquist, J. Virol. 63, 4055–4059 (1989).
110. Wathen, M. W. and L. M. K. Wathen, J. Virol. 58, 173–178 (1986).
111. Robbins, A. K., M. E. Whealy, M. E., R. J. Watson and L. W. Enquist, J. Virol. 59, 635–645 (1986).
112. Allen, W. P., and F. Rapp, J. Infect. Dis. 145, 413–421 (1982).
113. Bryson, Y. J., M. Dillon, M. Lovett, G. Acuna, S. Taylor, J. D. Cherry, B. L. Johnson, E. Wiesmeier, W. Growdon, T. Creagh-Kirk, and R. Keeney, N. Engl. J. Med. 308, 916–921 (1983).
114. Douglas, J. M., C. Critchlow, J. Benedetti, G. J. Mertz, J. D. Connor, M. A. Hintz, A. Fahnlander, M. Remington, C. Winter, and L. Corey, N. Engl. J. Med. 310, 1551–1556 (1984).
115. Roizman, B. and A. E. Sears, In: Virology, eds. Fields, B. N. and D. M. Knipe (Raven Press, Ltd., New York) pp. 1795–1841 (1990).

116. Stuve, L. L., S. Brown-Shimer, C. Pachl, R. Najarian, D. Dina, and R. L. Burke, J. Virol. 61, 326–335 (1987).
117. Dowbenko, D. J., and L. A. Lasky, J. Virol. 52, 154–163 (1984).
118. Watson, R. J., Gene 26, 307–312 (1983).
119. McGeoch, D. J., H. W. M. Moss, D. McNab and M. C. Frame, J. gen. Virol. RS, 19–38 (1987).
120. Chan, W., Immunol. 49, 343–352 (1983).
121. Davis, W. B., J. A. Taylor, and J. E. Oakes, J. Infect. Dis. 140, 534–540 (1979).
122. Oakes, J. E., and H. Rosemond-Hornbeak, Infect. Immun. 21, 489–495 (1978).
123. Balachandran, N., S. Bacchetti, and W. E. Rawls, Infect. Immun. 37, 1132–1137 (1982).
124. Oakes, J. E., W. B. Davis, J. A. Taylor, and W. W. Weppner, Infect. Immun. 29, 642–649 (1980).
125. McLaughlin-Taylor, E., D. E. Willey, E. M. Cantin, R. Eberle, B. Moss, and H. Openshaw, J. gen. Virol. 69, 1731–1734 (1988).
126. Weir, J. P., M. Bennett, E. M. Allen, K. L. Elkins, S. Martin, and B. T. Rouse, J. gen. Virol. 70, 2587–2594 (1989).
127. Gibbs, E. P. J., and M. M. Rweyemamu, Vet. Bull. 47, 317–343 (1977).
128. Yates, W. D. G., Can. J. Comp. Med. 46, 225–263 (1982).
129. Misra, V., R. M. Blumenthal and L. A. Babiuk, J. Virol. 40, 367–378 (1981).
130. Lawrence, W. C., R. C. D'Urso, C. A. Kundel, J. C. Whitbeck and L. J. Bello, J. Virol. 60, 405–414 (1986).
131. Zamb, T. 1987, Abstract No. 330, 68th Annual Meeting of Conference of Research Workers in Animal Disease, 16 and 17 Nov. 1987, Chicago, Ill., U.S.A.
132. Babiuk, L. A., J. L'Italien, S. van Drunen Littel-van den Hurk, T. Zamb, M. J. P. Lawman, G. Hughes, and G. A. Gifford, J. Virol. 159, 57–66 (1987).
133. van Drunen Littel-van den Hurk, S., and L. A. Babiuk, J. Virol. 59, 401–410 (1986).
134. Gaskel, R. M., and R. C. Povey, Res. Vet. Sci. 27, 167–174 (1978).
135. Povey R. C., and M. R. Wilson, Feline Practice 8, 35–42 (1978).
136. Chappuis, G., C. Benoit-Jeanin, and D. Fargeaud, In: Develop. biol. Standard., Vol. 52, eds. M. Bonneau, and W. Hennessen, (S. Karger, Basel) pp. 485–491 (1982).
137. Saint-Gerand, A. L., Vaccine 6, 508 (1988).
138. Sarmiento, M., M. Haffey, and P. G. Spear, J. Virol. 29, 1149–1158 (1979).
139. Ruyechan, W. T., L. S. Morse, D. M. Knipe, and B. Roizman, J. Virol. 29, 677–697 (1979).
140. Pereira, L., E. Cassai, R. W. Honess, B. Roizman, M. Terni, and A. Nahmias, Infect. Immun. 13, 211–220 (1976).
141. Eberle, R., and R. J. Courtney, J. Virol. 35, 902–917 (1980).
142. Papp-Vid, G., and J. B. Derbyshire, Can. J. Comp. Med. 43, 231–233 (1979).
143. Meas, R. K., S. L. Fritsch, L. L. Herr, and P. A. Rota, J. Virol. 51, 259–262 (1984).
144. Fargeaud, D., C. Benoit Jeannin, F. Kato, and G. Chappuis, Arch. Virol. 80, 69–82 (1984).
145. Compton, T., In: Cell Biology of Virus Entry, Replication, and Pathogenesis, eds. Compans, R. W., A. Helenius, and M. B. A. Oldstone (Alan R. Liss, Inc.) pp. 45–56 (1989).
146. Spatz, S. J., R. K. Meas, and C. E. Beisel, Abstracts of the 14$^{th}$ International Herpesvirus Workshop (Nyborg Strand Denmark) p. 128 (1989).
147. Little, S. P., J. T. Jofre, R. J. Courthey, and P. A. Schaffer, Virology 114, 149–160 (1981).
148. DeLuca, N., D. J. Bzik, V. C. Bond, S. Person, and W. Snipes, Virology 122, 411–423 (1982).
149. Cai, W., B. Gu, and S. Person, J. Virol. 62, 2596–2604 (1988).
150. Courtney, R. J., In: Immunobiology of Herpes Simplex Virus Infection, eds. B. T. Rouse and C. Lopez (CRC Press, Inc., Boca Raton, Fla.) pp. 33–44 (1984).
151. Kozak, M., Microbial Rev. 47, 1–45 (1983).
152. Pelletier, J., and N. Sonenberg, Nature 334, 320–325 (1988).
153. Rota, P. A., R. K. Maes, and W. T. Ruyechan, Virology 154, 168–179 (1986).
154. Henle, G., W. Henle, and V. Diehl, Proc. Natl. Acad. Sci. USA 59, 94–101 (1968).
155. Kozak, M., Cell 44, 283–292 (1986).
156. Miller, G., In: Virology, Second Edition, eds. Fields, B. N. et al, (Raven Press, Ltd., New York) pp. 1921–1958 (1990).
157. Hubbard, S. C., and R. J. Ivatt, Ann. Rev. Biochem. 50, 555–583 (1981).
158. McGeoch, D. J., M. A. Dalrymple, A. J. Davison, A. Dolan, M. C. Frame, D. McNab, L. J. Perry, J. E. Scott, and P. Taylor, J. gen. Virol. 69, 1531–1574 (1988).
159. Kieff, E., and D. Liebowitz, In: Virology, Second Edition, eds. Fields, B. N. et al. (Raven Press, Ltd., New York) pp. 889–1920 (1990).
160. Watson, R. J., J. H. Weis, J. S. Salstrom, and L. W. Enquist, Science 218, 381–384 (1982).
161. McGeoch, D. J. and A. J. Davison, Nucleic Acid Res. 50, 4281–292 (1986).
162. Lehner, R., H. Meyer, and M. Mach, J. Virol. 63, 3792–3800 (1989).
163. Biggin, M., P. J. Farrell, and B. G. Barrell, EMBO. J. 3, 1083–1090 (1984).
164. Beisel, C., J. Tanner, T. Matsuo, D. Thorley-Lawson, F. Kezdy, and E. Kieff, J. Virol. 54, 665–674 (1985).
165. Qualtiere, L. F., J. F. Decoteau, and M. Hassan Nasr-el-Din, J. gen. Virol. 68, 535–543 (1987).
166. Epstein, M. A., A. J. Morgan, S. Finerty, B. J. Randle, and J. K. Kirkwood, Nature 318, 287–289 (1985).
167. Morgan, A. J., M. Mackett, S. Finerty, J. R. Arrand, F. T. Scullion, and M. A. Epstein, J. Med. Virol. 25, 189–195 (1988).
168. Strnad, B. C., T. Schuster, R. Klein, R. F. Hopkins, T. Witmer, R. H. Neubauer, and H. Rabin, J. Virol. 41, 258–264 (1982).
169. Miller, N., and L. M. Hutt-Fletcher, J. Virol. 62, 2366–2372 (1988).
170. Plotkin, S. A., H. M. Friedman, S. E. Starr, and E. Gonczol, In: Contemporary Issues in Infectious Diseases, Vol. 8, eds. Root et al. (Churchill Livingstone, New York) pp. 65–92 (1989).
171. Plotkin, S. A., S. E. Starr, H. M. Friedman, E. Gonczol, and R. E. Weibel, J. Inf. Dis. 159, 860–865 (1989).
172. Gretch, D. R., B. Kari, L. Rasmussen, R. C. Gehrz, and M. F. Stinski, J. Virol. 62, 875–881 (1988).
173. Weston, K., and B. G. Barrell, J. Mol. Biol. 192, 177–208 (1986).
174. Pachl, C., W. S. Probert, K. M. Hermsen, F. R. Masiarz, L. Rasmussen, T. C. Merigan, and R. R. Spaete, Virology 169, 418–426 (1989).
175. Rasmussen, L., M. Nelson, M. Neff, and T. C. Merigan, Jr., Virology 163, 308–318 (1988).
176. Kari, B., N. Lussenhop, R. Goertz, M. Wabuke-Bunoti, R. Radeke, and R. Gehrz, J. Virol. 60, 345–352 (1986).

177. Boyle, D. B., and B. E. H. Coupar, Virus Res. 10, 343–356 (1988).
178. Nettleton, P. F., and J. M. Sharp, Vet. Rec. 107, 379 (1980).
179. Kahrs, R. F., J. Amer. Vet. Med. Assoc. 171, 1055–1064 (1977).
180. McLauchlan, J., D. Gaffney, J. L. Whitton, and J. B. Clements, Nucleic Acids Res. 13, 1347–1368 (1985).
181. Davison, A. J., EMBO J. 2, 2203–2209 (1983).
182. Todd, D. and J. B. McFerran, Arch. Virol. 86, 167–176 (1985).
183. Diamond, L., Int. J. Cancer 2, 143–152 (1967).
184. Guo, P., S. Goebel, S. Davis, M. E. Perkus, B. Languet, P. Desmettre, G. Allen, and E. Paoletti, J. Virol. 63, 4189–4198 (1989).
185. Russel, M., S. Kidd, and M. R. Kelley, Gene 45, 333–338 (1986).
186. Kunkel, T. A., J. D. Roberts, and R. A. Zakour, In: Methods in Enzymology, Vol. 154, eds. R. Wu, and L. Grossman (Academic Press, Inc.) pp. 367–382 (1987).
187. Schmitt, J. F. C. and H. G. Stunnenberg, J. Virol. 62, 1889–1897 (1988).
188. Pickup, D. J., B. S. Ink, W. Hu, C. A. Ray, and W. K. Joklik, Proc. Natl. Acad. Sci. USA 83, 7698–7702 (1986).
189. Southern, E. M., J. Mol. Biol. 98, 503–517 (1975).
190. Bucher, D., S. Popple, M. Baer, A. Mikhail, Y.-F. Gong, C. Whitaker, E. Paoletti, and A. Judd, J. Virol. 63, 3622–3633 (1989).
191. Joklik, W. K., Virology 18, 9–18 (1962).
192. Guilhot, S., A. Hampe, L. D'Auriol, and F. Galibert, Virology 161, 252–258 (1987).
193. Falkner, F. G., and B. Moss, J. Virol. 62, 1849–1854 (1988).
194. Boyle, D. B., and B. E. H. Coupar, Gene 65, 123–128 (1988).
195. Dreyfuss, G., S. A. Adam, and Y. D. Choi, Mol. Cell. Biol. 4, 15–423 (1984).
196. Kennedy, I. M., D. P. Leader, and W. S. Stevely, J. gen. Virol. 5, 1621–1624 (1984).
197. Powell, K. L. and D. H. Watson, J. gen. Virol. 29, 167–178 (1975).
198. Marsden, H. S., N. D. Stow, V. G. preston, M. C. Timbury, and N. M. Wilkie, J. Virol. 28, 624–642 (1978).
199. Marsden, H. S., A. Buckmaster, J. W. palfreyman, R. G. Hope, and A. C. Minson, J. Virol. 50, 547–554 (1984).
200. Zweig, M., S. D. Showalter, S. V. Bladen, C. J. Heilman, Jr. and B. Hampar, J. Virol. 47, 185–192 (1983).
201. Marshall, R. L., B. A. Israel, and G. J. Letchworth, III., Virology 165, 338–347 (1988).
202. Panicali, D., S. W. Davis, S. R. Mercer, and E. paoletti, J. Virol. 37, 1000–1010 (1981).
203. Misra V., R. Nelson, and M. Smith, Virology 166, 542–549 (1988).
204. Keller, P. M., A. J. Davison, R. S. Lowe, C. D. Bennett, and R. W. Ellis, Virology 152, 181–191 (1986).
205. Bzik, D. J., C. Debroy, B. A. Fox, N. E. pederson, and S. Person, Virology 155, 322–333 (1986).
206. Gong, M., T. Ooka, T. Matsuo, and E. Kieff, J. Virol. 61, 499–508 (1987).
207. Baer, R., A. T. Bankier, M. D. Biggin, P. L. Deininger, P. J. Farrell, T. J. Gibson, G. Hatfull, G. S. Hudson, S. C. Satchwell, C. Seguin, P. S. Tuffnell, and B. G. Barrell, Nature 310, 207–211 (1984).
208. Emini, E. A., J. Luka, M. E. Armstrong, P. M. Keller, R. W. Ellis, and G. R. Pearson, Virology 157, 552–555 (1987).
209. Heineman, T., M. Gong, J. Sample, and E. Kieff, J. Virol. 62, 1101–1107 (1988).
210. Patel, D. D., and D. F. Pickup, Embo J. 6, 3787–3794 (1987).

What is claimed is:

1. A vaccine for inducing a protective response in a host animal inoculated with said vaccine, said vaccine comprising a carrier and a recombinant vaccinia or avipox virus; said recombinant virus containing, in a nonessential region or regions thereof, DNA from equine herpesvirus and one or more promoters for expressing the DNA, wherein said DNA from equine herpesvirus encodes: glycoprotein gp13, glycoproteins gp13 and gp14, an N-terminal leader truncated glycoprotein gp14 which is exposed on the surface of cells infected with said recombinant virus, or glycoprotein gp13 and an N-terminal leader truncated glycoprotein gp14 which is exposed on the surface of cells infected with said recombinant virus.

2. A vaccine as in claim 1 wherein said DNA from equine herpesvirus encodes glycoprotein gp13.

3. A vaccine as in claim 1 wherein said DNA from equine herpesvirus encodes an N-terminal leader truncated glycoprotein gp14 which is exposed on the surface of cells infected with said recombinant virus.

4. A vaccine as in claim 1 wherein said DNA from equine herpesvirus encodes an N-terminal leader truncated glycoprotein gp14 which is exposed on the surface of cells infected with said recombinant virus, or glycoprotein gp13 and an N-terminal leader truncated glycoprotein gp14 which is exposed on the surface of cells infected with said recombinant virus; wherein said DNA encoding said truncated gp14 is equine herpesvirus 1 (EHV-1) DNA which has had deleted therefrom codons 2 through 34 with the substitution of four codons such that DNA contains the sequence ATG-CAT-GCA-TGC-ATT-GCT, wherein ATG is codon 1 of the EHV-1 gp14 sequence and GCT is codon 35 of the EHV-1 gp14 sequence.

5. A vaccine as in claim 1 wherein said DNA from equine herpesvirus encodes glycoprotein gp13 and an N-terminal leader truncated glycoprotein gp14 which is exposed on the surface of cells infected with said recombinant virus.

6. A vaccine as in claim 1 wherein said DNA from equine herpesvirus encodes glycoprotein gp13 and glycoprotein gp14.

7. A vaccine as in claim 1 wherein the virus is vaccinia virus.

8. A vaccine as in claim 1 wherein the virus is an avipox virus.

9. A vaccine as in claim 8 wherein the avipox virus is fowlpox virus or canarypox virus.

10. A vaccine as in claim 8 wherein the avipox virus is canarypox virus.

11. A vaccine as in claim 8 wherein the avipox virus is fowlpox virus.

* * * * *